(12) United States Patent
Shelton, IV et al.

(10) Patent No.: US 11,213,294 B2
(45) Date of Patent: *Jan. 4, 2022

(54) SURGICAL INSTRUMENT COMPRISING CO-OPERATING LOCKOUT FEATURES

(71) Applicant: Cilag GmbH International, Zug (CH)

(72) Inventors: Frederick E. Shelton, IV, Hillsboro, OH (US); Jason L. Harris, Lebanon, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 131 days.

This patent is subject to a terminal disclaimer.

(21) Appl. No.: 16/281,685

(22) Filed: Feb. 21, 2019

(65) Prior Publication Data

US 2019/0298341 A1    Oct. 3, 2019

Related U.S. Application Data

(60) Provisional application No. 62/807,310, filed on Feb. 19, 2019, provisional application No. 62/807,319, (Continued)

(51) Int. Cl.
*A61B 17/062* (2006.01)
*A61B 17/068* (2006.01)
(Continued)

(52) U.S. Cl.
CPC ........ *A61B 17/0682* (2013.01); *A61B 17/072* (2013.01); *A61B 17/07207* (2013.01); *A61B 17/29* (2013.01); *A61B 17/34* (2013.01); *A61B 17/105* (2013.01); *A61B 17/32* (2013.01); *A61B 34/30* (2016.02); *A61B 2017/00398* (2013.01); *A61B 2017/00473* (2013.01); *A61B 2017/00477* (2013.01); *A61B 2017/00862* (2013.01); *A61B 2017/0688* (2013.01); *A61B 2017/07221* (2013.01); *A61B 2017/07257* (2013.01); *A61B 2017/07271* (2013.01); *A61B 2017/2927* (2013.01); *A61B 2090/034* (2016.02);
(Continued)

(58) Field of Classification Search
CPC .............. A61B 17/0682; A61B 17/072; A61B 17/07207; A61B 2017/07271
See application file for complete search history.

(56) References Cited

U.S. PATENT DOCUMENTS

| | | |
|---|---|---|
| 1,853,416 A | 4/1932 | Hall |
| 2,222,125 A | 11/1940 | Stehlik |

(Continued)

FOREIGN PATENT DOCUMENTS

| | | |
|---|---|---|
| AU | 2015201140 A1 | 3/2015 |
| CA | 2795323 A1 | 5/2014 |

(Continued)

OTHER PUBLICATIONS

US 10,504,709 B2, 12/2019, Karancsi et al. (withdrawn)
(Continued)

*Primary Examiner* — Chelsea E Stinson

(57) ABSTRACT

A surgical system is disclosed that comprises a stapling instrument including a staple firing lockout and a staple cartridge configured to defeat the staple firing lockout when the staple cartridge is seated in the stapling instrument.

25 Claims, 122 Drawing Sheets

Related U.S. Application Data filed on Feb. 19, 2019, provisional application No. 62/807,309, filed on Feb. 19, 2019, provisional application No. 62/650,887, filed on Mar. 30, 2018, provisional application No. 62/649,302, filed on Mar. 28, 2018, provisional application No. 62/649,294, filed on Mar. 28, 2018, provisional application No. 62/649,300, filed on Mar. 28, 2018, provisional application No. 62/649,309, filed on Mar. 28, 2018, provisional application No. 62/649,310, filed on Mar. 28, 2018, provisional application No. 62/649,291, filed on Mar. 28, 2018, provisional application No. 62/649,296, filed on Mar. 28, 2018, provisional application No. 62/649,333, filed on Mar. 28, 2018, provisional application No. 62/649,327, filed on Mar. 28, 2018, provisional application No. 62/649,315, filed on Mar. 28, 2018, provisional application No. 62/649,313, filed on Mar. 28, 2018, provisional application No. 62/649,320, filed on Mar. 28, 2018, provisional application No. 62/649,307, filed on Mar. 28, 2018, provisional application No. 62/649,323, filed on Mar. 28, 2018.

(51) Int. Cl.
| | | |
|---|---|---|
| *A61B 17/072* | (2006.01) | |
| *A61B 17/29* | (2006.01) | |
| *A61B 17/34* | (2006.01) | |
| *A61B 34/30* | (2016.01) | |
| *A61B 90/00* | (2016.01) | |
| *A61B 17/10* | (2006.01) | |
| *A61B 17/32* | (2006.01) | |
| *A61B 17/00* | (2006.01) | |

(52) U.S. Cl.
CPC .............. *A61B 2090/0811* (2016.02); *A61B 2090/0814* (2016.02)

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,202,722 A | 5/1980 | Paquin |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,892,244 A | 1/1990 | Fox et al. |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,084,057 A | 1/1992 | Green et al. |
| 5,100,402 A | 3/1992 | Fan |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,197,962 A | 3/1993 | Sansom et al. |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,322,055 A | 6/1994 | Davison et al. |
| 5,342,349 A | 8/1994 | Kaufman |
| 5,383,880 A | 1/1995 | Hooven |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,503,320 A | 4/1996 | Webster et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A * | 12/1996 | Savage ............ A61B 17/07207 227/175.2 |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |

(56) References Cited

U.S. PATENT DOCUMENTS

| | | |
|---|---|---|
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,273,887 B1 | 8/2001 | Yamauchi et al. |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,341,164 B1 | 1/2002 | Dilkie et al. |
| 6,391,102 B1 | 5/2002 | Bodden et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,585,791 B1 | 7/2003 | Garito et al. |
| 6,618,626 B2 | 9/2003 | West, Jr. et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,208,005 B2 | 4/2007 | Frecker et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,422,139 B2 | 9/2008 | Shelton, IV et al. |
| 7,423,972 B2 | 9/2008 | Shaham et al. |
| 7,457,804 B2 | 11/2008 | Uber, III et al. |
| 7,464,847 B2 | 12/2008 | Viola et al. |
| 7,464,849 B2 | 12/2008 | Shelton, IV et al. |
| 7,515,961 B2 | 4/2009 | Germanson et al. |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |

(56) References Cited

U.S. PATENT DOCUMENTS

| | | |
|---|---|---|
| 7,753,245 B2 | 7/2010 | Boudreaux et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,942,300 B2 | 5/2011 | Rethy et al. |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| 8,128,625 B2 | 3/2012 | Odom |
| 8,131,565 B2 | 3/2012 | Dicks et al. |
| 8,136,712 B2 | 3/2012 | Zingman |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,241,322 B2 | 8/2012 | Whitman et al. |
| 8,255,045 B2 | 8/2012 | Gharib et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| 8,365,975 B1 | 2/2013 | Manoux et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,571,598 B2 | 10/2013 | Valavi |

(56) References Cited

U.S. PATENT DOCUMENTS

| | | |
|---|---|---|
| 8,573,459 B2 | 11/2013 | Smith et al. |
| 8,573,465 B2 | 11/2013 | Shelton, IV |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,055 B2 | 12/2013 | Barratt et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,918,207 B2 | 12/2014 | Prisco |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |

(56) References Cited

U.S. PATENT DOCUMENTS

| | | |
|---|---|---|
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,161,803 B2 | 10/2015 | Yates et al. |
| 9,168,054 B2 | 10/2015 | Turner et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,468,438 B2 | 10/2016 | Baber et al. |
| 9,480,492 B2 | 11/2016 | Aranyi et al. |
| 9,485,475 B2 | 11/2016 | Speier et al. |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,566,708 B2 | 2/2017 | Kurnianto |
| 9,572,592 B2 | 2/2017 | Price et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,138 B2 | 3/2017 | Thomas et al. |
| 9,603,024 B2 | 3/2017 | Wang et al. |
| 9,610,114 B2 | 4/2017 | Baxter, III et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |

(56) References Cited

U.S. PATENT DOCUMENTS

| | | |
|---|---|---|
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,470 B2 | 12/2017 | Gilbert et al. |
| 9,839,487 B2 | 12/2017 | Dachs, II |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondon et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |

(56) References Cited

U.S. PATENT DOCUMENTS

| | | |
|---|---|---|
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,105,140 B2 | 10/2018 | Malinouskas et al. |
| 10,105,142 B2 | 10/2018 | Baxter, III et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,143,526 B2 | 12/2018 | Walker et al. |
| 10,143,948 B2 | 12/2018 | Bonitas et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,169,862 B2 | 1/2019 | Andre et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,035 B2 | 4/2019 | Fehre et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |

(56) References Cited

U.S. PATENT DOCUMENTS

| | | |
|---|---|---|
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,941 B2 | 7/2019 | Marczyk et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |

(56) References Cited

U.S. PATENT DOCUMENTS

| | | |
|---|---|---|
| 10,555,769 B2 | 2/2020 | Worrell et al. |
| 10,561,422 B2 | 2/2020 | Schellin et al. |
| 10,561,471 B2 | 2/2020 | Nichogi |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |
| 10,586,074 B2 | 3/2020 | Rose et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,691 B2 | 4/2020 | Wiener et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,454 B2 | 10/2020 | Kopp |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,835,247 B2 | 11/2020 | Shelton, IV et al. |
| 10,856,768 B2 | 12/2020 | Osadchy et al. |
| 10,864,037 B2 | 12/2020 | Mun et al. |
| 10,872,684 B2 | 12/2020 | McNutt et al. |
| 10,902,944 B1 | 1/2021 | Casey et al. |
| 10,905,418 B2 | 2/2021 | Shelton, IV et al. |
| 10,905,420 B2 | 2/2021 | Jasemian et al. |
| 10,932,784 B2 | 3/2021 | Mozdzierz et al. |
| 10,959,729 B2 | 3/2021 | Ehrenfels et al. |
| 10,987,102 B2 | 4/2021 | Gonzalez et al. |
| 10,992,698 B2 | 4/2021 | Patel et al. |
| 10,998,098 B2 | 5/2021 | Greene et al. |
| 11,058,501 B2 | 7/2021 | Tokarchuk et al. |
| 2002/0049551 A1 | 4/2002 | Friedman et al. |
| 2002/0072746 A1 | 6/2002 | Lingenfelder et al. |
| 2003/0009111 A1 | 1/2003 | Cory et al. |
| 2003/0093503 A1 | 5/2003 | Yamaki et al. |
| 2003/0114851 A1 | 6/2003 | Truckai et al. |
| 2003/0210812 A1 | 11/2003 | Khamene et al. |
| 2003/0223877 A1 | 12/2003 | Anstine et al. |
| 2004/0078236 A1 | 4/2004 | Stoodley et al. |

(56) References Cited

U.S. PATENT DOCUMENTS

| | | |
|---|---|---|
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0192633 A1 | 9/2005 | Montpetit |
| 2005/0222631 A1 | 10/2005 | Dalal et al. |
| 2005/0236474 A1 | 10/2005 | Onuma et al. |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0079874 A1 | 4/2006 | Faller et al. |
| 2006/0116908 A1 | 6/2006 | Dew et al. |
| 2006/0184160 A1 | 8/2006 | Ozaki et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0049947 A1 | 3/2007 | Menn et al. |
| 2007/0078678 A1 | 4/2007 | DiSilvestro et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0191713 A1 | 8/2007 | Eichmann et al. |
| 2007/0225556 A1 | 9/2007 | Ortiz et al. |
| 2007/0225690 A1 | 9/2007 | Sekiguchi et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0255413 A1 | 10/2008 | Zemlok et al. |
| 2008/0262654 A1 | 10/2008 | Omori et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0065604 A1 | 3/2010 | Weng |
| 2010/0069942 A1 | 3/2010 | Shelton, IV |
| 2010/0070417 A1 | 3/2010 | Flynn et al. |
| 2010/0132334 A1 | 6/2010 | Duclos et al. |
| 2010/0137845 A1 | 6/2010 | Ramstein et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198248 A1 | 8/2010 | Vakharia |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0292535 A1 | 11/2010 | Paskar |
| 2010/0292684 A1 | 11/2010 | Cybulski et al. |
| 2011/0022032 A1 | 1/2011 | Zemlok et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0166883 A1 | 7/2011 | Palmer et al. |
| 2011/0237883 A1 | 9/2011 | Chun |
| 2011/0264000 A1 | 10/2011 | Paul et al. |
| 2011/0306840 A1 | 12/2011 | Allen et al. |
| 2012/0022519 A1 | 1/2012 | Huang et al. |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0116265 A1 | 5/2012 | Houser et al. |
| 2012/0116381 A1 | 5/2012 | Houser et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0191091 A1 | 7/2012 | Allen |
| 2012/0191162 A1 | 7/2012 | Villa |
| 2012/0203785 A1 | 8/2012 | Awada |
| 2012/0211542 A1 | 8/2012 | Racenet |
| 2012/0245958 A1 | 9/2012 | Lawrence et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0098965 A1* | 4/2013 | Kostrzewski .......... A61B 90/08 227/175.2 |
| 2013/0105552 A1 | 5/2013 | Weir et al. |
| 2013/0116218 A1 | 5/2013 | Kaplan et al. |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0006943 A1 | 1/2014 | Robbins et al. |
| 2014/0013565 A1 | 1/2014 | MacDonald et al. |
| 2014/0029411 A1 | 1/2014 | Nayak et al. |
| 2014/0033926 A1 | 2/2014 | Fassel et al. |

(56) References Cited

U.S. PATENT DOCUMENTS

| | | |
|---|---|---|
| 2014/0035762 A1 | 2/2014 | Shelton, IV et al. |
| 2014/0066700 A1 | 3/2014 | Wilson et al. |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R. et al. |
| 2014/0148729 A1 | 5/2014 | Schmitz et al. |
| 2014/0166724 A1 | 6/2014 | Schellin et al. |
| 2014/0187856 A1 | 7/2014 | Holoien et al. |
| 2014/0194864 A1 | 7/2014 | Martin et al. |
| 2014/0204190 A1 | 7/2014 | Rosenblatt, III et al. |
| 2014/0243799 A1 | 8/2014 | Parihar |
| 2014/0243809 A1 | 8/2014 | Gelfand et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0263569 A1* | 9/2014 | Williams ......... A61B 17/07207 227/180.1 |
| 2014/0303660 A1 | 10/2014 | Boyden et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051617 A1 | 2/2015 | Takemura et al. |
| 2015/0053737 A1 | 2/2015 | Leimbach et al. |
| 2015/0066000 A1 | 3/2015 | An et al. |
| 2015/0070187 A1 | 3/2015 | Wiesner et al. |
| 2015/0108198 A1 | 4/2015 | Estrella |
| 2015/0133945 A1 | 5/2015 | Dushyant et al. |
| 2015/0196295 A1 | 7/2015 | Shelton, IV et al. |
| 2015/0199109 A1 | 7/2015 | Lee |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0324114 A1 | 11/2015 | Hurley et al. |
| 2015/0332003 A1 | 11/2015 | Stamm et al. |
| 2015/0332196 A1 | 11/2015 | Stiller et al. |
| 2016/0000437 A1 | 1/2016 | Giordano et al. |
| 2016/0015471 A1 | 1/2016 | Piron et al. |
| 2016/0034648 A1 | 2/2016 | Mohlenbrock et al. |
| 2016/0038253 A1 | 2/2016 | Piron et al. |
| 2016/0066913 A1 | 3/2016 | Swayze et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0158468 A1 | 6/2016 | Tang et al. |
| 2016/0180045 A1 | 6/2016 | Syed |
| 2016/0192960 A1 | 7/2016 | Bueno et al. |
| 2016/0206202 A1 | 7/2016 | Frangioni |
| 2016/0224760 A1 | 8/2016 | Petak et al. |
| 2016/0228204 A1 | 8/2016 | Quaid et al. |
| 2016/0235303 A1 | 8/2016 | Fleming et al. |
| 2016/0249910 A1 | 9/2016 | Shelton, IV et al. |
| 2016/0256160 A1 | 9/2016 | Shelton, IV et al. |
| 2016/0278841 A1 | 9/2016 | Panescu et al. |
| 2016/0287912 A1 | 10/2016 | Warnking |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0361070 A1 | 12/2016 | Ardel et al. |
| 2016/0367305 A1 | 12/2016 | Hareland |
| 2016/0374665 A1 | 12/2016 | DiNardo et al. |
| 2016/0374723 A1 | 12/2016 | Frankhouser et al. |
| 2016/0374762 A1 | 12/2016 | Case et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0068792 A1 | 3/2017 | Reiner |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0151026 A1 | 6/2017 | Panescu et al. |
| 2017/0156076 A1 | 6/2017 | Eom et al. |
| 2017/0164997 A1 | 6/2017 | Johnson et al. |
| 2017/0165012 A1 | 6/2017 | Chaplin et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0290586 A1 | 10/2017 | Wellman |
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0303419 A1 | 10/2017 | Collins et al. |
| 2017/0303984 A1 | 10/2017 | Malackowski |
| 2017/0304020 A1 | 10/2017 | Ng et al. |
| 2017/0312456 A1 | 11/2017 | Phillips |
| 2017/0325813 A1 | 11/2017 | Aranyi et al. |
| 2017/0325876 A1 | 11/2017 | Nakadate et al. |
| 2017/0325878 A1 | 11/2017 | Messerly et al. |
| 2017/0360438 A1 | 12/2017 | Cappola |
| 2017/0360439 A1 | 12/2017 | Chen et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367697 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |

(56) References Cited

U.S. PATENT DOCUMENTS

| | | |
|---|---|---|
| 2018/0014848 A1 | 1/2018 | Messerly et al. |
| 2018/0050196 A1 | 2/2018 | Pawsey et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168601 A1 | 6/2018 | Bakos et al. |
| 2018/0168603 A1 | 6/2018 | Morgan et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168621 A1 | 6/2018 | Shelton, IV et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168632 A1 | 6/2018 | Harris et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168715 A1 | 6/2018 | Strobl |
| 2018/0177383 A1 | 6/2018 | Noonan et al. |
| 2018/0199995 A1 | 7/2018 | Odermatt et al. |
| 2018/0206884 A1 | 7/2018 | Beaupre |
| 2018/0206905 A1 | 7/2018 | Batchelor et al. |
| 2018/0207307 A1 | 7/2018 | Schwartz et al. |
| 2018/0214025 A1 | 8/2018 | Homyk et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0242967 A1 | 8/2018 | Meade |
| 2018/0250084 A1 | 9/2018 | Kopp et al. |
| 2018/0263710 A1 | 9/2018 | Sakaguchi et al. |
| 2018/0263717 A1 | 9/2018 | Kopp |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0317826 A1 | 11/2018 | Muhsin et al. |
| 2018/0317915 A1 | 11/2018 | Mcdonald, II |
| 2018/0360449 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000448 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0029712 A1 | 1/2019 | Stoddard et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0053801 A1 | 2/2019 | Wixey et al. |
| 2019/0053866 A1 | 2/2019 | Seow et al. |
| 2019/0069949 A1 | 3/2019 | Vrba et al. |
| 2019/0069962 A1 | 3/2019 | Tabandeh et al. |
| 2019/0069964 A1 | 3/2019 | Hagn |
| 2019/0070550 A1 | 3/2019 | Lalomia et al. |
| 2019/0070731 A1 | 3/2019 | Bowling et al. |
| 2019/0087544 A1 | 3/2019 | Peterson |
| 2019/0090969 A1 | 3/2019 | Jarc et al. |
| 2019/0104919 A1 | 4/2019 | Shelton, IV et al. |
| 2019/0110828 A1 | 4/2019 | Despatie |
| 2019/0115108 A1 | 4/2019 | Hegedus et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125344 A1 | 5/2019 | DiNardo et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125381 A1 | 5/2019 | Scheib et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |

(56) References Cited

U.S. PATENT DOCUMENTS

| | | |
|---|---|---|
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0162179 A1 | 5/2019 | O'Shea et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201117 A1 | 7/2019 | Yates et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0290389 A1 | 9/2019 | Kopp |
| 2019/0298340 A1* | 10/2019 | Shelton, IV ............... A61F 2/82 |
| 2019/0298342 A1* | 10/2019 | Shelton, IV ........... A61B 17/29 |

(56) References Cited

U.S. PATENT DOCUMENTS

| | | | |
|---|---|---|---|
| 2019/0298343 A1* | 10/2019 | Shelton, IV | A61B 17/34 |
| 2019/0298346 A1 | 10/2019 | Shelton, IV et al. | |
| 2019/0298347 A1* | 10/2019 | Shelton, IV | A61F 2/82 |
| 2019/0298350 A1* | 10/2019 | Shelton, IV | A61B 17/07207 |
| 2019/0298351 A1 | 10/2019 | Shelton, IV et al. | |
| 2019/0298352 A1 | 10/2019 | Shelton, IV et al. | |
| 2019/0298353 A1 | 10/2019 | Shelton, IV et al. | |
| 2019/0298354 A1* | 10/2019 | Shelton, IV | A61B 90/39 |
| 2019/0298355 A1 | 10/2019 | Shelton, IV et al. | |
| 2019/0298356 A1* | 10/2019 | Shelton, IV | A61B 17/07207 |
| 2019/0298357 A1* | 10/2019 | Shelton, IV | A61B 17/29 |
| 2019/0298464 A1 | 10/2019 | Abbott | |
| 2019/0298481 A1 | 10/2019 | Rosenberg et al. | |
| 2019/0307520 A1 | 10/2019 | Peine et al. | |
| 2019/0311802 A1 | 10/2019 | Kokubo et al. | |
| 2019/0314015 A1 | 10/2019 | Shelton, IV et al. | |
| 2019/0314016 A1 | 10/2019 | Huitema et al. | |
| 2019/0321117 A1 | 10/2019 | Itkowitz et al. | |
| 2019/0333626 A1 | 10/2019 | Mansi et al. | |
| 2019/0343594 A1 | 11/2019 | Garcia Kilroy et al. | |
| 2019/0374140 A1 | 12/2019 | Tucker et al. | |
| 2020/0000470 A1 | 1/2020 | Du et al. | |
| 2020/0046353 A1 | 2/2020 | Deck et al. | |
| 2020/0054317 A1 | 2/2020 | Pisarnwongs et al. | |
| 2020/0054320 A1 | 2/2020 | Harris et al. | |
| 2020/0054321 A1 | 2/2020 | Harris et al. | |
| 2020/0054322 A1 | 2/2020 | Harris et al. | |
| 2020/0054323 A1 | 2/2020 | Harris et al. | |
| 2020/0054326 A1 | 2/2020 | Harris et al. | |
| 2020/0054327 A1 | 2/2020 | Harris et al. | |
| 2020/0054328 A1 | 2/2020 | Harris et al. | |
| 2020/0054329 A1 | 2/2020 | Shelton, IV et al. | |
| 2020/0054330 A1 | 2/2020 | Harris et al. | |
| 2020/0054331 A1 | 2/2020 | Harris et al. | |
| 2020/0078096 A1 | 3/2020 | Barbagli et al. | |
| 2020/0100830 A1 | 4/2020 | Henderson et al. | |
| 2020/0162896 A1 | 5/2020 | Su et al. | |
| 2020/0178971 A1 | 6/2020 | Harris et al. | |
| 2020/0261075 A1 | 8/2020 | Boudreaux et al. | |
| 2020/0261076 A1 | 8/2020 | Boudreaux et al. | |
| 2020/0261077 A1 | 8/2020 | Shelton, IV et al. | |
| 2020/0261078 A1 | 8/2020 | Bakos et al. | |
| 2020/0261080 A1 | 8/2020 | Bakos et al. | |
| 2020/0261081 A1 | 8/2020 | Boudreaux et al. | |
| 2020/0261082 A1 | 8/2020 | Boudreaux et al. | |
| 2020/0261083 A1 | 8/2020 | Bakos et al. | |
| 2020/0261084 A1 | 8/2020 | Bakos et al. | |
| 2020/0261085 A1 | 8/2020 | Boudreaux et al. | |
| 2020/0261086 A1 | 8/2020 | Zeiner et al. | |
| 2020/0261087 A1 | 8/2020 | Timm et al. | |
| 2020/0261088 A1 | 8/2020 | Harris et al. | |
| 2020/0261089 A1 | 8/2020 | Shelton, IV et al. | |
| 2020/0275928 A1 | 9/2020 | Shelton, IV et al. | |
| 2020/0275930 A1 | 9/2020 | Harris et al. | |
| 2020/0281665 A1 | 9/2020 | Kopp | |
| 2020/0405375 A1 | 12/2020 | Shelton, IV et al. | |
| 2021/0000555 A1 | 1/2021 | Shelton, IV et al. | |
| 2021/0007760 A1 | 1/2021 | Reisin | |
| 2021/0015568 A1 | 1/2021 | Liao et al. | |
| 2021/0022731 A1 | 1/2021 | Eisinger | |
| 2021/0022738 A1 | 1/2021 | Weir et al. | |
| 2021/0022809 A1 | 1/2021 | Crawford et al. | |
| 2021/0059674 A1 | 3/2021 | Shelton, IV et al. | |
| 2021/0153889 A1 | 5/2021 | Nott et al. | |
| 2021/0169516 A1 | 6/2021 | Houser et al. | |
| 2021/0176179 A1 | 6/2021 | Shelton, IV | |
| 2021/0177452 A1 | 6/2021 | Nott et al. | |
| 2021/0177489 A1 | 6/2021 | Yates et al. | |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 1214913 A2 | 6/2002 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2037167 A1 | 7/1980 |
| GB | 2509523 A | 7/2014 |
| JP | S5373315 A | 6/1978 |
| JP | 2007123394 A | 5/2007 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014134196 A1 | 9/2014 |
| WO | WO-2015129395 A1 | 9/2015 |
| WO | WO-2016100719 A1 | 6/2016 |
| WO | WO-2016206015 A1 | 12/2016 |
| WO | WO-2017011382 A1 | 1/2017 |
| WO | WO-2017011646 A1 | 1/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018152141 A1 | 8/2018 |
| WO | WO-2018176414 A1 | 10/2018 |

OTHER PUBLICATIONS

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Slocinski et al., "Distance measure for impedance spectra for quantified evaluations," Lecture Notes on Impedance Spectroscopy, vol. 3, Taylor and Francis Group (Jul. 2012)—Book Not Attached.

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of

(56) References Cited

OTHER PUBLICATIONS

Translational Engineering in Health and Medicine, vol. 3, pp. 1-9, Oct. 21, 2015.
Benkmann et al., "Concept of iterative optimization of minimally invasive surgery," 2017 22nd International Conference on Methods and Models in Automation and Robotics (MMAR), IEEE pp. 443-446, Aug. 28, 2017.
Trautman, Peter, "Breaking the Human-Robot Deadlock: Surpassing Shared Control Performance Limits with Sparse Human-Robot Interaction," Robotics: Science and Systems XIII, pp. 1-10, Jul. 12, 2017.
Miksch et al., "Utilizing temporal data abstraction for data validation and therapy planning for artificially ventilated newborn infants," Artificial Intelligence in Medicine, vol. 8, No. 6, pp. 543-576 (1996).
Horn et al., "Effective data validation of high-frequency data: Time-point-time-interval-, and trend-based methods," Computers in Biology and Medic, New York, NY, vol. 27, No. 5, pp. 389-409 (1997).
Stacey et al., "Temporal abstraction in intelligent clinical data analysis: A survey," Artificial Intelligence in Medicine, vol. 39, No. 1, pp. 1-24 (2006).
Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.
Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Phumzile Malindi, "5. QoS in Telemedicine," "Telemedicine," Jun. 20, 2011, IntechOpen, pp. 119-138.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.

Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from internet: <https://www.youtube.com/watch?v=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.
"Surgical instrumentation: the true cost of instrument trays and a potential strategy for optimization"; Mhlaba et al.; Sep. 23, 2015 (Year: 2015).

(56) References Cited

OTHER PUBLICATIONS

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

Roy D Cullum, "Handbook of Engineering Design", ISBN: 9780408005586, Jan. 1, 1988 (Jan. 1, 1988), XP055578597, ISBN: 9780408005586, 10-20, Chapter6, p. 138, right-hand column, paragraph 3.

Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

\* cited by examiner

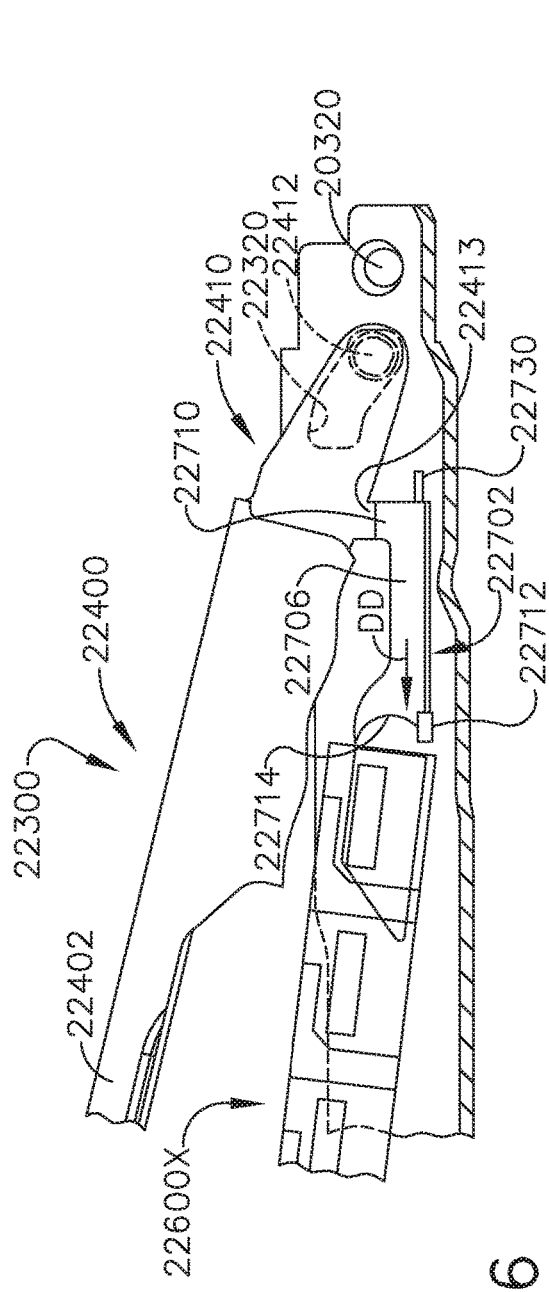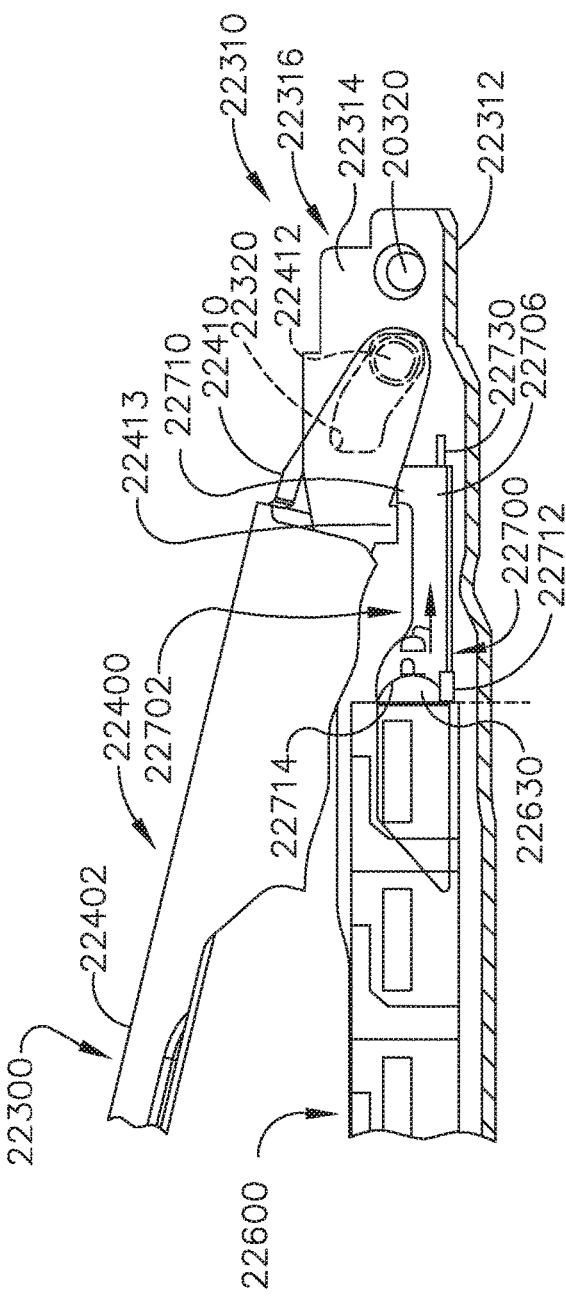

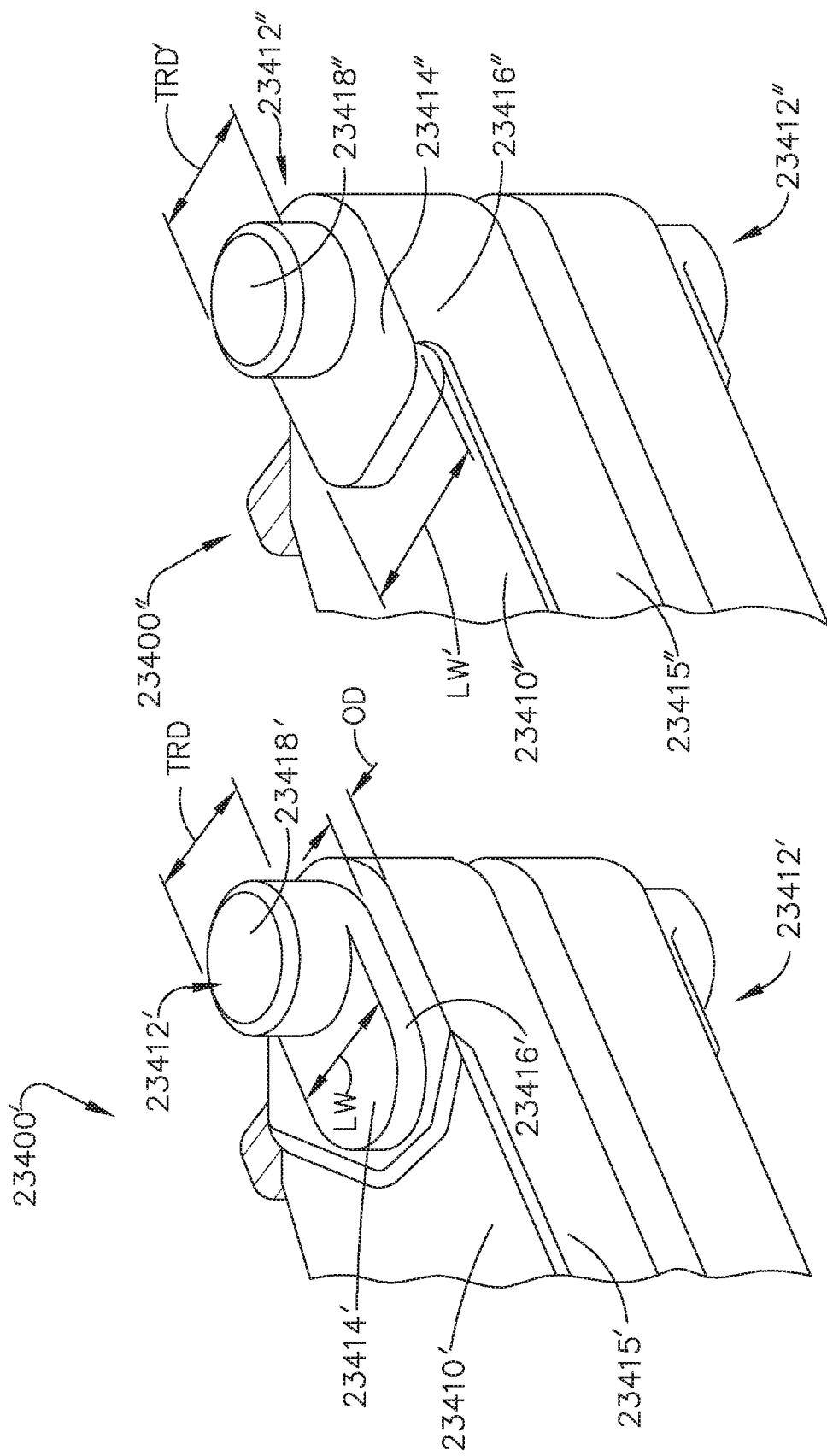

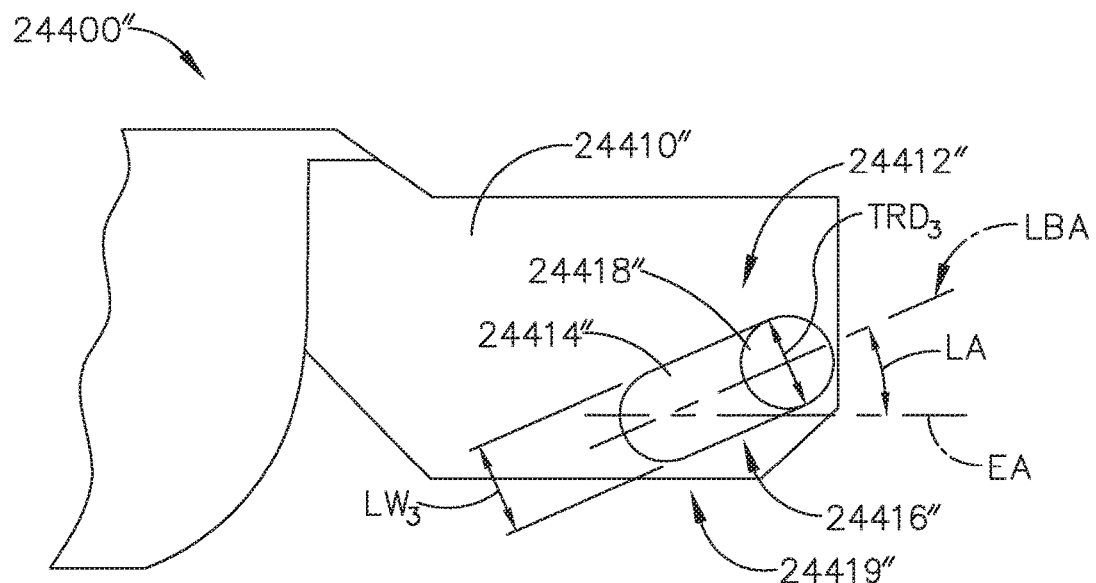
FIG. 53
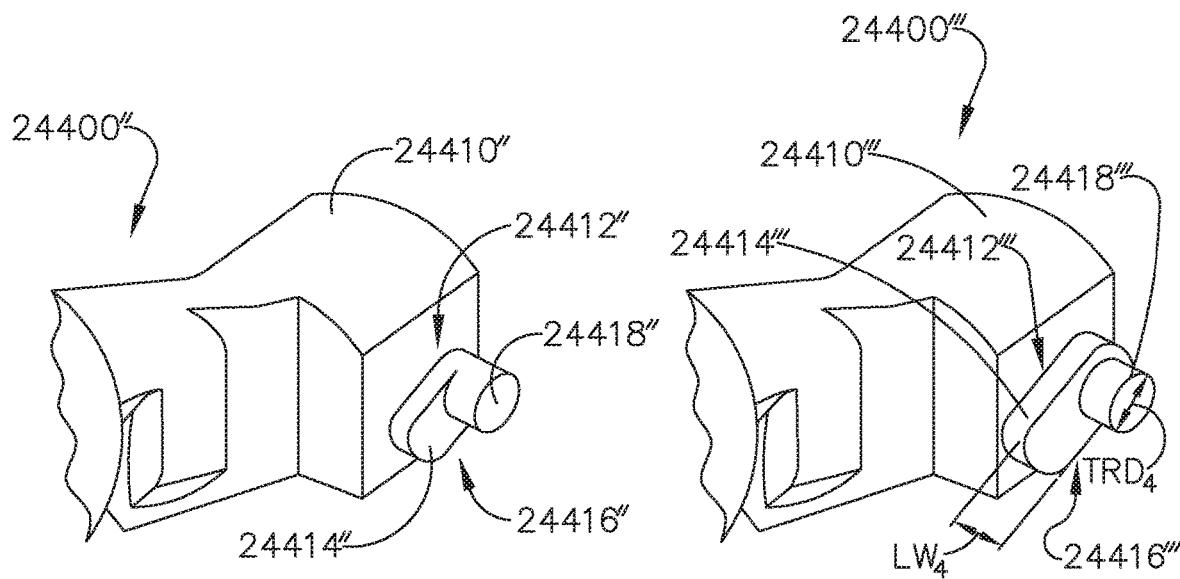
FIG. 54
FIG. 58

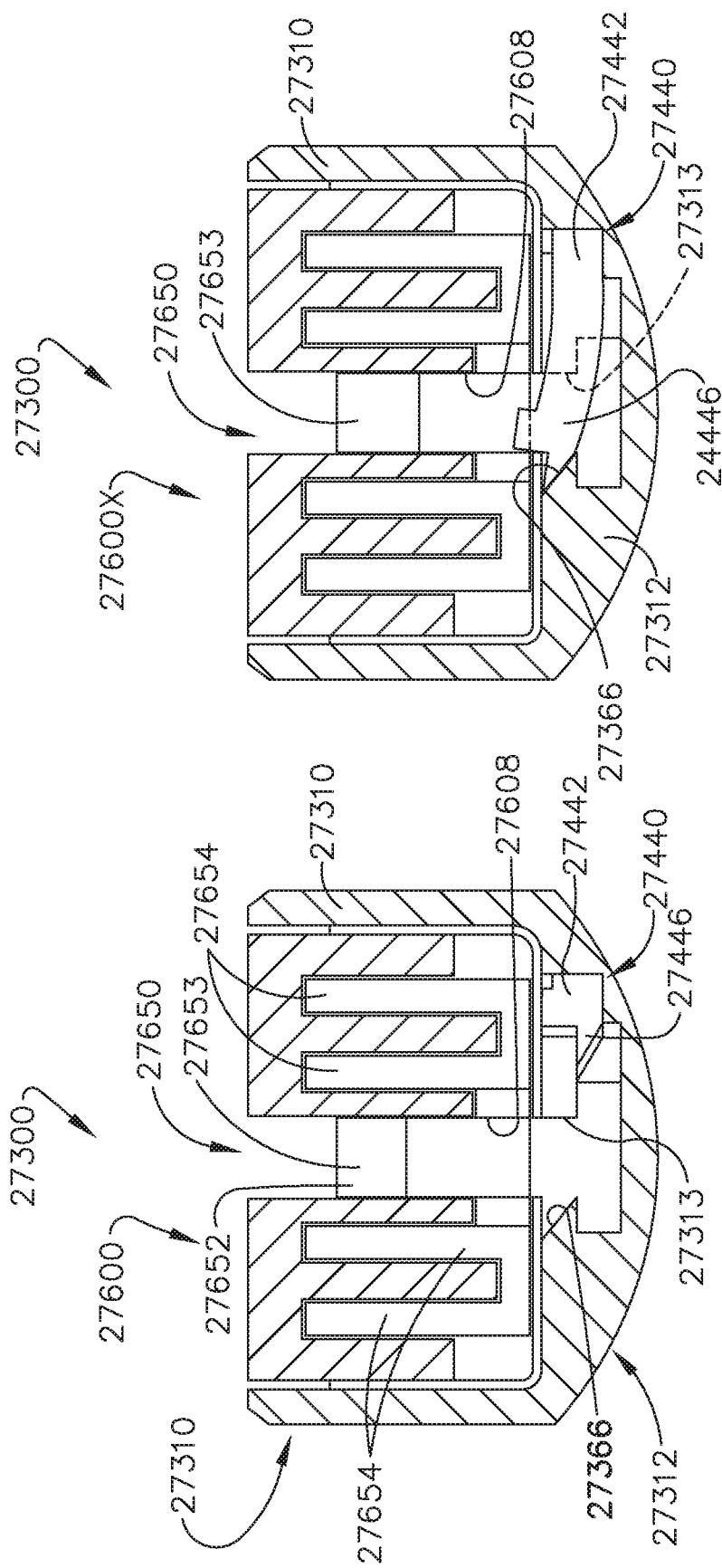

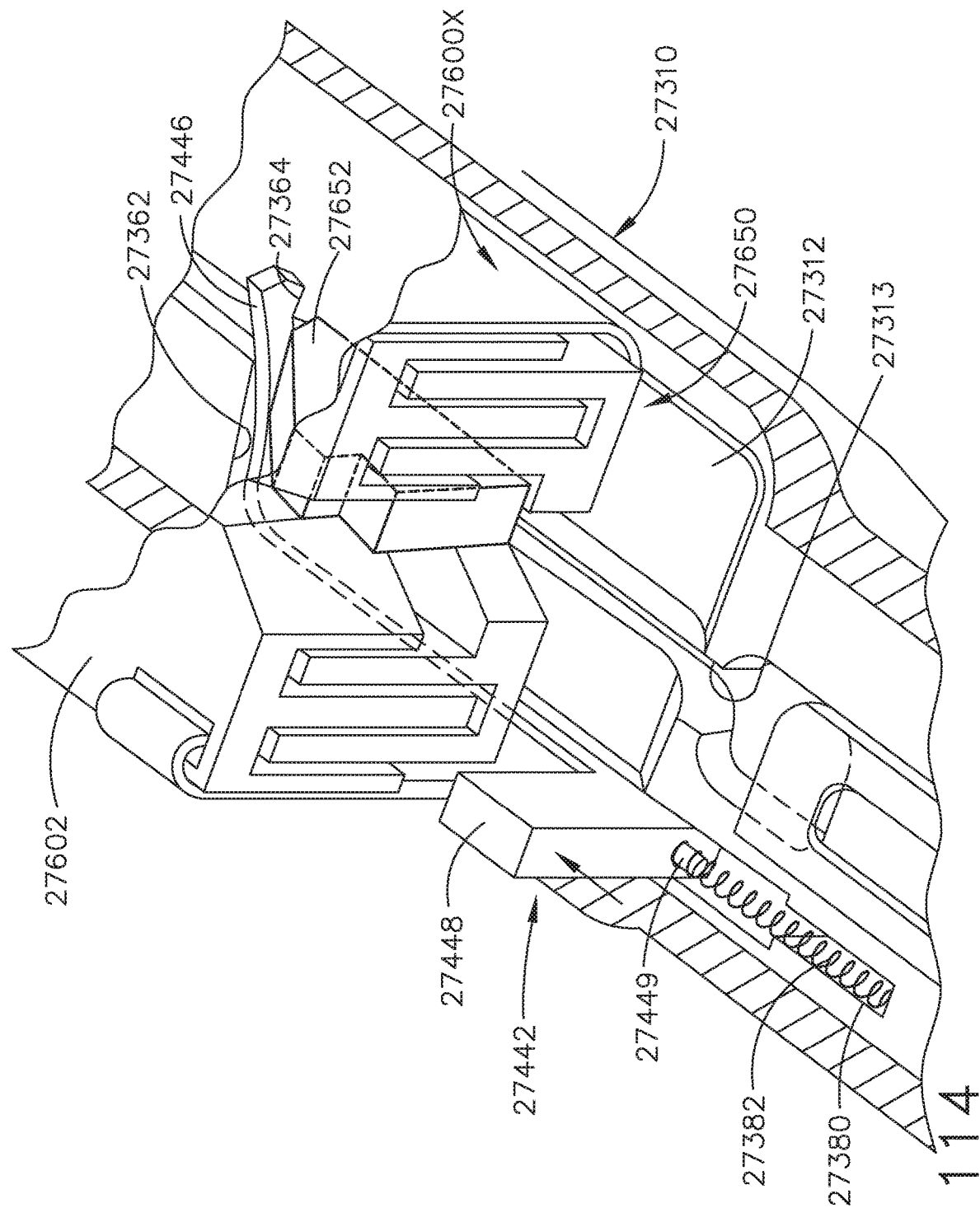

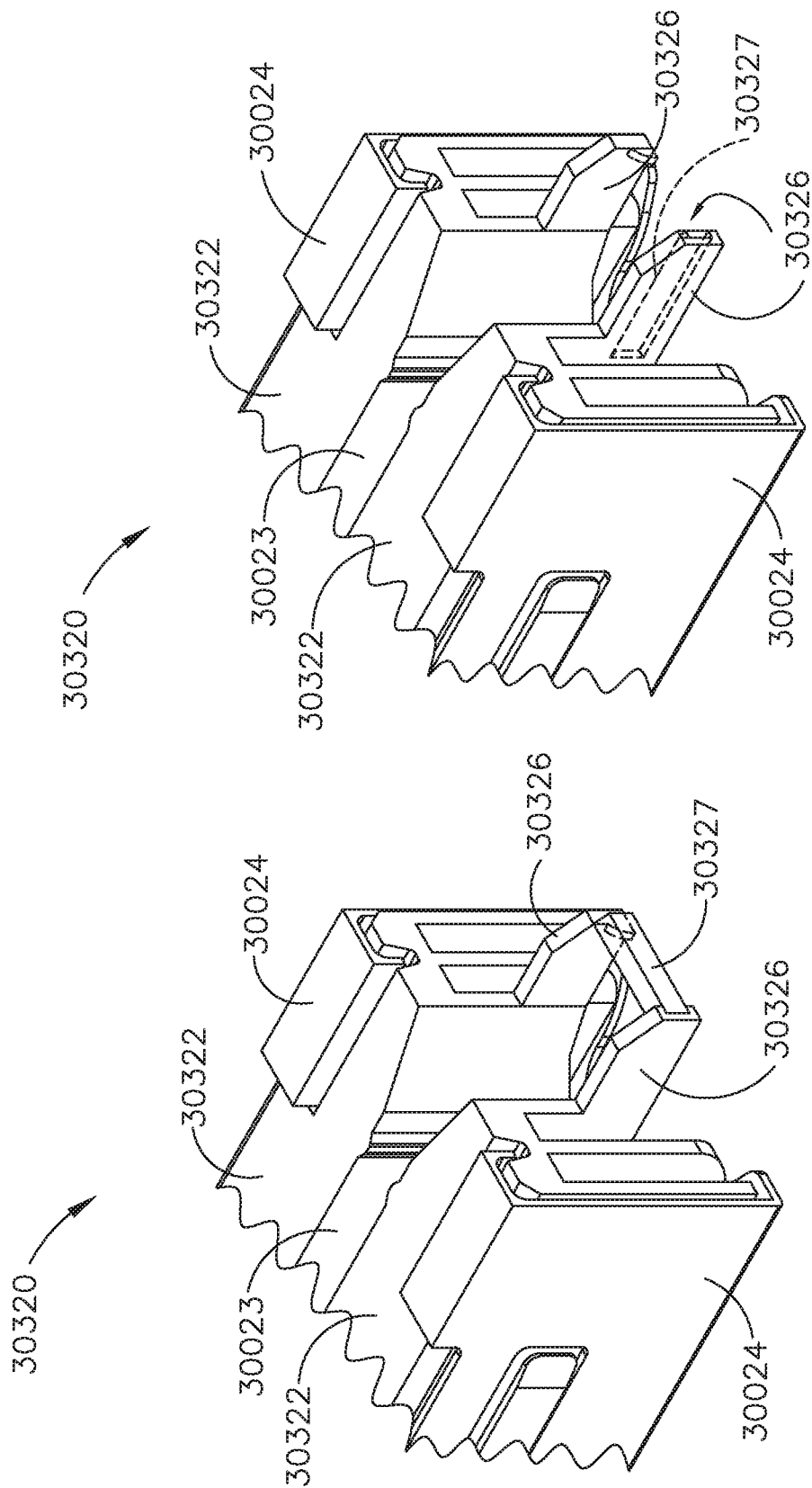

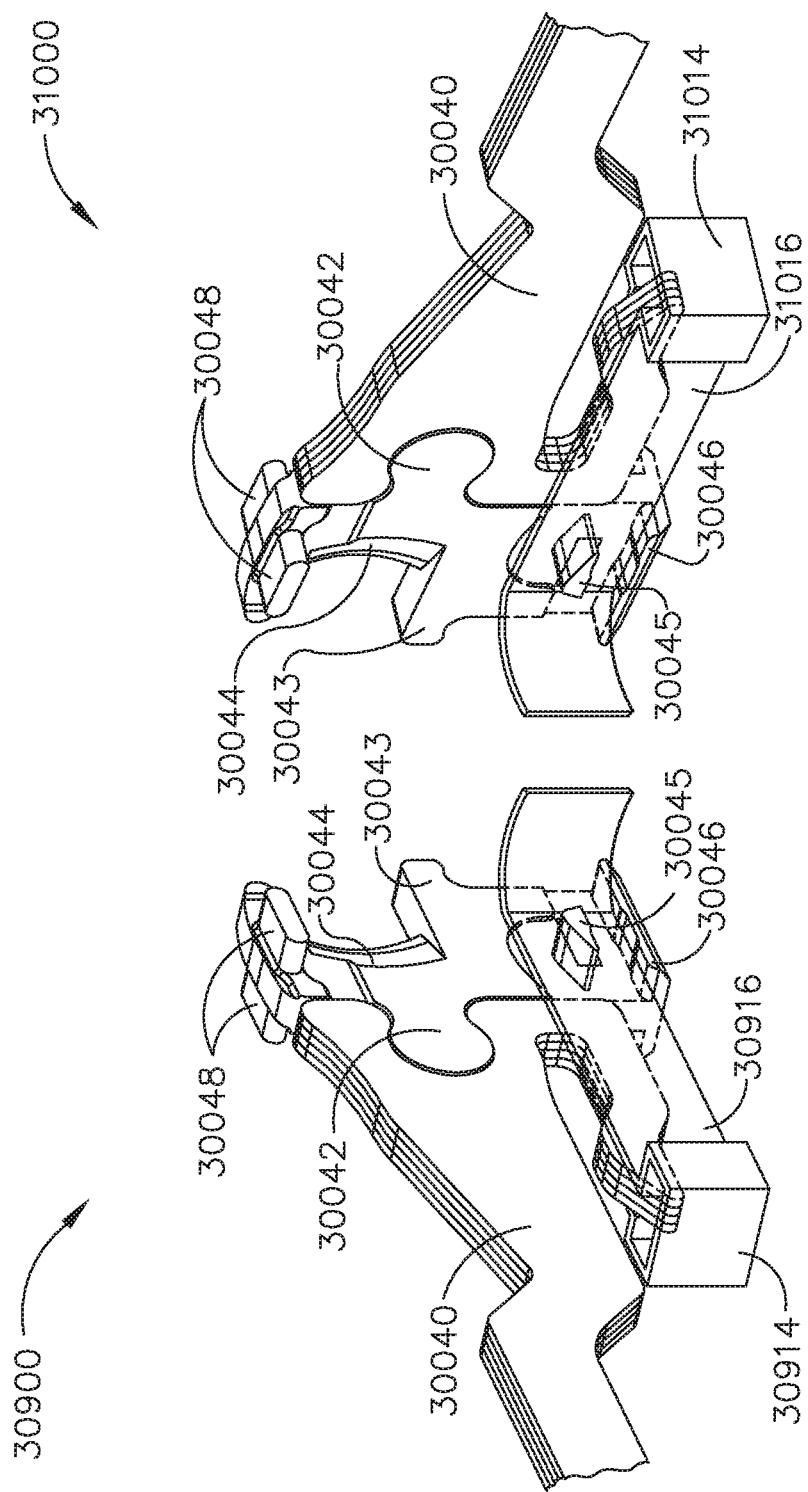

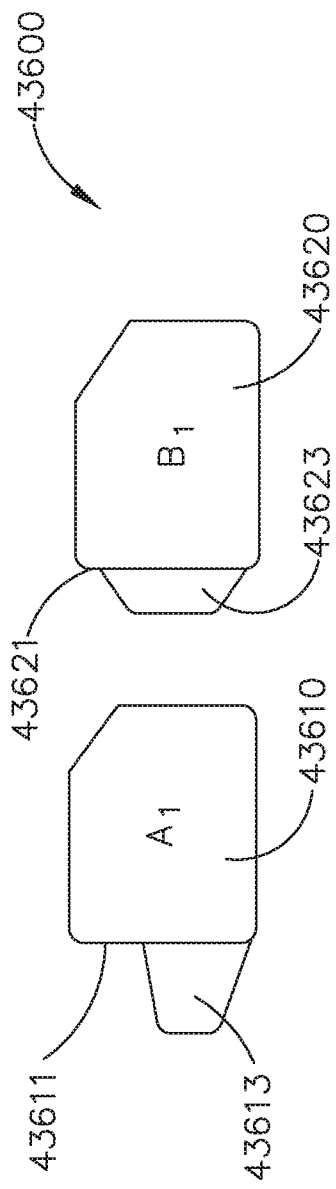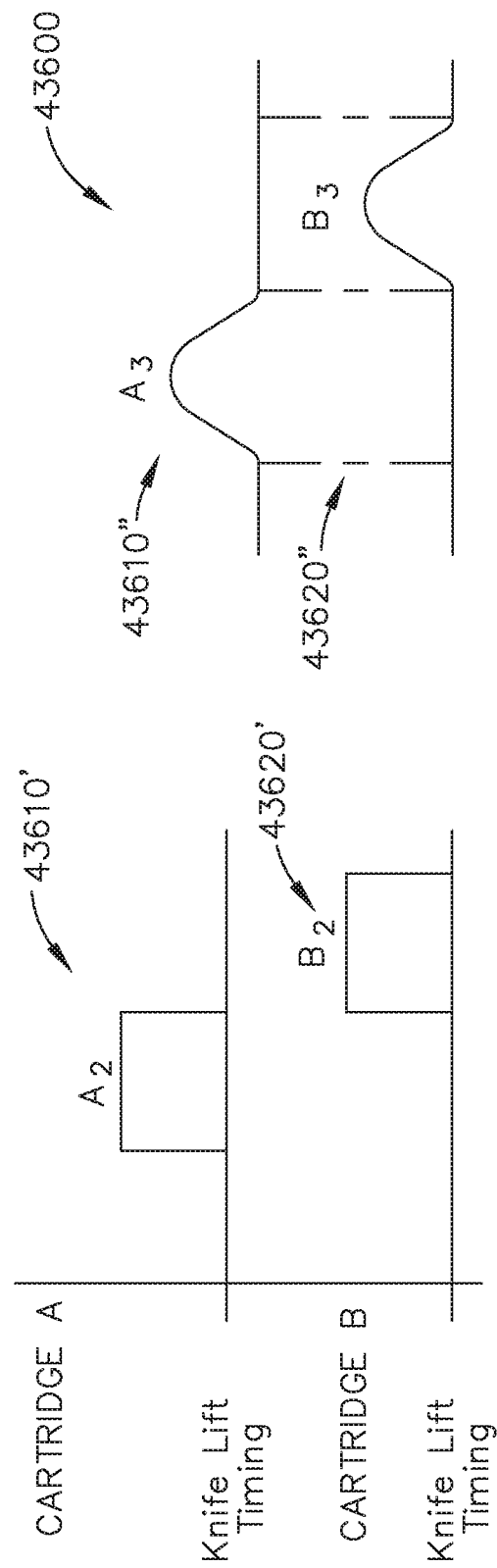

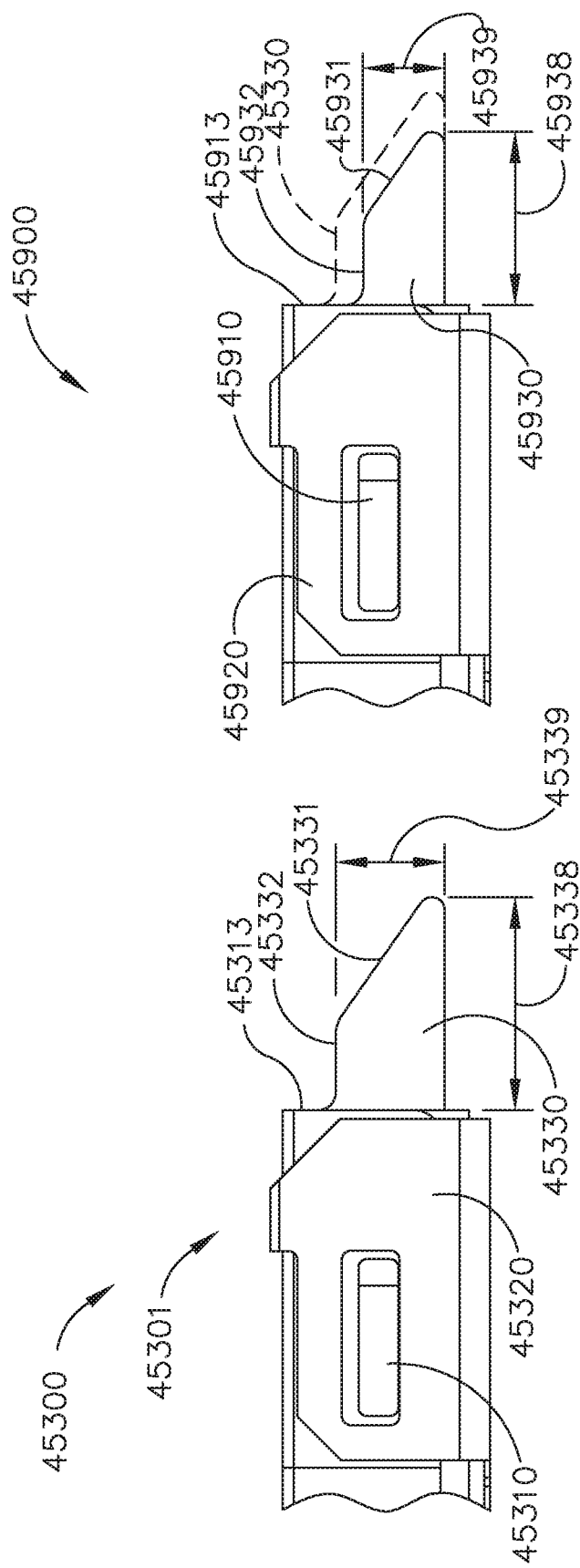

SURGICAL INSTRUMENT COMPRISING CO-OPERATING LOCKOUT FEATURES

CROSS-REFERENCE TO RELATED APPLICATIONS

This application claims the benefit of U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS, filed Feb. 19, 2019, of U.S. Provisional Patent Application Ser. No. 62/807,319, entitled SURGICAL STAPLING DEVICES WITH IMPROVED LOCKOUT SYSTEMS, filed Feb. 19, 2019, and of U.S. Provisional Patent Application Ser. No. 62/807,309, entitled SURGICAL STAPLING DEVICES WITH IMPROVED ROTARY DRIVEN CLOSURE SYSTEMS, filed Feb. 19, 2019, the disclosures of which are incorporated by reference herein in their entireties. This application claims the benefit of U.S. Provisional Patent Application Ser. No. 62/650,887, entitled SURGICAL SYSTEMS WITH OPTIMIZED SENSING CAPABILITIES, filed Mar. 30, 2018, the disclosure of which is incorporated by reference herein in its entirety. This application claims the benefit of U.S. Provisional Patent Application Ser. No. 62/649,302, entitled INTERACTIVE SURGICAL SYSTEMS WITH ENCRYPTED COMMUNICATION CAPABILITIES, filed Mar. 28, 2018, of U.S. Provisional Patent Application Ser. No. 62/649,294, entitled DATA STRIPPING METHOD TO INTERROGATE PATIENT RECORDS AND CREATE ANONYMIZED RECORD, filed Mar. 28, 2018, of U.S. Provisional Patent Application Ser. No. 62/649,300, entitled SURGICAL HUB SITUATIONAL AWARENESS, filed Mar. 28, 2018, of U.S. Provisional Patent Application Ser. No. 62/649,309, entitled SURGICAL HUB SPATIAL AWARENESS TO DETERMINE DEVICES IN OPERATING THEATER, filed Mar. 28, 2018, of U.S. Provisional Patent Application Ser. No. 62/649,310, entitled COMPUTER IMPLEMENTED INTERACTIVE SURGICAL SYSTEMS, filed Mar. 28, 2018, of U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT, filed Mar. 28, 2018, of U.S. Provisional Patent Application Ser. No. 62/649,296, entitled ADAPTIVE CONTROL PROGRAM UPDATES FOR SURGICAL DEVICES, filed Mar. 28, 2018, of U.S. Provisional Patent Application Ser. No. 62/649,333, entitled CLOUD-BASED MEDICAL ANALYTICS FOR CUSTOMIZATION AND RECOMMENDATIONS TO A USER, filed Mar. 28, 2018, of U.S. Provisional Patent Application Ser. No. 62/649,327, entitled CLOUD-BASED MEDICAL ANALYTICS FOR SECURITY AND AUTHENTICATION TRENDS AND REACTIVE MEASURES, filed Mar. 28, 2018, of U.S. Provisional Patent Application Ser. No. 62/649,315, entitled DATA HANDLING AND PRIORITIZATION IN A CLOUD ANALYTICS NETWORK, filed Mar. 28, 2018, of U.S. Provisional Patent Application Ser. No. 62/649,313, entitled CLOUD INTERFACE FOR COUPLED SURGICAL DEVICES, filed Mar. 28, 2018, of U.S. Provisional Patent Application Ser. No. 62/649,320, entitled DRIVE ARRANGEMENTS FOR ROBOT-ASSISTED SURGICAL PLATFORMS, filed Mar. 28, 2018, of U.S. Provisional Patent Application Ser. No. 62/649,307, entitled AUTOMATIC TOOL ADJUSTMENTS FOR ROBOT-ASSISTED SURGICAL PLATFORMS, filed Mar. 28, 2018, and of U.S. Provisional Patent Application Ser. No. 62/649,323, entitled SENSING ARRANGEMENTS FOR ROBOT-ASSISTED SURGICAL PLATFORMS, filed Mar. 28, 2018, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 33 is a cross-sectional side view of another surgical end effector with an anvil thereof in an open position and with a compatible surgical staple cartridge installed therein;

FIG. 36 is another cross-sectional side view of the surgical end effector of FIG. 33, with the anvil thereof in an open position during initial installation of an incompatible surgical staple cartridge therein;

FIG. 41 is a partial perspective view of a proximal end portion of an anvil;

FIG. 42 is a partial perspective view of a proximal end portion of another anvil;

FIG. 50 is a partial perspective view of a proximal end portion of the anvil of the surgical end effector of FIG. 49;

FIG. 53 is a side elevational view of a portion of the anvil of the surgical end effector of FIG. 52;

FIG. 54 is a partial perspective view of a portion of the anvil of FIG. 53;

FIG. 58 is a partial perspective view of another anvil;

FIG. 112 is a partial cross-sectional end view of the surgical end effector and compatible surgical staple cartridge of FIG. 110;

FIG. 113 is another partial cross-sectional surgical end view of the end effector of FIG. 110 with an incompatible surgical staple cartridge installed therein;

FIG. 114 is another partial cross-sectional perspective view of portions of the surgical end effector of FIG. 110 with an incompatible surgical staple cartridge installed therein;

FIG. 119 is another partial cross-sectional perspective view of a portion of the surgical staple cartridge of FIG. 116 with the camming assembly thereof in an unlocked position;

FIG. 120 is a partial elevational view of a stapling instrument including a cartridge channel, a staple cartridge positioned in the cartridge channel, and a firing member in accordance with at least one embodiment illustrated with some components removed, wherein the firing member is in an unfired position;

FIG. 121 is a partial elevational view of the stapling instrument of FIG. 120 illustrating the firing member in a locked-out position;

FIG. 122 is a partial elevational view of a stapling instrument including a cartridge channel, a staple cartridge positioned in the cartridge channel, and a firing member in accordance with at least one embodiment illustrated with some components removed, wherein the firing member is in an unfired position;

FIG. 123 is a partial elevational view of the stapling instrument of FIG. 122 illustrating the firing member in an unlocked position;

FIG. 124 is a partial elevational view of the stapling instrument of FIG. 122 illustrating the firing member in a locked-out position;

FIG. 125 is a partial bottom view of the stapling instrument of FIG. 122 illustrating the firing member in an unfired position;

FIG. 126 is a partial perspective view of the staple cartridge of FIG. 122;

FIG. 127 is a partial perspective view of a staple cartridge in accordance with at least one embodiment;

FIG. 128 is a partial elevational view of a stapling instrument including a cartridge channel, a staple cartridge positioned in the cartridge channel, and a firing member in accordance with at least one embodiment illustrated with some components removed, wherein the firing member is in an unfired position;

FIG. 129 is a partial elevational view of the stapling instrument of FIG. 128 illustrating the firing member in an unlocked position;

FIG. 130 is a partial top view of the stapling instrument of FIG. 128 illustrated in the unfired position of FIG. 128;

Figure 128:
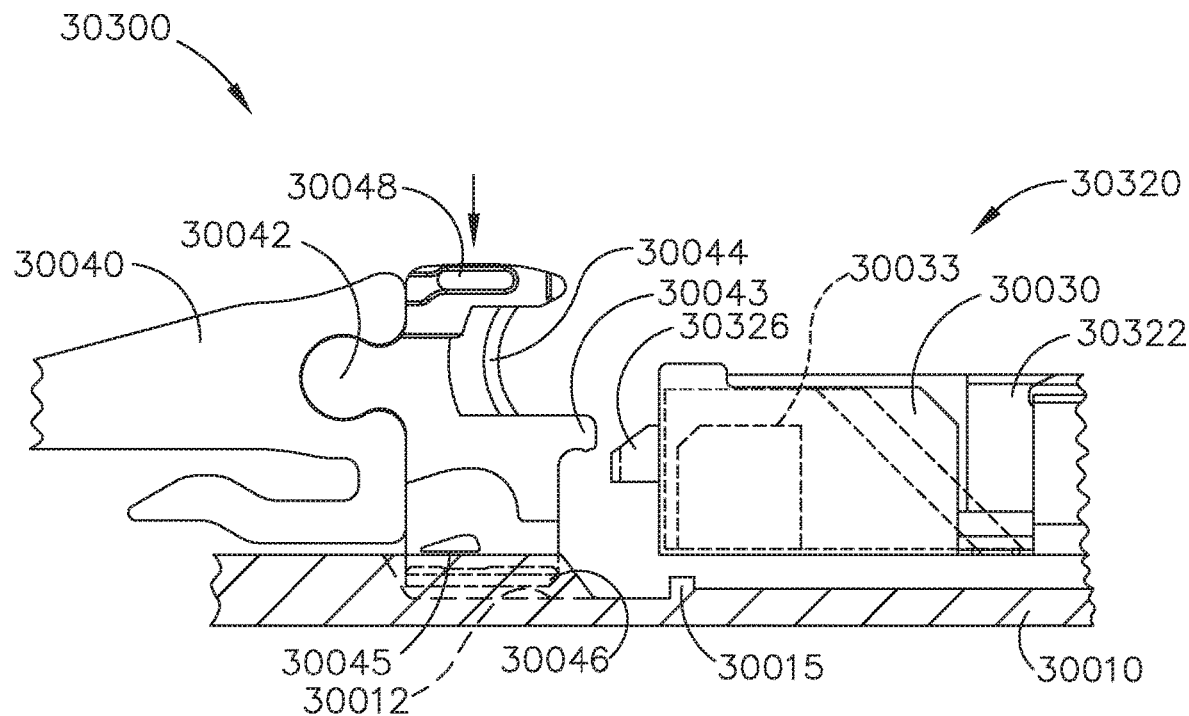
Figure 129:
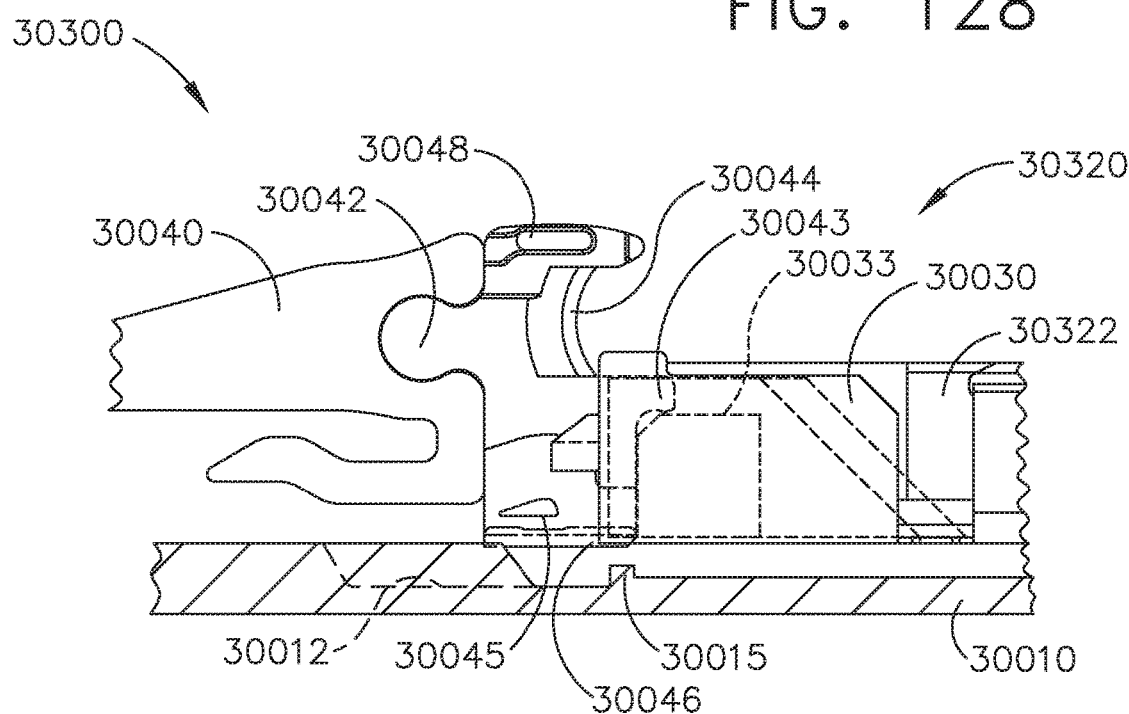
Figure 131:
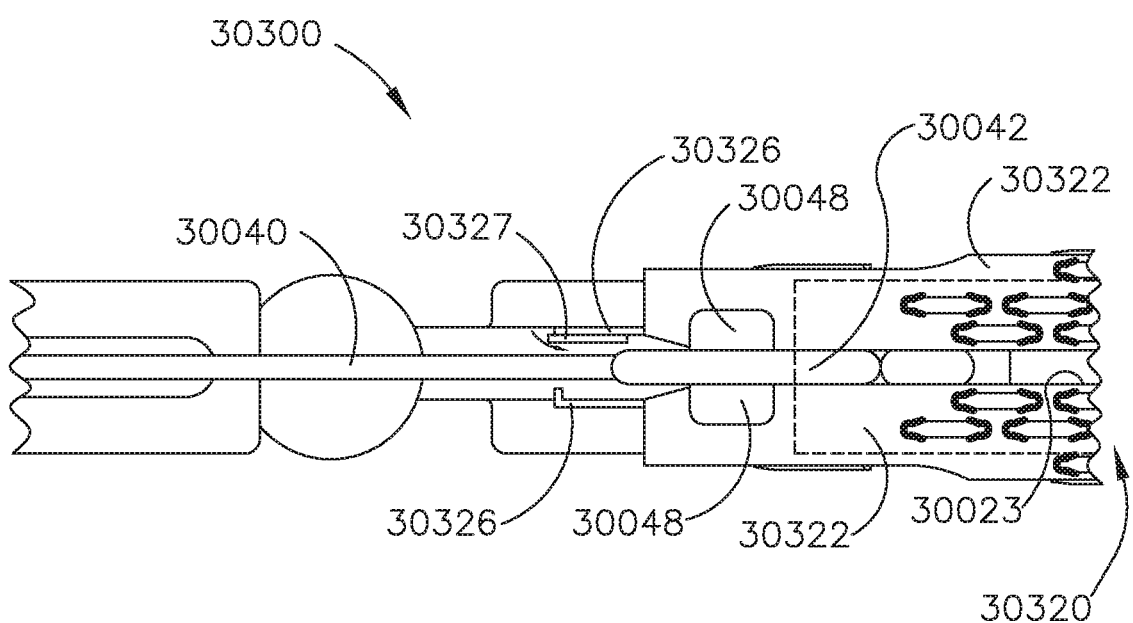
Figure 134:
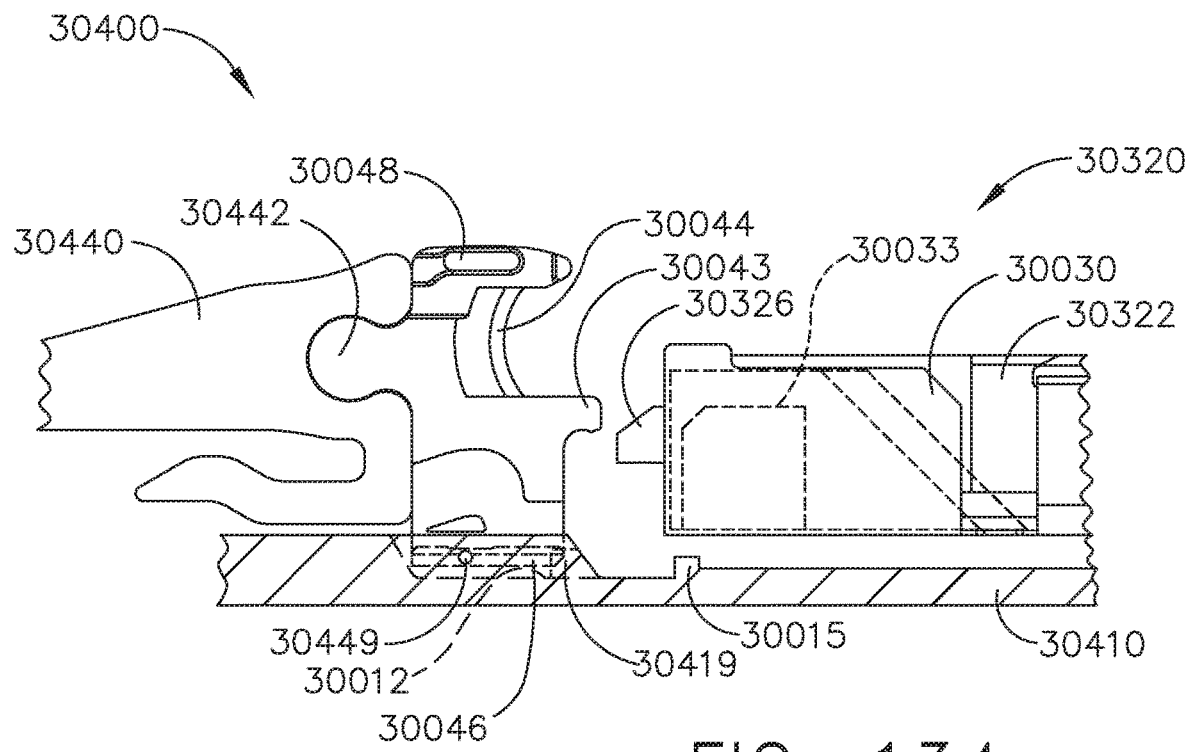
Figure 135:
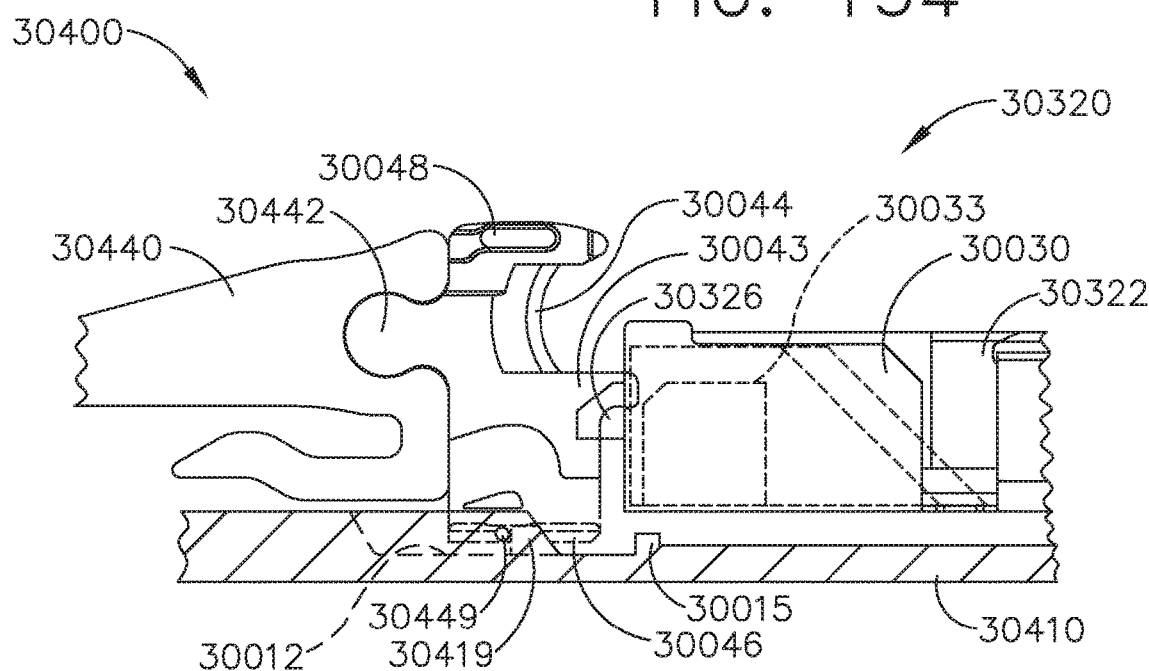
Figure 136:
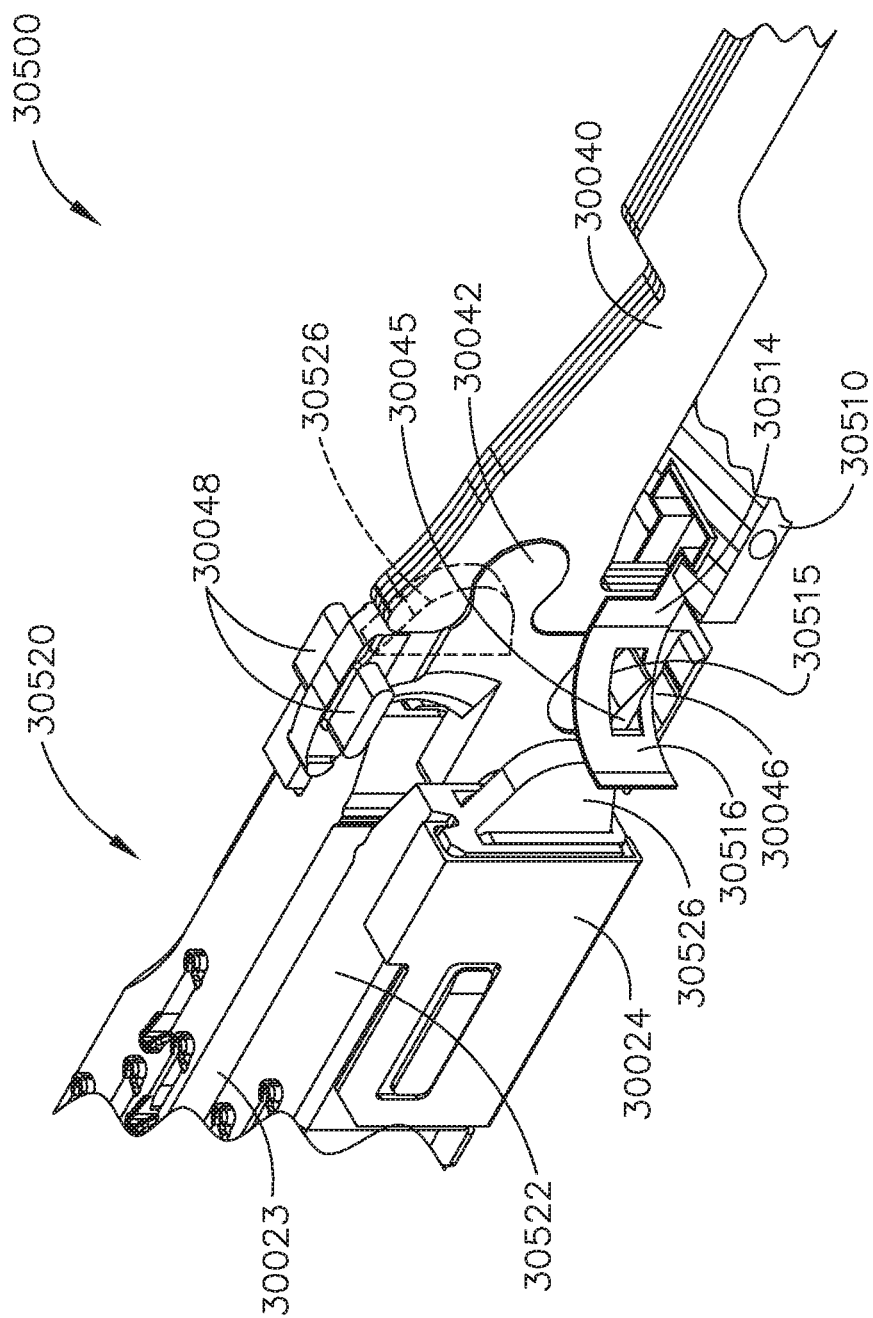
Figure 137:
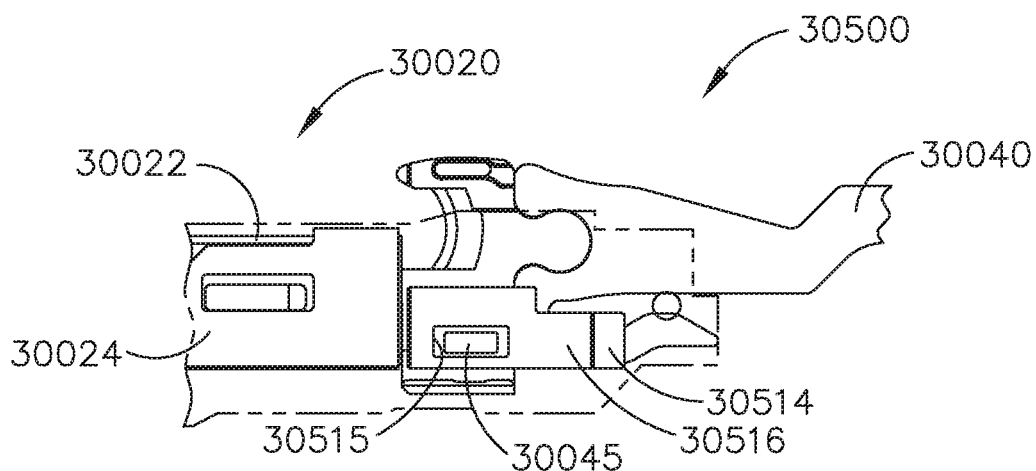
Figure 138:
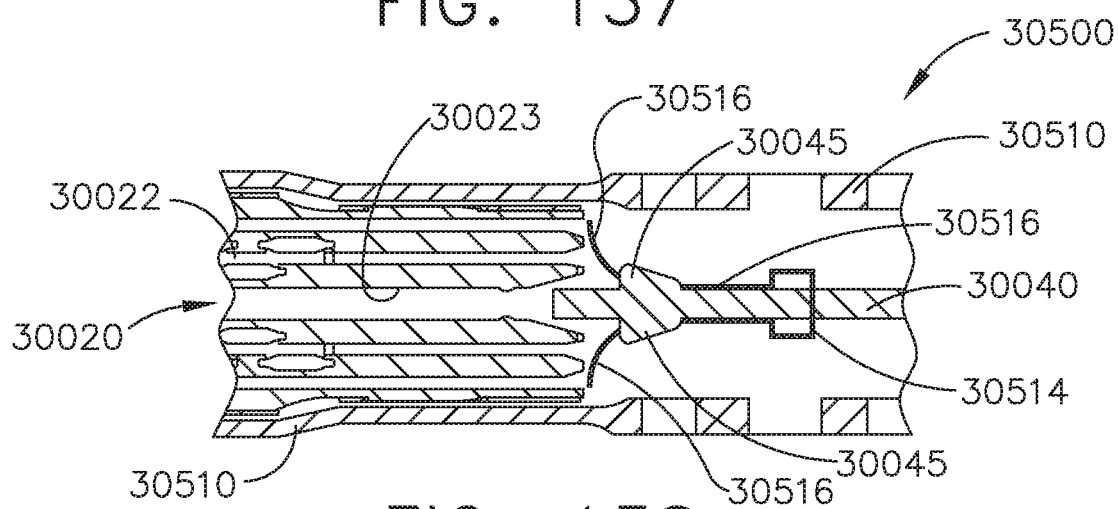
Figure 139:
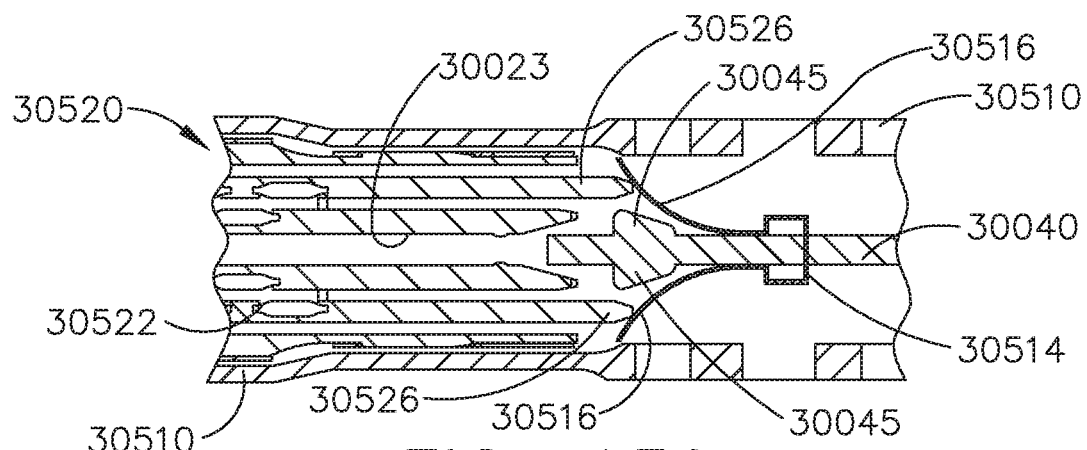
Figure 140:
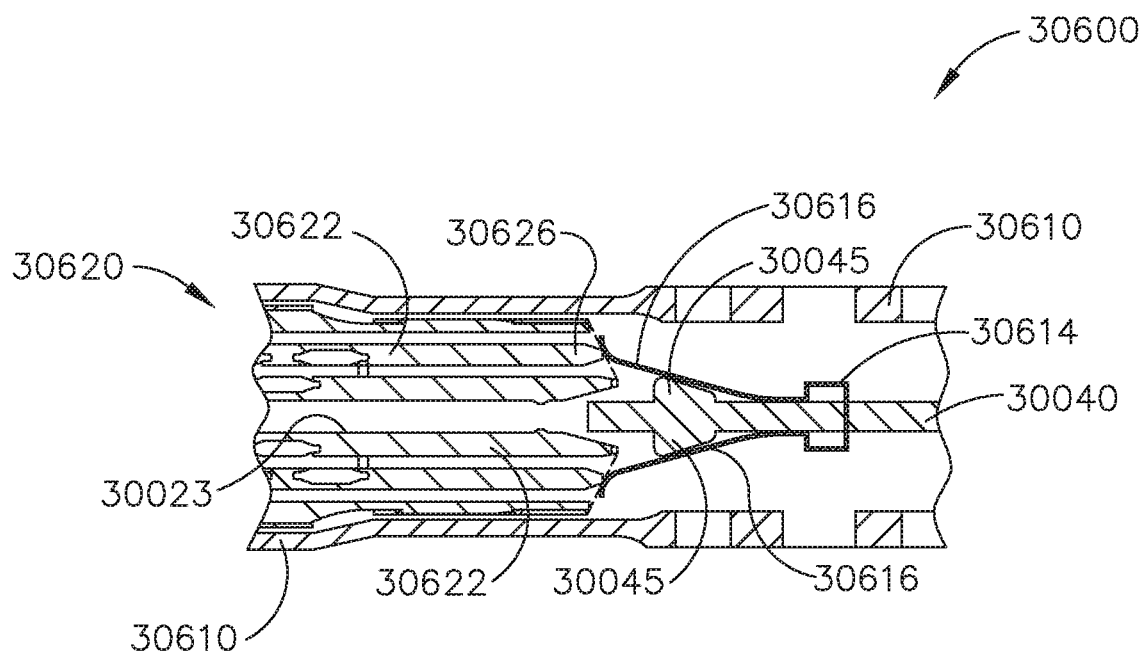
Figure 141:
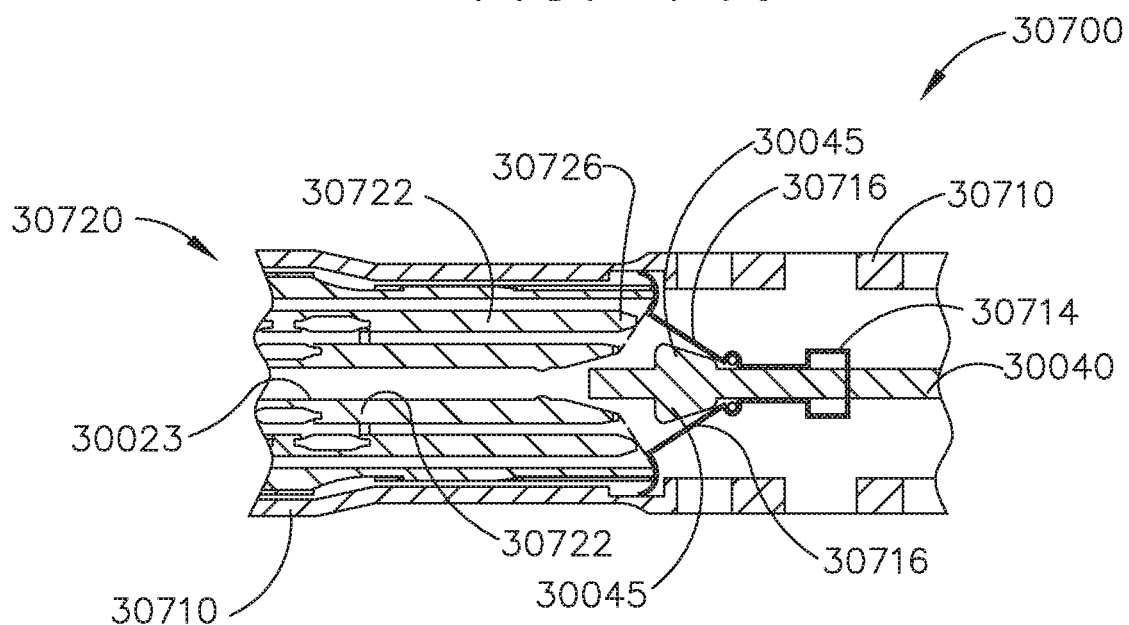
Figure 143:
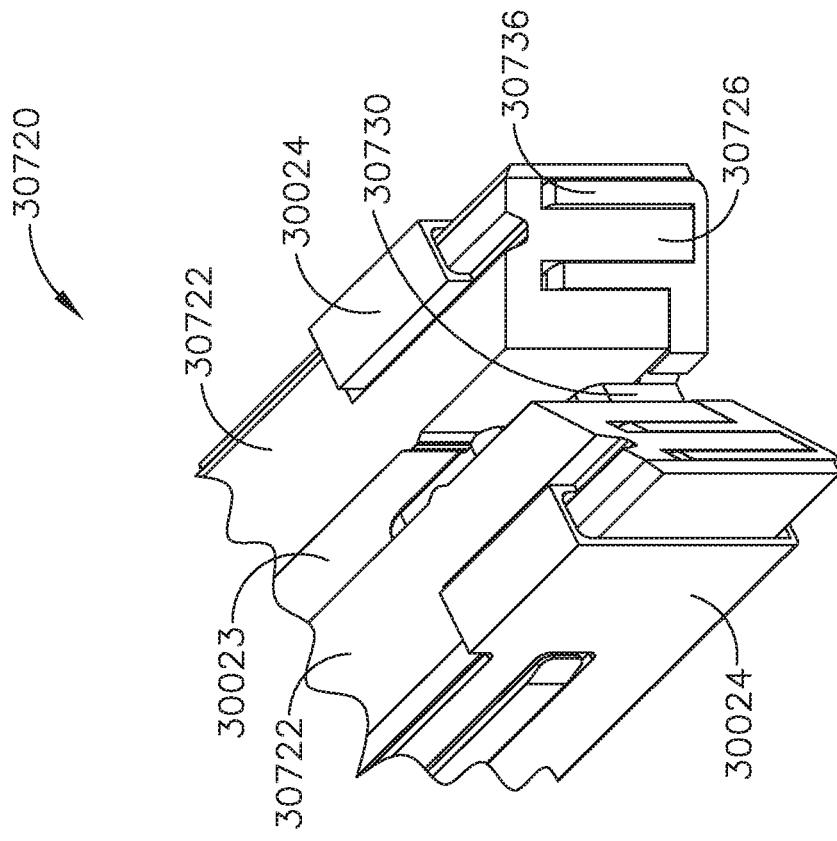
Figure 142:
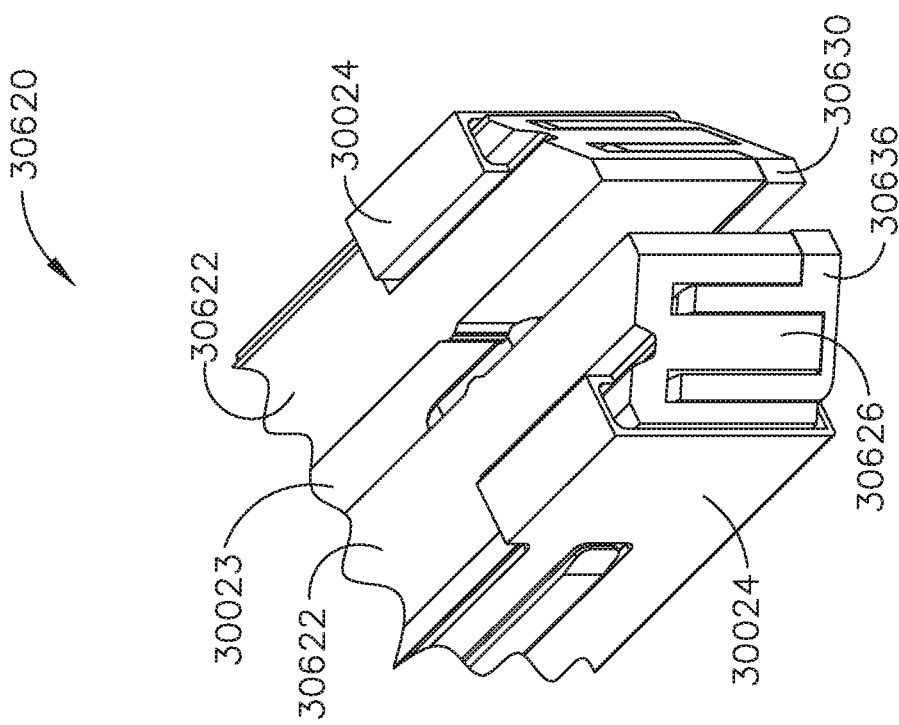
Figure 144:
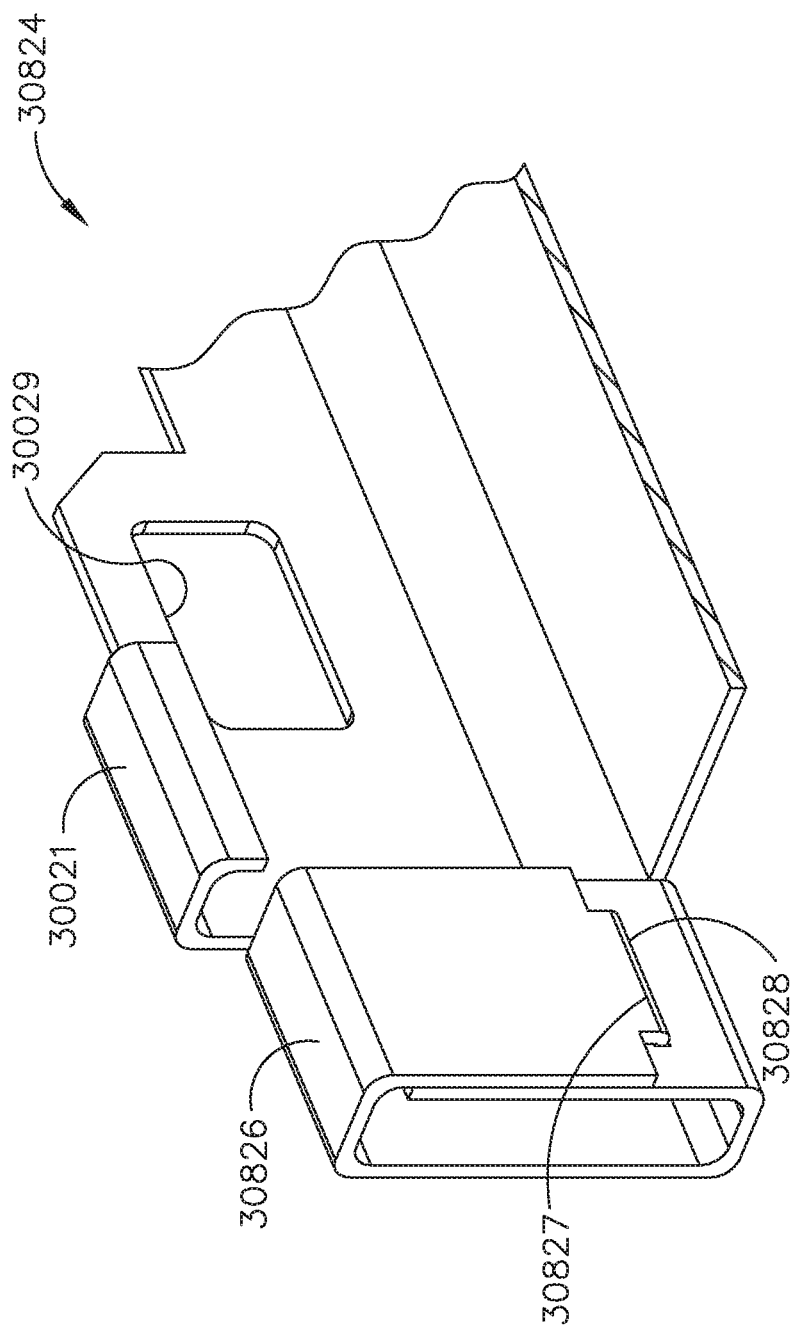
Figure 145:
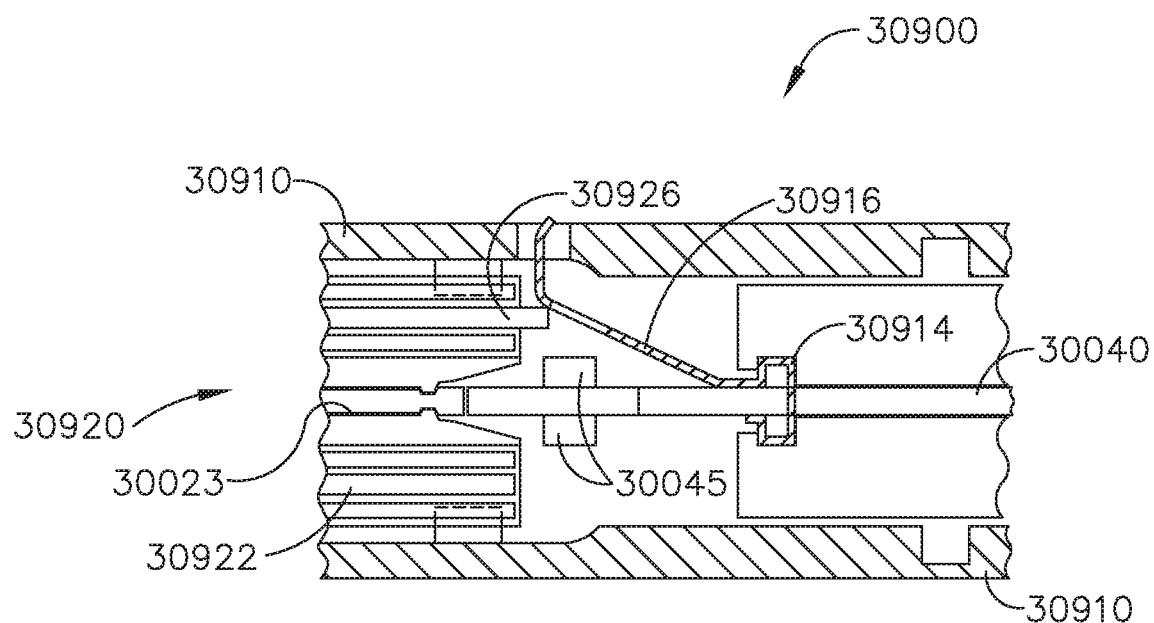
Figure 146:
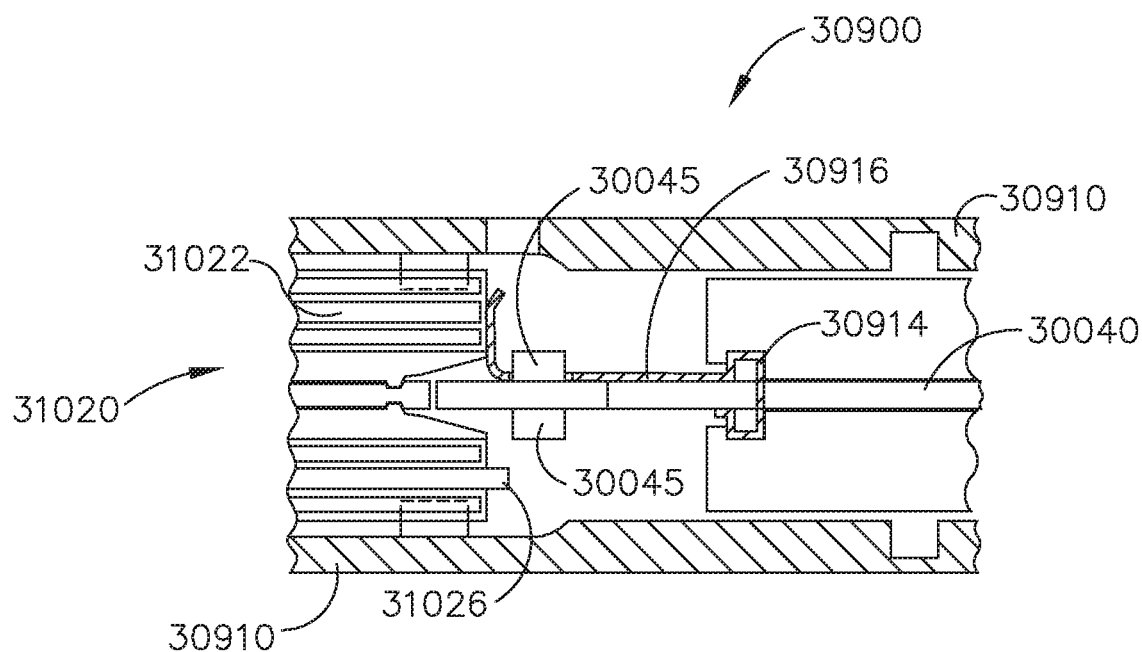
Figure 149:
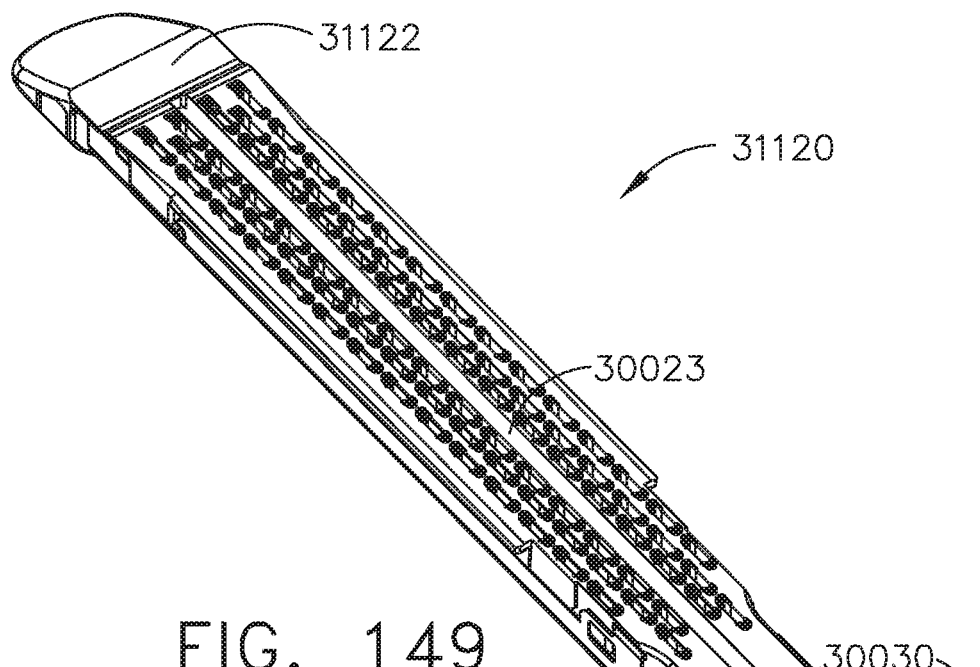
Figure 150:
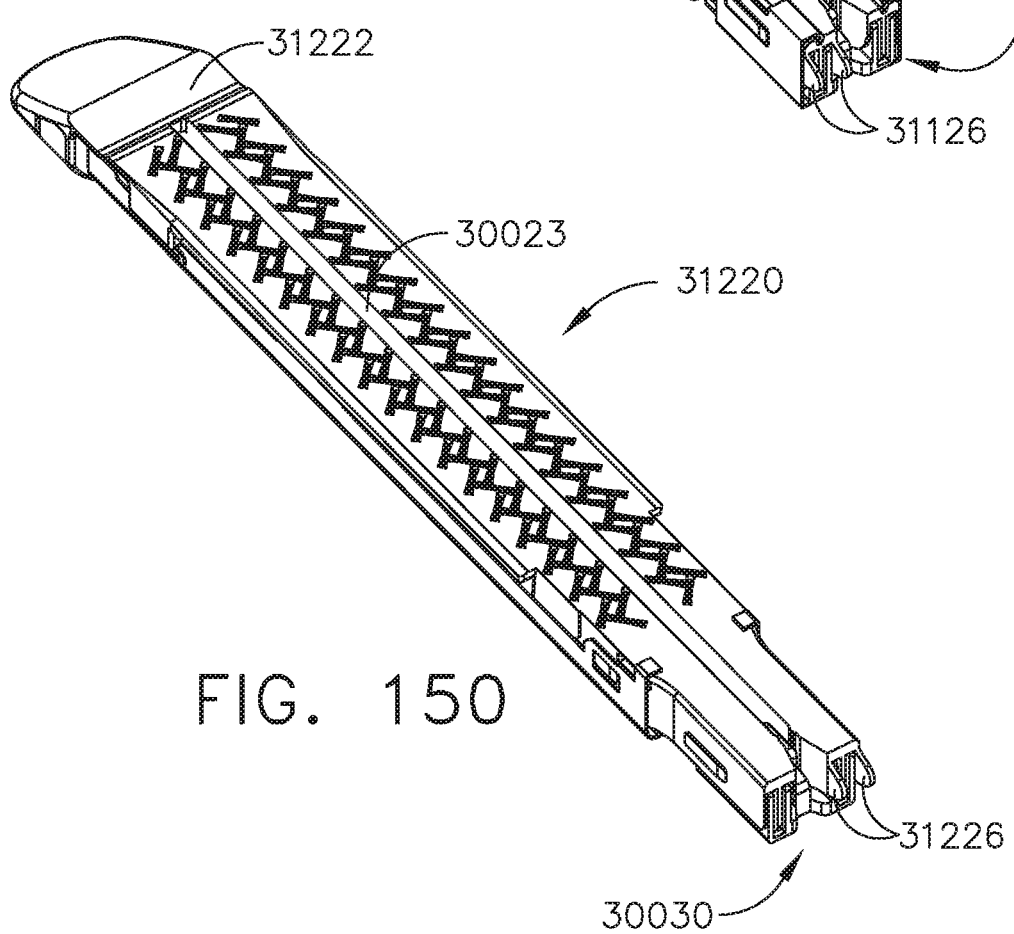
Figure 151:
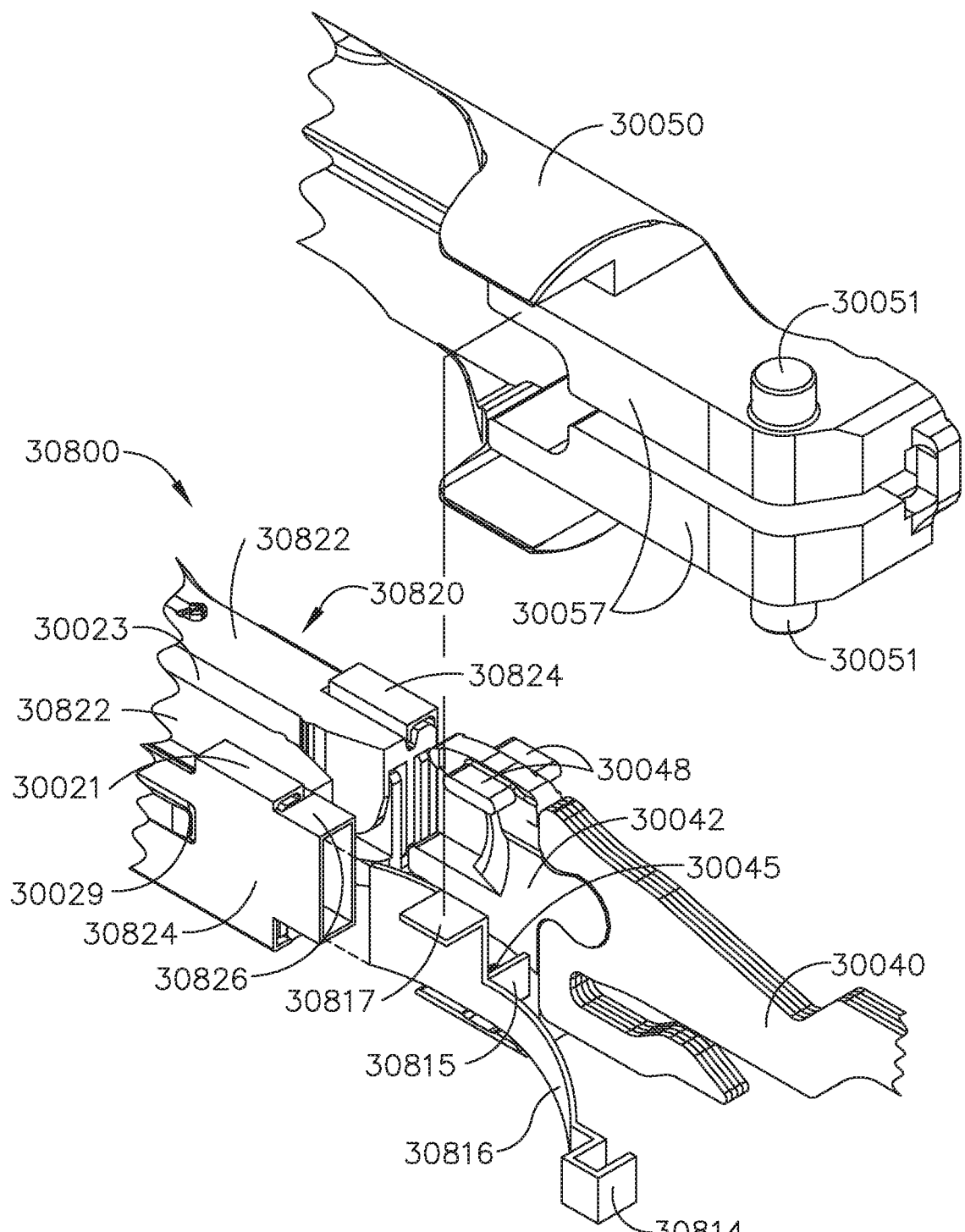
Figure 152:
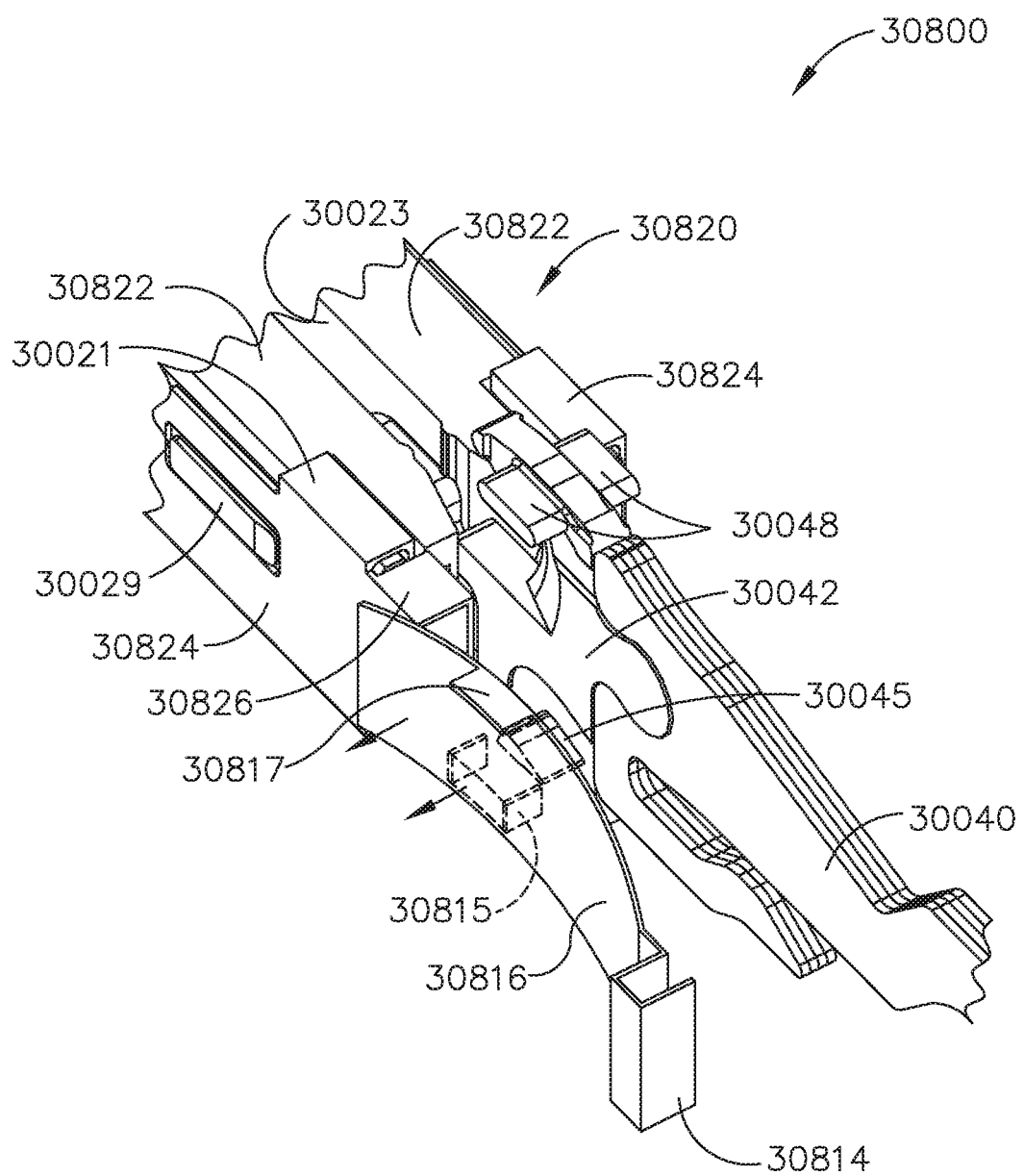
Figure 153:
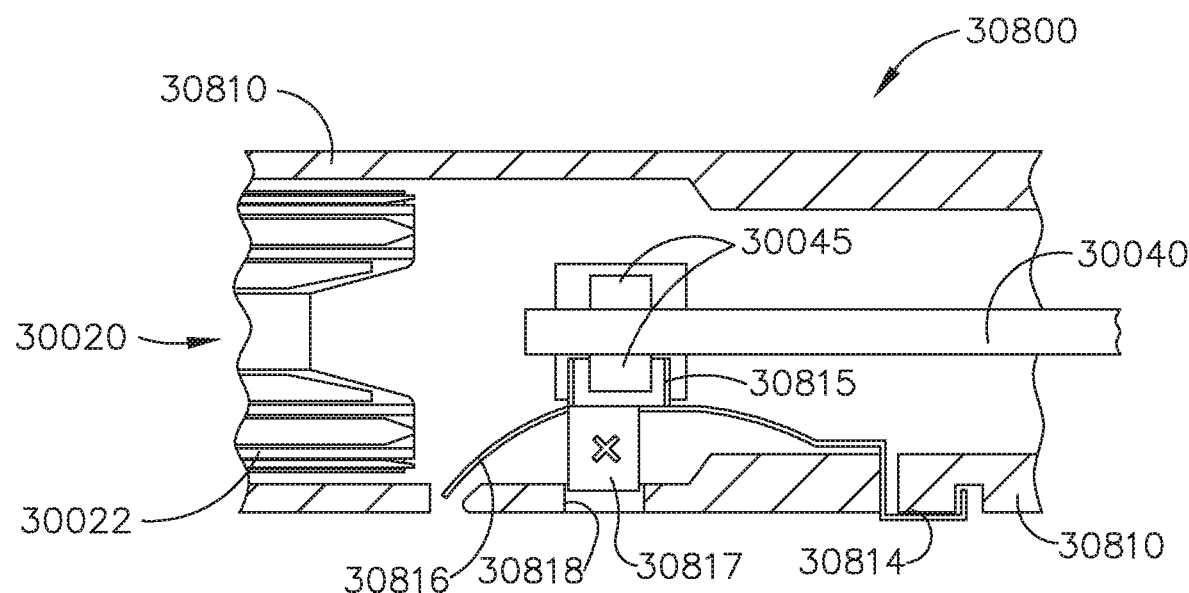
Figure 154:
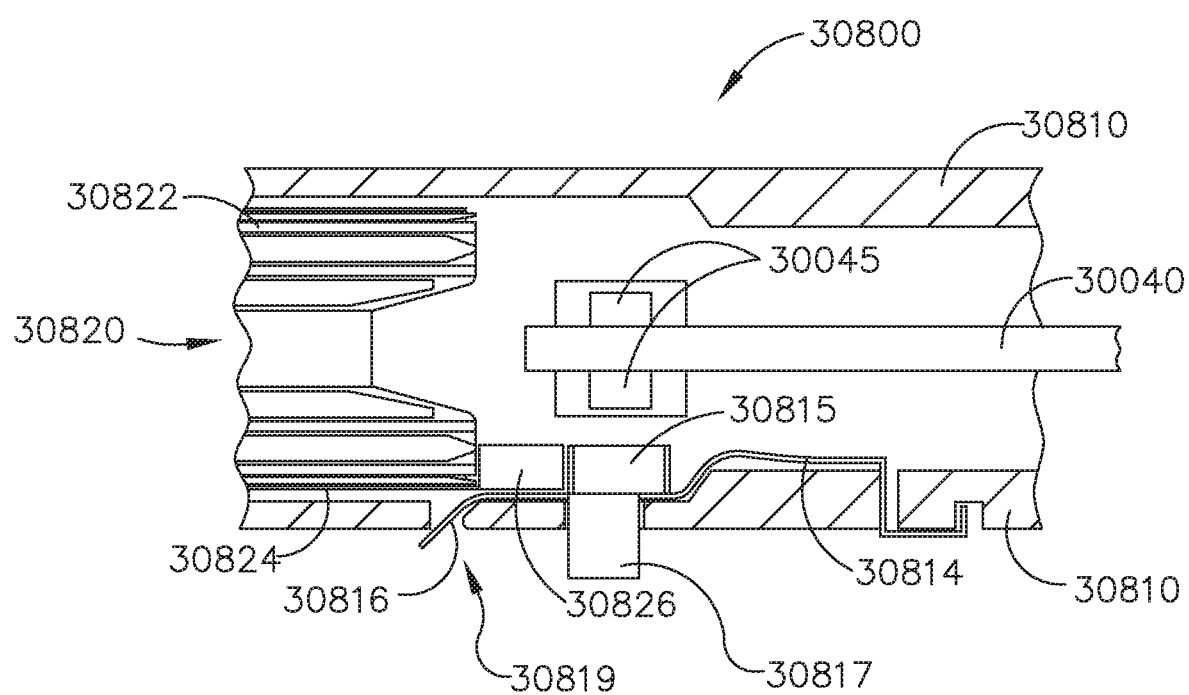
Figure 155:
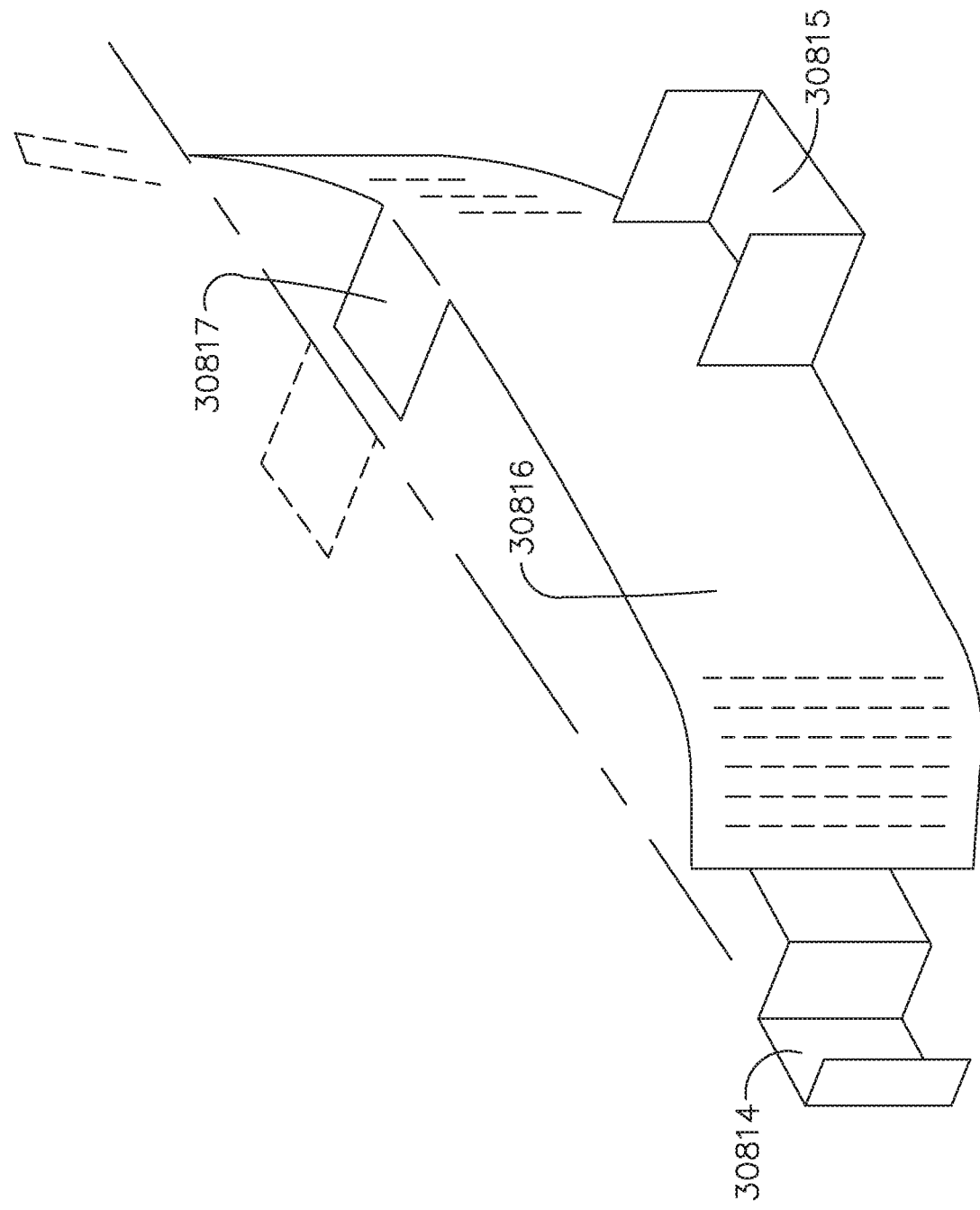
Figure 155A:
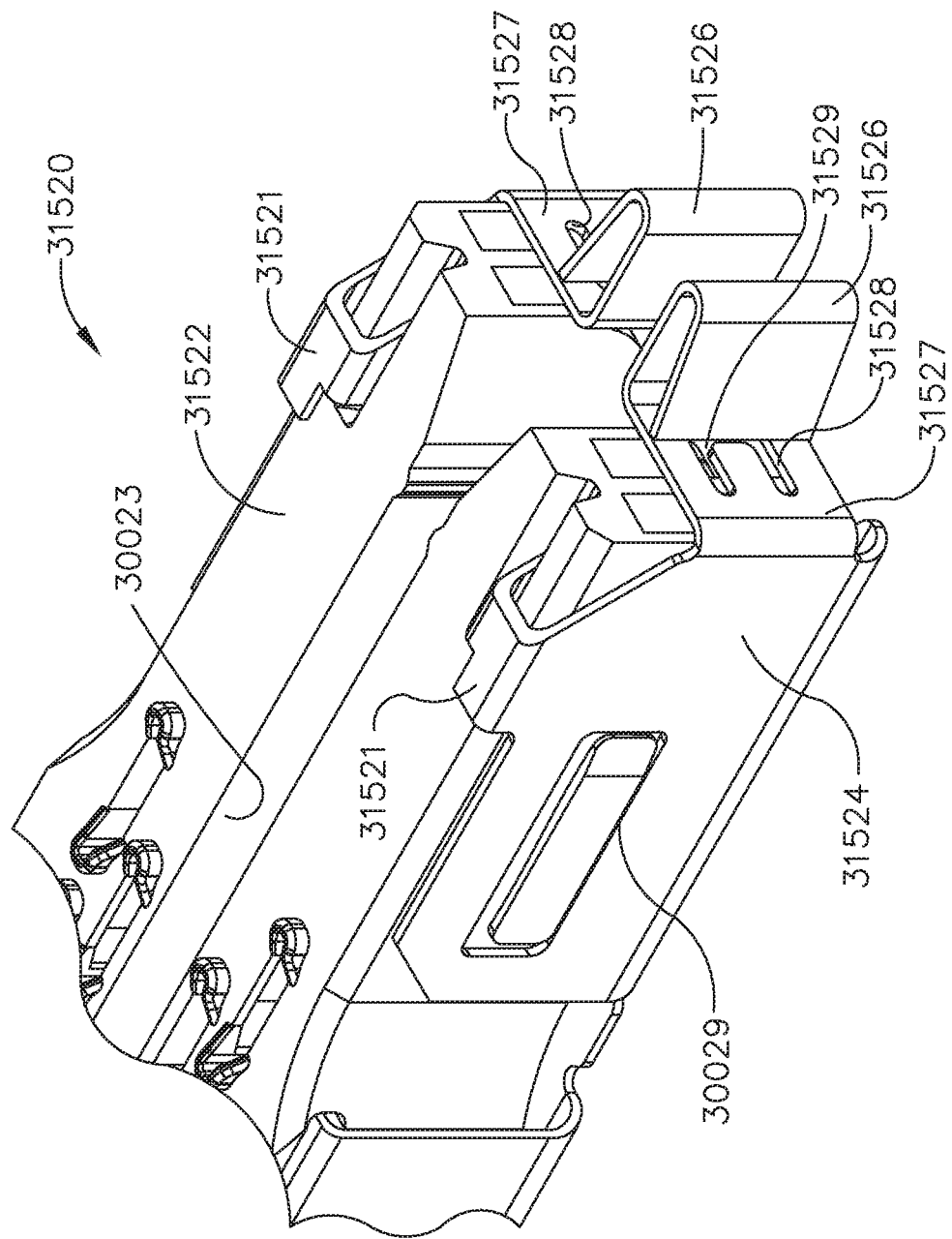
Figure 155B:
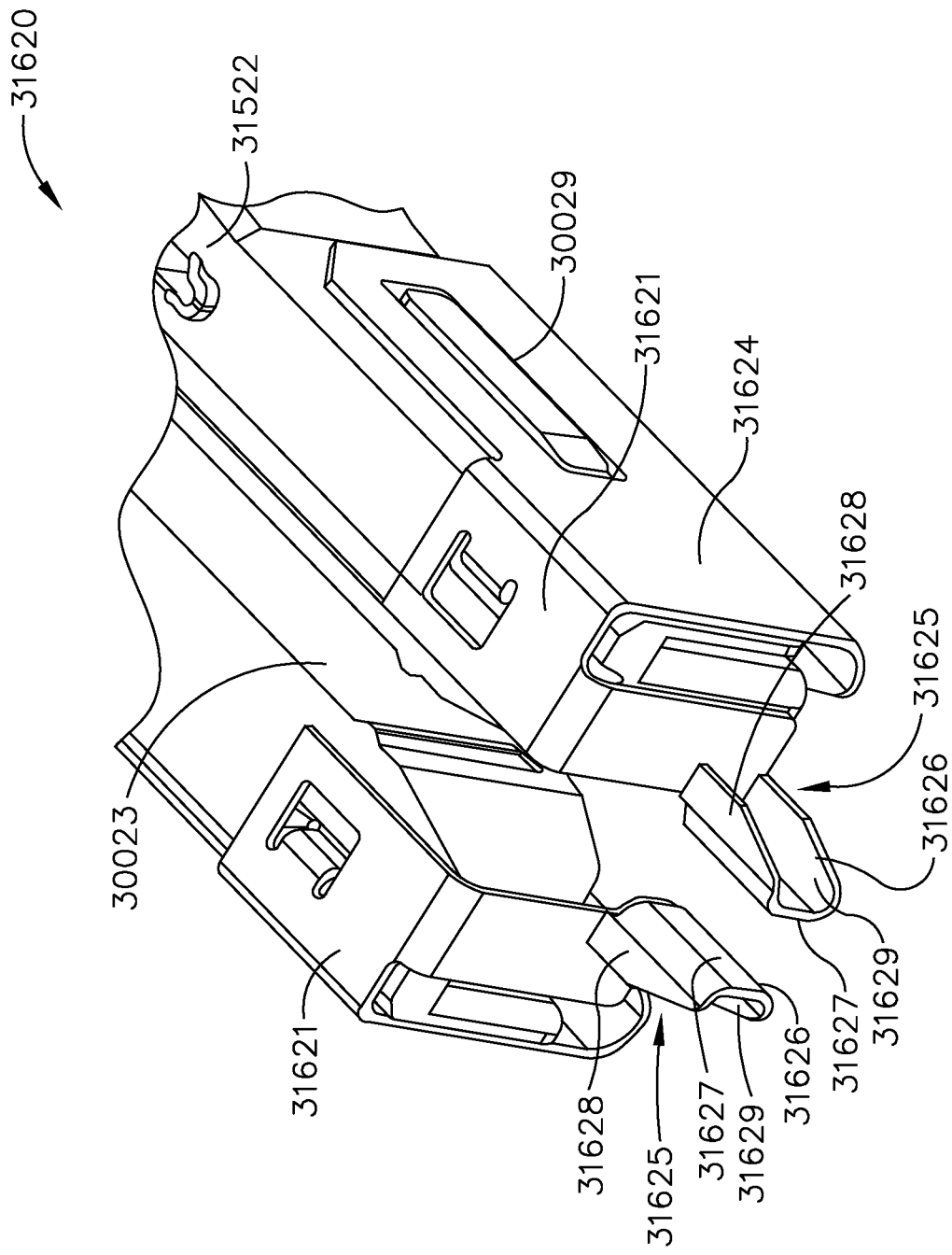
Figure 155C:
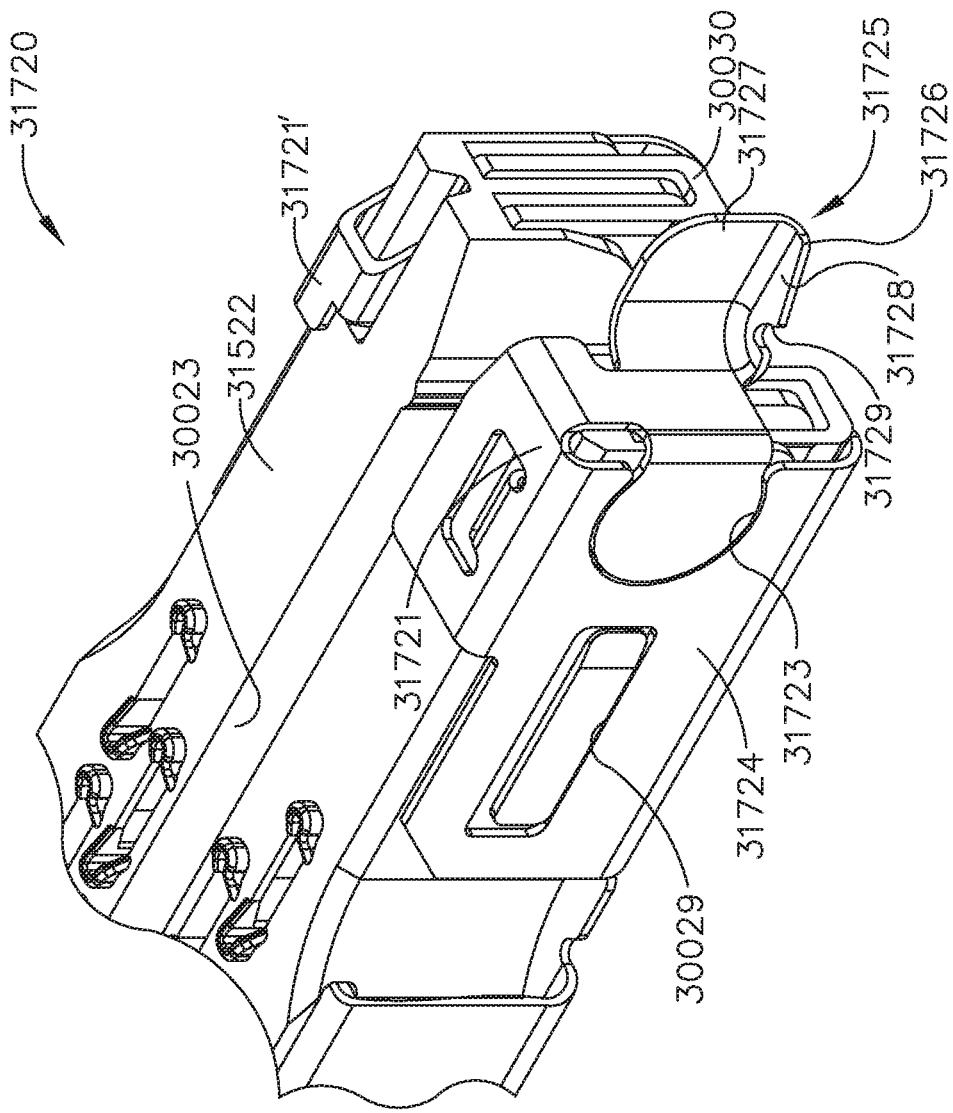
Figure 155D:
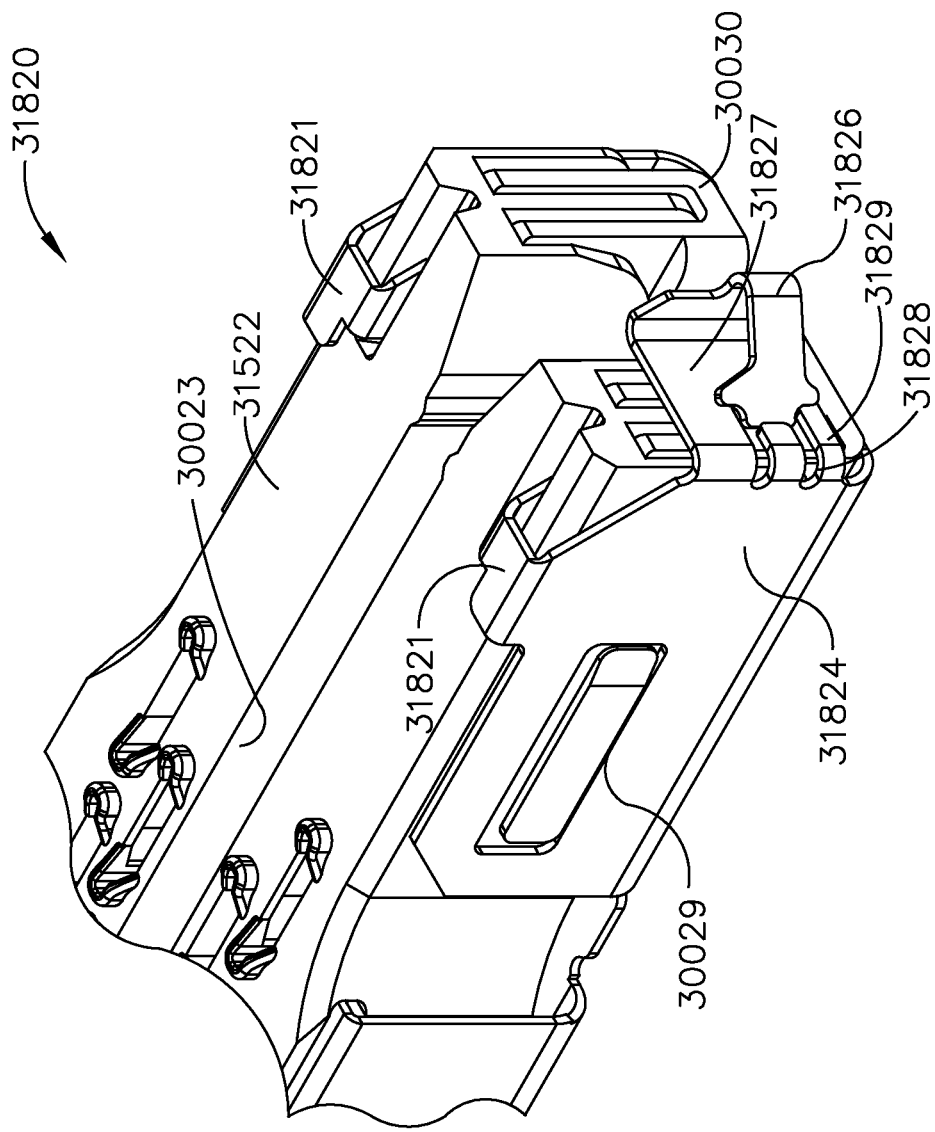
Figure 155E:
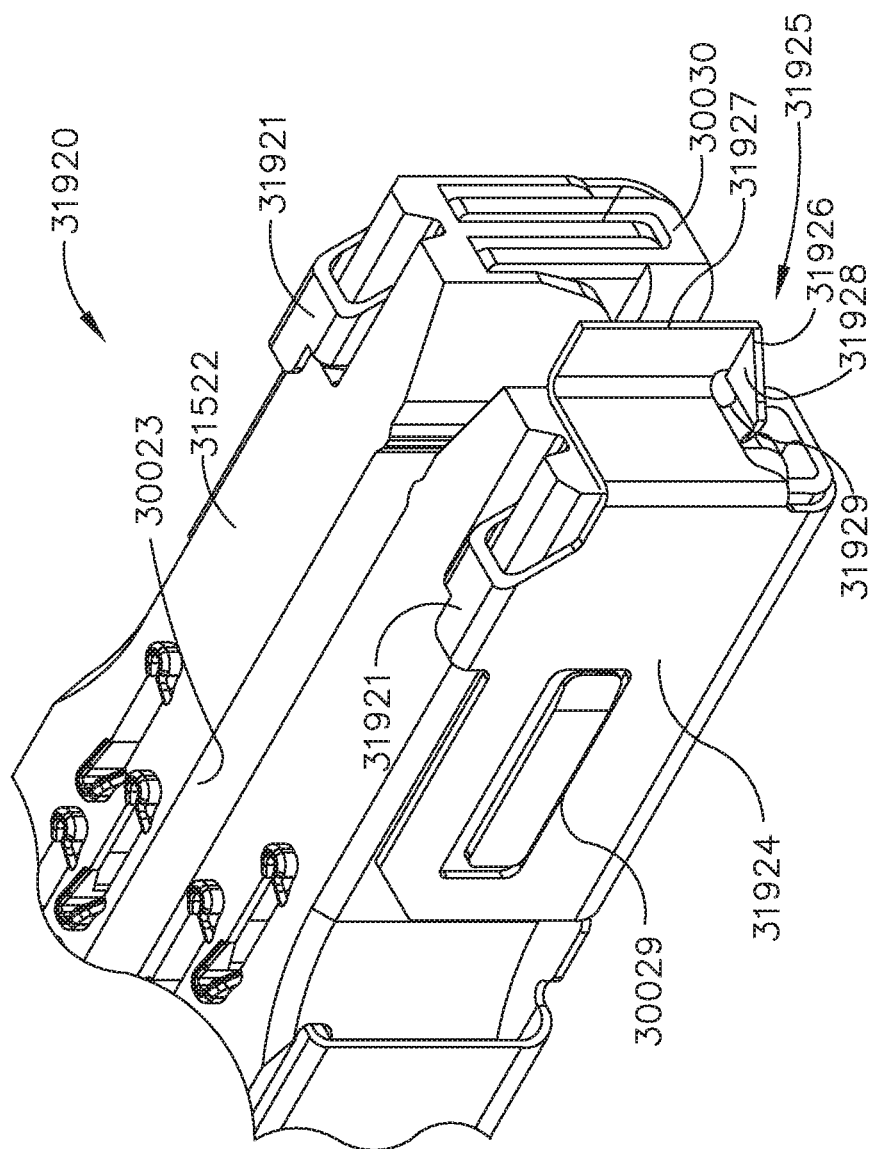
Figure 156:
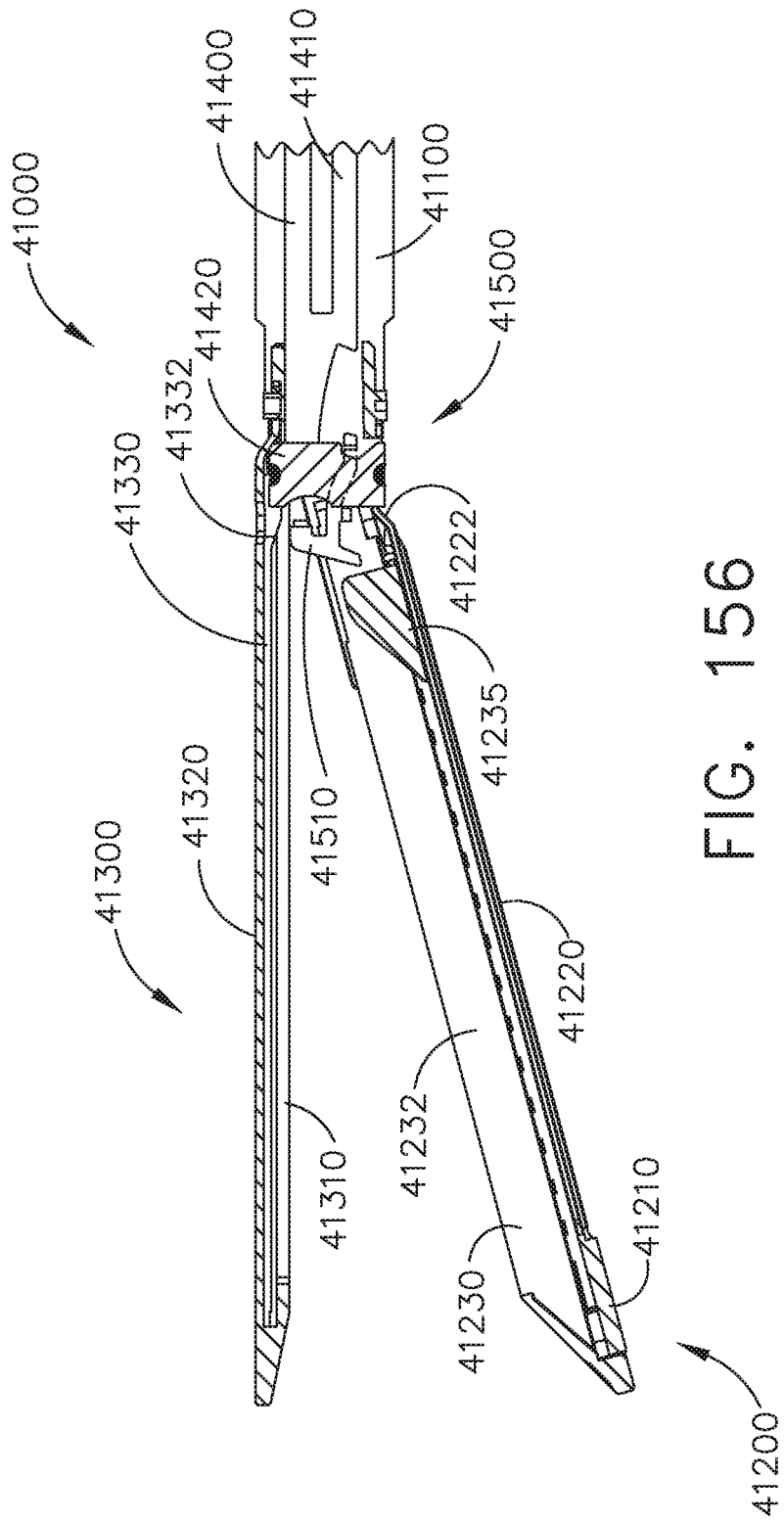
Figure 157:
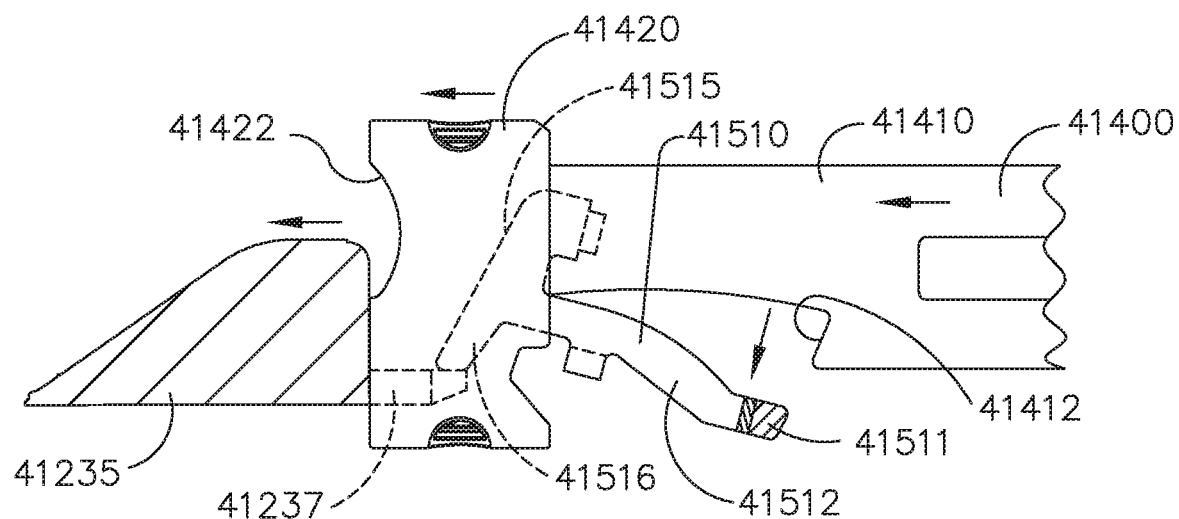
Figure 158:
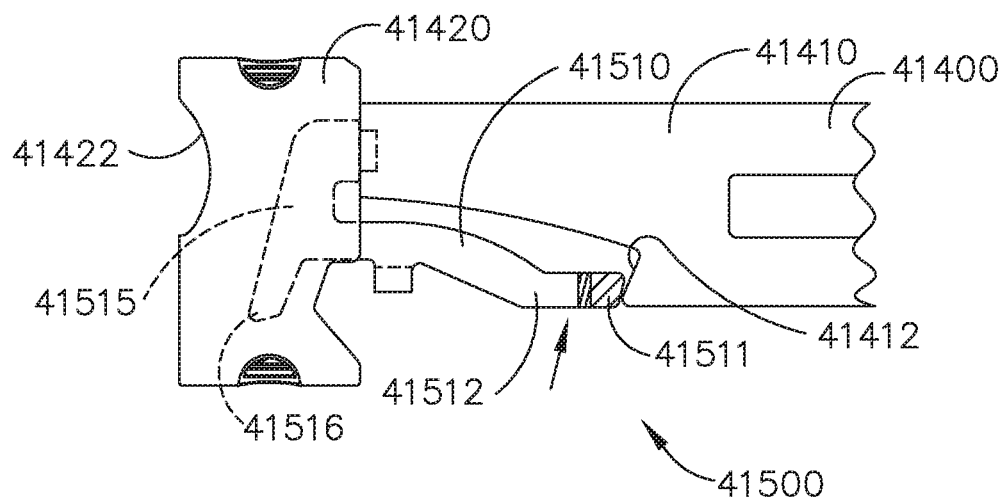
Figure 159:
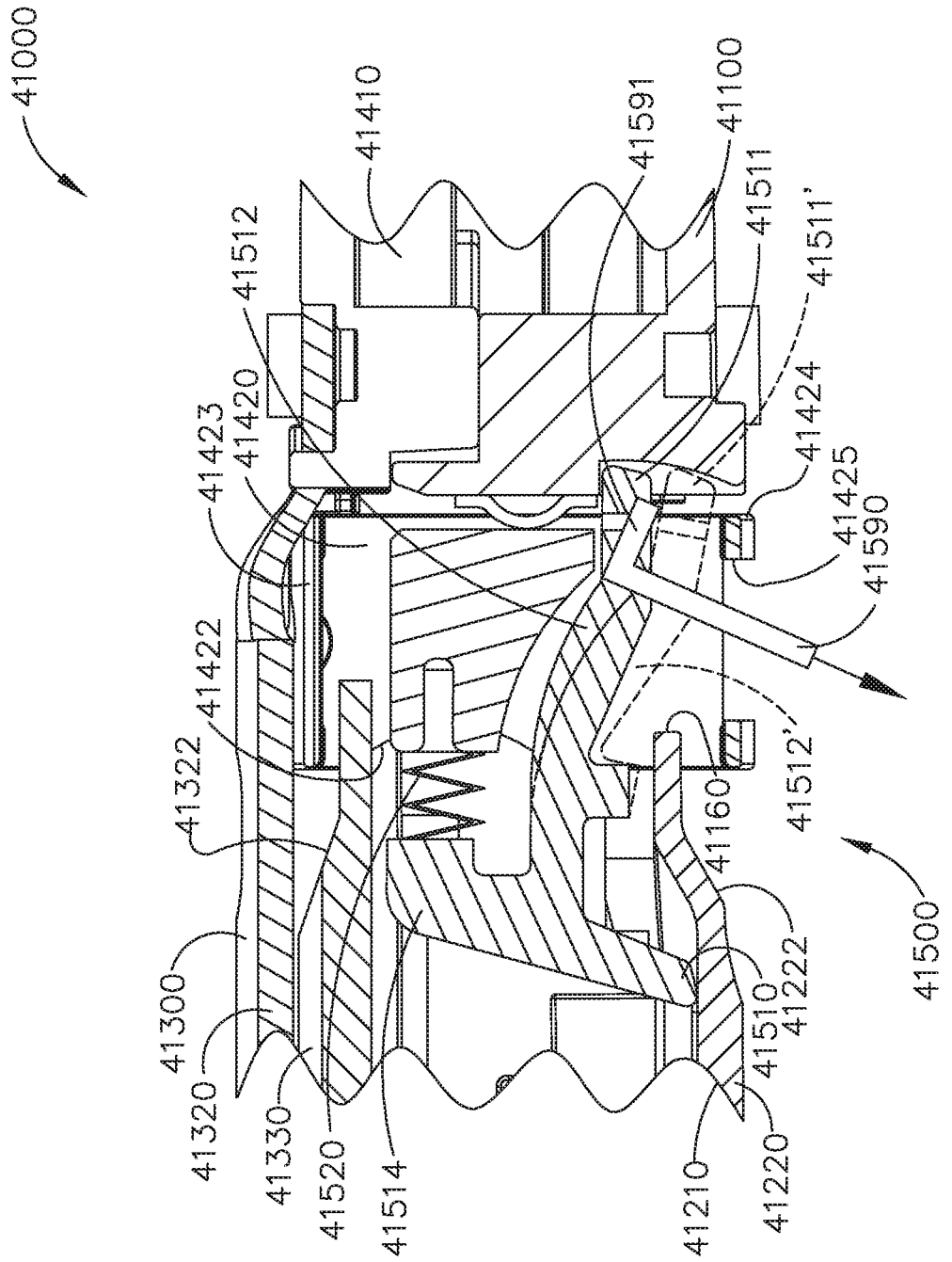
Figure 160:
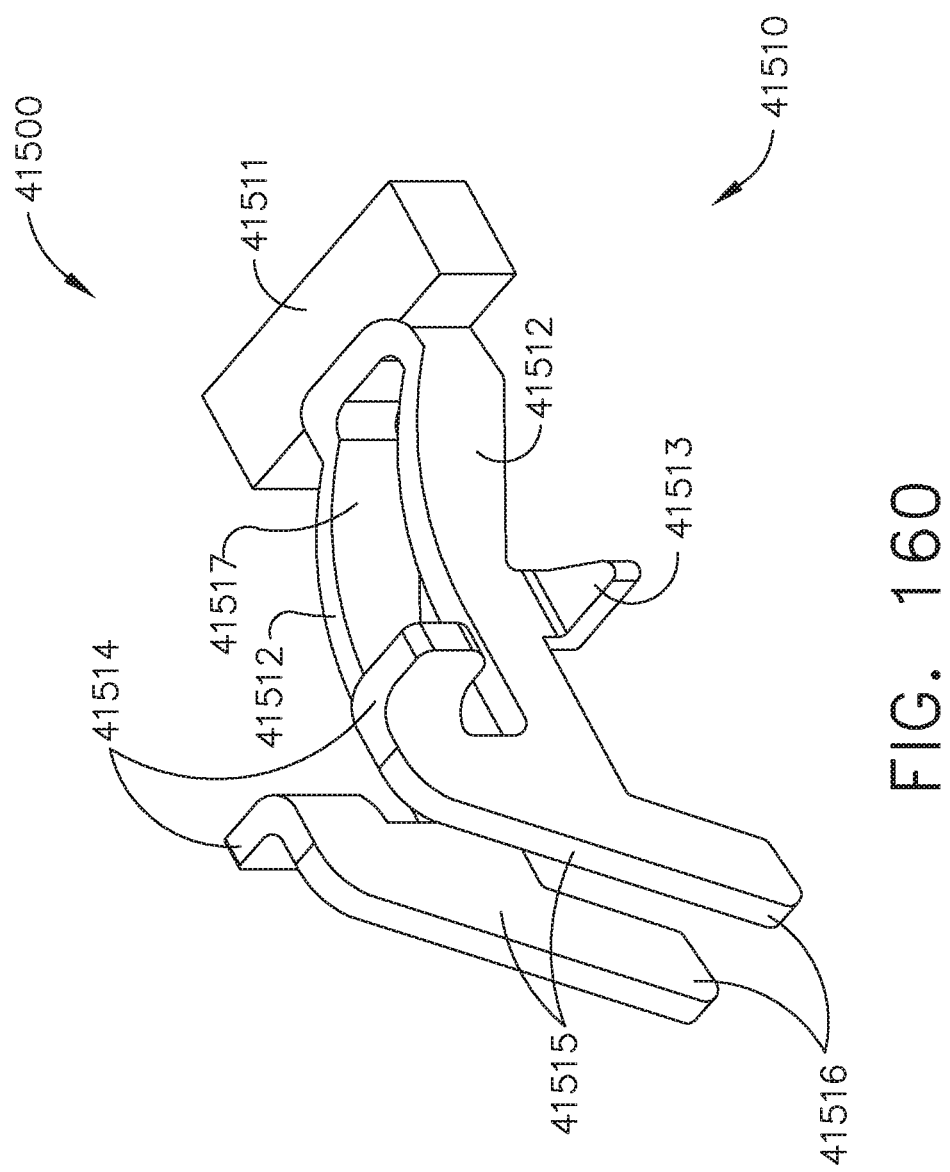
Figure 161:
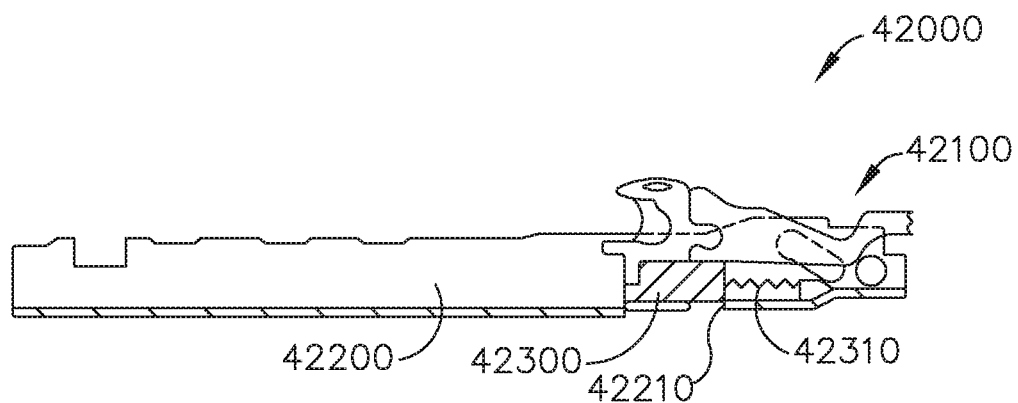
Figure 162:
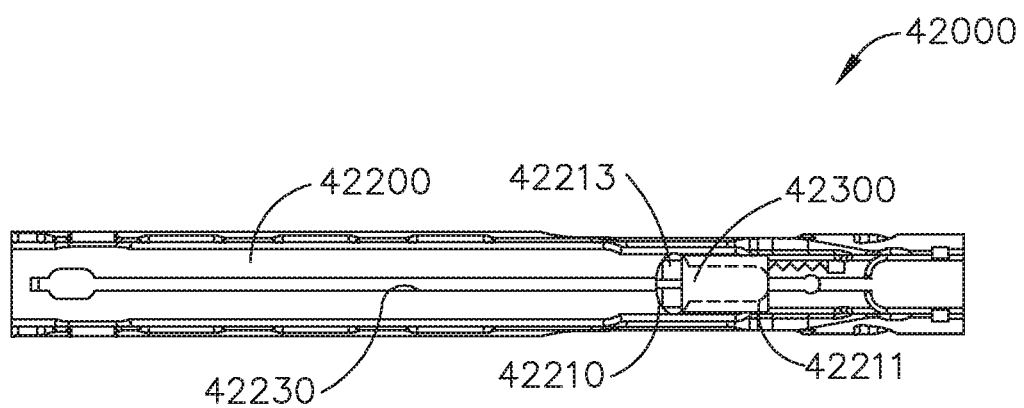
Figure 163:
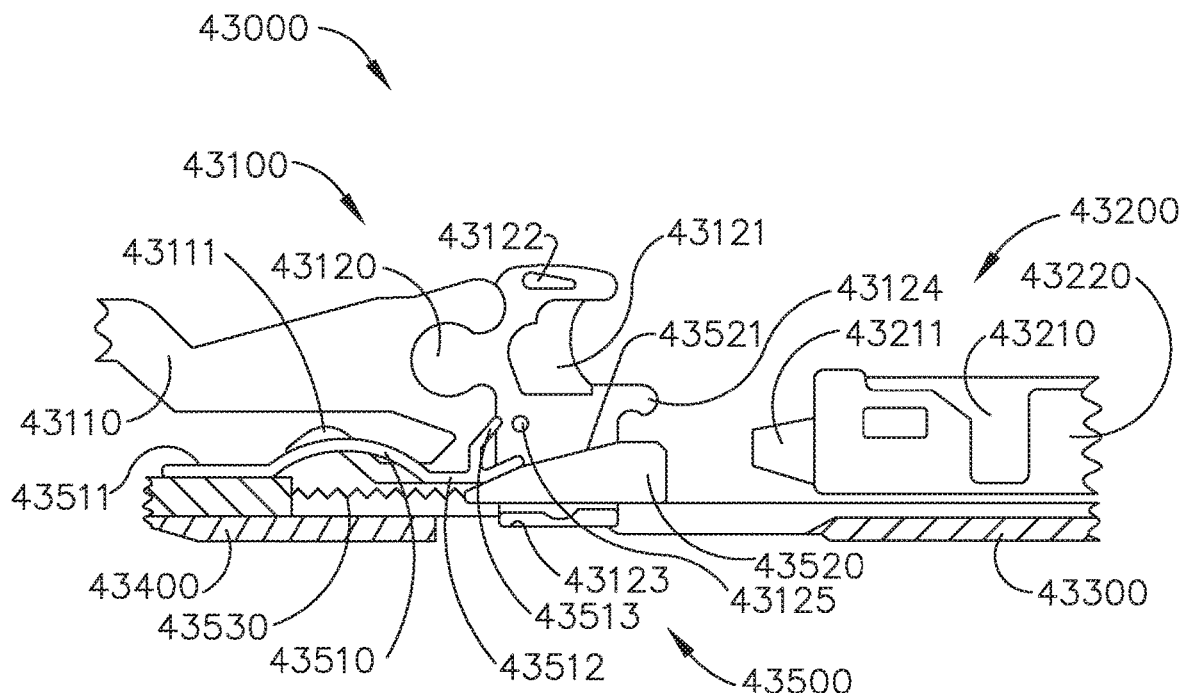
Figure 164:
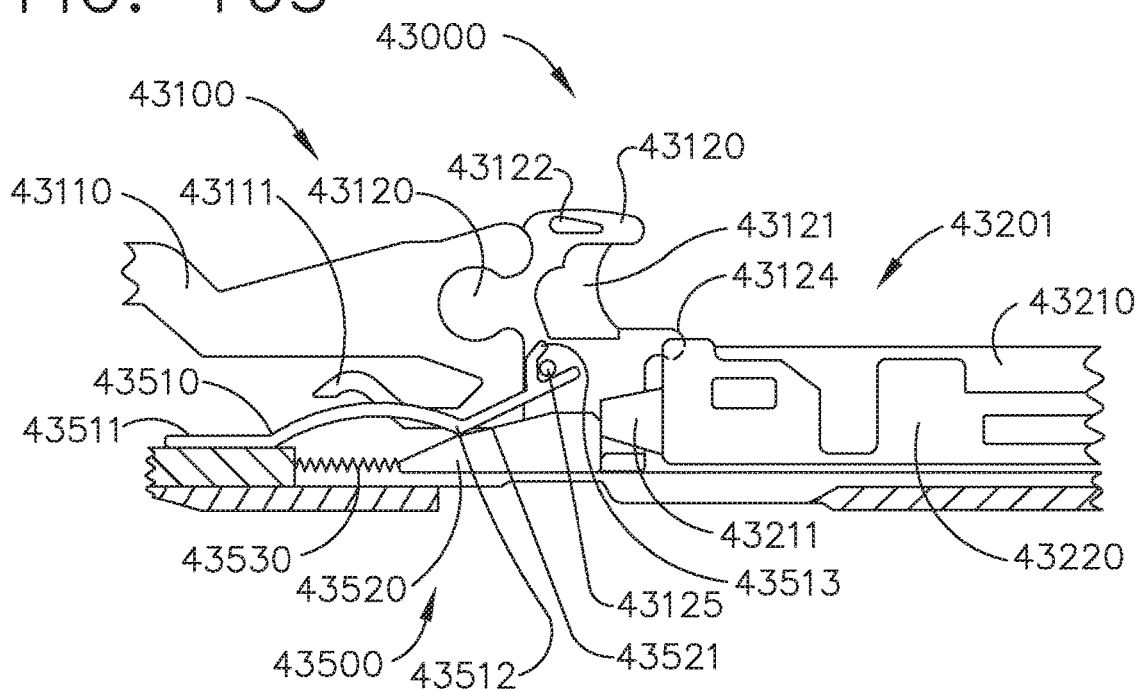
Figure 168:
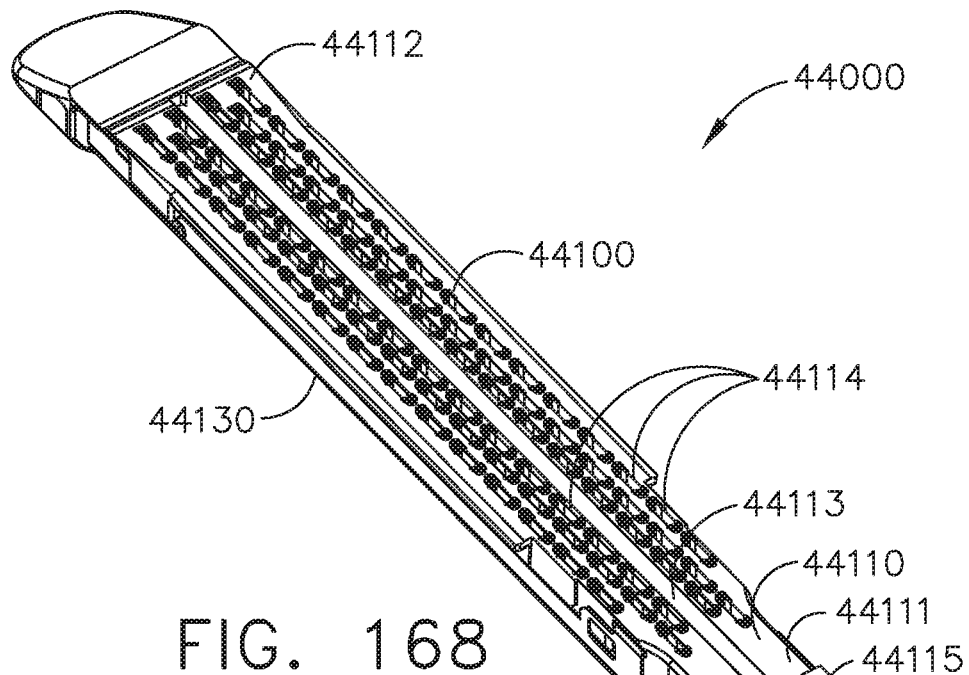
Figure 169:
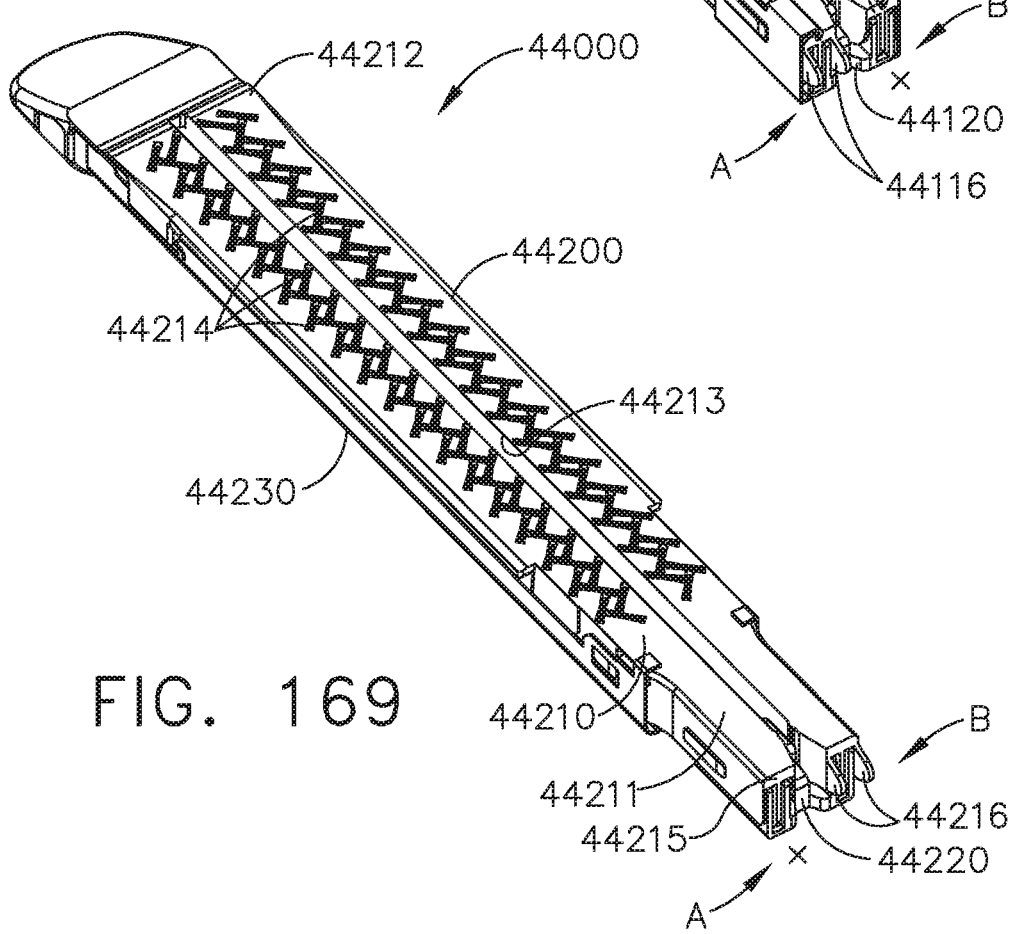
Figure 170:
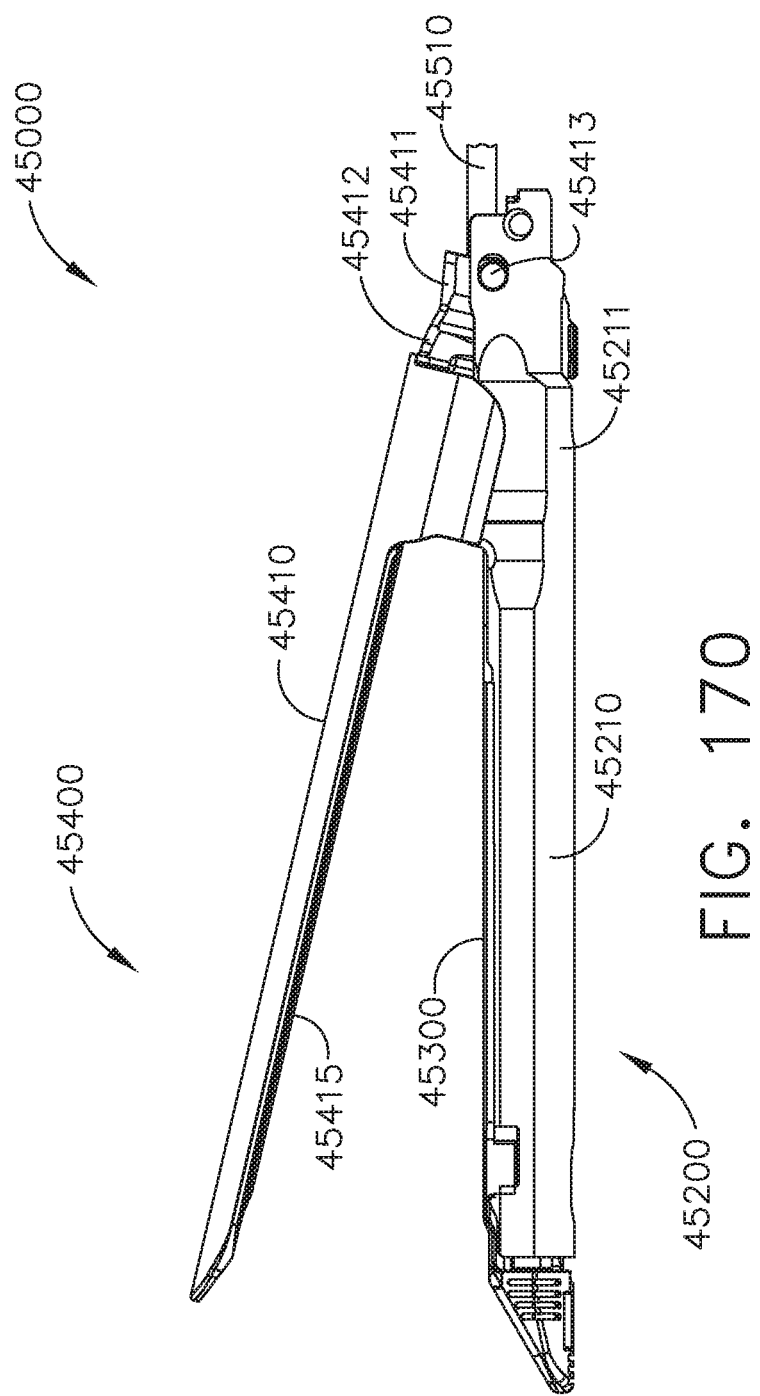
Figure 171:
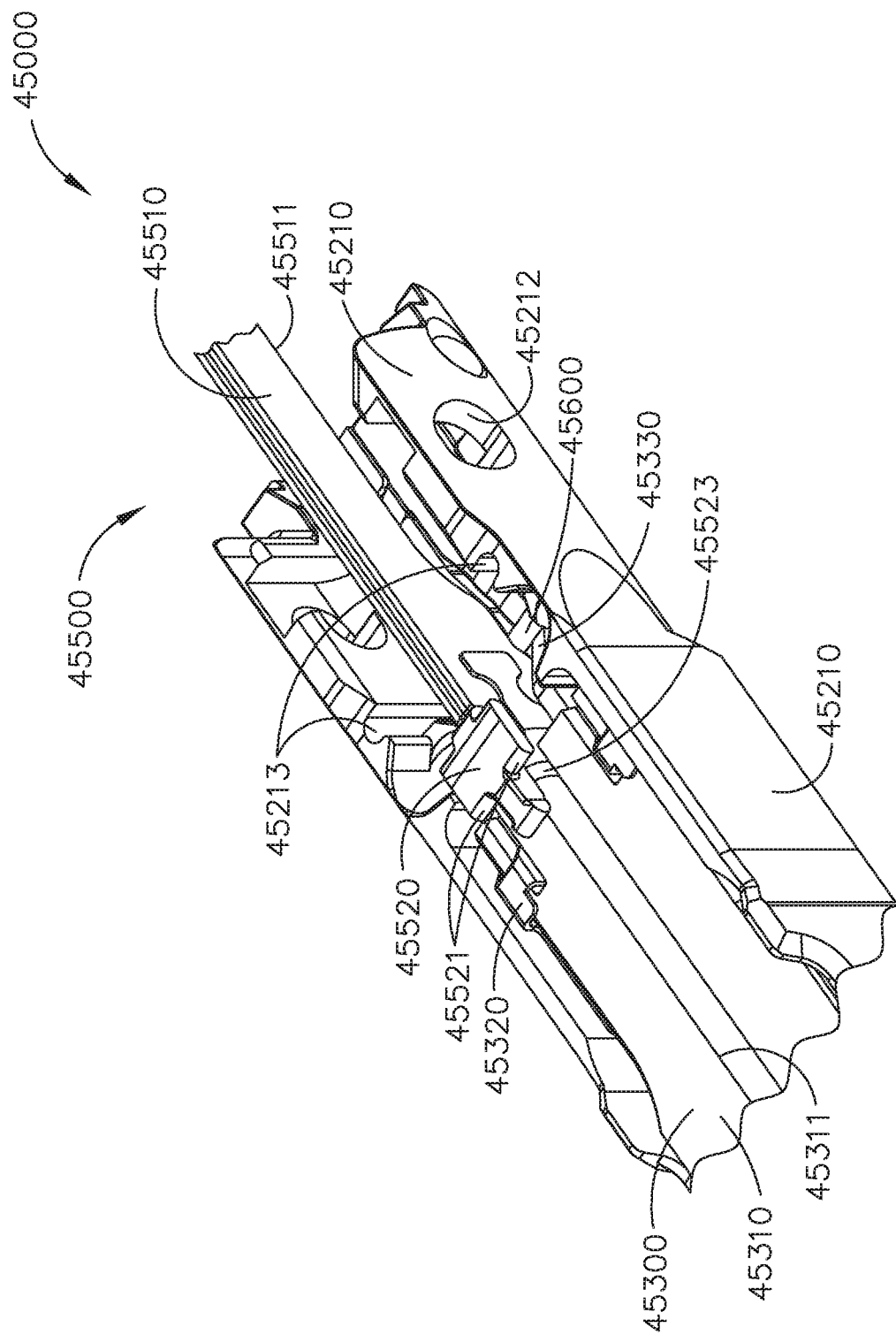
Figure 172:
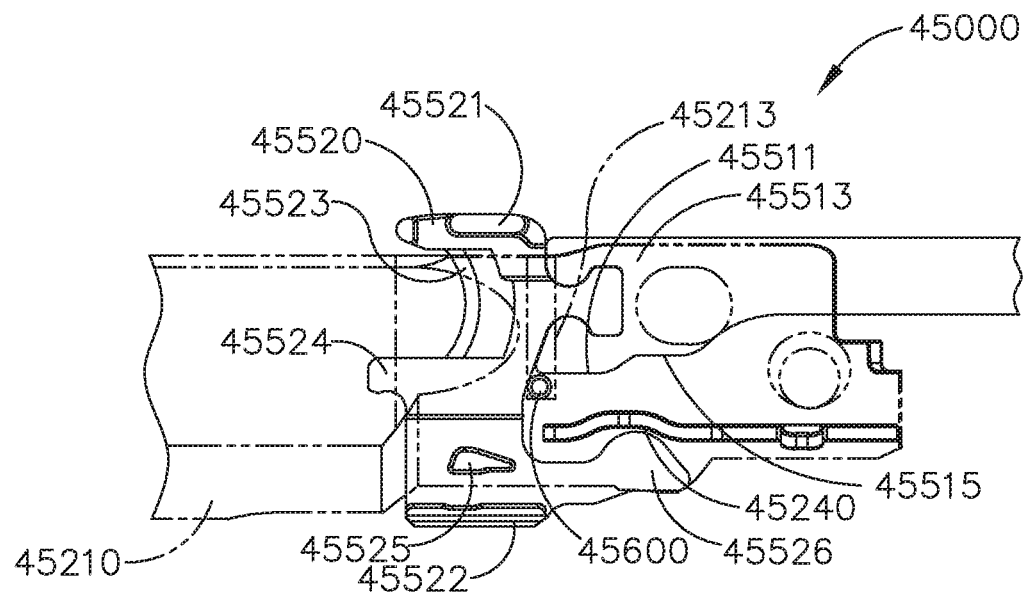
Figure 173:
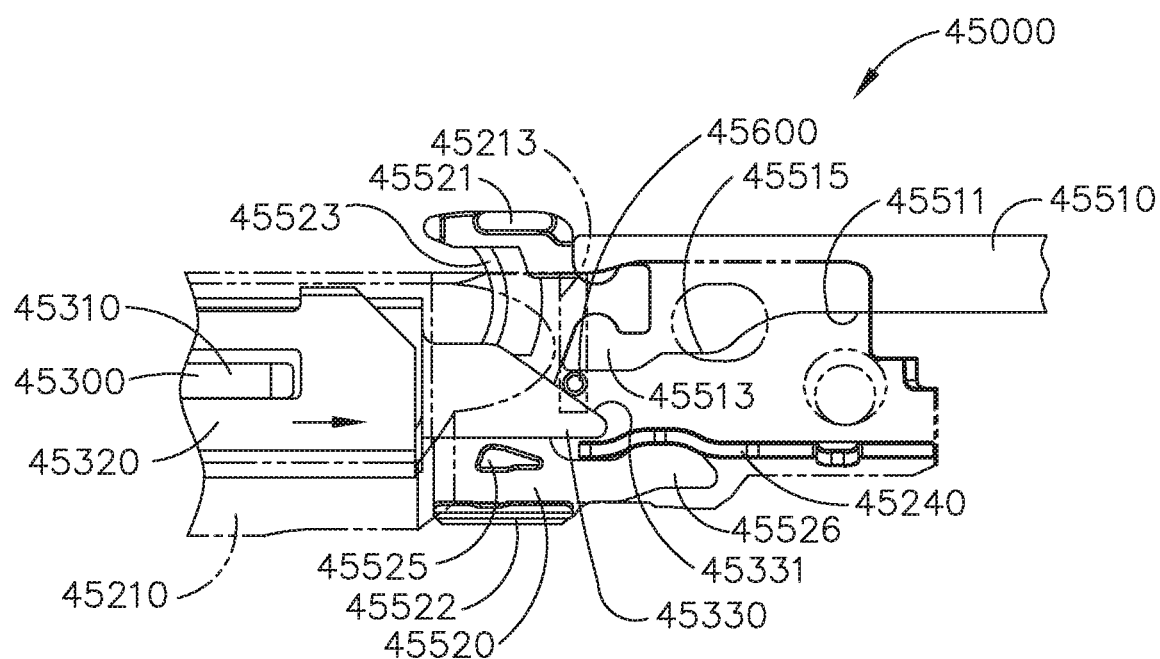
Figure 174:
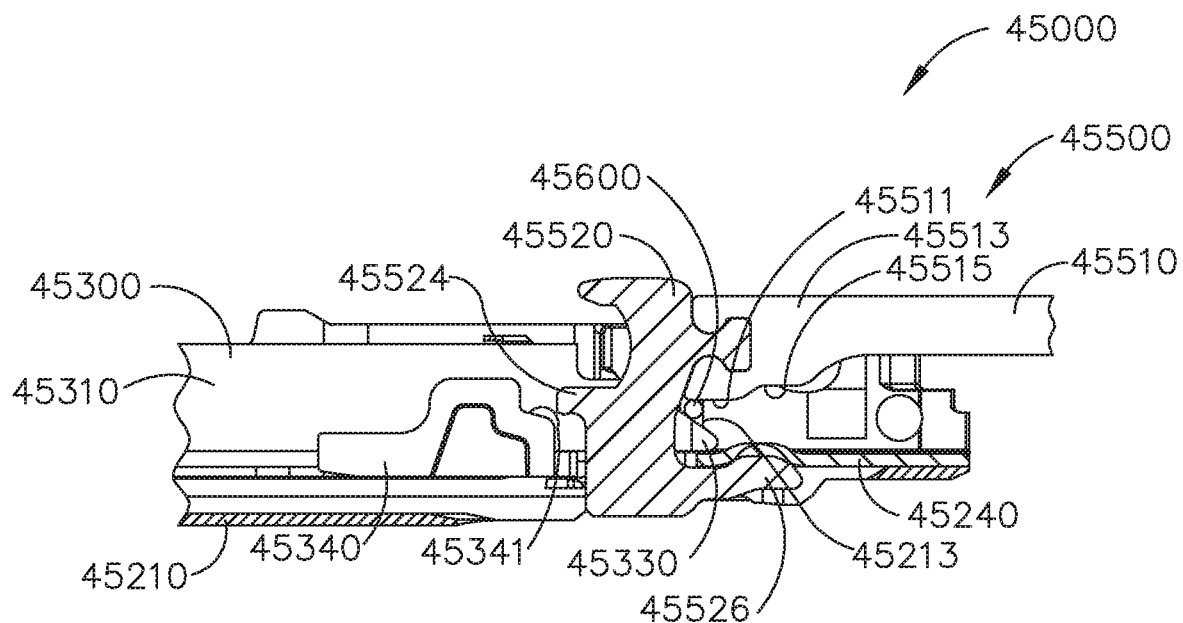
Figure 175:
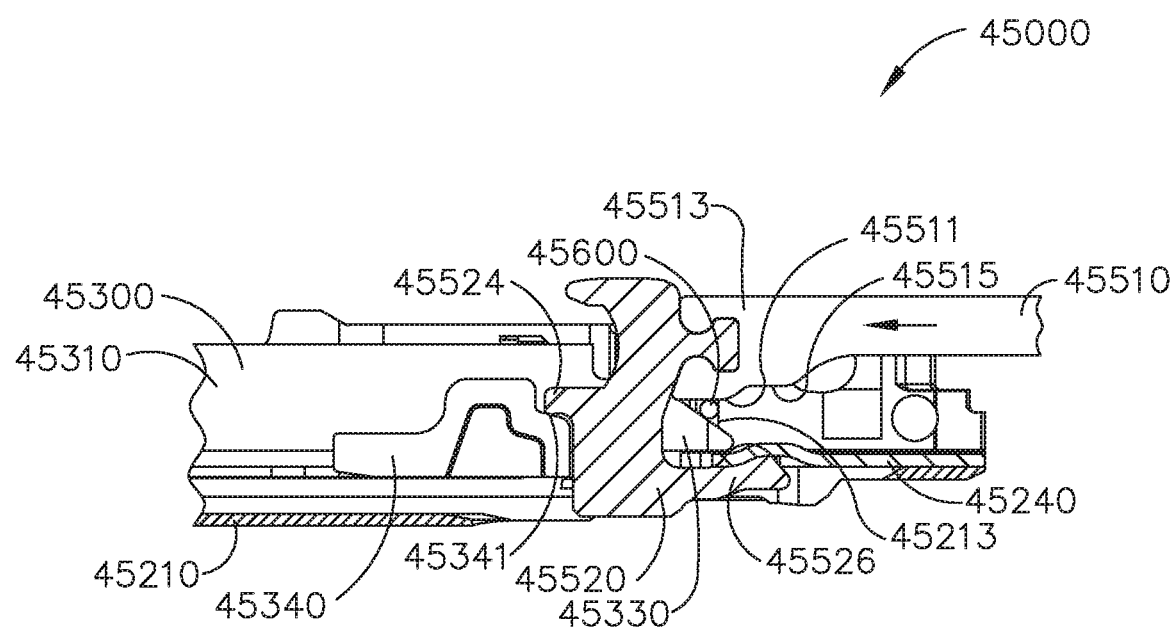
Figure 176:
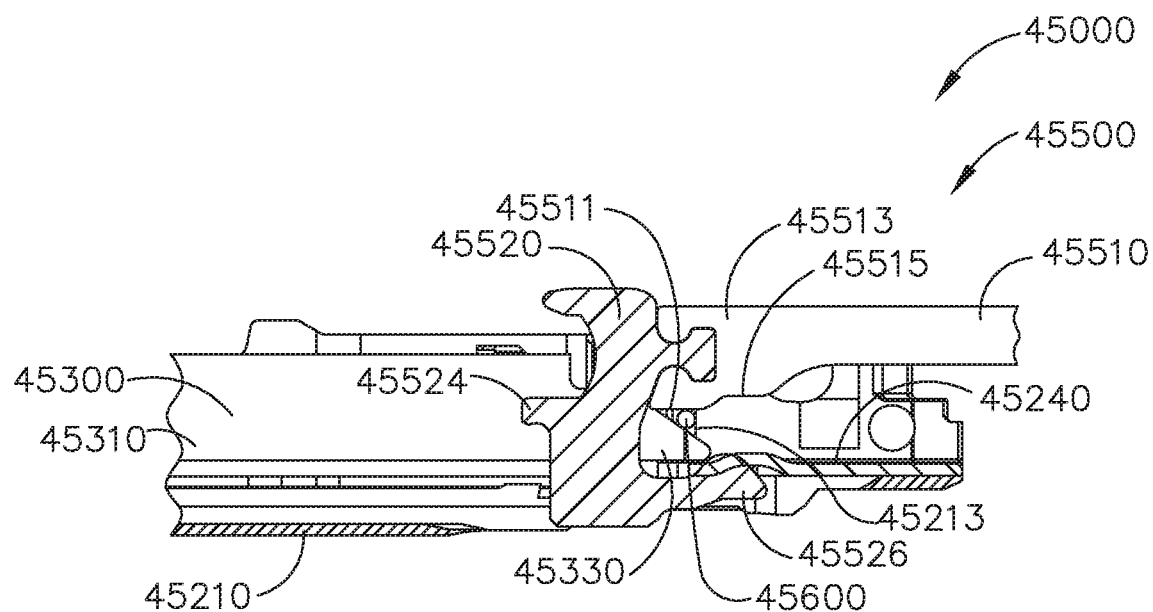
Figure 177:
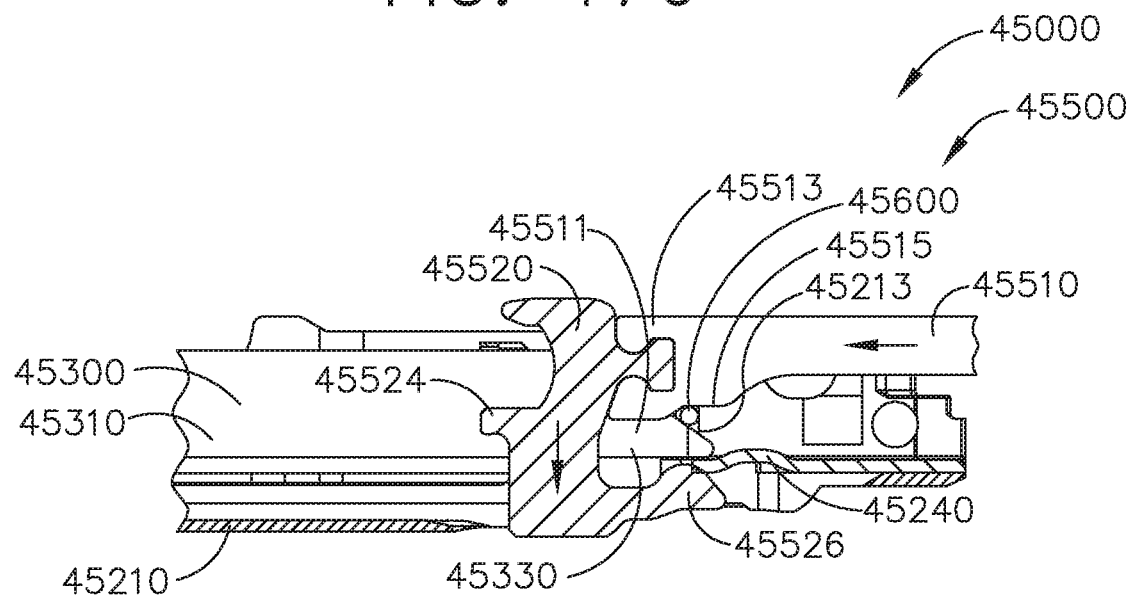
Figure 178:
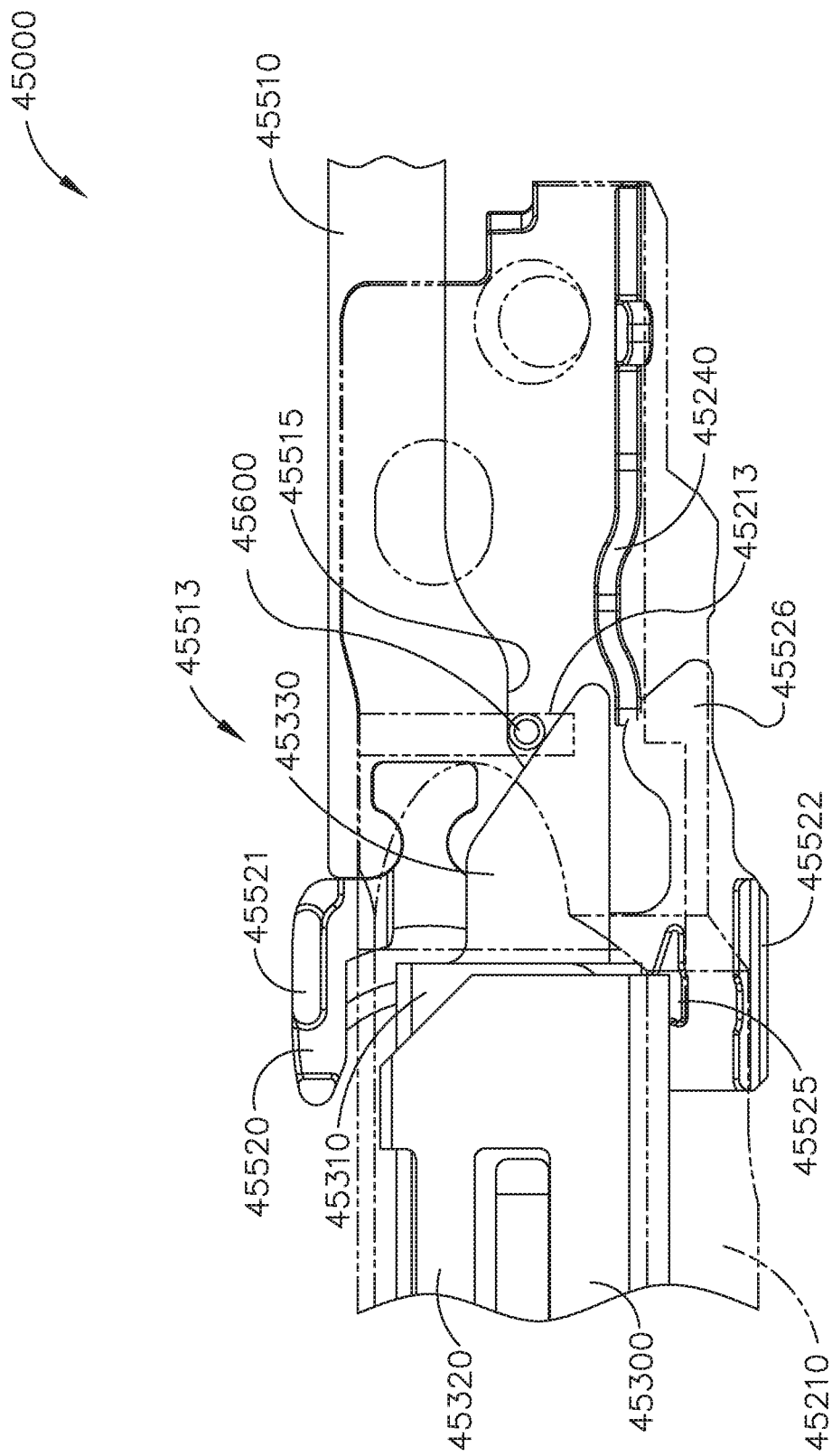
Figure 179:
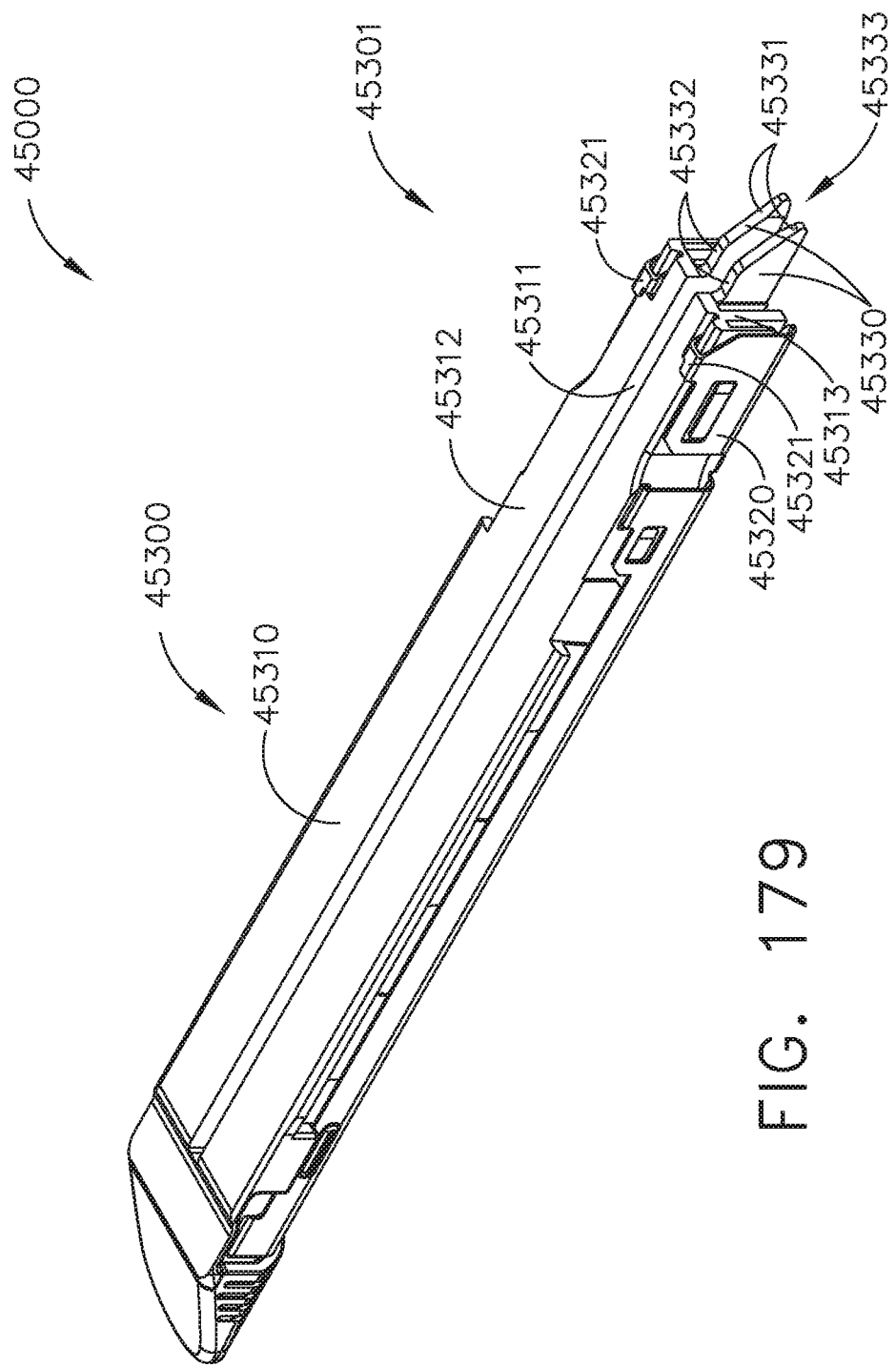

FIG. 131 is a partial top view of the stapling instrument of FIG. 128 illustrated in the unlocked position of FIG. 129;

FIG. 132 is a partial perspective view of the staple cartridge of FIG. 128 in an unspent configuration;

FIG. 133 is a partial perspective view of the staple cartridge of FIG. 128 in a spent configuration;

FIG. 134 is a partial elevational view of a stapling instrument including a cartridge channel, a staple cartridge positioned in the cartridge channel, and a firing member in accordance with at least one embodiment illustrated with some components removed, wherein the firing member is in an unfired position;

FIG. 135 is a partial elevational view of the stapling instrument of FIG. 134 illustrating the firing member in a locked-out position;

FIG. 136 is a partial perspective view of a stapling instrument including a cartridge channel, a staple cartridge positioned in the cartridge channel, a firing member, and a firing member lock in accordance with at least one embodiment illustrated with some components removed, wherein the firing member has been unlocked by the staple cartridge;

FIG. 137 is a partial elevational view of the stapling instrument of FIG. 136 illustrated with an improper staple cartridge seated in the cartridge channel;

FIG. 138 is a partial cross-sectional plan view of the stapling instrument of FIG. 136 illustrated with an improper staple cartridge seated in the cartridge channel;

FIG. 139 is a partial cross-sectional plan view of the stapling instrument of FIG. 136 illustrating the firing member lock unlocked by the staple cartridge;

FIG. 140 is a partial cross-sectional view of a stapling instrument in accordance with at least one embodiment that has been unlocked by a staple cartridge;

FIG. 141 is a partial cross-sectional view of a stapling instrument in accordance with at least one embodiment that has been unlocked by a staple cartridge;

FIG. 142 is a partial perspective view of the staple cartridge of FIG. 140;

FIG. 143 is a partial perspective view of the staple cartridge of FIG. 141;

FIG. 144 is a partial cross-sectional perspective view of a staple cartridge pan in accordance with at least one embodiment;

FIG. 145 is a partial perspective view of a stapling instrument including a cartridge channel, a staple cartridge positioned in the cartridge channel, a firing member, and a firing member lock in accordance with at least one embodiment illustrated with some components removed, wherein the firing member is unlocked by the staple cartridge;

FIG. 146 is a partial perspective view of the stapling instrument of FIG. 145 illustrating a different staple cartridge positioned in the cartridge channel which does not unlock the firing member;

FIG. 147 is a partial perspective view of the stapling instrument of FIG. 145 illustrating the firing member in a locked configuration;

FIG. 148 is a partial perspective view of a stapling instrument configured to be unlocked by the different staple cartridge of FIG. 146;

FIG. 149 is a perspective view of a staple cartridge which is similar to the staple cartridge of FIG. 146 and configured to unlock the stapling instrument of FIG. 148;

FIG. 150 is a perspective view of a staple cartridge which is similar to the staple cartridge of FIG. 145 and configured to unlock the stapling instrument of FIG. 145;

FIG. 151 is a partial exploded view of a stapling instrument comprising a cartridge channel, a staple cartridge positioned in the cartridge channel, a firing member, an anvil, and a dual-purpose firing member/anvil lock in accordance with at least one embodiment illustrated with some components removed, wherein the stapling instrument is illustrated in a locked state;

FIG. 152 is a partial perspective view of the stapling instrument of FIG. 151 being unlocked by the insertion of the staple cartridge into the cartridge channel;

FIG. 153 is a partial cross-sectional view of the stapling instrument of FIG. 151 illustrating the stapling instrument in the locked state of FIG. 151;

FIG. 154 is a partial cross-sectional view of the stapling instrument of FIG. 151 illustrating the stapling instrument in the unlocked state of FIG. 152;

FIG. 155 is a perspective view of the firing member/anvil lock of FIG. 151;

FIG. 155A is a partial perspective view of a staple cartridge in accordance with at least one embodiment;

FIG. 155B is a partial perspective view of a staple cartridge in accordance with at least one embodiment;

FIG. 155C is a partial perspective view of a staple cartridge in accordance with at least one embodiment;

FIG. 155D is a partial perspective view of a staple cartridge in accordance with at least one embodiment;

FIG. 155E is a partial perspective view of a staple cartridge in accordance with at least one embodiment;

FIG. 156 is a partial cross-sectional view of a surgical stapling assembly comprising an anvil, a staple cartridge, a firing member, and a firing lockout;

FIG. 157 is a partial cross-sectional view of the firing member and the firing lockout of FIG. 156 illustrated in an unlocked configuration;

FIG. 158 is a partial cross-sectional view of the firing member and the firing lockout of FIG. 156 illustrated in a locked configuration;

FIG. 159 is a partial cross-sectional view of the surgical stapling assembly of FIG. 156, wherein the surgical stapling assembly further comprises an exterior access aperture configured to permit a user to artificially move the firing lockout into the unlocked configuration with a separate lockout key;

FIG. 160 is a perspective view of a lockout member of the firing lockout of FIG. 156;

FIG. 161 is a partial cross-sectional view of a surgical stapling assembly comprising a lockout and an exterior access orifice configured to permit a user to artificially move the firing lockout into an unlocked configuration with a separate lockout key;

FIG. 162 is a bottom plan view of the surgical stapling assembly of FIG. 161;

FIG. 163 is a partial cross-sectional view of a surgical stapling assembly comprising a firing member, a cartridge channel, a staple cartridge configured be installed into the cartridge channel, and a lockout, wherein the lockout is illustrated in an unengaged configuration;

FIG. 164 is a partial cross-sectional view of the surgical stapling assembly of FIG. 163, wherein the lockout is illustrated in an engaged configuration;

FIG. 165 comprises elevational views of two staple cartridges each comprising a different lockout key;

FIG. 166 is a graph depicting knife lift timing provided by each lockout key of the staple cartridges of FIG. 165;

FIG. 167 is a graph depicting knife lift displacement provided by each lockout key of the staple cartridges of FIG. 165;

FIG. 168 is a perspective view of a first staple cartridge for use with a surgical stapling system, wherein the first staple cartridge comprises a cartridge body, a pan, a sled, and a first lockout key;

FIG. 169 is a perspective view of a second staple cartridge for use with the surgical stapling system with which the first staple cartridge of FIG. 168 is to be used, wherein the second staple cartridge comprises a cartridge body, a pan, a sled, and a second lockout key;

FIG. 170 is an elevational view of a surgical stapling assembly comprising a firing member, a first jaw comprising a staple cartridge, a second jaw comprising an anvil movable relative to the first jaw, and a lockout;

FIG. 171 is partial perspective view of the surgical stapling assembly of FIG. 170;

FIG. 172 is a partial elevational view of the surgical stapling assembly of FIG. 170 where the staple cartridge is not installed within the first jaw;

FIG. 173 is a partial elevational view of the surgical stapling assembly of FIG. 170 where the staple cartridge is installed within the first jaw;

FIG. 174 is a partial cross-sectional view of the surgical stapling assembly of FIG. 170 where the staple cartridge is installed within the first jaw and the firing member is in an unfired position;

FIG. 175 is a partial cross-sectional view of the surgical stapling assembly of FIG. 170 where the staple cartridge is installed within the first jaw and the firing member is in a partially fired position;

FIG. 176 is a partial cross-sectional view of the surgical stapling assembly of FIG. 170 where the staple cartridge is not installed within the first jaw and the firing member is in the unfired position;

FIG. 177 is a partial cross-sectional view of the surgical stapling assembly of FIG. 170 where the staple cartridge is not installed within the first jaw and the firing member is in a locked position;

FIG. 178 is a partial elevational view of the surgical stapling assembly of FIG. 170 where the staple cartridge is installed within the first jaw and the firing member is in the partially fired position, wherein some components are illustrated with hidden lines;

FIG. 179 is a perspective view of the staple cartridge of the surgical stapling assembly of FIG. 170 comprising a lockout key extending from a proximal end thereof;

FIG. 180 is a partial plan view of the staple cartridge of FIG. 179; and

FIG. 181 is a partial plan view of a second staple cartridge configured for use with a system including the staple cartridge of FIG. 179, wherein the second staple cartridge comprises a lockout key comprising a different configuration than the lockout key of the staple cartridge of FIG. 179.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. patent applications that were filed on even date herewith and which are each herein incorporated by reference in their respective entireties:

U.S. patent application entitled METHODS FOR CONTROLLING A POWERED SURGICAL STAPLER THAT HAS SEPARATE ROTARY CLOSURE AND FIRING SYSTEMS, U.S. patent application Ser. No. 16/281,658, U.S. Published Patent Application No. 2019-0298350;

U.S. patent application entitled STAPLE CARTRIDGE COMPRISING A LOCKOUT KEY CONFIGURED TO LIFT A FIRING MEMBER, U.S. patent application Ser. No. 16/281,670, U.S. Published Patent Application No. 2019-0298340;

U.S. patent application entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN, U.S. patent application Ser. No. 16/281,675, U.S. Published Patent Application No. 2019-0298354;

U.S. patent application entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT, U.S. patent application Ser. No. 16/281,693, U.S. Published Patent Application No. 2019-0298342;

U.S. patent application entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN, U.S. patent application Ser. No. 16/281,704, U.S. Published Patent Application No. 2019-0298356;

U.S. patent application entitled STAPLING INSTRUMENT COMPRISING A DEACTIVATABLE LOCKOUT, U.S. patent application Ser. No. 16/281,707, U.S. Published Patent Application No. 2019-0298347;

U.S. patent application entitled SURGICAL INSTRUMENT COMPRISING A JAW CLOSURE LOCKOUT, U.S. patent application Ser. No. 16/281,741, U.S. Published Patent Application No. 2019-0298357;

U.S. patent application entitled SURGICAL STAPLING DEVICES WITH CARTRIDGE COMPATIBLE CLOSURE AND FIRING LOCKOUT ARRANGEMENTS, U.S. patent application Ser. No. 16/281,762, U.S. Published Patent Application No. 2019-0298343;

U.S. patent application entitled SURGICAL STAPLE CARTRIDGE WITH FIRING MEMBER DRIVEN CAMMING ASSEMBLY THAT HAS AN ONBOARD TISSUE CUTTING FEATURE, U.S. patent application Ser. No. 16/281,660, U.S. Published Patent Application No. 2019-0298351;

U.S. patent application entitled SURGICAL STAPLING DEVICES WITH IMPROVED ROTARY DRIVEN CLOSURE SYSTEMS, U.S. patent application Ser. No. 16/281,666, U.S. Published Patent Application No. 2019-0298352;

U.S. patent Application entitled SURGICAL STAPLING DEVICES WITH ASYMMETRIC CLOSURE FEATURES, U.S. patent application Ser. No. 16/281,672, U.S. Published Patent Application No. 2019-0298353;

U.S. patent Application entitled ROTARY DRIVEN FIRING MEMBERS WITH DIFFERENT ANVIL AND CHANNEL ENGAGEMENT FEATURES, U.S. patent application Ser. No. 16/281,678, U.S. Published Patent Application No. 2019-0298355; and U.S. patent Application entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING, U.S. patent application Ser. No. 16/281,682, U.S. Published Patent Application No. 2019-0298346.

Applicant of the present application owns the following U.S. Provisional patent applications that were filed on Feb. 19, 2019 and which are each herein incorporated by reference in their respective entireties:

U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;

U.S. Provisional Patent Application Ser. No. 62/807,319, entitled SURGICAL STAPLING DEVICES WITH IMPROVED LOCKOUT SYSTEMS; and U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional patent applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional patent application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. patent application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS.

Applicant of the present application owns the following U.S. patent applications that were filed on Aug. 20, 2018 and which are each herein incorporated by reference in their respective entireties:

U.S. patent application Ser. No. 16/105,101, entitled METHOD FOR FABRICATING SURGICAL STAPLER ANVILS;

U.S. patent application Ser. No. 16/105,183, entitled REINFORCED DEFORMABLE ANVIL TIP FOR SURGICAL STAPLER ANVIL;

U.S. patent application Ser. No. 16/105,150, entitled SURGICAL STAPLER ANVILS WITH STAPLE DIRECTING PROTRUSIONS AND TISSUE STABILITY FEATURES;

U.S. patent application Ser. No. 16/105,098, entitled FABRICATING TECHNIQUES FOR SURGICAL STAPLER ANVILS;

U.S. patent application Ser. No. 16/105,140, entitled SURGICAL STAPLER ANVILS WITH TISSUE STOP FEATURES CONFIGURED TO AVOID TISSUE PINCH;

U.S. patent application Ser. No. 16/105,081, entitled METHOD FOR OPERATING A POWERED ARTICULATABLE SURGICAL INSTRUMENT;

U.S. patent application Ser. No. 16/105,094, entitled SURGICAL INSTRUMENTS WITH PROGRESSIVE JAW CLOSURE ARRANGEMENTS;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM;

U.S. patent application Ser. No. 16/105,119, entitled ARTICULATABLE MOTOR POWERED SURGICAL INSTRUMENTS WITH DEDICATED ARTICULATION MOTOR ARRANGEMENTS;

U.S. patent application Ser. No. 16/105,160, entitled SWITCHING ARRANGEMENTS FOR MOTOR POWERED ARTICULATABLE SURGICAL INSTRUMENTS; and U.S. Design patent application Ser. No. 29/660,252, entitled SURGICAL STAPLER ANVILS.

Applicant of the present application owns the following U.S. patent applications and U.S. patents that are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Patent Application Publication No. 2018/0168642;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Patent Application Publication No. 2018/0168646;

U.S. patent application Ser. No. 15/386,209, entitled SURGICAL END EFFECTORS AND FIRING MEMBERS THEREOF, now U.S. Patent Application Publication No. 2018/0168645;

U.S. patent application Ser. No. 15/386,198, entitled LOCKOUT ARRANGEMENTS FOR SURGICAL END EFFECTORS AND REPLACEABLE TOOL ASSEMBLIES, now U.S. Patent Application Publication No. 2018/0168644;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S. Patent Application Publication No. 2018/0168629;

U.S. patent application Ser. No. 15/385,941, entitled SURGICAL TOOL ASSEMBLIES WITH CLUTCH- ING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Patent Application Publication No. 2018/0168630;

U.S. patent application Ser. No. 15/385,943, entitled SURGICAL STAPLING INSTRUMENTS AND STAPLE-FORMING ANVILS, now U.S. Patent Application Publication No. 2018/0168631;

U.S. patent application Ser. No. 15/385,950, entitled SURGICAL TOOL ASSEMBLIES WITH CLOSURE STROKE REDUCTION FEATURES, now U.S. Patent Application Publication No. 2018/0168635;

U.S. patent application Ser. No. 15/385,945, entitled STAPLE CARTRIDGES AND ARRANGEMENTS OF STAPLES AND STAPLE CAVITIES THEREIN, now U.S. Patent Application Publication No. 2018/0168632;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Patent Application Publication No. 2018/0168636;

U.S. patent application Ser. No. 15/385,953, entitled METHODS OF STAPLING TISSUE, now U.S. Patent Application Publication No. 2018/0168637;

U.S. patent application Ser. No. 15/385,954, entitled FIRING MEMBERS WITH NON-PARALLEL JAW ENGAGEMENT FEATURES FOR SURGICAL END EFFECTORS, now U.S. Patent Application Publication No. 2018/0168638;

U.S. patent application Ser. No. 15/385,955, entitled SURGICAL END EFFECTORS WITH EXPANDABLE TISSUE STOP ARRANGEMENTS, now U.S. Patent Application Publication No. 2018/0168639;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Patent Application Publication No. 2018/0168640;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Patent Application Publication No. 2018/0168641;

U.S. patent application Ser. No. 15/385,947, entitled STAPLE CARTRIDGES AND ARRANGEMENTS OF STAPLES AND STAPLE CAVITIES THEREIN, now U.S. Patent Application Publication No. 2018/0168634;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Patent Application Publication No. 2018/0168599;

U.S. patent application Ser. No. 15/385,899, entitled SURGICAL INSTRUMENT COMPRISING IMPROVED JAW CONTROL, now U.S. Patent Application Publication No. 2018/0168600;

U.S. patent application Ser. No. 15/385,901, entitled STAPLE CARTRIDGE AND STAPLE CARTRIDGE CHANNEL COMPRISING WINDOWS DEFINED THEREIN, now U.S. Patent Application Publication No. 2018/0168602;

U.S. patent application Ser. No. 15/385,902, entitled SURGICAL INSTRUMENT COMPRISING A CUTTING MEMBER, now U.S. Patent Application Publication No. 2018/0168603;

U.S. patent application Ser. No. 15/385,904, entitled STAPLE FIRING MEMBER COMPRISING A MISSING CARTRIDGE AND/OR SPENT CARTRIDGE LOCKOUT, now U.S. Patent Application Publication No. 2018/0168605;

U.S. patent application Ser. No. 15/385,905, entitled FIRING ASSEMBLY COMPRISING A LOCKOUT, now U.S. Patent Application Publication No. 2018/0168606;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Patent Application Publication No. 2018/0168620;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Patent Application Publication No. 2018/0168594;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Patent Application Publication No. 2018/0168626;

U.S. patent application Ser. No. 15/385,911, entitled SURGICAL STAPLERS WITH INDEPENDENTLY ACTUATABLE CLOSING AND FIRING SYSTEMS, now U.S. Patent Application Publication No. 2018/0168612;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Patent Application Publication No. 2018/0168601;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Patent Application Publication No. 2018/0168616;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Patent Application Publication No. 2018/0168622;

U.S. patent application Ser. No. 15/385,924, entitled SURGICAL INSTRUMENT WITH PRIMARY AND SAFETY PROCESSORS, now U.S. Patent Application Publication No. 2018/0168624;

U.S. patent application Ser. No. 15/385,910, entitled ANVIL HAVING A KNIFE SLOT WIDTH, now U.S. Patent Application Publication No. 2018/0168611;

U.S. patent application Ser. No. 15/385,903, entitled CLOSURE MEMBER ARRANGEMENTS FOR SURGICAL INSTRUMENTS, now U.S. Patent Application Publication No. 2018/0168604;

U.S. patent application Ser. No. 15/385,906, entitled FIRING MEMBER PIN CONFIGURATIONS, now U.S. Patent Application Publication No. 2018/0168607;

U.S. patent application Ser. No. 15/386,188, entitled STEPPED STAPLE CARTRIDGE WITH ASYMMETRICAL STAPLES, now U.S. Patent Application Publication No. 2018/0168585;

U.S. patent application Ser. No. 15/386,192, entitled STEPPED STAPLE CARTRIDGE WITH TISSUE RETENTION AND GAP SETTING FEATURES, now U.S. Patent Application Publication No. 2018/0168643;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Patent Application Publication No. 2018/0168589;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Patent Application Publication No. 2018/0168591;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Patent Application Publication No. 2018/0168593;

U.S. patent application Ser. No. 15/385,894, entitled SHAFT ASSEMBLY COMPRISING A LOCKOUT, now U.S. Patent Application Publication No. 2018/0168595;

U.S. patent application Ser. No. 15/385,895, entitled SHAFT ASSEMBLY COMPRISING FIRST AND SECOND ARTICULATION LOCKOUTS, now U.S. Patent Application Publication No. 2018/0168596;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Patent Application Publication No. 2018/0168621;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Patent Application Publication No. 2018/0168576;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Patent Application Publication No. 2018/0168580;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Patent Application Publication No. 2018/0168581;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Patent Application Publication No. 2018/0168582;

U.S. patent application Ser. No. 15/385,936, entitled ARTICULATABLE SURGICAL INSTRUMENTS WITH ARTICULATION STROKE AMPLIFICATION FEATURES, now U.S. Patent Application Publication No. 2018/0168583;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, now U.S. Patent Application Publication No. 2015/0297232;

U.S. patent application Ser. No. 14/318,997, entitled FASTENER CARTRIDGE COMPRISING DEPLOYABLE TISSUE ENGAGING MEMBERS, now U.S. Patent Application Publication No. 2015/0297229;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Patent Application Publication No. 2015/0297235.

Applicant of the present application owns the following U.S. patent applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695;

U.S. patent application Ser. No. 15/191,807, entitled STAPLING SYSTEM FOR USE WITH WIRE STAPLES AND STAMPED STAPLES, now U.S. Patent Application Publication No. 2017/0367696;

U.S. patent application Ser. No. 15/191,834, entitled STAMPED STAPLES AND STAPLE CARTRIDGES USING THE SAME, now U.S. Patent Application Publication No. 2017/0367699;

U.S. patent application Ser. No. 15/191,788, entitled STAPLE CARTRIDGE COMPRISING OVERDRIVEN STAPLES, now U.S. Patent Application Publication No. 2017/0367698; and U.S. patent application Ser. No. 15/191,818, entitled STAPLE CARTRIDGE COMPRISING OFFSET LONGITUDINAL STAPLE ROWS, now U.S. Patent Application Publication No. 2017/0367697.

Applicant of the present application owns the following U.S. patent applications that were filed on Jun. 24, 2016 and which are each herein incorporated by reference in their respective entireties:

U.S. Design patent application Ser. No. 29/569,218, entitled SURGICAL FASTENER, now U.S. Design Pat. No. D826,405;

U.S. Design patent application Ser. No. 29/569,227, entitled SURGICAL FASTENER, now U.S. Design Pat. No. D822,206;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Patent Application Publication No. 2017/0281163;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Patent Application Publication No. 2017/0281172;

U.S. patent application Ser. No. 15/089,263, entitled SURGICAL INSTRUMENT HANDLE ASSEMBLY WITH RECONFIGURABLE GRIP PORTION, now U.S. Patent Application Publication No. 2017/0281165;

U.S. patent application Ser. No. 15/089,262, entitled ROTARY POWERED SURGICAL INSTRUMENT WITH MANUALLY ACTUATABLE BAILOUT SYSTEM, now U.S. Patent Application Publication No. 2017/0281161;

U.S. patent application Ser. No. 15/089,277, entitled SURGICAL CUTTING AND STAPLING END EFFECTOR WITH ANVIL CONCENTRIC DRIVE MEMBER, now U.S. Patent Application Publication No. 2017/0281166;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Patent Application Publication No. 2017/0281168;

U.S. patent application Ser. No. 15/089,258, entitled SURGICAL STAPLING SYSTEM COMPRISING A SHIFTABLE TRANSMISSION, now U.S. Patent Application Publication No. 2017/0281178;

U.S. patent application Ser. No. 15/089,278, entitled SURGICAL STAPLING SYSTEM CONFIGURED TO PROVIDE SELECTIVE CUTTING OF TISSUE, now U.S. Patent Application Publication No. 2017/0281162;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;

U.S. patent application Ser. No. 15/089,300, entitled SURGICAL STAPLING SYSTEM COMPRISING AN UNCLAMPING LOCKOUT, now U.S. Patent Application Publication No. 2017/0281179;

U.S. patent application Ser. No. 15/089,196, entitled SURGICAL STAPLING SYSTEM COMPRISING A JAW CLOSURE LOCKOUT, now U.S. Patent Application Publication No. 2017/0281183;

U.S. patent application Ser. No. 15/089,203, entitled SURGICAL STAPLING SYSTEM COMPRISING A JAW ATTACHMENT LOCKOUT, now U.S. Patent Application Publication No. 2017/0281184;

U.S. patent application Ser. No. 15/089,210, entitled SURGICAL STAPLING SYSTEM COMPRISING A SPENT CARTRIDGE LOCKOUT, now U.S. Patent Application Publication No. 2017/0281185;

U.S. patent application Ser. No. 15/089,324, entitled SURGICAL INSTRUMENT COMPRISING A SHIFTING MECHANISM, now U.S. Patent Application Publication No. 2017/0281170;

U.S. patent application Ser. No. 15/089,335, entitled SURGICAL STAPLING INSTRUMENT COMPRISING MULTIPLE LOCKOUTS, now U.S. Patent Application Publication No. 2017/0281155;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Patent Application Publication No. 2017/0281177;

U.S. patent application Ser. No. 15/089,304, entitled SURGICAL STAPLING SYSTEM COMPRISING A GROOVED FORMING POCKET, now U.S. Patent Application Publication No. 2017/0281188;

U.S. patent application Ser. No. 15/089,331, entitled ANVIL MODIFICATION MEMBERS FOR SURGICAL STAPLERS, now U.S. Patent Application Publication No. 2017/0281180;

U.S. patent application Ser. No. 15/089,336, entitled STAPLE CARTRIDGES WITH ATRAUMATIC FEATURES, now U.S. Patent Application Publication No. 2017/0281164;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Patent Application Publication No. 2017/0281169; and U.S. patent application Ser. No. 15/089,349, entitled CIRCULAR STAPLING SYSTEM COMPRISING LOAD CONTROL, now U.S. Patent Application Publication No. 2017/0281174.

Applicant of the present application also owns the U.S. patent applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Patent Application Publication No. 2017/0189018;

U.S. patent application Ser. No. 14/984,525, entitled MECHANISMS FOR COMPENSATING FOR DRIVETRAIN FAILURE IN POWERED SURGICAL INSTRUMENTS, now U.S. Patent Application Publication No. 2017/0189019; and U.S. patent application Ser. No. 14/984,552, entitled SURGICAL INSTRUMENTS WITH SEPARABLE MOTORS AND MOTOR CONTROL CIRCUITS, now U.S. Patent Application Publication No. 2017/0189020.

Applicant of the present application also owns the U.S. patent applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Patent Application Publication No. 2017/0224333;

U.S. patent application Ser. No. 15/019,228, entitled SURGICAL INSTRUMENTS WITH MULTIPLE LINK ARTICULATION ARRANGEMENTS, now U.S. Patent Application Publication No. 2017/0224342;

U.S. patent application Ser. No. 15/019,196, entitled SURGICAL INSTRUMENT ARTICULATION MECHANISM WITH SLOTTED SECONDARY CONSTRAINT, now U.S. Patent Application Publication No. 2017/0224330;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Patent Application Publication No. 2017/0224331;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Patent Application Publication No. 2017/0224336;

U.S. patent application Ser. No. 15/019,230, entitled ARTICULATABLE SURGICAL INSTRUMENTS WITH OFF-AXIS FIRING BEAM ARRANGEMENTS, now U.S. Patent Application Publication No. 2017/0224335; and U.S. patent application Ser. No. 15/019,245, entitled SURGICAL INSTRUMENTS WITH CLOSURE STROKE REDUCTION ARRANGEMENTS, now U.S. Patent Application Publication No. 2017/0224343.

Applicant of the present application also owns the U.S. patent applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Patent Application Publication No. 2017/0231623;

U.S. patent application Ser. No. 15/043,259, entitled MECHANISMS FOR COMPENSATING FOR DRIVETRAIN FAILURE IN POWERED SURGICAL INSTRUMENTS, now U.S. Patent Application Publication No. 2017/0231626;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Patent Application Publication No. 2016/0367256;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,914, entitled MOVABLE FIRING BEAM SUPPORT ARRANGEMENTS FOR ARTICULATABLE SURGICAL INSTRUMENTS, now U.S. Patent Application Publication No. 2016/0367255;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Patent Application Publication No. 2016/0367254;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Patent Application Publication No. 2016/0367246; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Pat. No. 9,993,258; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWREEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO IDENTIFY CARTRIDGE TYPE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL SYSTEM COMPRISING FIRST AND SECOND DRIVE SYSTEMS, now U.S. Pat. No. 9,844,368;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled SURGICAL INSTRUMENT COMPRISING A GAP SETTING SYSTEM, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 1:
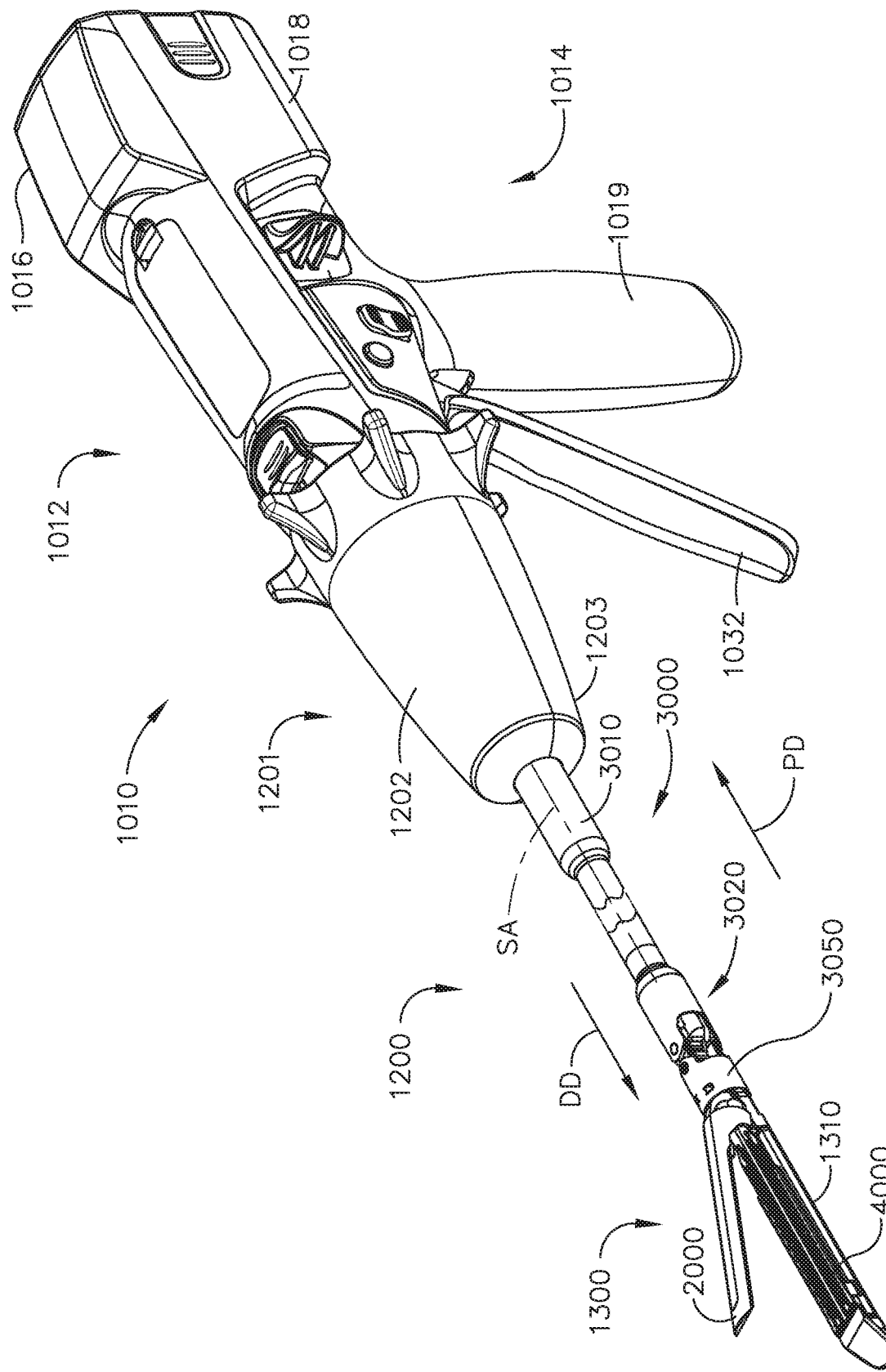
FIG. 1 is a perspective view of a powered surgical stapling system.
Figure 2:
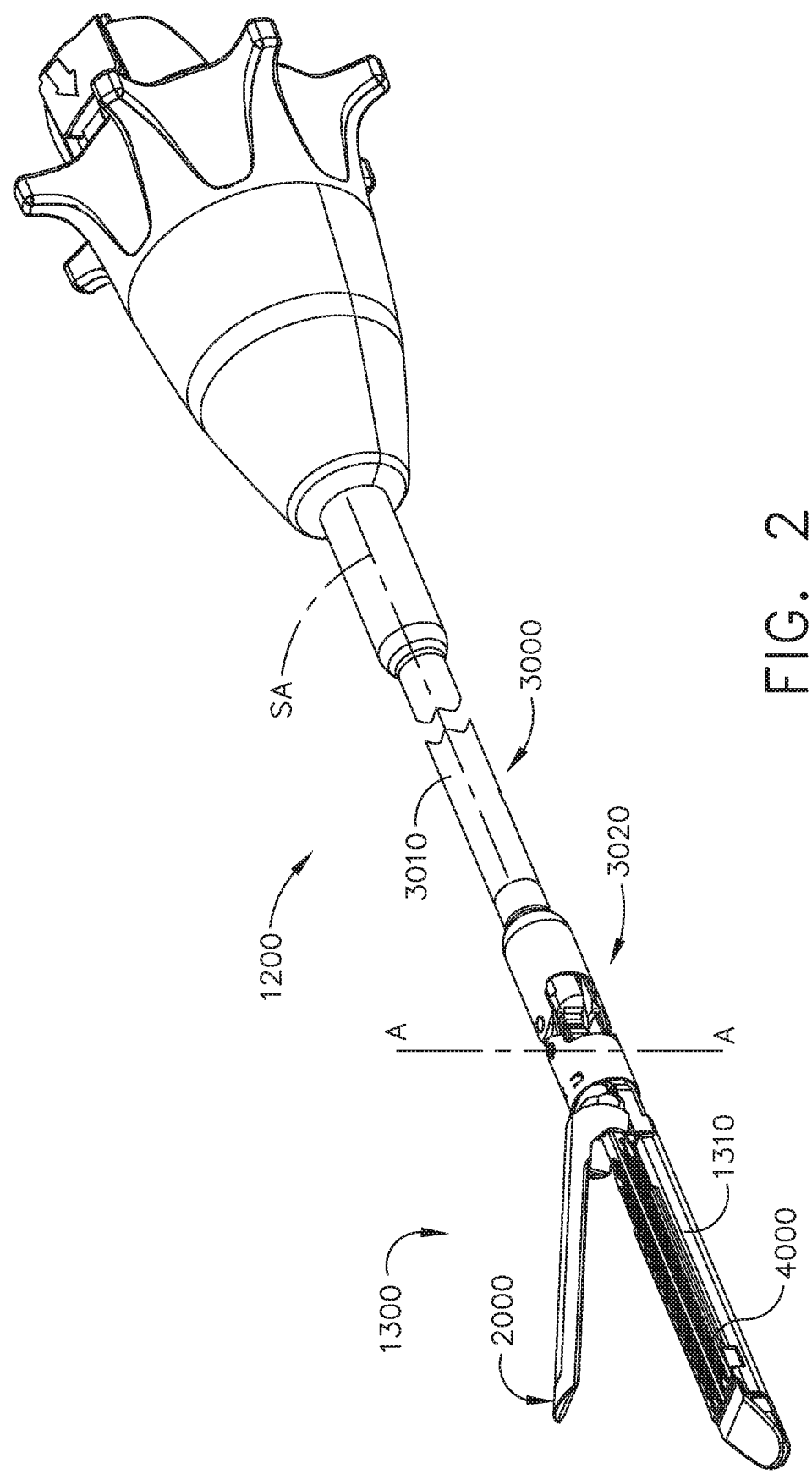
FIG. 2 is a perspective view of an interchangeable surgical shaft assembly of the powered surgical stapling system of FIG. 1.
Figure 3:
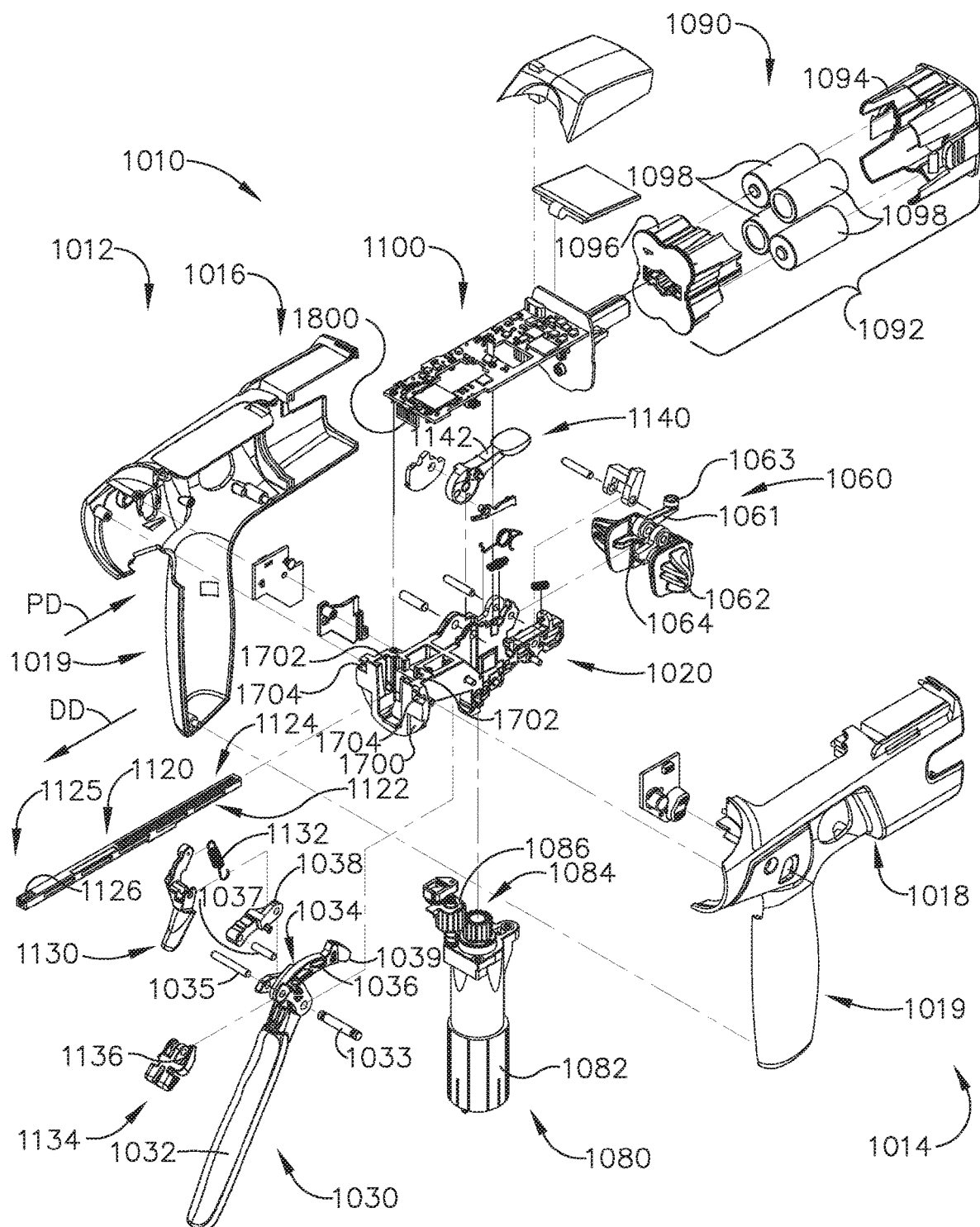
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a previous housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

The previous housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 4000 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the release button assembly 1062. A magnetic element 1063, such as a permanent magnet, for example, may be mounted to the arm 1061. When the release button assembly 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the release button assembly 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a with a set, or rack, of drive teeth 1122 on a longitudinally-movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 82 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. See FIG. 3. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
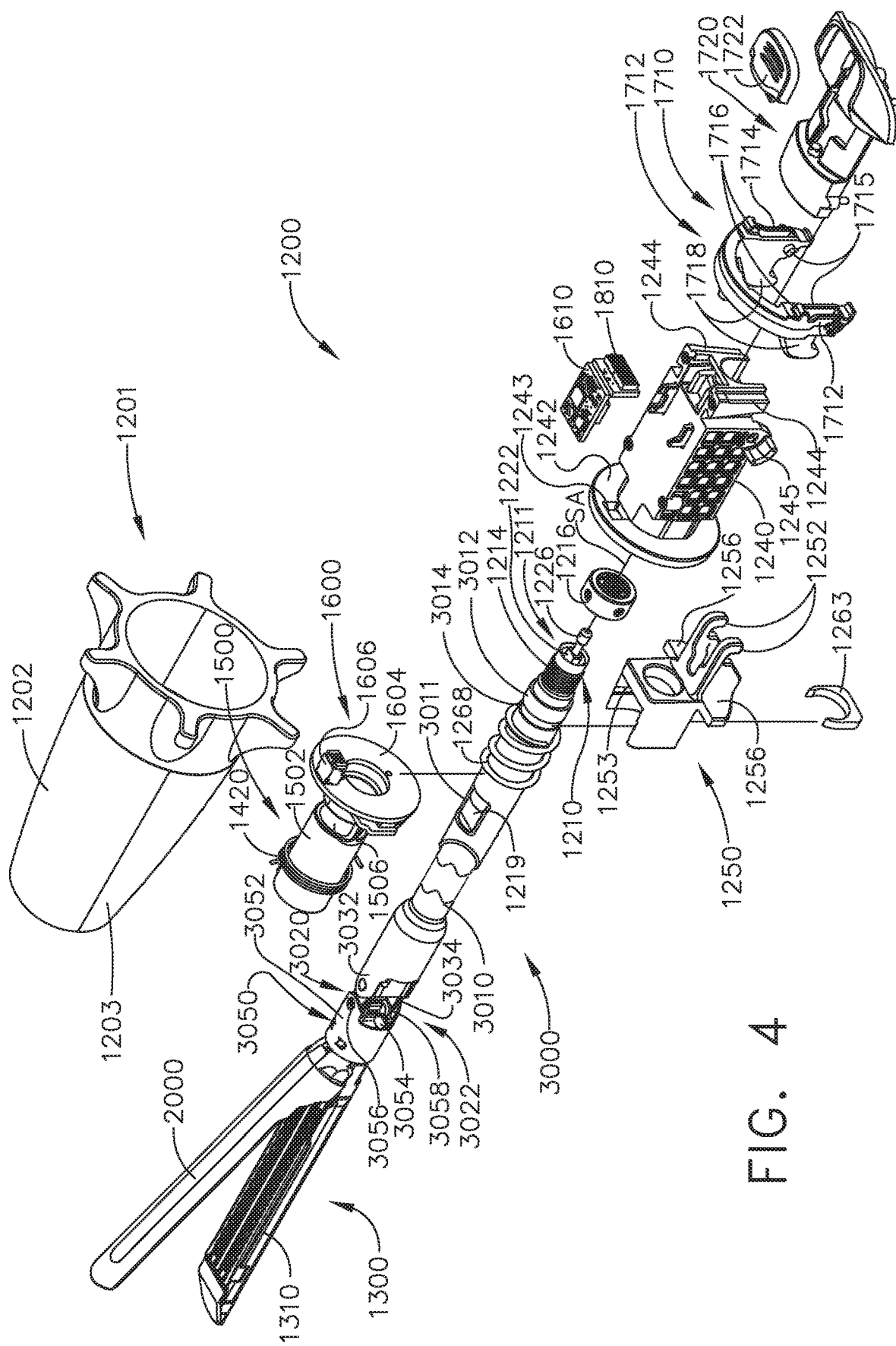
FIG. 4 is an exploded assembly view of the interchangeable surgical shaft assembly of FIG. 2.
Figure 5:
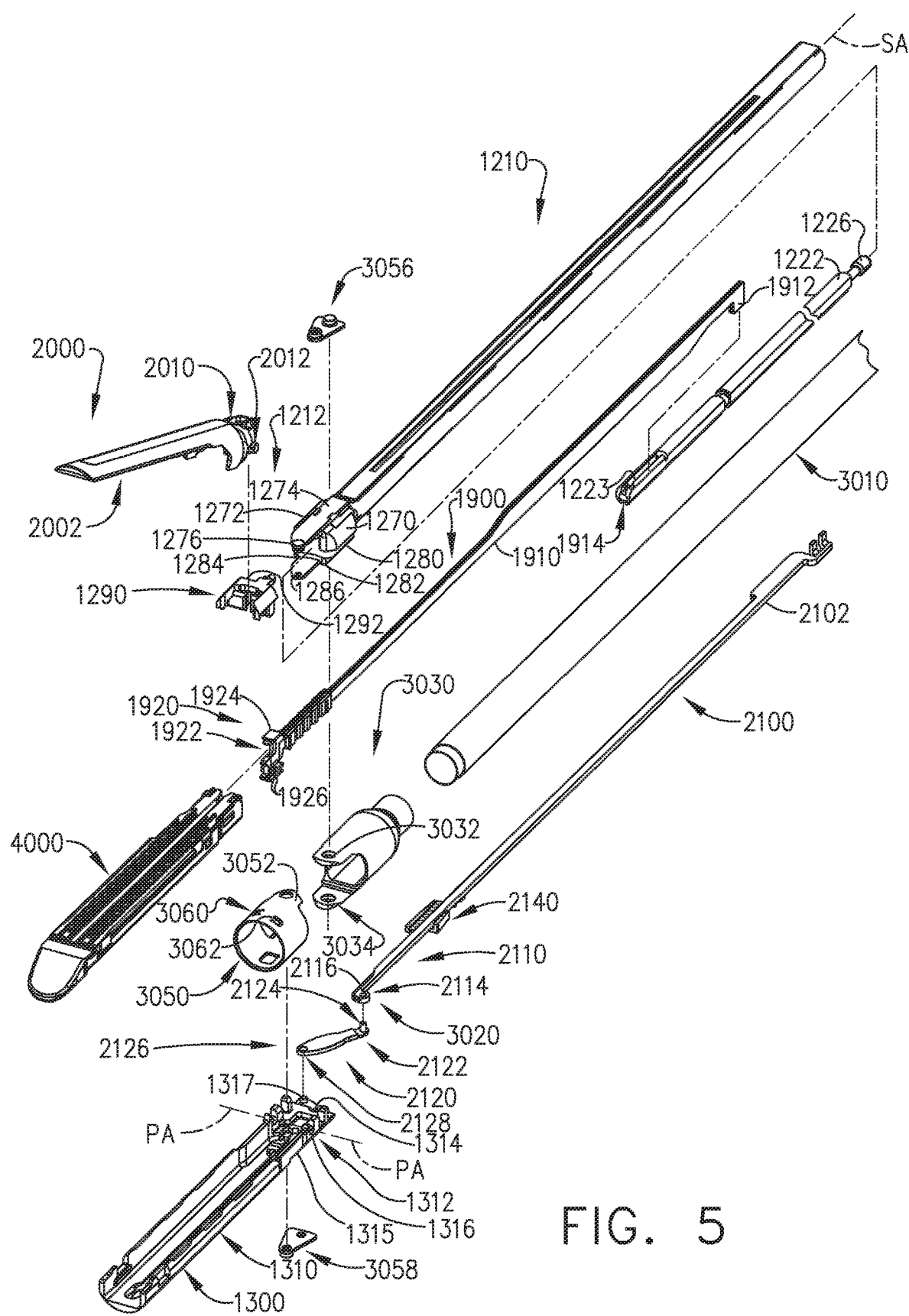
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate channel 1310 that is configured to operably support a staple cartridge 4000 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure tube 3050 to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 4000 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receive an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, now U.S. Patent Application Publication No. 2014/0263541, entitled ARTICULATABLE SURGICAL INSTRUMENT COMPRISING AN ARTICULATION LOCK and U.S. Pat. No. 9,913,642, entitled SURGICAL INSTRUMENT COMPRISING A SENSOR SYSTEM, the entire disclosures of each being hereby incorporated by reference herein. For example, when the closure member segment 3010 is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange portion 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail receiving slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame or spine of the shaft assembly 1200 with the frame 1020 of the handle 1014. Another system can comprise a closure drive system 1030 which can operably connect the closure trigger 1032 of the handle 1014 and the closure tube 1260 and the anvil 2000 of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the handle control board 1100. Further details regaining the circuitry and control systems may be found in U.S. patent application Ser. No. 13/803,086, now U.S. Patent Application Publication No. 2014/0263541, and U.S. patent application Ser. No. 14/226,142, now U.S. Pat. No. 9,913,642, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

Figure 6:
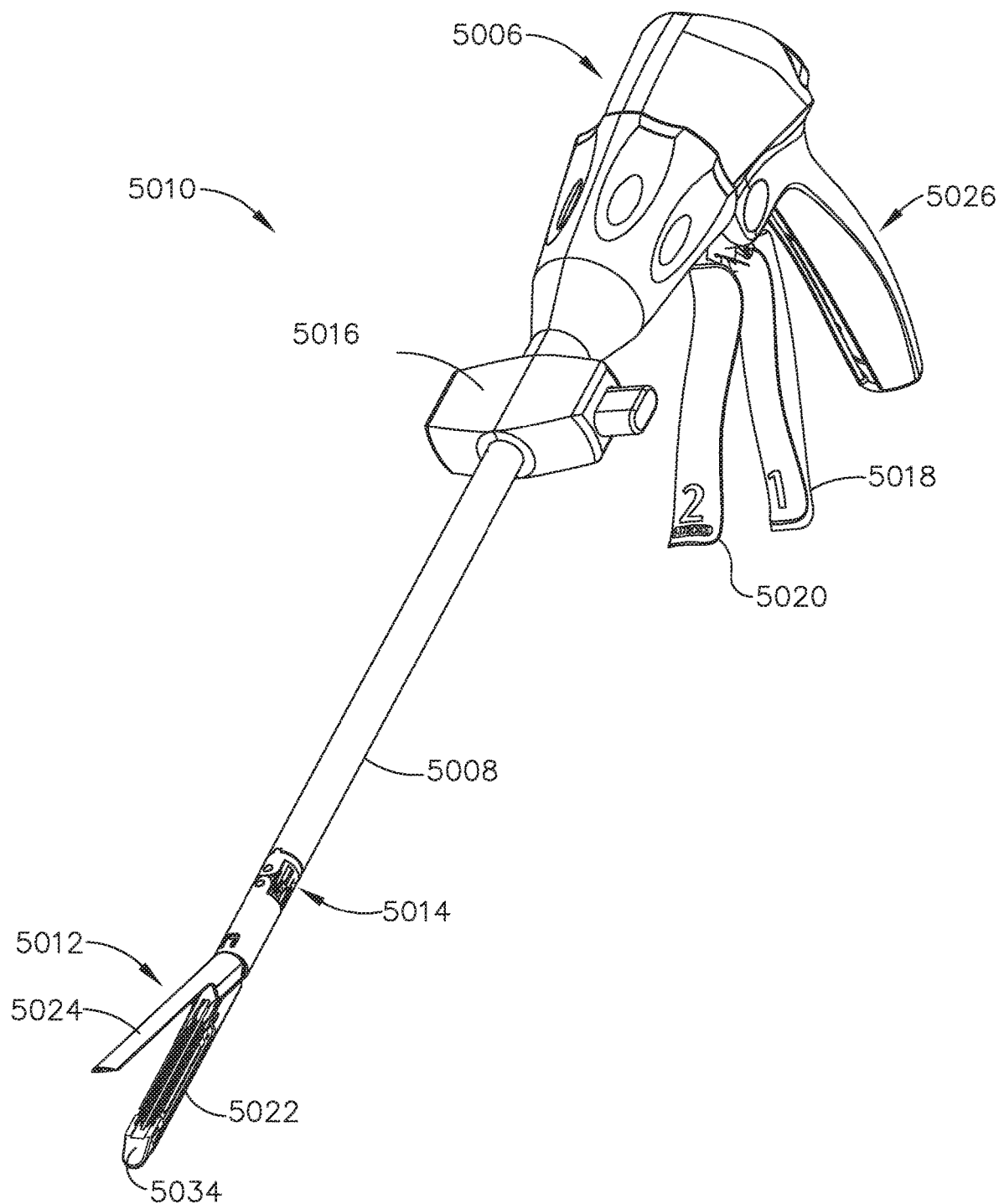
FIG. 6 is a perspective view of another powered surgical stapling system.
Figure 7:
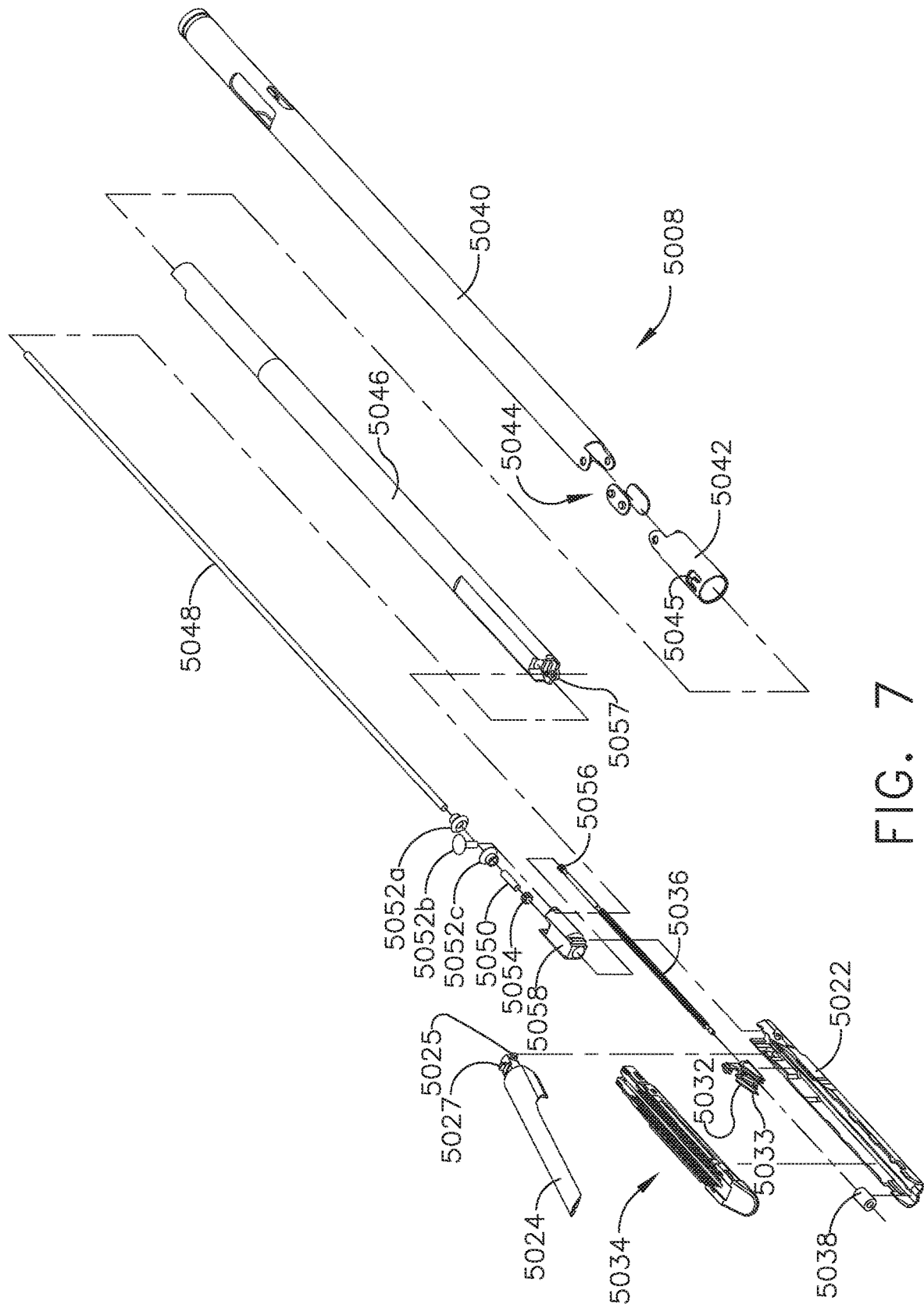
FIG. 7 is an exploded assembly view of portion of a shaft assembly of the powered surgical stapling system of FIG. 6.
Figure 8:
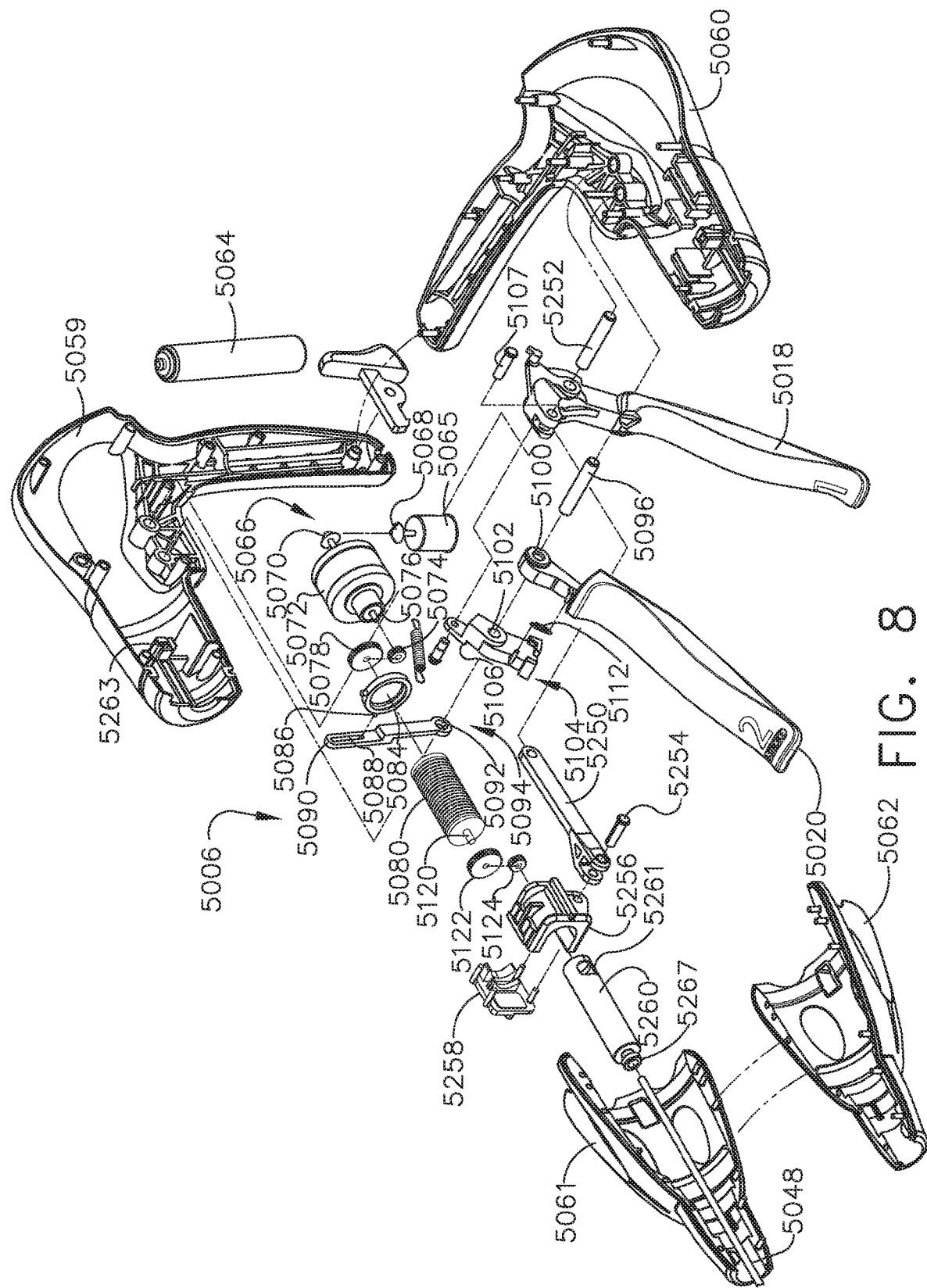
FIG. 8 is an exploded assembly view of portions of a handle assembly of the powered surgical stapling system of FIG. 6.
Figure 9:
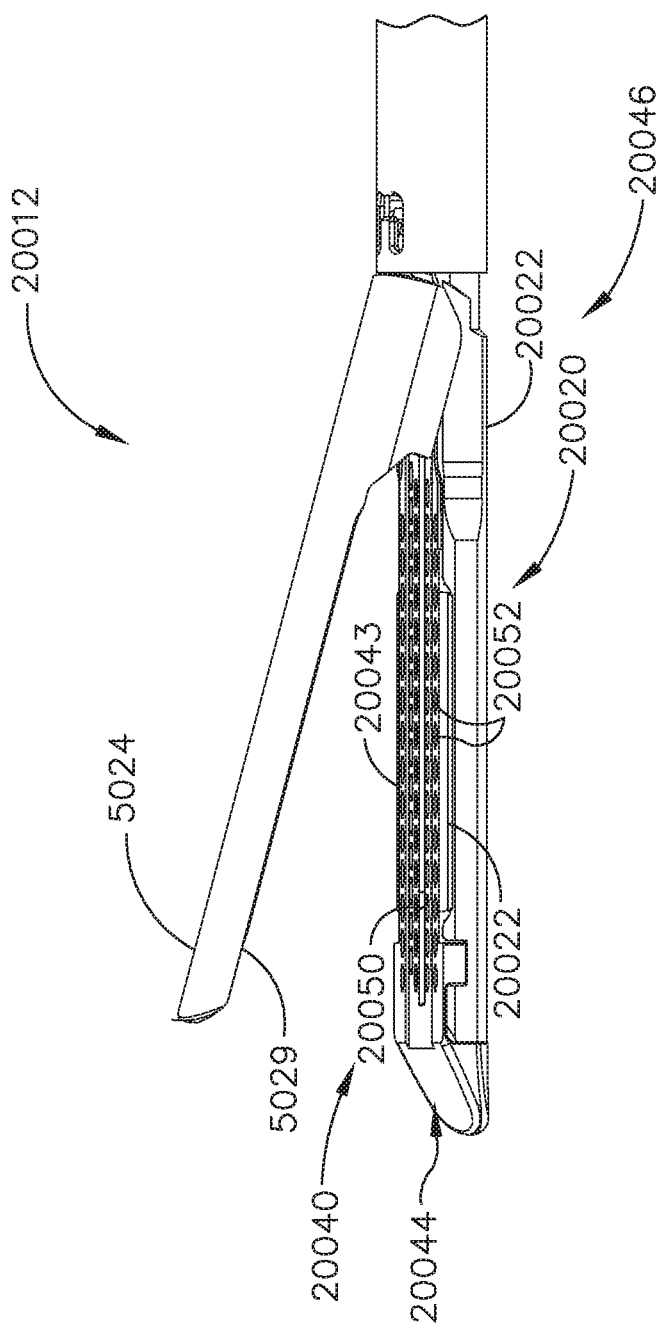
FIG. 9 is a side elevational view of another surgical end effector that may be employed with a rotary powered surgical stapling system.

FIGS. 6-8 depict a previous surgical cutting and fastening instrument 5010 that is configured to generate rotary drive motions for operating a surgical end effector 5012. The endoscopic surgical instrument 5010 comprises a handle 5006, a shaft 5008, and an articulating surgical end effector 5012 pivotally connected to the shaft 5008 at an articulation pivot 5014. An articulation control 5016 may be provided adjacent to the handle 5006 to effect rotation of the end effector 5012 about the articulation pivot 5014. It will be appreciated that various embodiments may include a non-pivoting end effector, and therefore may not have an articulation pivot 5014 or articulation control 5016.

The handle 5006 of the instrument 5010 may include a closure trigger 5018 and a firing trigger 5020 for actuating the end effector 5012. It will be appreciated that instruments having end effectors directed to different surgical tasks may have different numbers or types of triggers or other suitable controls for operating the end effector 5012. In one embodiment, a clinician or operator of the instrument 5010 may articulate the end effector 5012 relative to the shaft 5008 by utilizing the articulation control 5016, as described in more detail in pending U.S. Pat. No. 7,670,334, entitled SURGICAL INSTRUMENT HAVING AN ARTICULATING END EFFECTOR, the entire disclosure of which is incorporated herein by reference. The end effector 5012 includes in this example, among other things, a staple channel 5022 and a pivotally translatable clamping member, such as an anvil 5024, which are maintained at a spacing that assures effective stapling and severing of tissue clamped in the end effector 5012. The handle 5006 includes a pistol grip 5026 toward which the closure trigger 5018 is pivotally drawn by the clinician to cause clamping or closing of the anvil 5024 towards the staple channel 5022 of the end effector 5012 to thereby clamp tissue positioned between the anvil 5024 and channel 5022.

In the arrangement depicted in FIG. 7, the end effector 5012 includes, in addition to the previously-mentioned channel 5022 and anvil 5024, a cutting instrument 5032, a sled 5033, a staple cartridge 5034 that is removably seated in the channel 5022, and a helical screw shaft 5036. The cutting instrument 5032 may be, for example, a knife. The anvil 5024 includes pivot pins 5025 that are movably supported in corresponding slots in the channel 5022. In one arrangement, the anvil 5024 includes a tab 5027 at its proximate end that is inserted into a component of the mechanical closure system (described further below) to open and close the anvil 5024.

Still referring to FIG. 7, the shaft 5008 includes a proximal closure tube 5040 and a distal closure tube 5042 pivotably linked by a pivot link 5044. The distal closure tube 5042 includes an opening 5045 into which the tab 5027 on the anvil 5024 is inserted in order to open and close the anvil 5024, as further described below. Disposed inside the closure tubes 5040, 5042 may be a proximate spine tube 5046. Disposed inside the proximate spine tube 5046 may be a main rotational (or proximate) drive shaft 5048 that communicates with a secondary (or distal) drive shaft 5050 via a bevel gear assembly 5052a-c. The secondary drive shaft 5050 is connected to a drive gear 5054 that engages a proximate drive gear 5056 of the helical screw shaft 5036. The vertical bevel gear 5052b may sit and pivot in an opening 5057 in the distal end of the proximate spine tube 5046. A distal spine tube 5058 may be used to enclose the secondary drive shaft 5050 and the drive gears 5054, 5056.

Collectively, the main drive shaft 5048, the secondary drive shaft 5050, and the articulation assembly (e.g., the bevel gear assembly 5052a-c) are sometimes referred to herein as the "main drive shaft assembly."

A bearing 5038, positioned at a distal end of the staple channel 5022, receives the helical screw shaft 5036, allowing the helical screw shaft 5036 to freely rotate with respect to the channel 5022. The helical screw shaft 5036 may interface a threaded opening (not shown) of the knife 5032 such that rotation of the helical screw shaft 5036 causes the knife 5032 to translate distally or proximately (depending on the direction of the rotation) through the staple channel 5022.

Turning next to FIG. 8, the handle 5006 includes exterior lower side pieces 5059, 5060 and nozzle pieces 5061, 5062 that fit together to form, in general, the exterior of the handle 5006. A battery 5064, such as a Li ion battery, may be provided in the pistol grip 5026 of the handle 5006. The battery 5064 powers a motor 5065 disposed in an upper portion of the pistol grip portion 5026 of the handle 5006. The motor 5065 may drive a 90° bevel gear assembly 5066 comprising a first bevel gear 5068 and a second bevel gear 5070. The bevel gear assembly 5066 may drive a planetary gear assembly 5072. The planetary gear assembly 5072 may include a pinion gear 5074 connected to a drive shaft 5076. The pinion gear 5074 may drive a mating ring gear 5078 that drives a helical gear drum 5080 via a drive shaft. A ring 5084 may be threaded on the helical gear drum 5080. Thus, when the motor 5065 rotates, the ring 5084 is caused to travel along the helical gear drum 5080 by means of the interposed bevel gear assembly 5066, planetary gear assembly 5072 and ring gear 5078.

The handle 5006 may include a middle handle piece 5104 adjacent to the upper portion of the firing trigger 5020. The handle 5006 also may comprise a bias spring 5112 connected between posts on the middle handle piece 5104 and the firing trigger 5020. The bias spring 5112 may bias the firing trigger 5020 to its fully open position. In that way, when the operator releases the firing trigger 5020, the bias spring 5112 will pull the firing trigger 5020 to its open position. The distal end of the helical gear drum 5080 includes a distal drive shaft 5120 that drives a ring gear 5122, which mates with a pinion gear 5124. The pinion gear 5124 is connected to the main drive shaft 5048 of the main drive shaft assembly. In that way, rotation of the motor 5065 causes the main drive shaft assembly to rotate, which causes actuation of the end effector 5012. The ring 5084 threaded on the helical gear drum 5080 may include a post 5086 that is disposed within a slot 5088 of a slotted arm 5090. The slotted arm 5090 has an opening 5092 in its opposite end 5094 that receives a pivot pin 5096 that is connected between the handle exterior side pieces 5059, 5060. The pivot pin 5096 is also disposed through an opening 5100 in the firing trigger 5020 and an opening 5102 in the middle handle piece 5104.

The middle handle piece 5104 includes a backside shoulder 5106 that engages the slotted arm 5090. The middle handle piece 5104 also has a forward motion stop 5107 that engages the firing trigger 5020. The movement of the slotted arm 5090 is controlled by rotation of the motor 5065. When the slotted arm 5090 rotates counter clockwise as the ring 5084 travels from the proximate end of the helical gear drum 5080 to the distal end, the middle handle piece 5104 will be free to rotate counter clockwise. Thus, as the user draws in the firing trigger 5020, the firing trigger 5020 will engage the forward motion stop 5107 of the middle handle piece 5104, causing the middle handle piece 5104 to rotate counter clockwise. Due to the backside shoulder 5106 engaging the slotted arm 5090, however, the middle handle piece 5104 will only be able to rotate counter clockwise as far as the slotted arm 5090 permits. In that way, if the motor 5065 should stop rotating for some reason, the slotted arm 5090 will stop rotating, and the user will not be able to further draw in the firing trigger 5020 because the middle handle piece 5104 will not be free to rotate counter clockwise due to the slotted arm 5090.

Components of an exemplary closure system for closing (or clamping) the anvil 5024 of the end effector 5012 by retracting the closure trigger 5018 are also shown in FIG. 8. In the illustrated embodiment, the closure system includes a yoke 5250 connected to the closure trigger 5018. A pivot pin 5252 is inserted through aligned openings in both the closure trigger 5018 and the yoke 5250 such that they both rotate about the same point. The distal end of the yoke 5250 is connected, via a pin 5254, to a first closure bracket 5256. The first closure bracket 5256 connects to a second closure bracket 5258. Collectively, the closure brackets 5256, 5258 define an opening in which the proximate end of the proximal closure tube 5040 (see FIG. 7) is seated and held such that longitudinal movement of the closure brackets 5256, 5258 causes longitudinal motion by the proximal closure tube 5040. The instrument 5010 also includes a closure drive shaft 5260 disposed inside the proximal closure tube 5040. The closure drive shaft 5260 may include a window 5261 into which a post 5263 on one of the handle exterior pieces, such as exterior lower side piece 5059 in the illustrated embodiment, is disposed to fixedly connect the closure drive shaft 5260 to the handle 5006. In that way, the proximal closure tube 5040 is capable of moving longitudinally relative to the closure drive shaft 5260. The closure drive shaft 5260 may also include a distal collar 5267 that fits into a cavity in proximate spine tube 5046 and is retained therein by a cap.

In operation, when the yoke 5250 rotates due to retraction of the closure trigger 5018, the closure brackets 5256, 5258 cause the proximal closure tube 5040 to move distally (i.e., away from the handle end of the instrument 5010), which causes the distal closure tube 5042 to move distally, which causes the anvil 5024 to rotate about the pivot pins 5025 into the clamped or closed position. When the closure trigger 5018 is unlocked from the locked position, the proximal closure tube 5040 is caused to slide proximately, which causes the distal closure tube 5042 to slide proximately, which, by virtue of the tab 5027 being inserted in the opening 5045 of the distal closure tube 5042, causes the anvil 5024 to pivot about the pivot pins 5025 into the open or unclamped position. In that way, by retracting and locking the closure trigger 5018, an operator may clamp tissue between the anvil 5024 and channel 5022, and may unclamp the tissue following the cutting/stapling operation by unlocking the closure trigger 5018 from the locked position. Further details concerning the construction and operation of the existing surgical instrument 5010 may be found in U.S. Pat. No. 7,845,537, entitled SURGICAL INSTRUMENT HAVING RECORDING CAPABILITIES, the entire disclosure of which is hereby incorporated by reference herein. Other rotary drive arrangements configured for use with various forms of robotic systems are disclosed in U.S. Patent Application Publication No. 2016/0287251, entitled STAPLING END EFFECTOR CONFIGURED TO COMPENSATE FOR AN UNEVEN GAP BETWEEN A FIRST JAW AND A SECOND JAW, the entire disclosure of which is hereby incorporated by reference herein.

Figure 10:
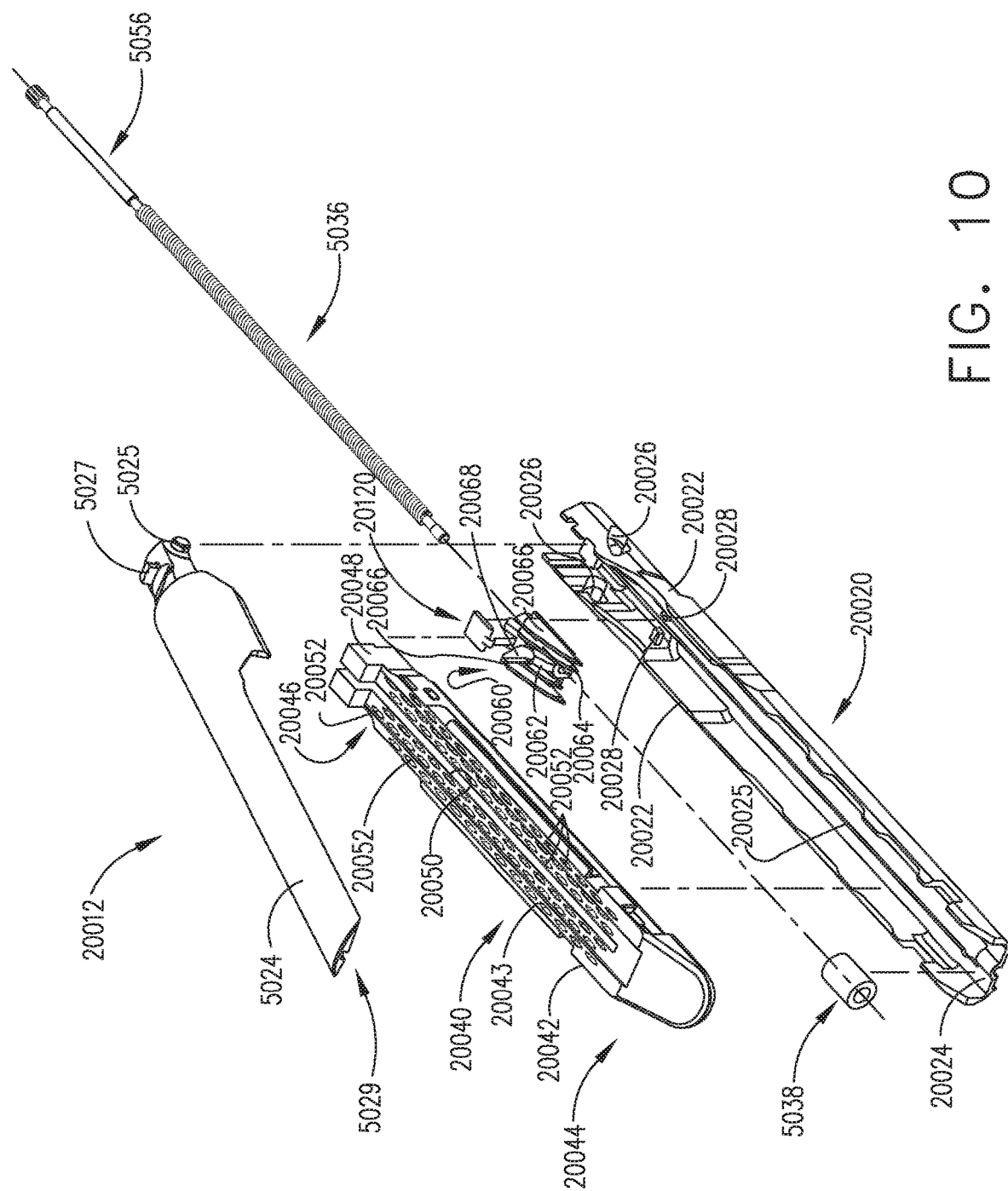
FIG. 10 is an exploded assembly view of the surgical end effector of FIG. 9.

FIGS. 9-16 depict a surgical end effector 20012 that may be used for example in connection with the powered surgical instrument 5010 described above. The surgical end effector 20012 may also be effective employed with various other rotary powered or robotically powered surgical systems which are disclosed in the various references incorporated herein by reference. Those components shown in FIGS. 9-16 that are identical to the components of the powered surgical instrument 5010 have been labeled with like component numbers. In the illustrated example, the surgical end effector 20012 comprises an elongate channel 20020 that is configured to operably support a surgical staple cartridge 20040 therein. The elongate channel 20020 is similar to channel 5022 described above, except for the noted differences. Turning to FIG. 10, the elongate channel 20020 comprises a pair of spaced upstanding walls 20022 and a bottom 20024. A helical screw shaft 5036 is supported in the channel 20020 by a bearing 5038 which enables the helical screw shaft 5036 to freely rotate with respect to the channel 20020. The surgical end effector 20012 further comprises an anvil 5024 that has pivot pins or trunnions 5025 that are received in corresponding slots 20026 provided in the upstanding channel walls 20022.

In the illustrated arrangement, the staple cartridge 20040 includes an elongate cartridge body 20042 that is sized to be removably seated in the elongate channel 20020. The cartridge body 20042 includes a cartridge slot 20050 that extends from a proximal end portion 20046 to a distal end portion 20044 of the cartridge body 20042. The cartridge body 20042 further comprises a cartridge deck surface 20043 that confronts a staple-forming undersurface 5029 of the anvil 5024 when the cartridge 20040 is seated in the channel 20020 and the anvil 5024 is pivoted to a closed position. Also in the illustrated example, three lines of surgical staple pockets 20052 are formed on each side of the cartridge slot 20050 and open through the cartridge deck surface 20043. Each staple pocket 20052 may have a staple driver (not shown) associated therewith that supports a surgical staple or fastener (not shown) thereon.

Still referring to FIG. 10, the staple cartridge 20040 further includes a camming assembly 20060 that comprises a camming assembly body 20062 that has a passage 20064 therethrough that is configured to straddle the helical screw shaft 5036 without affecting the rotation thereof. In other embodiments, the camming assembly 20060 may have a series of internal threads (not shown) that are configured to threadably engage the helical screw shaft 5036 to be driven thereby. In such arrangements, for example, the helical screw shaft 5036 may be provided with an unthreaded portion that corresponds to a starting position of the camming assembly 20060. Such camming assembly arrangements are further described in various references that have been herein incorporated by reference. In the illustrated example, the camming assembly 20060 is driven distally through the cartridge body 20042 by a firing member 20120.

As can further be seen in FIG. 10, the camming assembly body 20062 includes a series of cam members 20066 that are aligned with corresponding staple drivers supported in lines within the staple cartridge body 20042. In the illustrated example, the camming assembly 20060 includes an onboard tissue cutting member or blade 20068. The tissue cutting member 20068 extends above the deck surface 20043 so that as the camming assembly 20060 is driven distally, the tissue cutting member 20068 cuts the tissue that is clamped between the anvil 5024 and the staple cartridge 20040. When the staple cartridge is "fresh" or new (i.e., the cartridge has never been fired and contains staples or fasteners therein ready to be fired), the camming assembly 20060 is in a starting position within the cartridge 20040. When the camming assembly 20060 is in the starting position, the tissue cutting member 20068 is located within a garage portion 20048 formed on the proximal end portion 20046 of the cartridge body 20042 to prevent injury when handling the fresh cartridge 20040. In one aspect, the cam members 20066 extend distally beyond the tissue cutting member 20068 such that the staples or fasteners are deployed through the tissue before the tissue cutting member 20068 cuts through the tissue. Thus, the clamped tissue is stapled and thereafter cut as the firing member 20120 and camming assembly 20060 are driven distally. Once the firing member 20120 and the camming assembly 20060 have been driven into their distal-most ending positions, the firing member 20120 may be retracted back to its starting position by rotating the helical screw shaft 5036 in a reverse rotary direction while the camming assembly 20060 remains in its ending position. In at least one arrangement, the tissue cutting member 20068 is movable from a deployed cutting position to a storage position wherein the tissue cutting member 20068 is stored below the cartridge deck surface 20043 to prevent injury when handling the fired or spent cartridge 20040. For example, a retraction member (not shown) may be strategically located in the distal end 20044 of the cartridge body 20042 to contact and move the tissue cutting member 20068 from the deployed position to the storage position when a portion of the tissue cutting member 20068 is brought into contact with the retraction member.

Figure 11:
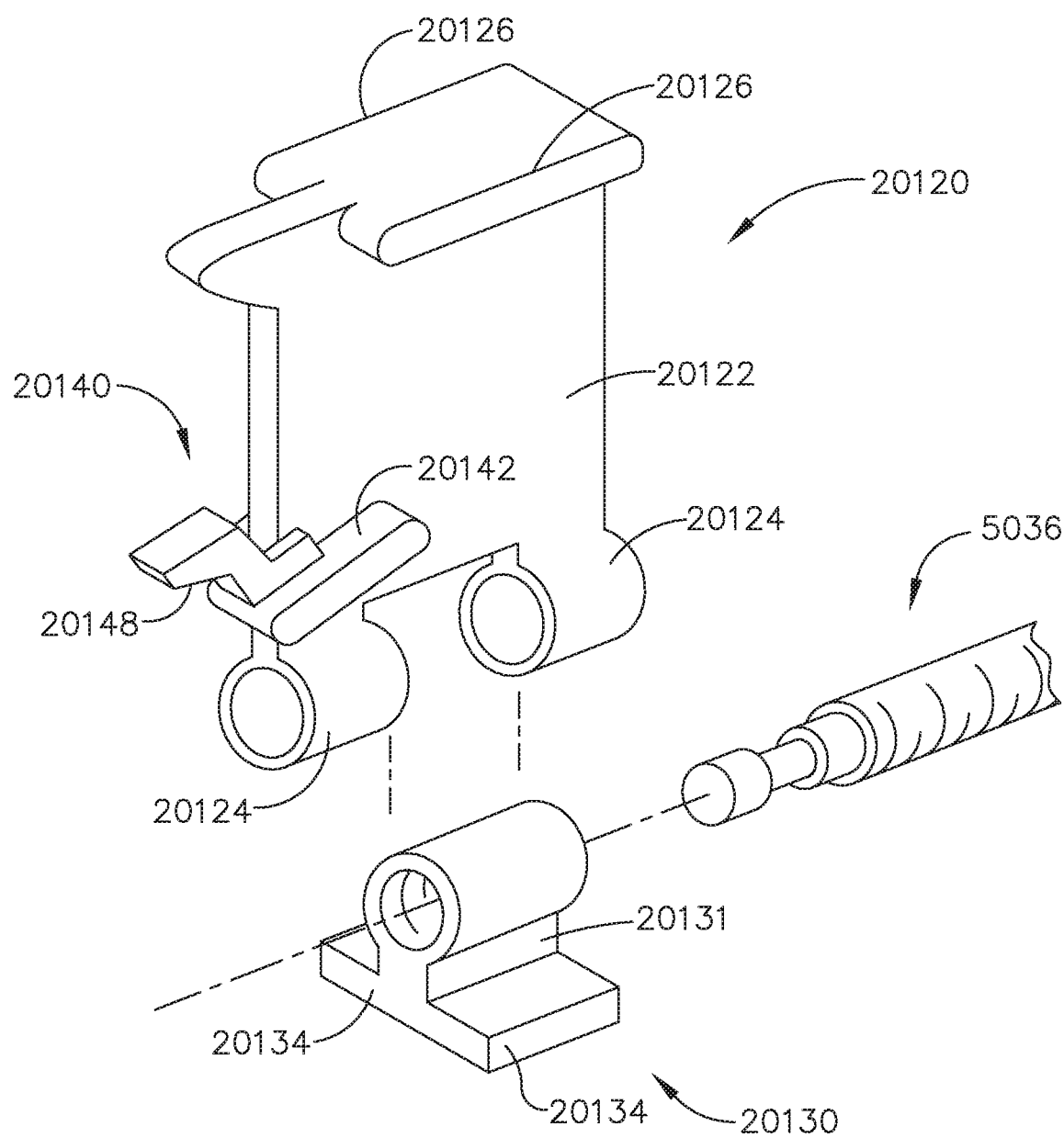
FIG. 11 is an exploded assembly view of a rotary powered firing member that may be employed with the surgical end effector of FIGS. 9 and 10.

FIG. 11 depicts one form of a firing member 20120. As can be seen in FIG. 11, the firing member 20120 comprises a body portion 20122 that includes two downwardly extending hollow mounting portions 20124 that are unthreaded and spaced from each other to receive a threaded drive nut 20130 therebetween. The threaded drive nut 20130 is configured to threadably engage the helical screw shaft 5036. The drive nut 20130 includes a vertical tab portion 20131 that is sized to extend through an axial slot 20025 (FIG. 10) in the bottom 20024 of the elongate channel 20020. Two laterally extending retention flanges 20134 are formed on the threaded drive nut 20130 and are configured to engage the bottom 20024 of the elongate channel 20020. In addition, two laterally extending anvil engagement tabs 20126 are formed on the top of the firing member body 20122 and are configured to engage corresponding ledges 20102 formed in the anvil 5024 as the firing member 20120 is axially moved within the surgical end effector 20012.

Figure 12:
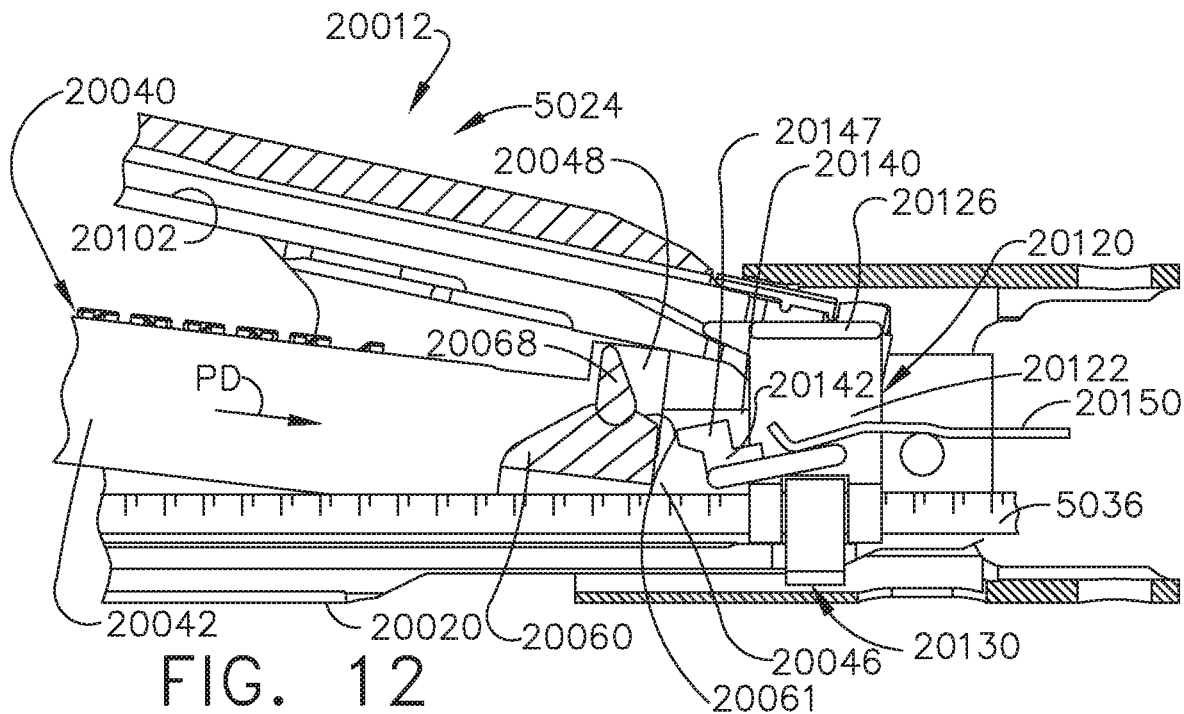
FIG. 12 is a partial cross-sectional view of the surgical end effector of FIG. 9 illustrating initial insertion of a fresh, unfired surgical staple cartridge therein.
Figure 13:
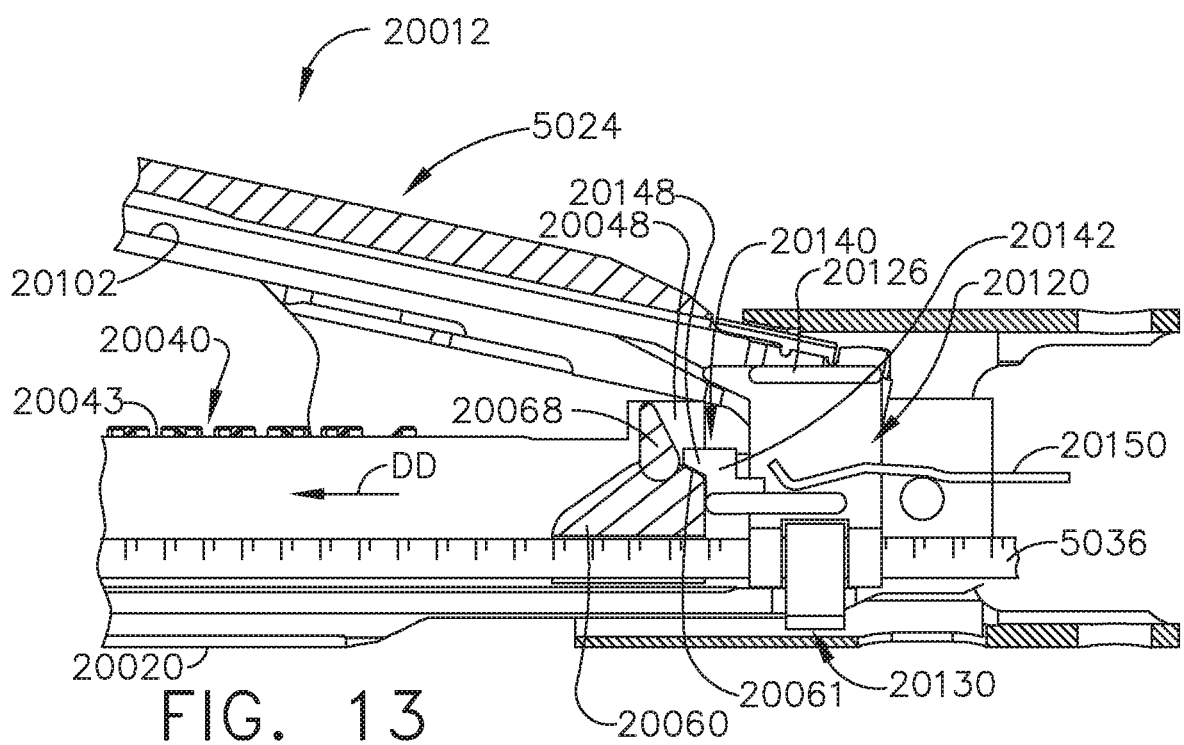
FIG. 13 is another partial cross-sectional view of the surgical end effector of FIG. 12, after the surgical staple cartridge has been operably installed therein.

As can also be seen in FIG. 11, the firing member 20120 may also be equipped with an onboard firing member lockout assembly 20140 that comprises a lockout member 20142 that is pivotally coupled to the firing member body 20122. The lockout member 20142 includes a sled latch 20148 that is configured to be engaged by the camming assembly 20060 when the camming assembly 20060 is in an unfired position. As can be seen in FIGS. 12 and 13, the camming assembly 20060 includes a firing member ledge 20061 configured to engage the sled latch 20148 on the lockout member 20142. A lockout spring 20150 is mounted in the elongate channel 20020 and is configured to bias the lockout member 20142 downward such that if the camming assembly 20060 is not in its unfired starting position, the lockout member 20142 contacts lockout lugs 20028 that are formed on portions of the inside surface of each upstanding sidewall 20022 of the elongate channel 20020. See FIG. 15. When in that position, should the user inadvertently attempt to distally advance the firing member 20120, the lockout member 20142 contacts the lockout lugs 20028 on the channel 20020 to prevent the distal advancement of the firing member 20120.

Figure 14:
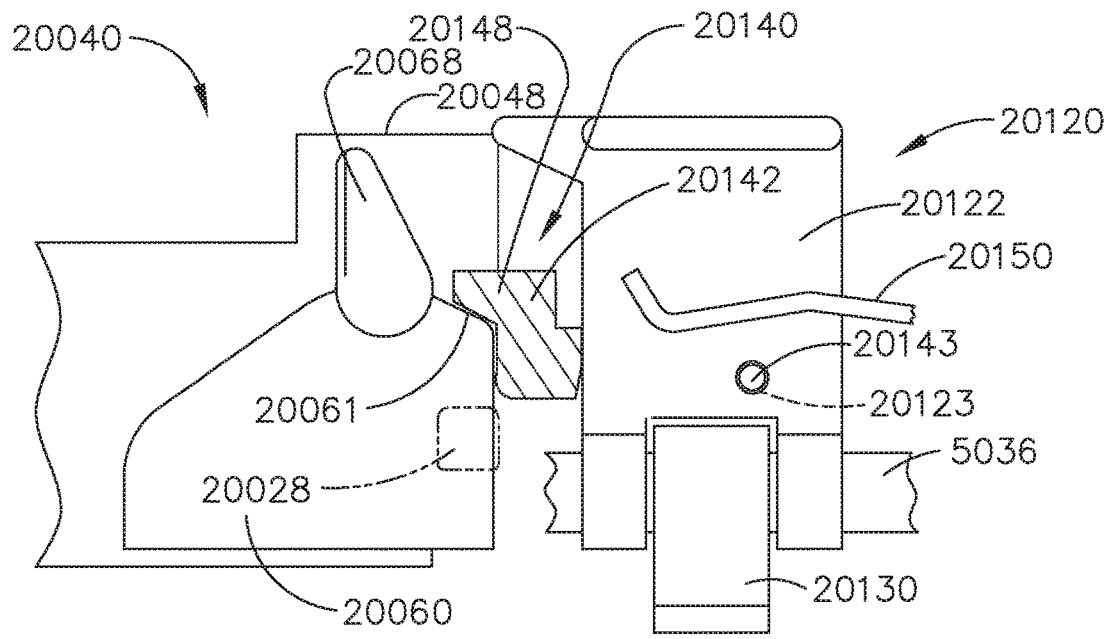
FIG. 14 is an enlarged partial cross-sectional view illustrating a firing member and a camming assembly of the end effector of FIG. 13.
Figure 15:
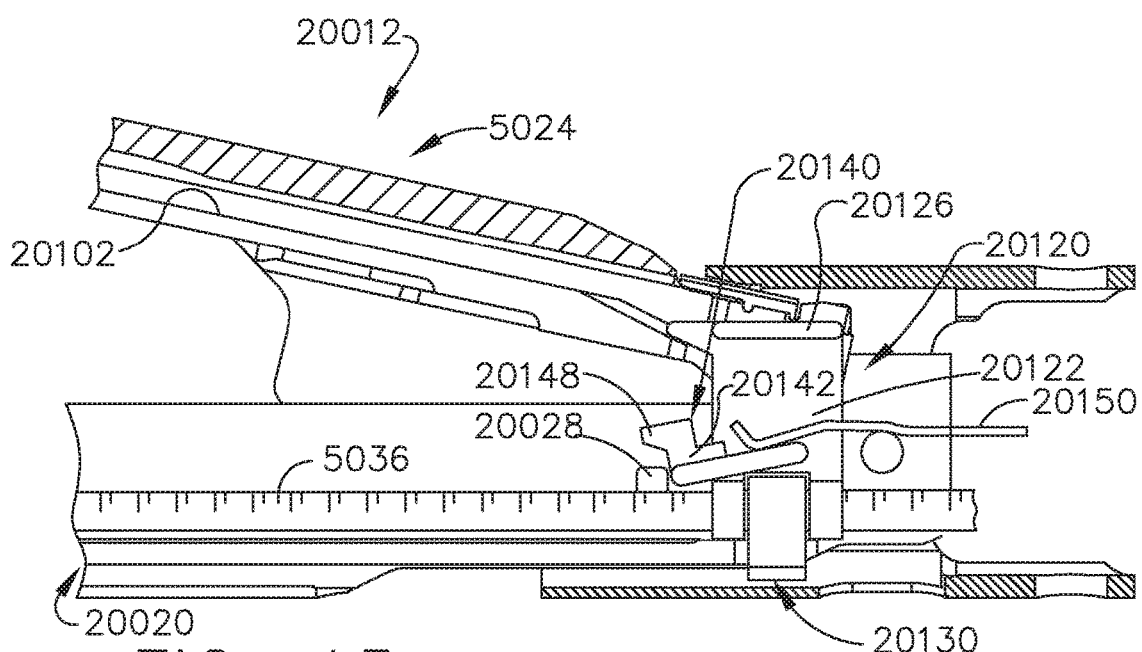
FIG. 15 is another partial cross-sectional view of the surgical end effector of FIG. 9, prior to insertion of a fresh surgical staple cartridge therein and with a firing member lockout assembly thereof in a locked position.

FIG. 12 illustrates the initial insertion of a fresh unfired surgical staple cartridge 20040 into the channel 20020. As can be seen in FIG. 12, the camming assembly 20060 is in a starting position and the proximal end portion 20046 of the surgical staple cartridge 20040 is inserted at an angle relative to the channel 20020 and then pushed in the proximal direction PD until the firing member ledge 20061 on the camming assembly 20060 unlockingly engages the sled latch portion 20148 of the lockout member 20142. FIGS. 13 and 14 illustrate the surgical staple cartridge 20040 in a properly installed position. As can be seen in FIG. 13, the firing member lockout assembly 20140 is in an unlocked position. Rotary actuation of the helical screw shaft 5036 in a first rotary direction will cause the firing member 20120 to move distally in the distal direction DD. As the firing member 20120 moves distally, the camming assembly 20060 is also driven distally thereby. The cam members 20066 cam the drivers stored in the cartridge 20040 upward in the cartridge body 20042. As the drivers are cammed upwardly, the staples or fasteners supported thereon are driven through the tissue that has been clamped between the anvil 5024 and the cartridge 20040 and into forming contact with the staple-forming undersurface 5029 on the anvil 5024. The stapled tissue is then cut by the tissue cutting member 20068. Once the firing member 20120 has been driven to its distalmost position in the cartridge 20040, the helical screw shaft 5036 may be rotated in a second opposite rotary direction to retract the firing member 20120 back to its beginning position. The camming assembly 20060 remains in the distal end portion 20044 of the cartridge body 20042. The spent cartridge 20040 may then be removed from the channel 20020.

FIG. 14 illustrates the end effector 20012 after the spent cartridge has been removed from the channel 20020. As can be seen in FIG. 14, the spring 20150 biases the lockout member 20142 of the firing member lockout assembly 20140 into locking engagement with the lockout lugs 20028 in the channel 20020. Should the user attempt to fire the surgical end effector 20012 (distally advance the firing member 20120), the lockout member 20142 will prevent the firing member 20120 from moving distally. Likewise, should the user attempt to reuse the spent cartridge, because the camming assembly 20060 is not in the starting position, the firing member lockout assembly 20140 will prevent the distal advancement of the firing member 20120.

Figure 16:
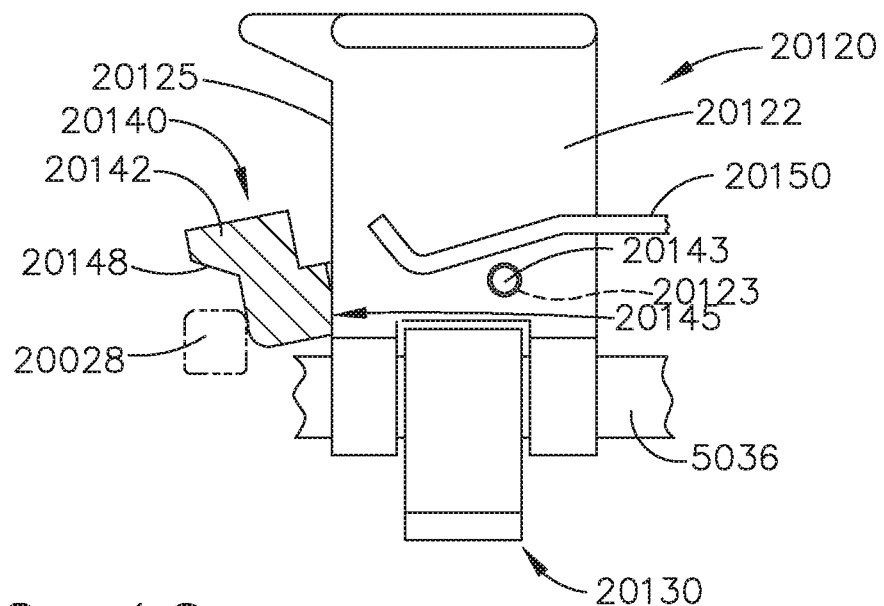
FIG. 16 is an enlarged partial cross-sectional view illustrating a firing member and lockout lugs of the end effector of FIG. 15, with a camming assembly and end effector channel omitted for clarity.

In the illustrated arrangement, the lockout member 20142 is pivotally coupled to the firing member body 20122 by pivot pins 20143 that are received in a hole 20123 extending through the firing member body 20122. See FIGS. 14 and 16. In at least one arrangement, the pivot pins 20143 are sized relative to the holes 20123 in the firing member body 20122 to facilitate free pivotal travel of the lockout member 20142 and to account for tolerance differences of the components. As can be seen in FIG. 14, the firing member 20120 includes a proximally-facing, firing surface 20145 that is configured to abut a distal-facing bearing surface 20125 on the firing member body 20122 when the firing member lockout assembly 20140 is in the unlocked position. Thus, when the firing member 20120 is advanced distally, the resistive forces encountered by the camming assembly 20060 during its distal movement are directly applied to the distal-facing bearing surface 20125 on the firing member body 20122. Such arrangement may prevent the transfer of these resistive forces back to the pivot pins 20143, which might cause the pivot pins 20143 to fail under such load. Similarly, as can be seen in FIG. 16, the proximally-facing angled bearing surface 20145 of the firing member 20120 is configured to abut the distal-facing bearing surface 20125 on the firing member body 20122 when the firing member lockout assembly 20140 is in the locked position. Such arrangement may prevent the transfer of the resistive locking forces resulting from the locking engagement of the lockout member 20142 with the lock lugs 20028 back to the pivot pins 20143, which might cause the pivot pins 20143 to fail under such load. The loose fit between the pins 20143 and the hole 20123 in the firing member body 20122 facilitate some translation of the lockout member 20142 when under load to facilitate transfer of the loads into the firing member body 20122 and not to the pins 20143 themselves.

In another arrangement, or in addition to the foregoing described lockout member 20142 arrangement, the amount of current being drawn by the motor used to apply the rotary motions to the helical screw shaft 5036 is monitored. Once the current increases beyond a predetermined threshold, a control circuit for the surgical instrument or robotic system, etc., may stop the motor to prevent any further rotation of the helical screw shaft 5036 and movement of the firing member 20120 to prevent damage to the above-described components.

Some previous firing member lockout arrangements that are configured to prevent advancement of a firing member of the end effector unless a fresh unfired staple cartridge has been properly installed in the surgical end effector, require the user to actively retract the firing member back to is proximal-most beginning position before the anvil is permitted to open. If the user attempts to open the anvil before the firing member is moved back to its proximal-most position, the may not understand why the anvil cannot come open. The above-described arrangement may prevent such confusion.

FIGS. 17-21 depict a surgical end effector 20300 that may be used for example in connection with the powered surgical instrument 1010 described above. The surgical end effector 20300 may also be effective employed with various other robotically powered surgical systems which are disclosed in the various references incorporated herein by reference. Those components shown in FIGS. 17-21 that are identical to the components of surgical instrument 1010 have been labeled with like component numbers. Those construction and function of those components of surgical instrument 1010 that are not necessary to understand the operation of the surgical end effector 20300 will not be repeated herein for the sake of brevity.

Figure 17:
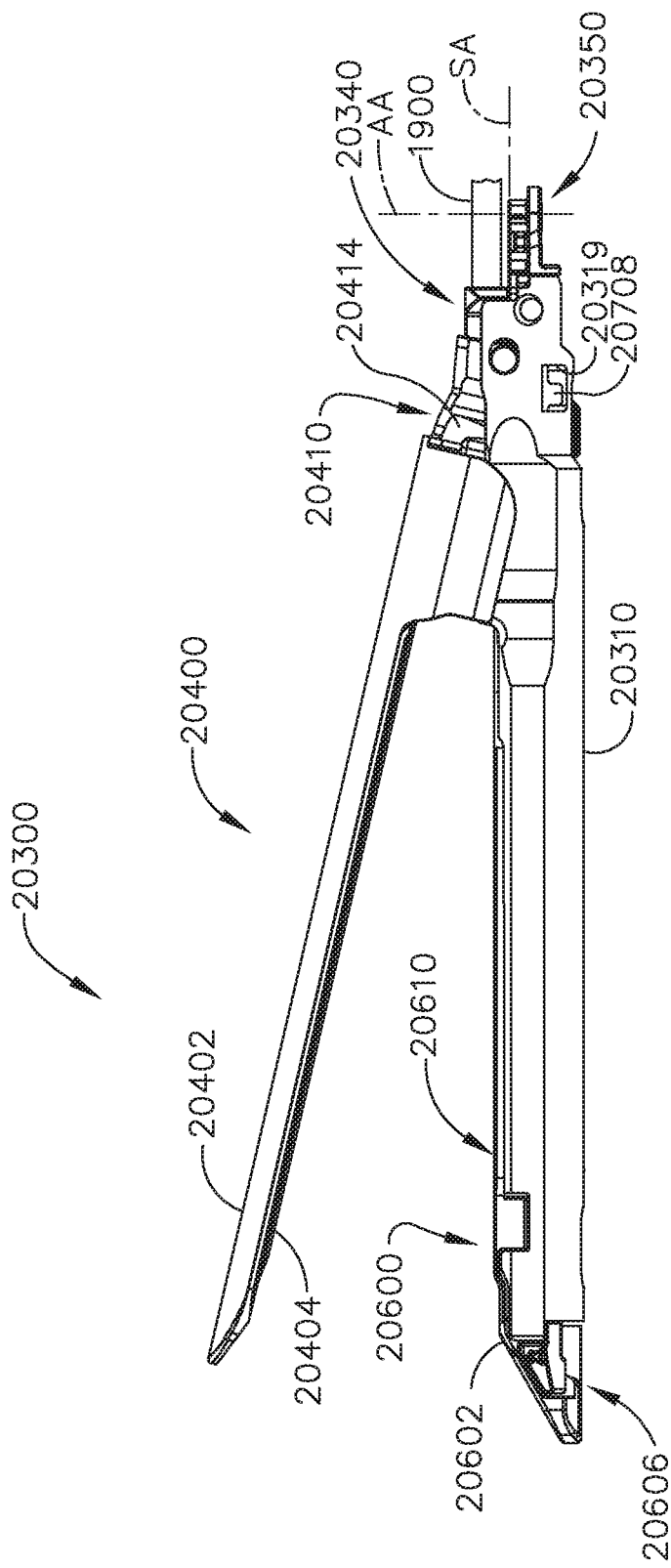
FIG. 17 is a side elevational view of another surgical end effector with an anvil thereof in an open position.
Figure 18:
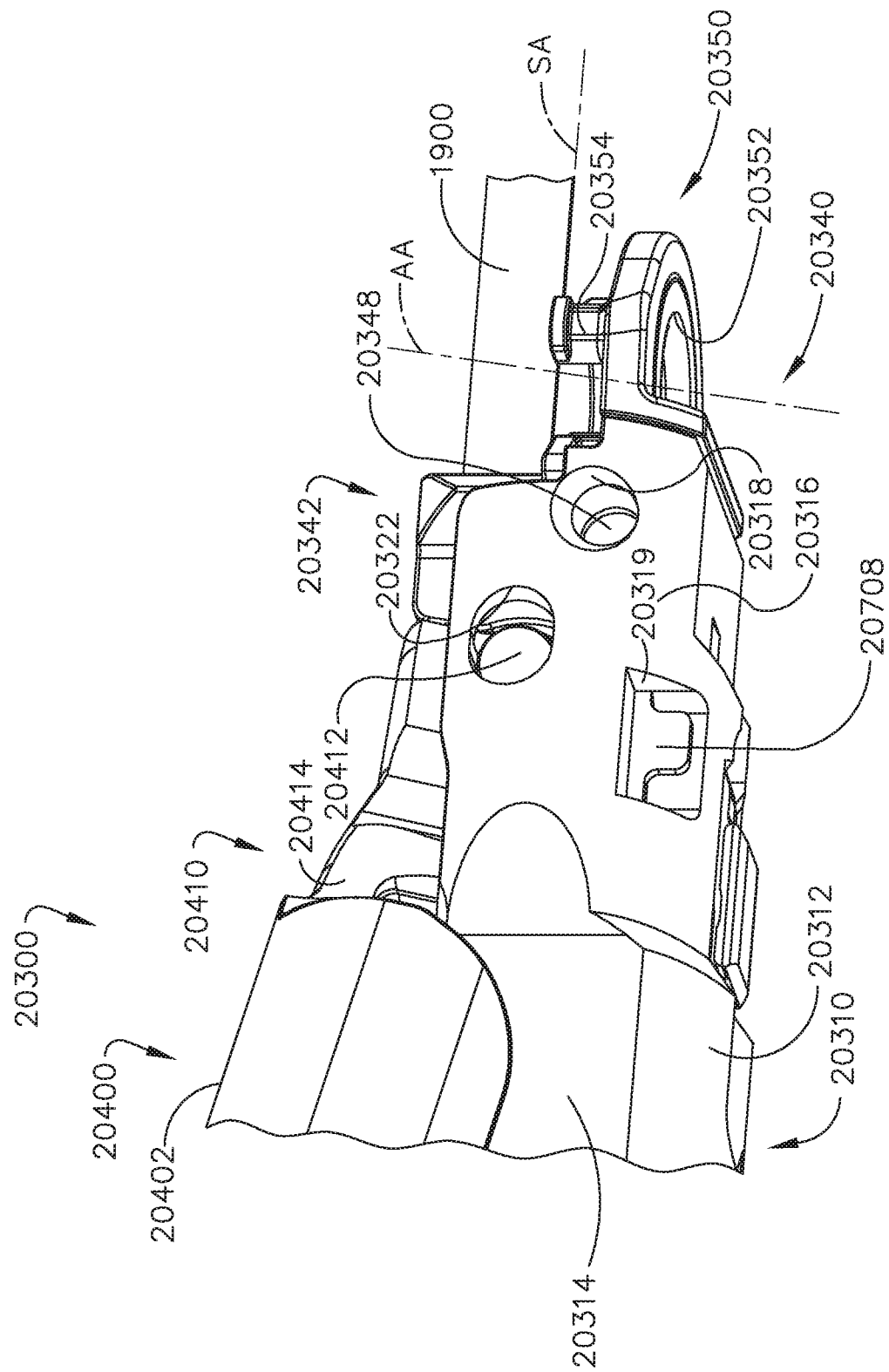
FIG. 18 is a partial bottom perspective view of the surgical end effector of FIG. 17.
Figure 19:
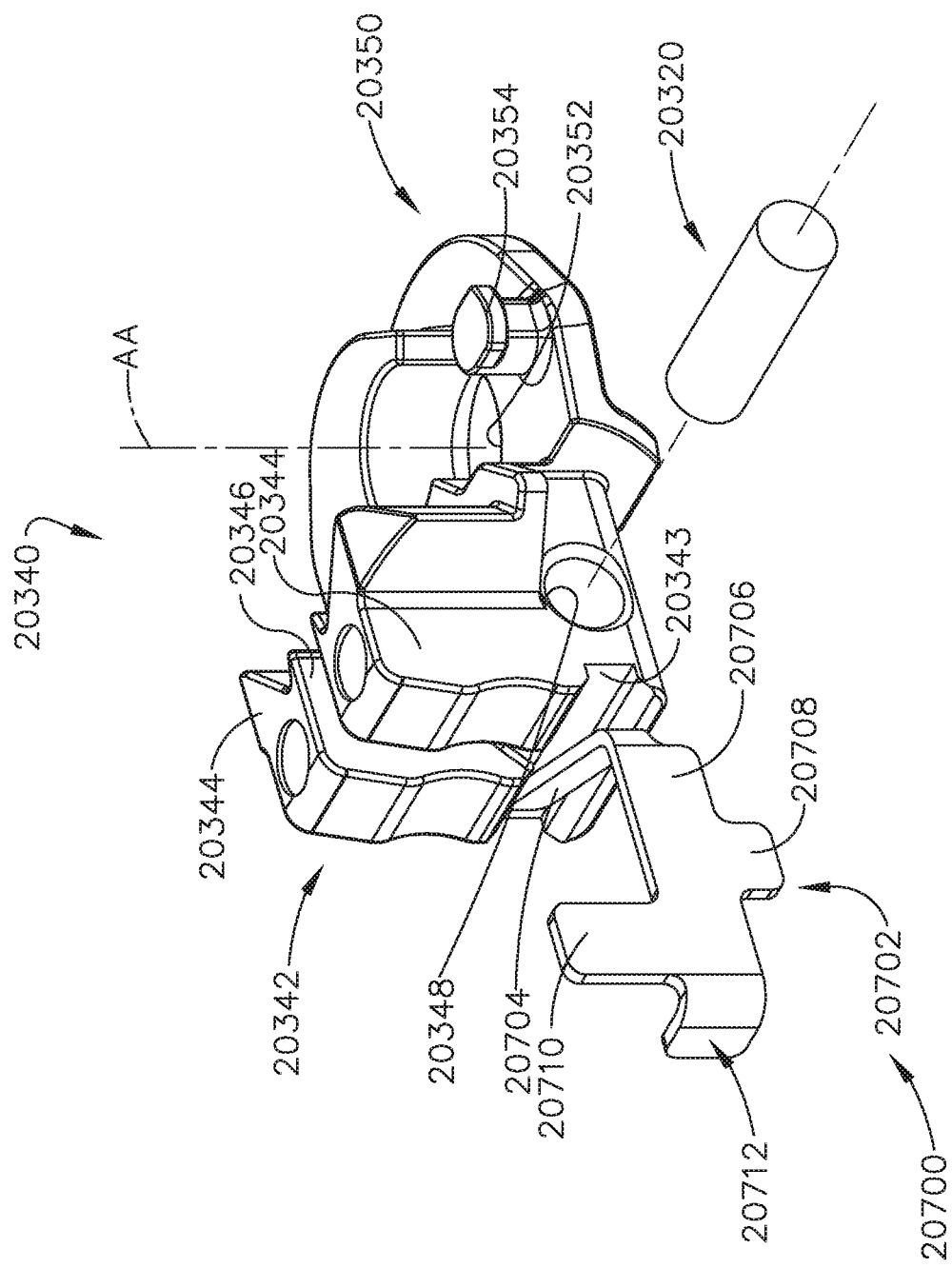
FIG. 19 is a perspective view of a channel mount feature and anvil lockout spring of the surgical end effector of FIG. 17.

Referring to FIGS. 17-21, the surgical end effector 20300 comprises an elongate channel 20310 that is configured to operably support a surgical staple cartridge 20600 therein. In the illustrated example, the elongate channel 20310 comprises a channel bottom 20312 and a pair of upstanding sidewalls 20314. The channel 20310 is coupled to the elongate shaft assembly 1200 (FIG. 5) by a channel mount feature 20340 which may facilitate articulation thereof about articulation joint 3020 (FIG. 5). As can be seen in FIG. 19, in one arrangement for example, the channel mount feature 20340 comprises a body portion 20342 that consists of an upstanding support 20344 that has a slot 20346 extending therethrough to receive the firing member beam 1900 (FIG. 5) therethrough. The channel mount feature 20340 may be movably or pivotally mounted to a proximal end 20316 of the channel 20310 by a channel mount feature, or channel pin 20320. In particular, the channel mount feature 20320 further includes a transverse pin opening 20348 that is configured to be coaxially aligned with holes 20318 in the sidewalls 20314 of the channel 20310 to receive the channel pin 20320 therethrough.

As described above, the shaft assembly 1200 includes a spine 1210 that terminates in an upper lug mount feature 1270 and in a lower lug mount feature 1280. See FIG. 5. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to the proximal end portion 20316 of the elongate channel 20310. As can be seen in FIG. 19, the channel mount feature 20340 further includes a shaft mount flange 20350 that extends proximally therefrom. In one arrangement for example, the shaft mount flange 20350 has a centrally disposed pivot hole 20352 therethrough that may pivotally receive the lower pivot pin 1286 on the lower mounting link 1284 of the lower lug mount feature 1280 (FIG. 5). The lower pivot pin 1286 is vertically aligned with the pivot socket 1276 to define an articulation axis AA about which the surgical end effector 20300 may articulate relative to the spine 1210. In one arrangement, the proximal articulation driver 2102 (FIG. 5) may be directly coupled to an articulation lug 20354 formed on the shaft mount flange 20350. In other arrangements, the proximal articulation driver 2102 may be attached to one or more articulation links that are attached to the shaft mount flange 20350. In either case, axial movement of the proximal articulation driver 2102 in the above-described manner will cause the channel mount feature to pivot about the articulation axis relative to the spine 1210 (FIG. 5) to articulate the end effector 20300 about the articulation axis AA.

The surgical end effector 20300 further comprises an anvil 20400 that is very similar to anvil 2000 described above, except for the differences discussed below. The anvil 20400 includes an elongate anvil body portion 20402 that has a staple-forming undersurface 20404 and an anvil mounting portion 20410 that is configured to interact with the end effector closure tube 3050 (FIG. 5) in the manner described above. The anvil 20400 is pivotally mounted on the elongate channel 20310 by a pair of laterally extending anvil pins or trunnions 20412 that are received in corresponding elongate trunnion slots 20322 formed in the upstanding channel walls 20314. Axial movement of the end effector closure tube 3050 in a distal direction will cause the anvil 20400 to pivot to a closed position about a pivot axis defined by the anvil trunnions 20412 and movement of the end effector closure tube 3050 in a proximal direction will cause the anvil to pivot to an open position relative to the elongate channel 20310.

Figure 22:
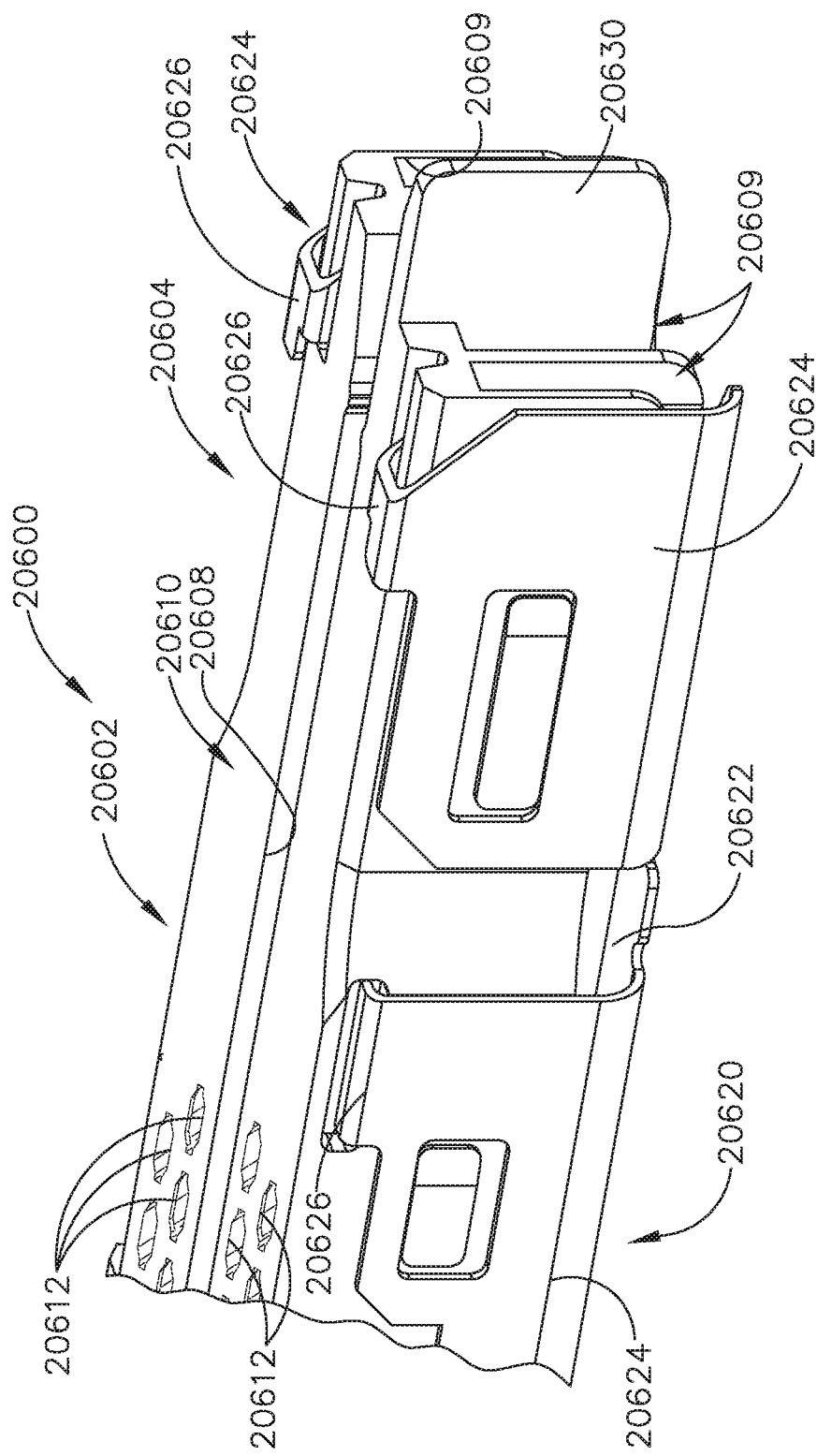
FIG. 22 is a perspective view of a proximal end portion of the surgical staple cartridge depicted in FIG. 21.

FIG. 22 illustrates one form of a staple cartridge 20600 that may be used in connection with the surgical end effector 20300. In at least one arrangement, the surgical staple cartridge 20600 comprises an elongate cartridge body 20602 that is sized to be removably seated in the elongate channel 20310. The cartridge body 20602 includes a cartridge slot 20608 that extends from a proximal end portion 20604 to a distal end portion 20606 (FIG. 17) of the cartridge body 20602. The cartridge body 20602 further comprises a cartridge deck surface 20610 that confronts the staple-forming undersurface 20404 of the anvil 20400 when the cartridge 20600 is seated in the channel 20310 and the anvil 20400 is pivoted to a closed position. Also in the illustrated example, three lines of surgical staple pockets 20612 are formed on each side of the cartridge slot 20608 and open through the cartridge deck surface 20610. Each staple pocket 20612 may have a staple driver (not shown) associated therewith that supports a surgical staple or fastener (not shown) thereon. In at least one example, the cartridge body 20602 is molded from a polymer material with the staple pockets 20612 molded or machined therein. In one arrangement, the staple pockets 20612 also open through a bottom of the cartridge body 20602 to facilitate installation of the drivers and fasteners into their respective pockets 20612. Once the drivers and fasteners are inserted into their respective staple pockets 20612, a cartridge pan 20620 is attached to the bottom of the cartridge body 20602. In one form, the cartridge pan 20620 is fabricated from a metal material and includes a bottom 20622 that spans across the bottom of the cartridge body 20602 and two upstanding sidewalls 20624 that correspond to each side of the cartridge body 20602. The cartridge pan 20620 may be removably affixed to the cartridge body 20602 by a series of hooks 20626 that are formed on the sidewalls 20624 and configured to hookingly engage corresponding portions of the cartridge body 20602. See FIG. 22. When installed, the cartridge pan 20620 may, among other things, prevent the drivers and fasteners from falling out of the bottom of the cartridge body 20602 during handling and installation of the cartridge 20600 into the elongate channel 20310.

As was discussed above in connection with cartridge 20040, cartridge 20600 operably supports a camming assembly therein. The camming assembly comprises a series of spaced cam members that are configured to move axially within corresponding cam slots 20609 formed on each side of the cartridge slot 20608 in the cartridge body 20602. The cam slots 20609 are aligned with corresponding lines of drivers in the cartridge body 20602 to facilitate camming contact with a corresponding cam member as the camming assembly is driven through the staple cartridge 20600 from a beginning position within the proximal end portion 20604 of the cartridge body 20602 to an ending position within the distal end portion 20606.

Figure 20:
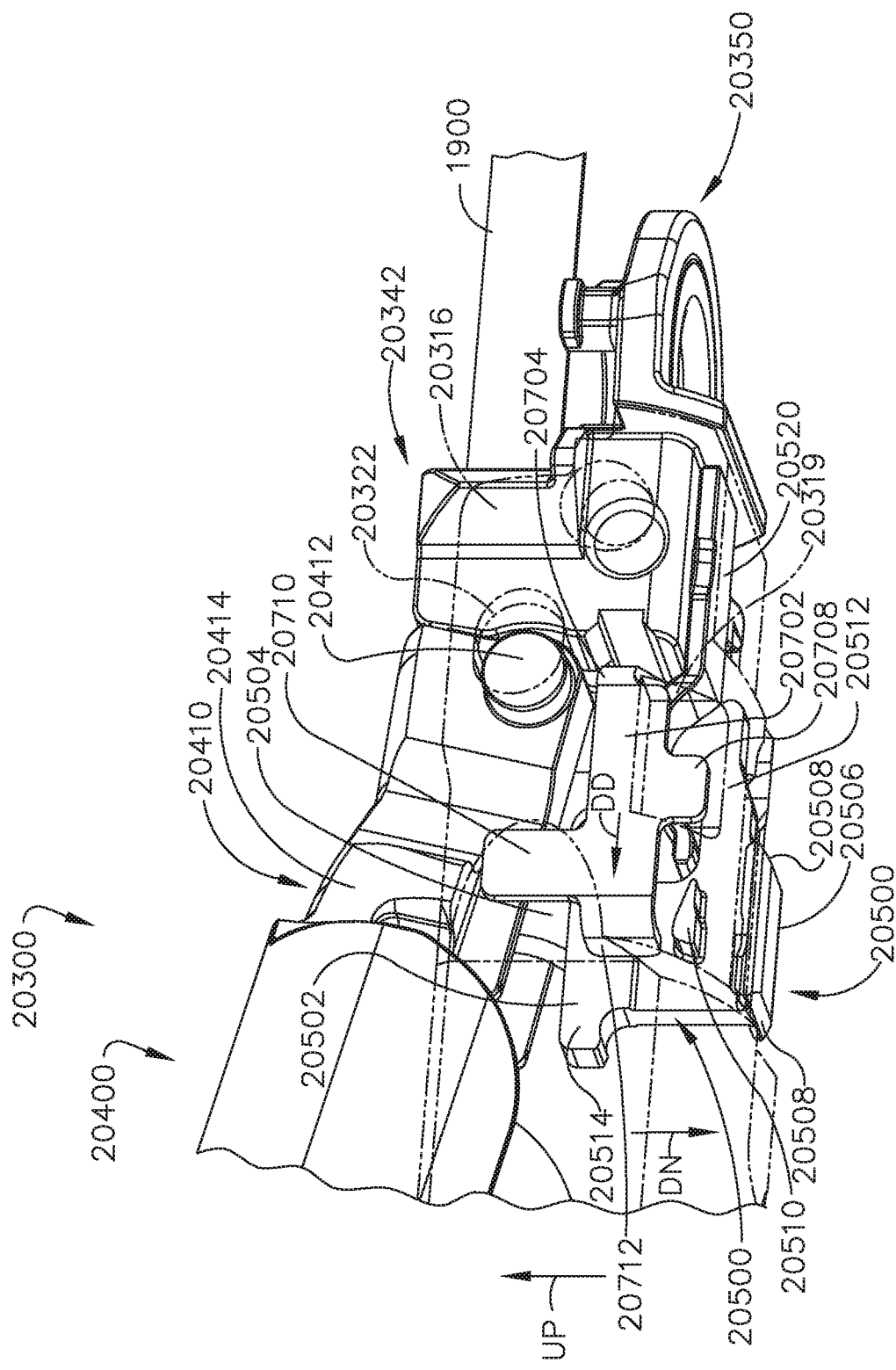
FIG. 20 is a partial bottom perspective view of the surgical end effector of FIG. 17 without a surgical staple cartridge installed therein and the anvil thereof in a locked position.
Figure 21:
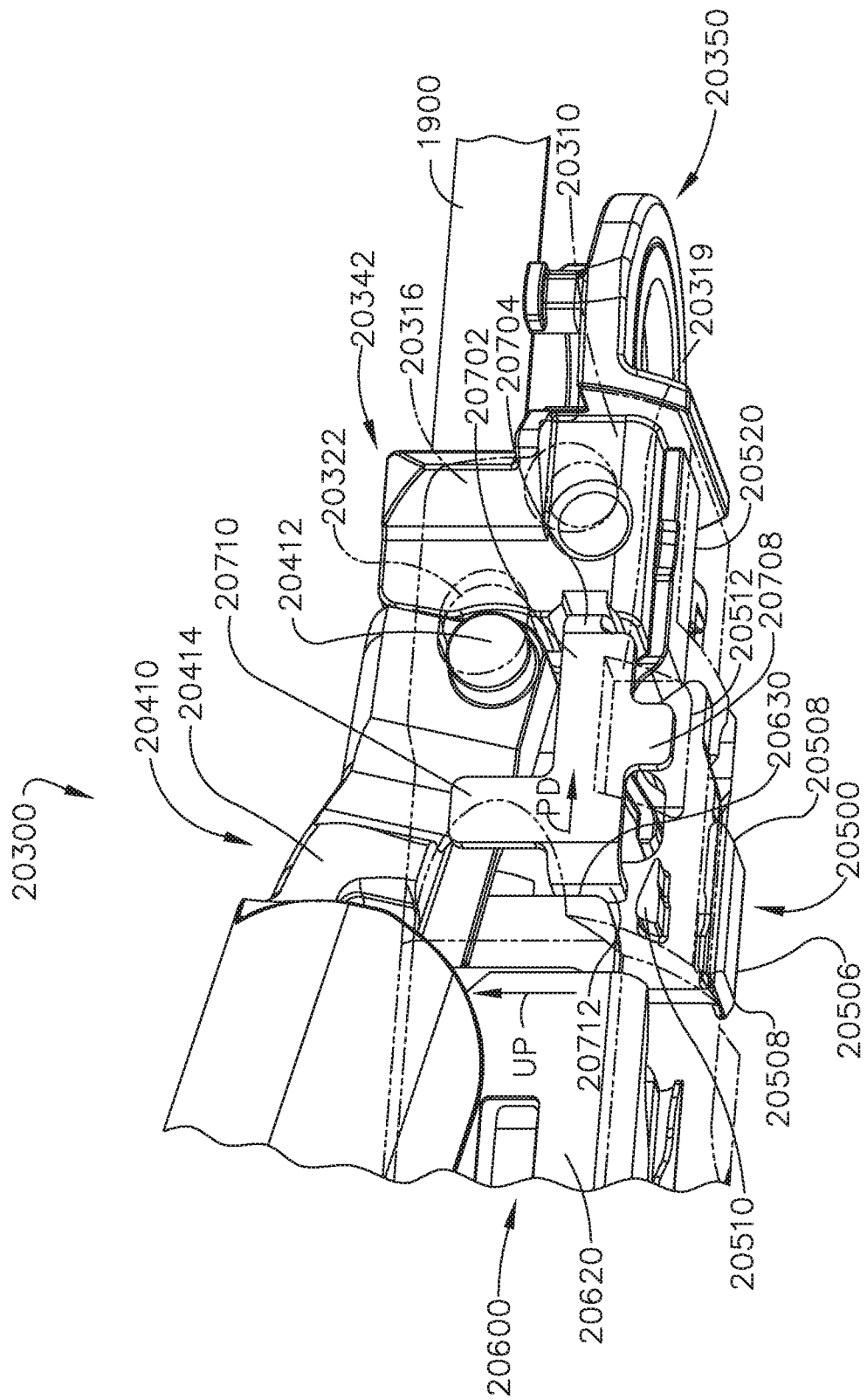
FIG. 21 is another partial bottom perspective view of the surgical end effector of FIG. 20 after a compatible surgical staple cartridge has been installed therein and the anvil lockout spring moved to an unlocked position.

The example illustrated in FIGS. 20 and 21 also employs a firing member 20500 that is attached to a distal end of the firing member beam 1900 and is configured to operably interface with the camming assembly in the staple cartridge 20600 to driven the camming assembly from its starting position to its ending position within the cartridge 20600. In at least one arrangement, the firing member 20500 is configured to interact with a camming assembly (not shown) in a staple cartridge 20600 that has been properly installed in the elongate channel 20310. For example, the firing member 20500 includes a firing member body 20502 that has a tissue cutting surface or blade 20504 formed thereon or attached thereto. The firing member body 20502 is sized to axially move within an axial anvil slot (not shown) in the anvil 20400 as well as the cartridge slot 20608 in the cartridge body 20602 and a channel slot (not shown) in the elongate channel 20310. A lower foot assembly 20506 that comprises a pair of laterally extending lower flanges 20508 extends from a bottom end of the firing member body 20502 to slidably engage corresponding channel ledges (not shown) that are formed on each side of the channel slot. An upper foot (not shown) that comprises two laterally extending anvil tabs may be formed on an upper end of the firing member body 20502 and is configured to slidably engage anvil ledges (not shown) that are formed on each side of the anvil slot. In at least one arrangement, the firing member 20500 further includes a pair of central tabs 20510 that extend laterally from each side of the firing member body 20502.

Still referring to FIGS. 20 and 21, in one arrangement, the firing member body 20502 is configured with a proximally extending spring tail 20512 that may be configured to operably interface with a firing member lockout spring 20520 that is mounted in the elongate channel 20310 and is configured to bias the firing member 20500 downward (arrow DN) in the elongate channel 20310 into a locked position. When in the locked position, the firing member foot 20506 and/or the central tabs 20510 are misaligned with corresponding passages in the channel 20310 and as such, should the user attempt to distally advance the firing member 20500 when in that locked out state, the firing member 20500 would not move distally due to such misalignment. That is, the foot 20506 and/or central tabs 20510 contact portions of the elongate channel to thereby prevent the distal advancement of the firing member 20500. In one arrangement, a sled latch 20514 is formed on the firing member body 20502 and is configured to be engaged by a corresponding portion formed on a camming assembly that is operably supported in the surgical staple cartridge 20600. When a fresh unfired staple cartridge 20600 with the camming assembly thereof in its starting position has been operably installed in the elongate channel 20310, a portion of the camming assembly engages the sled latch 20514 on the firing member body 20502 and moves the firing member 20500 upward (arrow UP in FIG. 20) into an unlocked position wherein the lower foot assembly 20506 and/or the central tabs 20510 are aligned with their respective passages in the channel 20310 to permit the firing member 20500 to axially advance therein. As the user distally advances the firing member 20500 into the cartridge 20600, the firing member 20500 also drives the camming assembly therein which cams the drivers upward to drive the staples or fasteners supported thereon into forming contact with the underside of the anvil. The tissue cutting member 20504 on the firing member 20500 then cuts through the stapled tissue. Once the firing member 20500 has been driven to its distal-most position corresponding to the ending position of the camming assembly, the firing member 20500 is retracted back to its proximal-most position, leaving the camming assembly in the distal end 20606 of the cartridge 20600. When the firing member 20500 returns to its proximal-most beginning position, the firing member lockout spring 20520 once again biases the firing member 20500 back into its locked position. Thus, should the user inadvertently try to reuse the spent cartridge 20600, the camming assembly is not in its starting position which is required to unlock the firing member 20500.

The surgical end effector 20300 may also employ a closure lockout system 20700 for preventing the anvil 20400 from being moved from an open position to a closed (clamped) position unless a corresponding compatible surgical staple cartridge 20600 has been operably installed in the elongate channel 20310. In the illustrated example, the closure lockout system 20700 comprises an anvil lock 20702 that is configured to move between an anvil locked position and an anvil unlocked position in response to installation of a staple cartridge 20600 therein. FIG. 19 illustrates one form of an anvil lock 20702. The anvil lock 20702 may be fabricated from spring steel or other suitable metal and include a proximal biasing arm 20704 that may be configured to be seated in a transverse spring mounting slot 20343 provided in the body portion 20342 of the channel mount feature 20340. The anvil lock 20702 further includes a distally extending body portion 20706 that has a downwardly extending mounting tab 20708 and an upwardly extending anvil lockout tab 20710 protruding therefrom. As can be seen in FIGS. 17, 18, and 20 the mounting tab 20708 extends into a clearance window 20319 that is formed in the elongate channel 20310.

FIG. 19 illustrates the surgical end effector 20300 without a surgical staple cartridge installed therein. As can be seen in FIG. 19, the proximal biasing arm 20704 has biased the anvil lock 20702 in the distal "anvil locked" position. When in this position, the anvil lockout tab 20710 is aligned with a portion of an anvil lock lug 20414 that is formed on the anvil mounting portion 20410 of the anvil 20400. Should the user attempt to close the anvil 20400, the anvil lock lug 20414 will contact the anvil lockout tab 20710 to thereby prevent any further travel of the anvil 20400 in the closure direction.

Returning to FIG. 21, in at least one arrangement, the staple cartridge 20600 includes an anvil unlocking feature or tab 20630 that protrudes proximally from the cartridge body 20602 and is aligned to unlockingly engage an actuation tab 20712 that is formed on the distal end of the anvil lock 20702 when the cartridge 20600 has been operably installed in the elongate channel 20310. FIG. 20 depicts the surgical staple cartridge 20600 operably installed in the elongate channel 20310. As can be seen in FIG. 21, the anvil unlocking tab 20630 on the staple cartridge body 20602 has contacted the actuation tab 20712 of the anvil lockout 20702 and biased the anvil lockout 20702 in the proximal direction PD to an unlocked position, wherein the anvil lockout tab 20710 is no longer aligned with the anvil lock lug 20414 on the anvil 20400. When in that position, the user may pivot the anvil 20400 to a closed position. Should the user attempt to install an inappropriate cartridge that lacks the anvil unlocking tab 20630 or similar feature designed to unlockingly engage the anvil lockout 20702, the user will be unable to close the anvil 20400 to complete the surgical stapling procedure.

Figure 23:
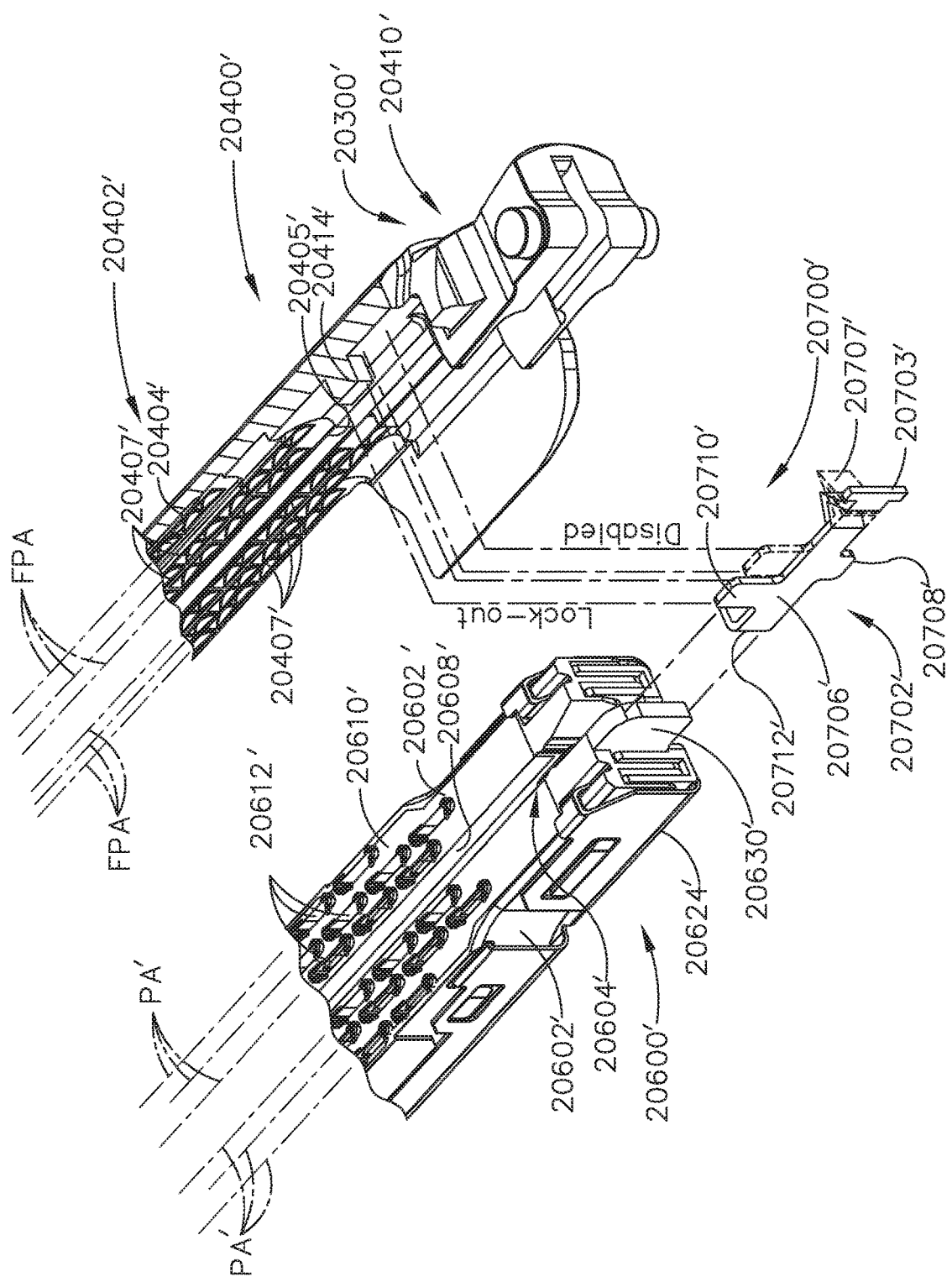
FIG. 23 is a partial exploded assembly view of a surgical staple cartridge and a corresponding anvil and anvil lockout system of a surgical end effector.

FIG. 23 illustrates an alternative closure lockout system 20700' for preventing an anvil 20400' of a surgical end effector 20300' from being moved from an open position to a closed (clamped) position unless a corresponding proper surgical staple cartridge 20600' has been operably installed in the corresponding elongate channel (not shown). The surgical end effector 20300' is substantially identical to surgical end effector 20300 described above, except for the differences discussed below. The closure lockout system 20700' comprises an anvil lockout 20702' that is substantially identical to anvil lockout 20702 described above, except for the following differences. For example, the anvil lockout 20702 may be fabricated from spring steel or other suitable metal and include a distally extending body portion 20706' that has a spring portion 20707' formed therein. A proximal end of the anvil lockout 20702' has an anchor tab 20703' formed thereon that serves to couple the anvil lockout 20702' to the channel mount feature 20340 (FIG. 19). Additionally, the body portion 20706' includes a downwardly extending mounting tab 20708' and an upwardly extending anvil lockout tab 20710' that protrudes therefrom. An actuation tab 20712' is formed on the distal end of the body portion 20706'.

The surgical staple cartridge 20600' is similar to the surgical staple cartridge 20600 described above and includes a cartridge body 20602' that is sized to be removably seated in the elongate channel 20310. The cartridge body 20602' includes a cartridge slot 20608' that extends from a proximal end portion 20604' to a distal end portion of the cartridge body 20602'. The cartridge body 20602' further comprises a cartridge deck surface 20610' and three lines of surgical staple pockets 20612' located on each side of the cartridge slot 20608'. As can be seen in FIG. 23, the staple pockets 20612', as well as the staples or fasteners therein (not shown) are aligned on pocket axes PA' that are parallel to the cartridge slot 20608'. Thus, the staples/fasteners are applied in lines that are approximately parallel to the cartridge slot 20608' and the tissue cutline. Like surgical staple cartridge 20600, surgical staple cartridge 20600' includes a cartridge pan 20624' and an anvil unlocking feature or tab 20630' that protrudes proximally from the cartridge body 20602'.

Still referring to FIG. 23, the anvil 20400' is similar to anvil 20400, except for the differences discussed below. The anvil 20400' includes an elongate anvil body portion 20402' and an anvil mounting portion 20410' that is configured to interact with the end effector closure tube 3050 (FIG. 5) in the manner described above. The anvil body portion 20402' includes a staple-forming undersurface 20404' that is bisected by an anvil slot 20405' that is configured to accommodate passage of the firing member 20500 therethrough. As can be seen in FIG. 23, the staple-forming undersurface 20404' comprises three lines of staple-forming pockets 20407' that are arranged on forming pocket axes FPA that are parallel with the anvil slot 20405'. When the anvil 20400' is moved to a closed position, the anvil slot 20405' is vertically aligned with the cartridge slot 20608' to permit passage of the firing member 20500 therethrough. The lines of staple-forming pockets 20407' are aligned with the staple pockets 20612' such that as the staples are driven from the cartridge 20600', they contact a corresponding pair of staple-forming pockets 20407' to be crimped. Thus, the array of staple-forming pockets in the anvil 20400' must correspond to the array of staple pockets 20612' in the cartridge 20600' to ensure that the staples are properly formed. As can be further seen in FIG. 23, in this arrangement, the anvil 20400' includes a downwardly extending anvil lock lug 20414' that is formed distal to the anvil mounting portion 20410' but is otherwise configured to contact the anvil lockout tab 20710' when the anvil lockout 20702' is in the locked position (e.g., no cartridge has been inserted into the channel 20310 or an improper cartridge has been seated in the channel 20310). When the cartridge 20600' has been properly seated in the elongate channel 20310, the anvil unlocking feature 20630' thereon contacts the actuation tab 20712' on the anvil lockout 20702' to bias the lockout 20702' proximally into the unlocked position wherein the anvil lockout tab 20710' is out of locking alignment with the anvil lock lug 20414' to permit the anvil 20400' to be pivoted to the closed position.

Figure 24:
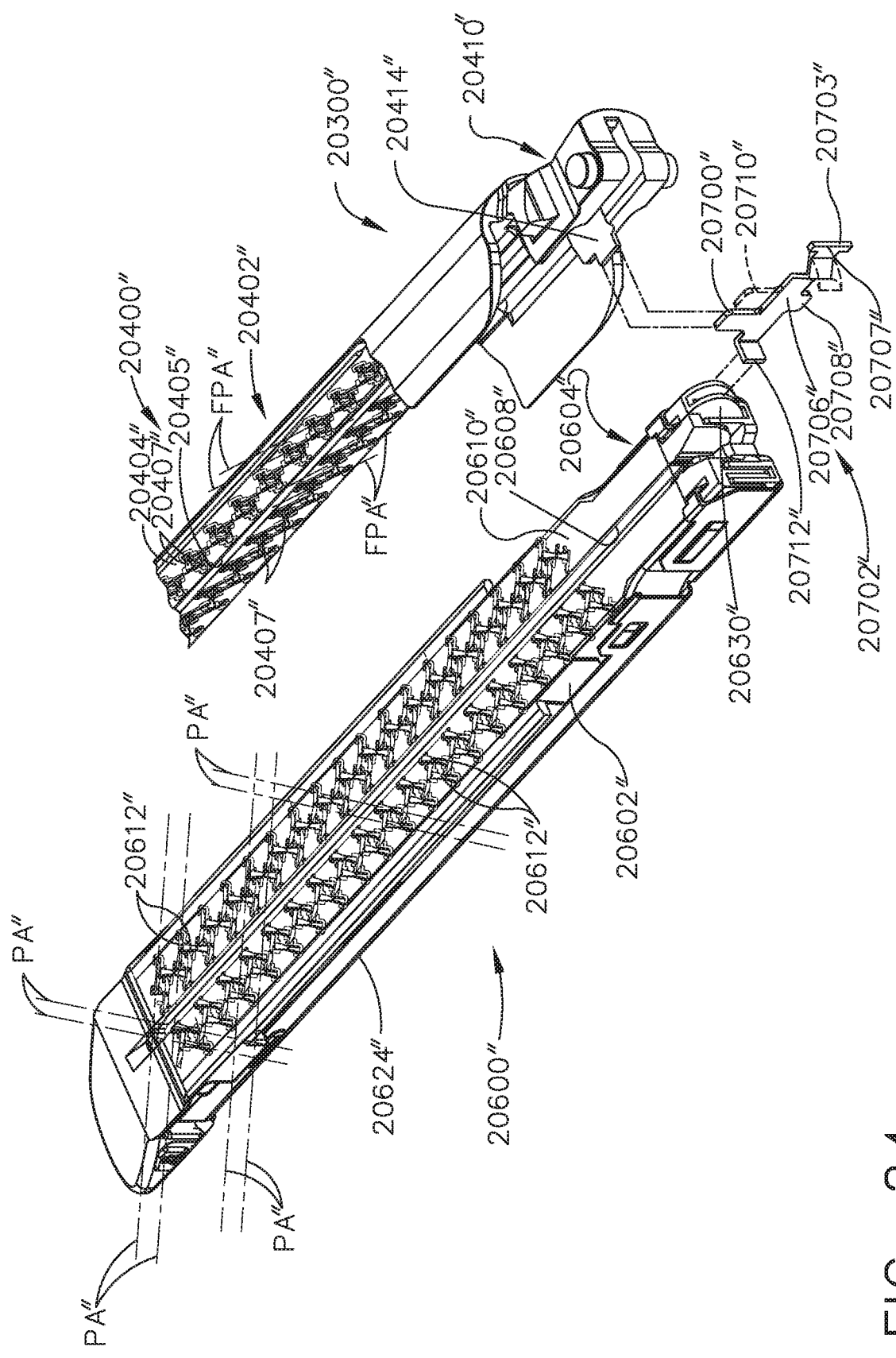
FIG. 24 is a partial exploded assembly view of a surgical staple cartridge and a corresponding anvil and anvil lockout system of another surgical end effector.

FIG. 24 illustrates an alternative closure lockout system 20700" for preventing an anvil 20400" of another surgical end effector 20300" from being moved from an open position to a closed (clamped) position unless a compatible surgical staple cartridge 20600" has been operably installed in the elongate channel 20310. The surgical end effector 20300" is substantially identical to surgical end effector 20300 described above, except for the differences discussed below. The closure lockout system 20700" comprises an anvil lockout 20702" that is substantially identical to anvil lockout 20702 described above, except for the following differences. For example, the anvil lockout 20702" may be fabricated from spring steel or other suitable metal and include a distally extending body portion 20706" that has a spring portion 20707" formed therein. A proximal end of the anvil lockout 20702" has an anchor tab 20703" formed thereon that serves to couple the anvil lockout 20702" to the channel mount feature 20340 (FIG. 19). Additionally, the body portion 20706" includes a downwardly extending mounting tab 20708" and an upwardly extending anvil lockout tab 20710" that protrudes therefrom. An actuation tab 20712" is formed on the distal end of the body portion 20706".

The surgical staple cartridge 20600" is similar to the surgical staple cartridge 20600 described above and includes a cartridge body 20602" that is sized to be removably seated in the elongate channel 20310. The cartridge body 20602" includes a cartridge slot 20608" that extends from a proximal end portion 20604" to a distal end portion of the cartridge body 20602". The cartridge body 20602" further comprises a cartridge deck surface 20610" and two lines of surgical staple pockets 20612" located on each side of the cartridge slot 20608". As can be seen in FIG. 24, the staple pockets 20612", as well as the staples or fasteners therein (not shown), are aligned on pocket axes PA" that are transverse to the cartridge slot 20608". Thus, the staples/fasteners are applied in lines that are approximately transverse to the cartridge slot 20608" and the tissue cutline. Such arrangements of fasteners create "flexible" or "stretchable" staple lines. Further details regarding cartridges for developing flexible or stretchable lines of staples may be found in U.S. patent application Ser. No. 14/498,121, entitled FASTENER CARTRIDGE FOR CREATING A FLEXIBLE STAPLE LINE, now U.S. Pat. No. 9,801,627, the entire disclosure of which is hereby incorporated by reference herein. Like surgical staple cartridge 20600, surgical staple cartridge 20600" includes a cartridge pan 20624" and an anvil unlocking feature or tab 20630" that protrudes proximally from the cartridge body 20602'.

Still referring to FIG. 24, the anvil 20400" is similar to anvil 20400, except for the differences discussed below. The anvil 20400" includes an elongate anvil body portion 20402" and an anvil mounting portion 20410" that is configured to interact with the end effector closure tube 3050 (FIG. 5) in the manner described above. The anvil body portion 20402" includes a staple-forming undersurface 20404" that is bisected by an anvil slot 20405" that is configured to accommodate passage of the firing member 20500 therethrough. As can be seen in FIG. 24, the staple-forming undersurface 20404" comprises lines of staple-forming pockets 20407" that are arranged on forming pocket axes FPA that are transverse to the anvil slot 20405". When the anvil 20400" is moved to a closed position, the anvil slot 20405" is vertically aligned with the cartridge slot 20608" to permit passage of the firing member 20500 therethrough. The lines of staple-forming pockets 20407" are aligned with the staple pockets 20612" such that as the staples are driven from the surgical staple cartridge 20600", they contact a corresponding pair of forming pockets 20407" to be crimped. Thus, the array of staple-forming pockets 20407" in the anvil 20400" must correspond to the array of staple pockets 20612" in the cartridge 20600" to ensure that the staples are properly formed. As can be further seen in FIG. 24, in this arrangement, the anvil 20400" includes a downwardly extending anvil lock lug 20414" that is formed or attached to the anvil mounting portion 20410" and is configured to contact the anvil lockout tab 20710" when the anvil lockout 20702" is in the locked position (e.g., no cartridge has been inserted into the channel 20310 or an improper cartridge is inserted in the channel 20310). When the cartridge 20600" has been properly seated in the elongate channel 20310, the anvil unlocking feature 20630" thereon contacts the actuation tab 20712" on the anvil lockout 20702" to bias the anvil lockout 20702" proximally into the unlocked position wherein the anvil lockout tab 20710" is out of locking alignment with the anvil lock lug 20414" to permit the anvil 20400" to be pivoted close.

As was discussed above, various surgical staple cartridges may have different arrays of and/or orientations of staples/fasteners therein. The sizes of the staples or fasteners, as well as the number of fasteners may vary from cartridge type to cartridge type depending upon a particular surgical procedure or application. To ensure that the staples are properly crimped or formed, the surgical staple cartridges must be used in connection with corresponding anvils that have the proper array of staple-forming pockets therein. Should a "non-compatible" cartridge be loaded into an end effector that has an anvil that is mismatched to the cartridge, the staples may not be properly formed during the firing process which could lead to catastrophic results. For example, the surgical staple cartridge 20600' depicted in FIG. 23 is matched to or "compatible with" the anvil 20400' shown in FIG. 23. The surgical staple cartridge 20600" shown in FIG. 24 is matched to or compatible with the anvil 20400" shown in FIG. 24. However, the surgical staple cartridge 20600" of FIG. 24 is incompatible with the anvil 20400' shown in FIG. 23, for example.

The closure lockout systems employed in the examples described above may avoid the activation of a mismatched cartridge that has otherwise been loaded into the end effector. For example, the anvil unlocking feature or tab 20630' on the staple cartridge 20600' is located on the left side of the cartridge slot 20608' and is positioned to contact the actuator tab 20712' on the anvil lockout spring 20707' when the cartridge 20600' is properly loaded in the channel 20310 of end effector 20300'. Conversely, the anvil unlocking feature or tab 20630" on the cartridge 20600" is located on the right side of the cartridge slot 20608" and aligned to contact the actuator tab 20712" on the anvil lockout 20702" when the cartridge 20600" is properly loaded in the channel 20310. Should the user load cartridge 20600" into the channel 20310 of the end effector 20300', anvil unlocking feature or tab 20630" on the staple cartridge 20600" will not contact the he actuator tab 20712' on the anvil lockout 20702' to move it into the unlocked position and the user will be unable to pivot the anvil 20400' closed. Likewise, should the user load cartridge 20600' into the channel of the end effector 20300", anvil unlocking feature or tab 20630' on the staple cartridge 20600' will not contact the he actuator tab 20712" on the anvil lockout 20702" to move it into the unlocked position and the user will be unable to pivot the anvil 20400" closed. If the user unwittingly loads another cartridge that lacks the proper anvil unlocking feature or tab that corresponds to the anvil lockout in the end effector, the user will be unable to close the anvil. The location, shape, length, etc. of the anvil unlocking feature(s) or tab(s) on a surgical staple cartridge may vary from cartridge type to cartridge type and be interrelated to the actuator member (size, location, shape, number, etc.) on the correspond anvil lockout located in a corresponding surgical end effector. For example, the anvil unlocking feature or tab may be integrally formed on the cartridge body, be machined or molded into the cartridge body, be attached to the cartridge body, be attached to or integrally formed on the camming assembly of the cartridge or comprise a portion of the cartridge pan, for example. All such variations are contemplated herein and are intended to be encompassed by the appended claims.

FIGS. 25-29 illustrate a surgical end effector 21300 that is very similar to the surgical end effectors 20300, 20300', 20300" described above, except for the differences discussed below. In this embodiment, for example, the end effector 21300 comprises an elongate channel 21310 that is configured to operably support a surgical staple cartridge 21600 therein. In the illustrated example, the elongate channel 21310 comprises a channel bottom 21312 and a pair of upstanding sidewalls 21314. Although not shown, the channel 21310 may be coupled to the elongate shaft assembly 1200 (FIG. 5) by a channel mount feature 20340 (described above) which may facilitate articulation thereof about articulation joint 3020 (FIG. 5). The surgical end effector 21300 further comprises an anvil 21400 that may be very similar to anvil 20400 described above, except for the differences discussed below. The anvil 21400 includes an elongate anvil body portion 21402 that has a staple-forming undersurface and an anvil mounting portion 21410 that is configured to interact with an end effector closure tube 3050 (FIG. 5) in the manner described above. The anvil 21400 is pivotally mounted on the elongate channel 21310 by a pair of laterally extending anvil pins or trunnions 21412 that are received in corresponding elongate trunnion slots 21320 that are formed in the upstanding channel walls 21314. Axial movement of the end effector closure tube 3050 in a distal direction will cause the anvil 21400 to translate distally until the trunnions 21412 contact the distal ends of their respective trunnion slots 21320 and pivot to a closed position. Conversely, movement of the end effector closure tube 3050 in a proximal direction will cause the anvil 21400 to pivot to an open position relative to the elongate channel 21310.

Figure 25:
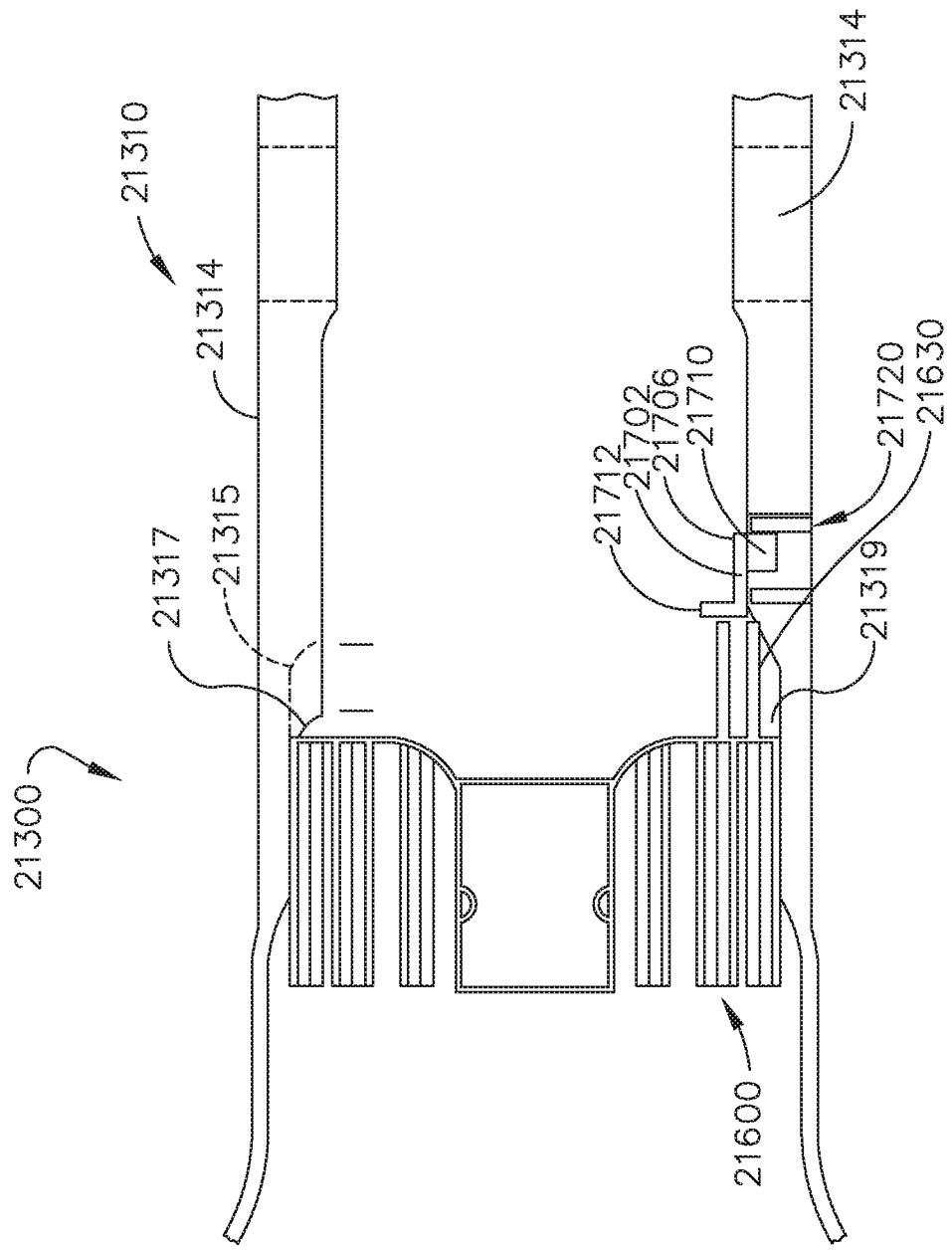
FIG. 25 is a partial bottom view of a channel of another end effector with a compatible surgical staple cartridge loaded therein with portions of the compatible surgical staple cartridge omitted for clarity.
Figure 26:
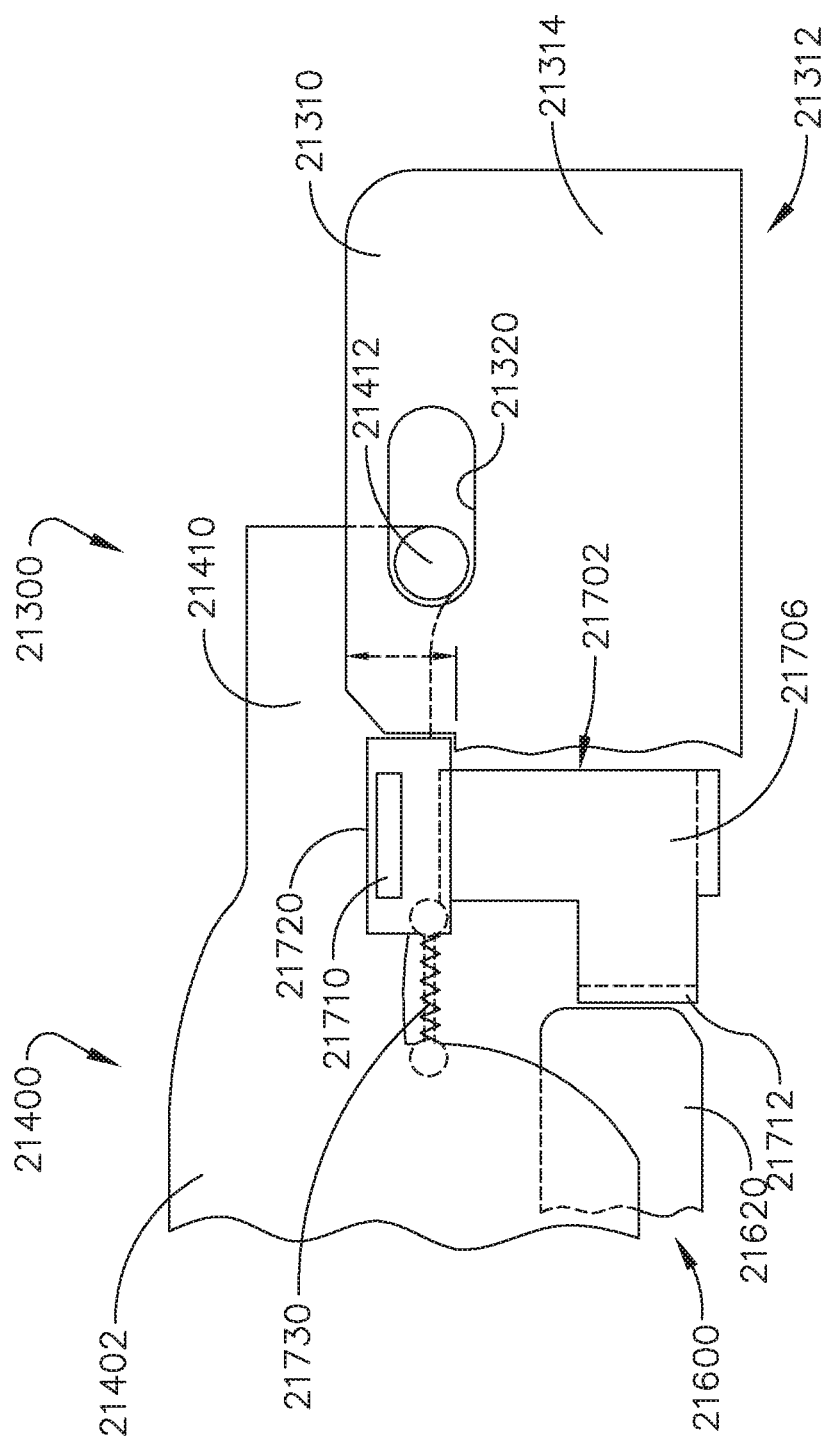
FIG. 26 is a side elevational view of a portion of the surgical end effector of FIG. 25, with portions of a channel, anvil and cartridge omitted for clarity.
Figures 27, 28:
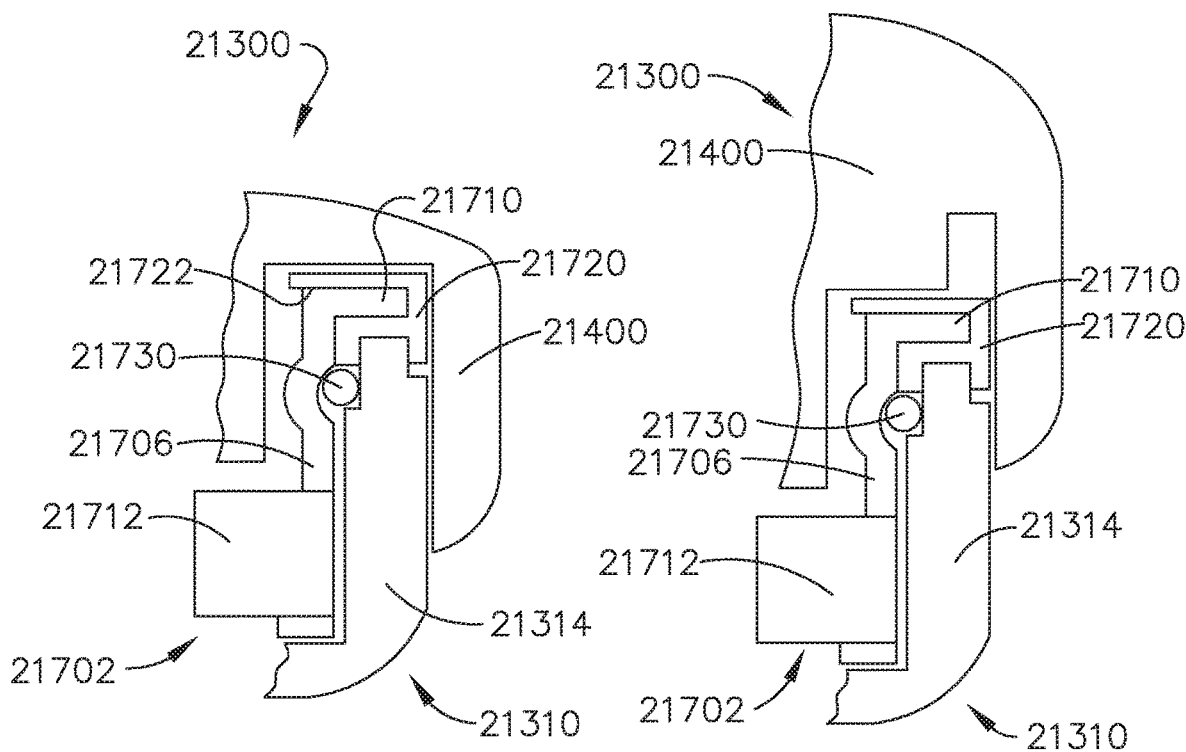
FIG. 27 is a partial cross-sectional end view of the surgical end effector of FIGS. 25 and 26 with the anvil shown in a closed position on a compatible surgical staple cartridge.
FIG. 28 is another partial cross-sectional end view of the surgical end effector of FIGS. 25 and 26 with the anvil thereof shown in a locked open position.
Figure 29:
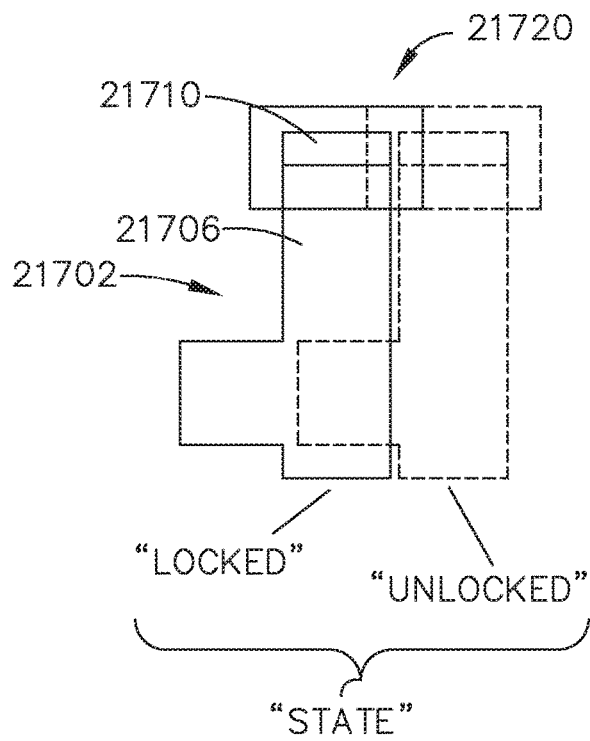
FIG. 29 is a side elevational of an anvil lock of the surgical end effector of FIGS. 25 and 26 shown in a locked configuration and an unlocked configuration (in phantom lines)

The end effector 21300 is configured to operably support a surgical staple cartridge 21600 that may be substantially the same as the surgical staple cartridge 20600, except that the anvil unlocking feature or tab 21630 comprises a portion of the cartridge pan 21620. The anvil unlocking feature 21630 is configured to operably interact with an axially movable anvil lock 21702 that is supported by the channel 21310. Turning to FIG. 27, the anvil lock 21702 is supported for axial movement between a distal locked position and a proximal locked position by a guide block 21720 that is attached to a portion of the channel 21310. In one example, anvil lock 21702 may be formed from metal and the guide block 21720 may be fabricated from 40% carbon filled Nylon 6/6 and be attached to the sidewall of 21314 of the channel 21310 by appropriate adhesive or other fastening means. The guide block 21720 may define a guide channel 21722 that is configured to support a locking tab portion 21710 of the anvil lock 21702. The anvil lock 21702 additionally comprises a vertical body portion 21706 that has an actuation tab 21712 formed on a distal end thereof. The anvil lock 21702 is biased to a distal locked position by an extension spring 21730 that is attached to the anvil lock 21702 and the channel sidewall 21314. When no cartridge is present, the extension spring 21730 biases the anvil lock 21702 into a distal locked position wherein the locking tab portion 21710 contacts a portion of the anvil 21400 to prevent the anvil 21400 from pivoting to a closed position. When a proper or compatible cartridge 21600 is loaded into the elongate channel 21310, the unlocking feature or tab 21630 of the cartridge pan 21620 contacts the actuation tab 21712 on the anvil lock 21702 to move the anvil lock 21702 proximally into an unlocked position wherein the locking tab portion 21710 of the anvil lock 21702 no longer prevents pivotal motion of the anvil 21400. As can be seen in FIG. 25, the anvil unlocking feature 21630 of the surgical staple cartridge 21600 is "asymmetric" in design. That is, the anvil unlocking feature 21630 is only located on one side of a proximal end of the cartridge 21600. FIG. 25 illustrates an old relief area 21315 that is present in previous channel arrangements and new relief areas 21317, 21319 that are provided in the channel 21310 to accommodate cartridge 21600 therein.

Figure 30:
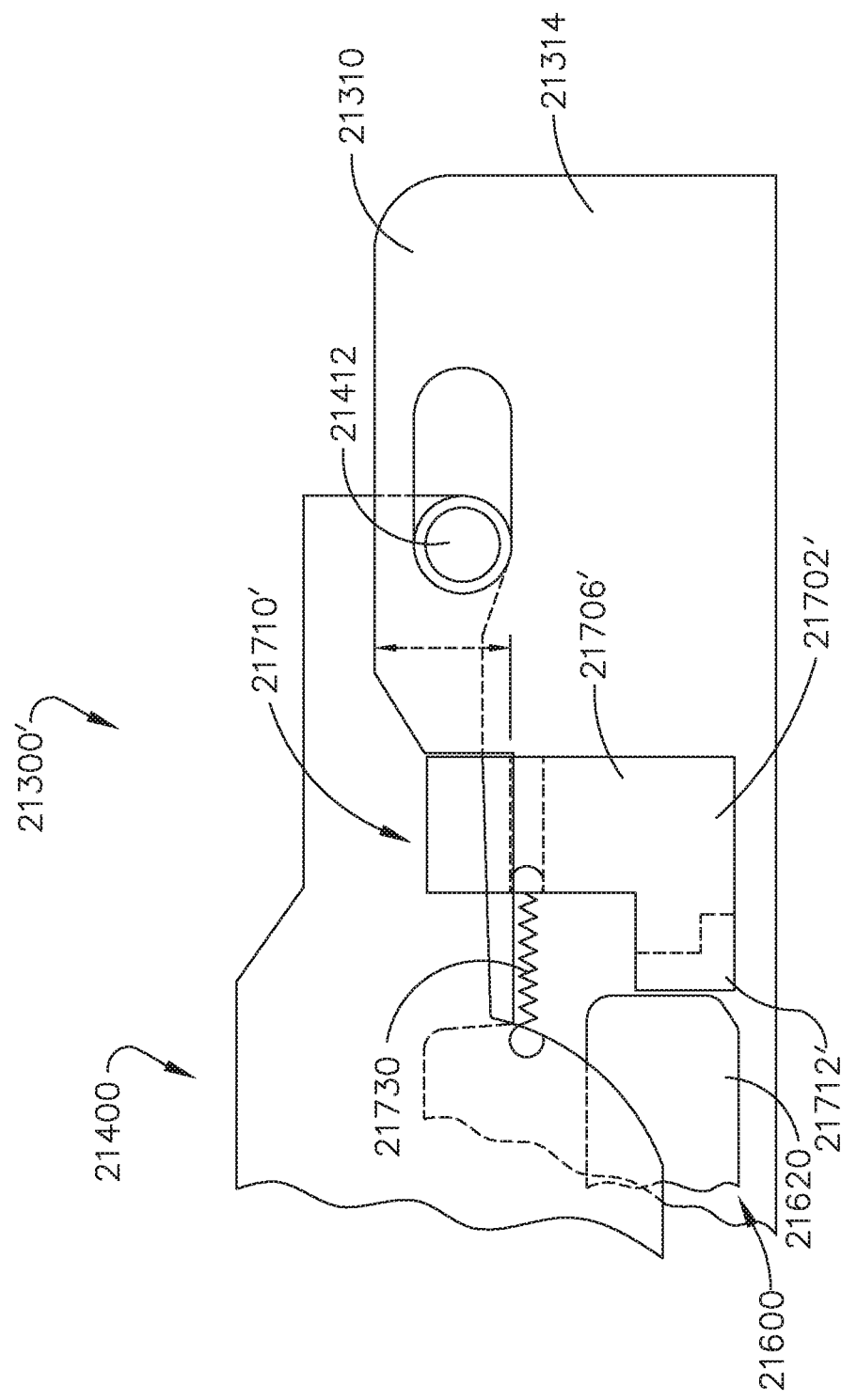
FIG. 30 is a side elevational view of a portion of another surgical end effector, with portions of a channel, anvil and cartridge omitted for clarity.
Figure 31:
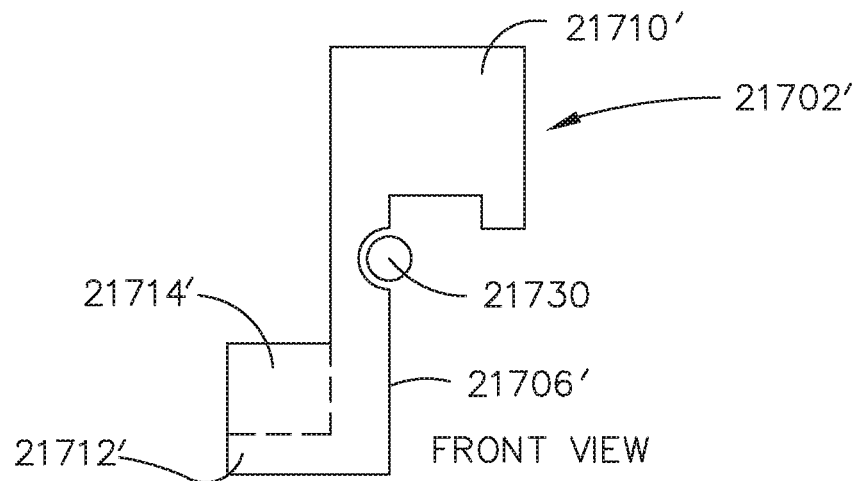
FIG. 31 is a front elevational view of an anvil lock of the surgical end effector of FIG. 30.
Figure 32:
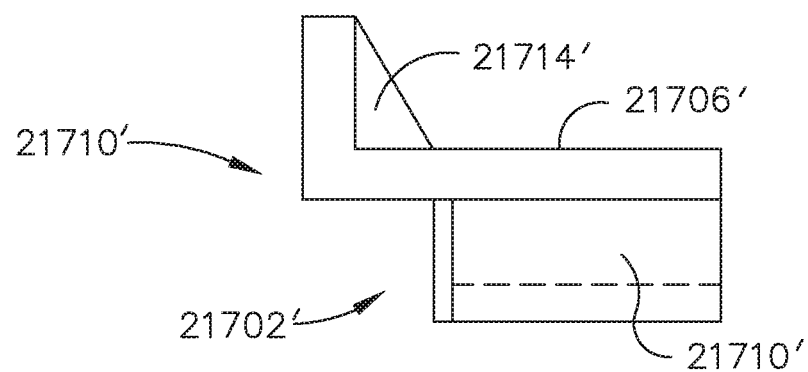
FIG. 32 is a top view of the anvil lock of FIG. 31.

FIG. 30 illustrates portions of a surgical end effector 21300' that is identical to end effector 21300, except that the end effector 21300' employs an anvil lock 21702' as depicted in FIGS. 31 and 32. In one example, the anvil lock 21702' may be fabricated from 40% carbon filled Nylon 6/6 and include a vertical body portion 21706' that has a locking portion 21710' formed on the upper end thereof. An actuation tab 21712' is formed on a distal end and a gusset 21714' is also employed to provide additional support to the actuation tab 21712'. As discussed above, when a proper or compatible surgical staple cartridge 21600 is loaded into the elongate channel 21310, the unlocking feature or tab 21630 of the cartridge pan 21620 contacts the actuation tab 21712' on the anvil lock 21702' to move the anvil lock 21702' proximally into an unlocked position wherein the locking portion 21710' of the anvil lock 21702' no longer prevents pivotal motion of the anvil 21400.

FIG. 33 illustrates another surgical end effector 22300 that employs an anvil lockout system 22700. The end effector 22300 is similar to the end effector 20300 described above, except for the noted differences. In this embodiment, the end effector 22300 comprises an elongate channel 22310 that is configured to operably support a surgical staple cartridge 22600 therein. In the illustrated example, the elongate channel 22310 comprises a channel bottom 22312 and a pair of upstanding sidewalls 22314. Although not shown, the channel 22310 may be coupled to the elongate shaft assembly 1200 (FIG. 5) by a channel mount feature 20340 (described above) which may facilitate articulation thereof about articulation joint 3020 (FIG. 5). The surgical end effector 22300 further comprises an anvil 22400 that is very similar to anvil 20400 described above, except for the differences discussed below. The anvil 22400 includes an elongate anvil body portion 22402 and an anvil mounting portion 22410 that is configured to interact with an end effector closure tube 3050 (FIG. 5) in the manner described above. The anvil 22400 is pivotally mounted on the elongate channel 22310 by a pair of laterally extending anvil pins or trunnions 22412 that are received in corresponding elongate trunnion slots 22320 formed in the upstanding channel sidewalls 22314. Axial movement of the end effector closure tube 3050 in a distal direction will cause the anvil trunnions 22412 to translate distally up the trunnion slots 22320 to pivot the anvil 22400 to a closed position. Conversely, movement of the end effector closure tube 3050 in a proximal direction will cause the anvil 22400 to pivot to an open position relative to the elongate channel 22310.

Figure 34:
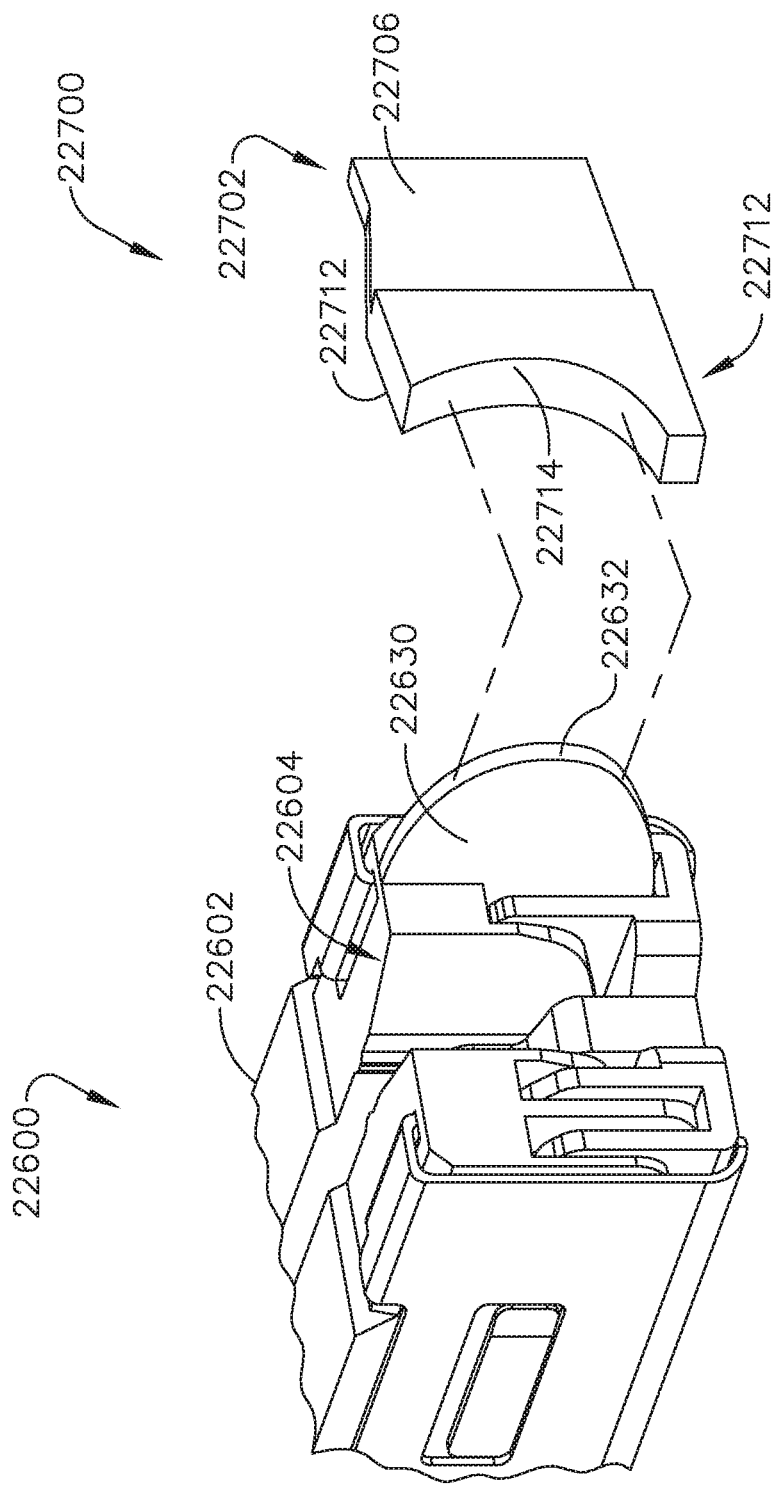
FIG. 34 is a partial perspective view of a proximal end of a compatible surgical staple cartridge of FIG. 33 in relation to a portion of an anvil lock feature of the surgical end effector of FIG. 33.

The end effector 22300 is configured to operably support a surgical staple cartridge 22600 that may be substantially the same as the surgical staple cartridge 20600, except that the anvil unlocking feature or tab 22630 is formed on a right side of a proximal end proximal end portion 22604 of the cartridge body 22602 and has a contoured proximal end surface 22632. In the illustrated example, the contoured proximal end surface 22632 has an arcuate shape. The anvil unlocking feature 22630 is configured to operably interact with an axially movable anvil lock 22702 of the anvil lockout system 22700 that is supported by the channel 22310. In the illustrated example, the anvil lock 22702 is supported for axial movement between a distal locked position and a proximal unlocked position within a proximal end portion 22316 of the elongate channel 22310. In the illustrated example, the anvil lock 22702 comprises an elongate body portion 22706 that has an anvil lock tab 22710 formed on a proximal end thereof and configured to lockingly interact with a lock lug 22413 formed on the anvil mounting portion 22410 of the anvil 22400. See FIG. 33. An actuation tab 22712 is formed on a distal end of the body portion 22706. The actuation tab 22712 has a contoured actuation surface 22714 formed therein that is configured to substantially match or mate with the contoured proximal end surface 22632 on the anvil unlocking feature 22630. See FIG. 34.

Figure 35:
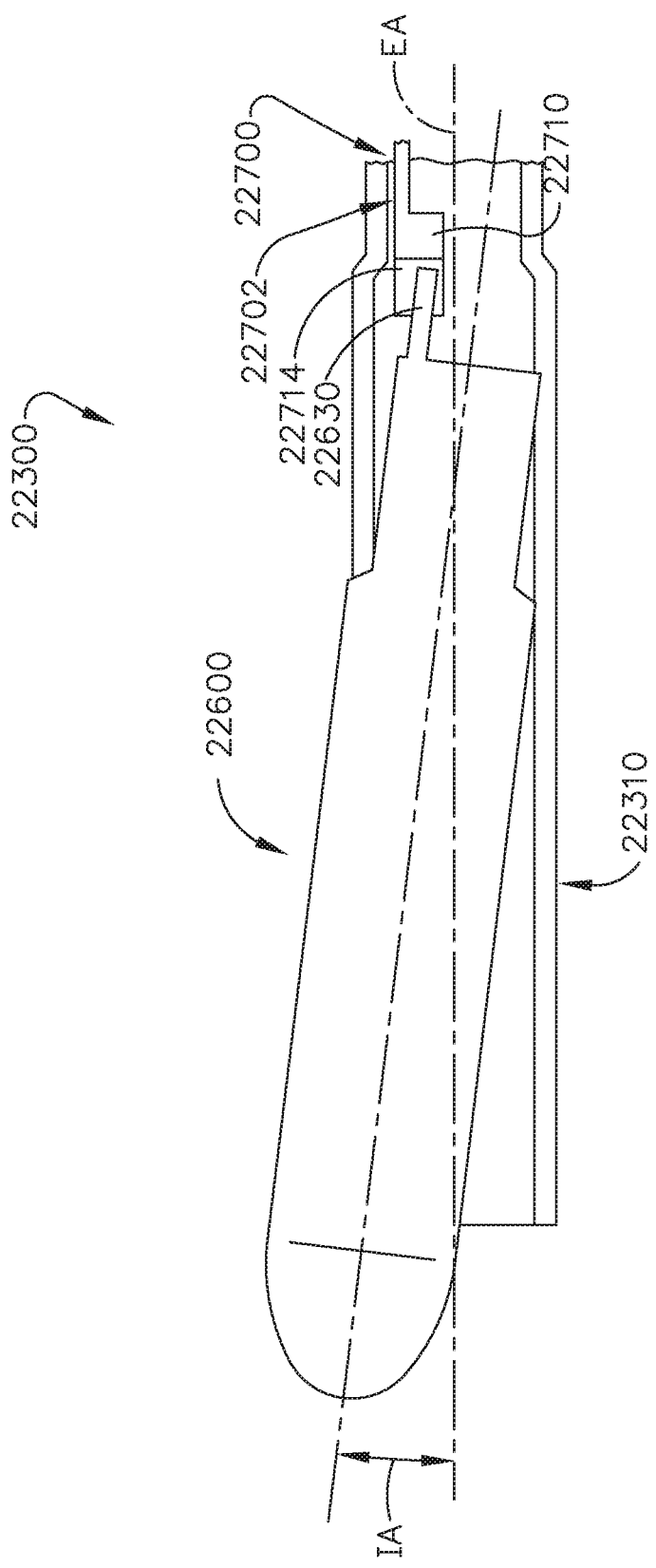
FIG. 35 is a top view of a portion of a channel of the surgical end effector of FIG. 33 and an outline of a compatible surgical staple cartridge of FIG. 33 being inserted therein.

In at least one arrangement, a spring or biasing member 22730 (leaf spring, coil spring, etc.) may be attached to or mounted within the channel 22310 and configured to bias the anvil lock 22702 in the distal direction DD to the locked position wherein the anvil lock tab 22710 thereon is in blocking alignment with the lock lug 22413 on the anvil mounting portion 22410 to prevent closing of the anvil 22400. When a proper or compatible surgical staple cartridge 22600 is operably loaded into the channel 22310, the anvil unlocking feature or tab 22630 is brought into engagement with the contoured surface 22714 on the actuation tab 22712 of the anvil lock 22702. The surgical staple cartridge 22600 is then moved proximally to seat the cartridge 22600 within the channel 22310. As the surgical staple cartridge 22600 is moved proximally, the anvil unlocking feature 22630 contacts the actuation tab 22712 of the anvil lock 22702 and biases the anvil lock 22702 proximally into the unlocked position wherein the anvil lock tab 22710 thereon is moved out of blocking alignment with the lock lug 22413 on the anvil mounting portion 22410 to permit the anvil 22400 to pivot closed. When the surgical staple cartridge 22600 is removed from the channel 22310, the spring 22730 biases the anvil lock 22702 distally back to the locked position. FIG. 35 illustrates that the contoured proximal end 22632 of the anvil unlocking feature 22630 formed on a right side of the proximal end portion 22604 of the cartridge body 22602 and the matching contoured surface 22714 on the actuation tab 22712 of the anvil lock 22702 enable the cartridge 22600 to facilitate unlocking interaction between the unlocking feature 22630 and actuation tab 22712 even when the cartridge is installed at an installation angle IA relative to the central axis EA of the end effector 22300. See FIG. 35.

FIG. 36 illustrates the attempted use of an incompatible cartridge 22600X that lacks an unlocking feature to move the anvil lock 22702 from the locked position to the unlocked position. As can be seen in FIG. 36, the lockout tab 22710 is in blocking alignment with the lock lug 22413 on the anvil 22400 to thereby prevent the anvil 22400 from being closed even after the cartridge 22600X has been seated in the channel 22310.

Figure 37:
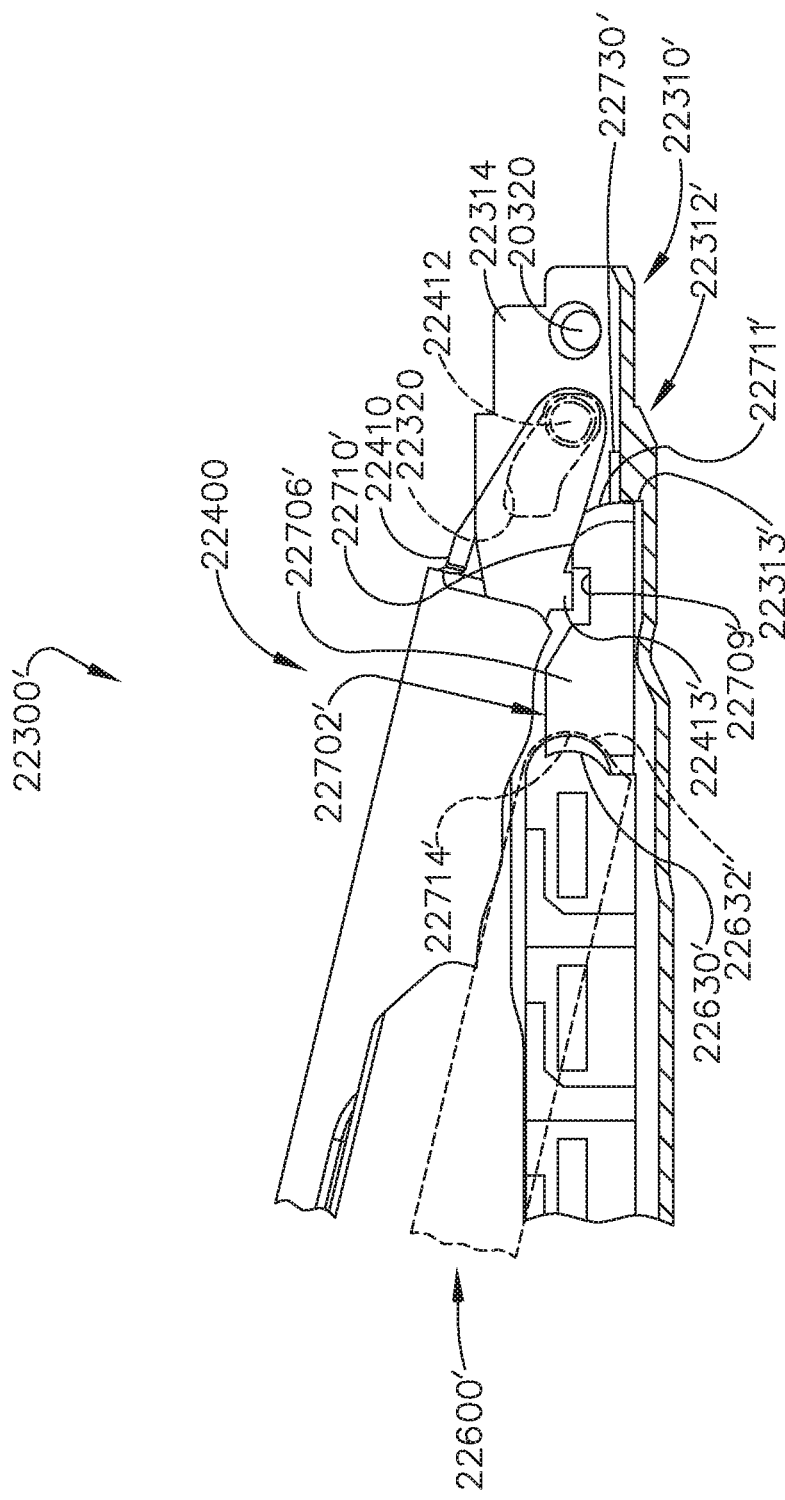
FIG. 37 is a cross-sectional side view of another surgical end effector with an anvil thereof in an open position during installation of a compatible surgical staple cartridge therein.

FIG. 37 illustrates another surgical end effector 22300' that is substantially identical to surgical end effector 22300 described above, except for the noted differences. The end effector 22300' is configured to operably support a staple cartridge 22600' that is substantially the same as cartridge 20600 and includes an anvil unlocking feature or tab 22630' that has a contoured proximal end surface 22632'. In the illustrated example, the anvil lock 22702' comprises an elongate body portion 22706' that has an anvil lock tab 22710' formed on a proximal end 22711' thereof and configured to lockingly interact with a lock lug 22413' formed on the anvil mounting portion 22410 of the anvil 22400. A distal end 22712' of the anvil lock 22702' includes a contoured actuation surface 22714' formed therein that is configured to substantially match or mate with the contoured proximal end surface 22632' on the anvil unlocking feature 22630' in the manners described above. A spring or biasing member 22730' (leaf spring, coil spring, etc.) may be attached to or mounted within the channel 22310' and configured to bias the anvil lock 22702' in the distal direction DD to the locked position wherein the anvil lock tab 22710' thereon is in blocking alignment with the lock lug 22413' on the anvil mounting portion 22410 to prevent closing of the anvil 22400.

When a proper or compatible surgical staple cartridge 22600' is operably loaded into the channel 22310', the anvil unlocking feature or tab 22630' is brought into engagement with the contoured surface 22714' of the anvil lock 22702'. The cartridge 22600' is then moved proximally in a proximal direction PD to seat the cartridge 22600' within the channel 22310'. As the cartridge 22600' is moved proximally, the anvil unlocking feature 22630' contacts the distal end of the anvil lock 22702' and biases the anvil lock 22702' proximally into the unlocked position wherein the anvil lock tab 22710' thereon is moved out of blocking alignment with the lock lug 22413' on the anvil mounting portion 22410 to permit the anvil 22400 to pivot closed. When the cartridge 22600' is removed from the channel 22310', the spring 22730' biases the anvil lock 22702' distally back to the locked position. As can be seen in FIG. 37, when compared to anvil lock 22702 described above, the anvil lock 22702' has a more robust body portion 22706'. In at least one example, a clearance notch 22709' is provided in the body portion 22706' to provide sufficient clearance for the lock lug 22413' when the anvil 22400 is pivoted to the closed position. In addition, a channel stop 22313' is formed on a bottom 22312' of the channel 22310' and is configured for contact with the proximal end 22711' of the anvil lock 22702' when the anvil lock 22702' is in the unlocked position to prevent the anvil lock 22702' from moving any further proximally to ensure that the lock lug 22413' remains aligned with the clearance notch 22709' in the anvil lock 22702' during closing of the anvil 22400.

Figure 38:
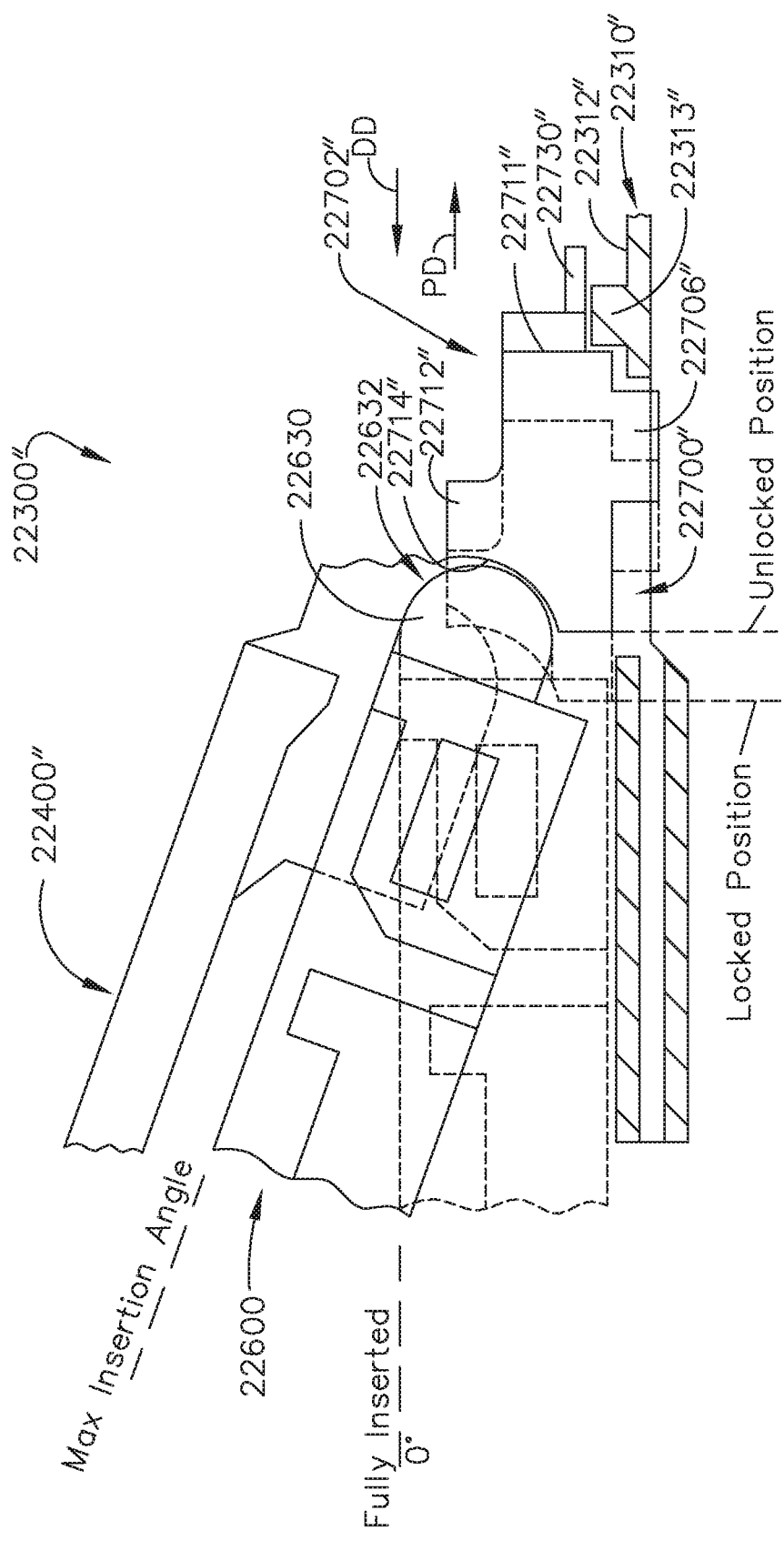
FIG. 38 is a cross-sectional side view of portions of another surgical end effector with an anvil thereof in an open position during installation of a compatible surgical staple cartridge therein.

FIG. 38 illustrates another surgical end effector 22300" that is substantially identical to surgical end effector 22300 described above, except for the noted differences. The end effector 22300" comprises an elongate channel 22310" that includes an anvil 22400" that is pivotally supported thereon. The channel 22310" is configured to operably support a surgical staple cartridge 22600 that is compatible with the staple-forming undersurface of the anvil 22400" and employs an anvil locking system 22700" that is configured to prevent closure of the anvil 22400" unless a surgical staple cartridge 22600 has been operably installed in the end effector 22300". In the illustrated example, the anvil locking system 22700" includes an anvil lock 22702" that comprises a body portion 22706" that has a distal end portion 22712" that is higher than a proximal portion of the body 22706". When the anvil lock 22702" is in its distal-most locked position, a portion of the anvil 22400" contacts the higher distal end portion 22712" to prevent the anvil 22400" from being closed. The distal end portion 22712" of the anvil lock 22702" includes a contoured actuation surface 22714" that is configured to substantially match or mate with the contoured proximal end surface 22632 on the anvil unlocking feature 22630 formed on the cartridge 22600 in the manners described above. A spring or biasing member 22730" (leaf spring, coil spring, etc.) may be attached to or mounted within the channel 22310" and be configured to bias the anvil lock 22702" in the distal direction DD to the locked position wherein the distal end portion 22712" is in blocking alignment with corresponding portion of the anvil 22400" to prevent closing of the anvil 22400".

When a proper or compatible surgical staple cartridge 22600 is operably loaded into the channel 22310", the anvil unlocking feature 22630 on the cartridge 22600 is brought into engagement with the contoured surface 22714" on the distal end 22712" of the anvil lock 22702". The cartridge 22600 is then moved proximally to seat the cartridge 22600 within the channel 22310". As the cartridge 22600 is moved proximally, the anvil unlocking feature 22630 contacts the distal end 22712" of the anvil lock 22702" and biases the anvil lock 22702" proximally into the unlocked position wherein the distal end portion 22712" is moved out of blocking alignment with the corresponding portion of the anvil 22400" to permit the anvil 22400" to pivot to a closed position. When the cartridge 22600 is removed from the channel 22310", the spring 22730" biases the anvil lock 22702" distally back to the locked position. As can also be seen in FIG. 38, a channel stop 22313" is formed on a bottom 22312" of the channel 22310" and is configured for contact with a proximal end 22711" of the anvil lock 22702" to prevent the cartridge 22600 from being inserted too far proximally into the end effector 22300".

Figure 39:
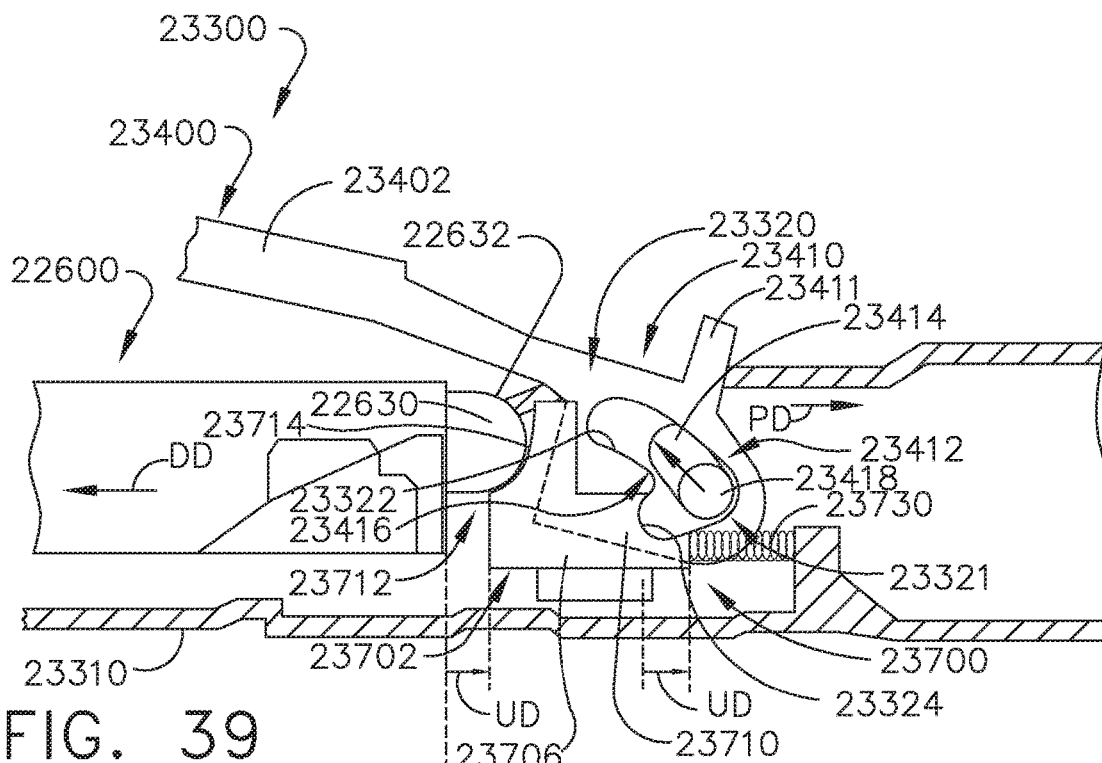
FIG. 39 is a cross-sectional side view of portions of another surgical end effector with an anvil thereof in an open position during installation of a compatible surgical staple cartridge therein.
Figure 40:
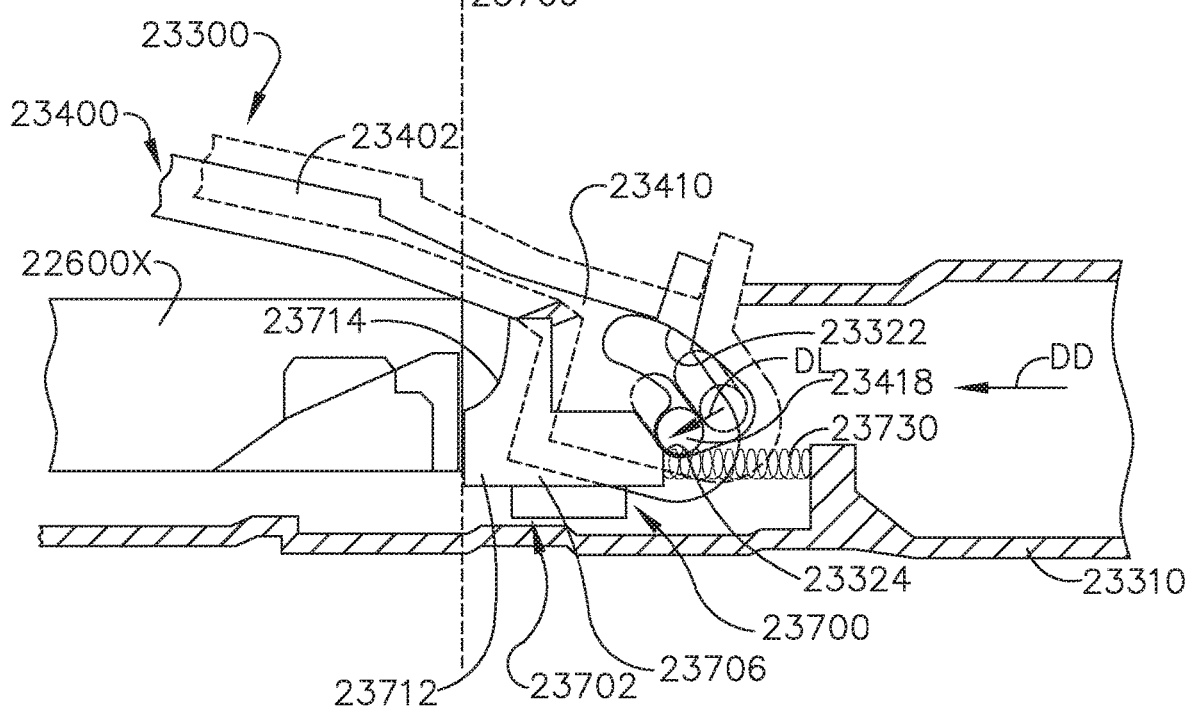
FIG. 40 is a cross-sectional side view of the end effector of FIG. 39 during installation of an incompatible cartridge therein.

FIGS. 39 and 40 illustrate another surgical end effector 23300 that is similar to the other surgical end effectors described herein with the exception of the various differences noted below. The end effector 23300 comprises an elongate channel 23310 that includes an anvil 23400 that is pivotally supported thereon. The channel 23310 is configured to operably support a surgical staple cartridge 22600 that is compatible to the staple-forming undersurface of the anvil 23400 and employs an anvil locking system 23700 that is configured to prevent closure of the anvil 23400 unless a cartridge 22600 has been operably installed in the end effector 23300. In the illustrated example, anvil locking system 23700 comprises an anvil lock 23702 comprising a body portion 23706 that has a distal end portion 23712. The distal end portion 23712 of the anvil lock 23702 includes a contoured actuation surface 23714 that is configured to substantially match or mate with the contoured proximal end surface 22632 on the anvil unlocking feature 22630 that is formed on the cartridge 22600 in the manners described above. A spring or biasing member 23730 is mounted within the channel 23310 and is configured to bias the anvil lock 23702 in the distal direction DD to a "locked" position.

In the illustrated example, the anvil 23400 includes an elongate anvil body 23402 that an anvil mounting portion 23410 that is configured to interact with the end effector closure tube 3050 (FIG. 5) in the manner described above. The anvil 23400 is pivotally mounted on the elongate channel 22310 by a pair of laterally extending trunnion formations 23412 that are received in corresponding trunnion slots 23320 formed in upstanding sidewalls of the channel 23310. At least one trunnion formation 23412 comprises a laterally protruding actuator lobe 23414 that defines an actuator ledge 23416. A trunnion pin 23418 protrudes outwardly from the actuator lobe 23414 and is sized to translate and pivot within a corresponding trunnion slot 23320.

As can be seen in FIG. 39, at least one trunnion slot 23320 comprises an arcuate actuation portion 23322 and a locking offset portion 23324 that is formed at a proximal end 23321 of the trunnion slot 23320. FIG. 39 illustrates insertion of a cartridge 22600 into the elongate channel 23310. To install a cartridge 22600 into the elongate channel 23310, the anvil 23400 is first moved to an open position. This may be accomplished by actuating the closure system to move the end effector closure tube 3050 (FIG. 5) in a proximal direction PD. As the closure tube 3050 is moved proximally, it interacts with an opening tab 23411 formed on the anvil mounting portion 23410. As the closure tube 3050 interacts with the anvil mounting portion 23410, the anvil 23400 translates proximally and starts to pivot open which results in the trunnion formation 23412 translating down the arcuate actuation portion 23322 of the corresponding trunnion slot 23320 and into the proximal end 23321 of the trunnion slots 23320 when the anvil 23400 reaches its fully open position.

During installation of a proper or compatible surgical staple cartridge 22600 into the channel 23310, the anvil unlocking feature or tab 22630 is brought into engagement with the contoured surface 23714 on the distal end 23712 of the anvil lock 23702. The cartridge 22600 is then moved proximally to seat the cartridge 22600 within the channel 22310. As the cartridge 22600 is moved proximally, the anvil unlocking feature 22630 contacts the distal end 23712 of the anvil lock 23702 and biases the anvil lock 23702 proximally an unlocking distance UD to bring a proximal end 23710 of the anvil lock body 23706 into engagement with actuator lobe 23414 on at least one trunnion formation 23412 to move the trunnion formation 23412 into a position wherein the trunnion formation 23412 can translate up the arcuate actuation portion 23322 of the corresponding trunnion slot 23320 when a closing motion is applied to the anvil mounting portion 23410. Stated another way, the proximal end 23710 of the anvil lock 23702 prevents the trunnion formation 23412 from entering the locking offset portion 23324 formed at the proximal end 23321 of the trunnion slot 23320 to enable the trunnion formation 23412 to progress into the arcuate actuation portion 23322 of the trunnion slot 23320.

FIG. 40 illustrates an attempted insertion of an incompatible cartridge 22600X that lacks the requisite unlocking feature or tab 22630 to move the anvil lock 23702 out of the distal locked position. If the user nonetheless seats the incompatible cartridge 22600X in the channel 23310 and then attempts to close the anvil 23400, the anvil locking system 23700 will prevent closure of the anvil 23400. For example, to close the anvil 23400, the closure system is activated to move the closure tube (or other closure member) distally into operably contact with the anvil mounting portion 23410 of the anvil 23400 to apply closure motions thereto. The initial application of closure motions to the anvil mounting portion 23410 causes the anvil mounting portion 23410 to move downwardly (arrow DL in FIG. 40) which results in the anvil trunnion formations 23412 entering the locking offset portions 23324 formed in the trunnion slots 23320. Thus, the anvil trunnion formations 23412 cannot translate into the arcuate actuation portion 23322 of the corresponding trunnion slot 23320 during the application of the closure motion to the anvil 23400 and the anvil 23400 is then prevented from closing.

FIG. 41 illustrates a portion of an alternative anvil 23400' that comprises an anvil mounting portion 23410' that has trunnion formations 23412' formed thereon. Each trunnion formation 23412' comprises a laterally protruding actuator lobe 23414' that defines an actuator ledge 23416' that is configured to interact with an anvil locking system 23700 in the manner described above. As can be seen in FIG. 41, the actuator ledge 23416' is vertically offset (distance OD) from a bottom surface 23415' of the anvil mounting portion 23410'. A trunnion pin 23418' protrudes outwardly from the actuator lobe 23414' and is sized to translate and pivot within a corresponding trunnion slot 23320. In this example, the trunnion pin 23418' has a trunnion pin diameter TRD that is approximately equal to the width LW of the actuator lobe 23414'.

FIG. 42 illustrates a portion of an alternative anvil 23400" that comprises an anvil mounting portion 23410" that has trunnion formations 23412" formed thereon. Each trunnion formation 23412" comprises a laterally protruding actuator lobe 23414" that defines an actuator ledge 23416" that is configured to interact with an anvil locking system 23700 in the manner described above. As can be seen in FIG. 42, the actuator ledge 23416" is coextensive with (e.g., not offset from) a bottom edge 23415" of the anvil mounting portion 23410". A trunnion pin 23418" protrudes outwardly from the actuator lobe 23414" and is sized to translate and pivot within a corresponding trunnion slot 23320. In this example, the trunnion pin 23418" has a trunnion pin diameter TRD' that is approximately equal to the width LW' of the actuator lobe 23414'.

Figure 43:
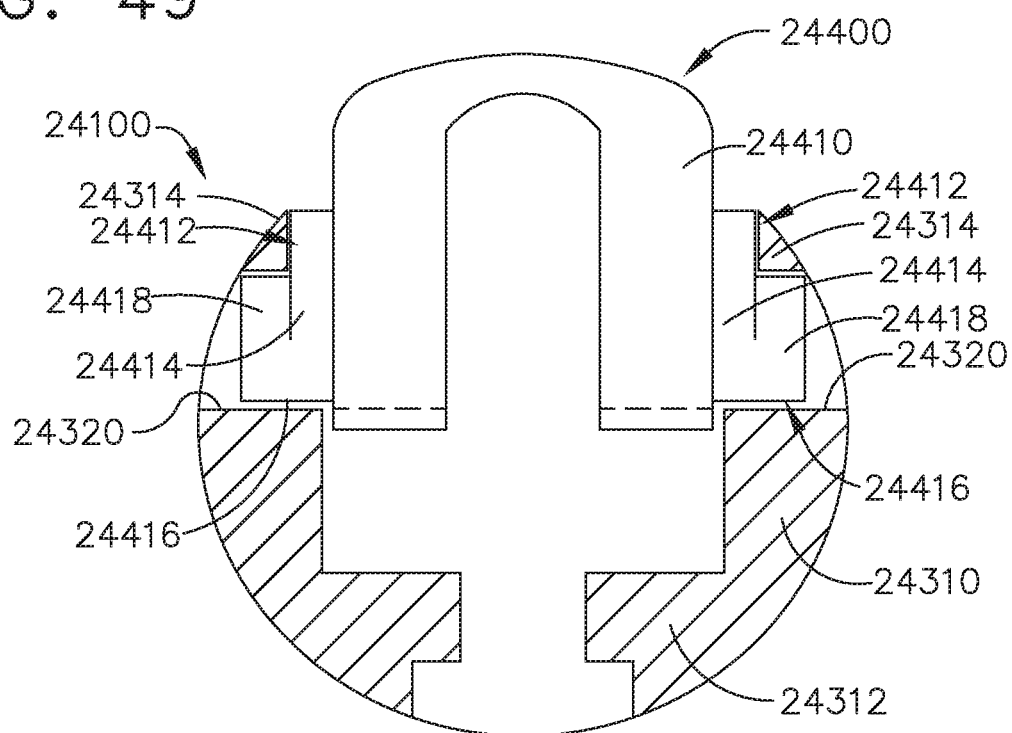
FIG. 43 is a partial cross-sectional end view of portions of another surgical end effector.
Figure 44:
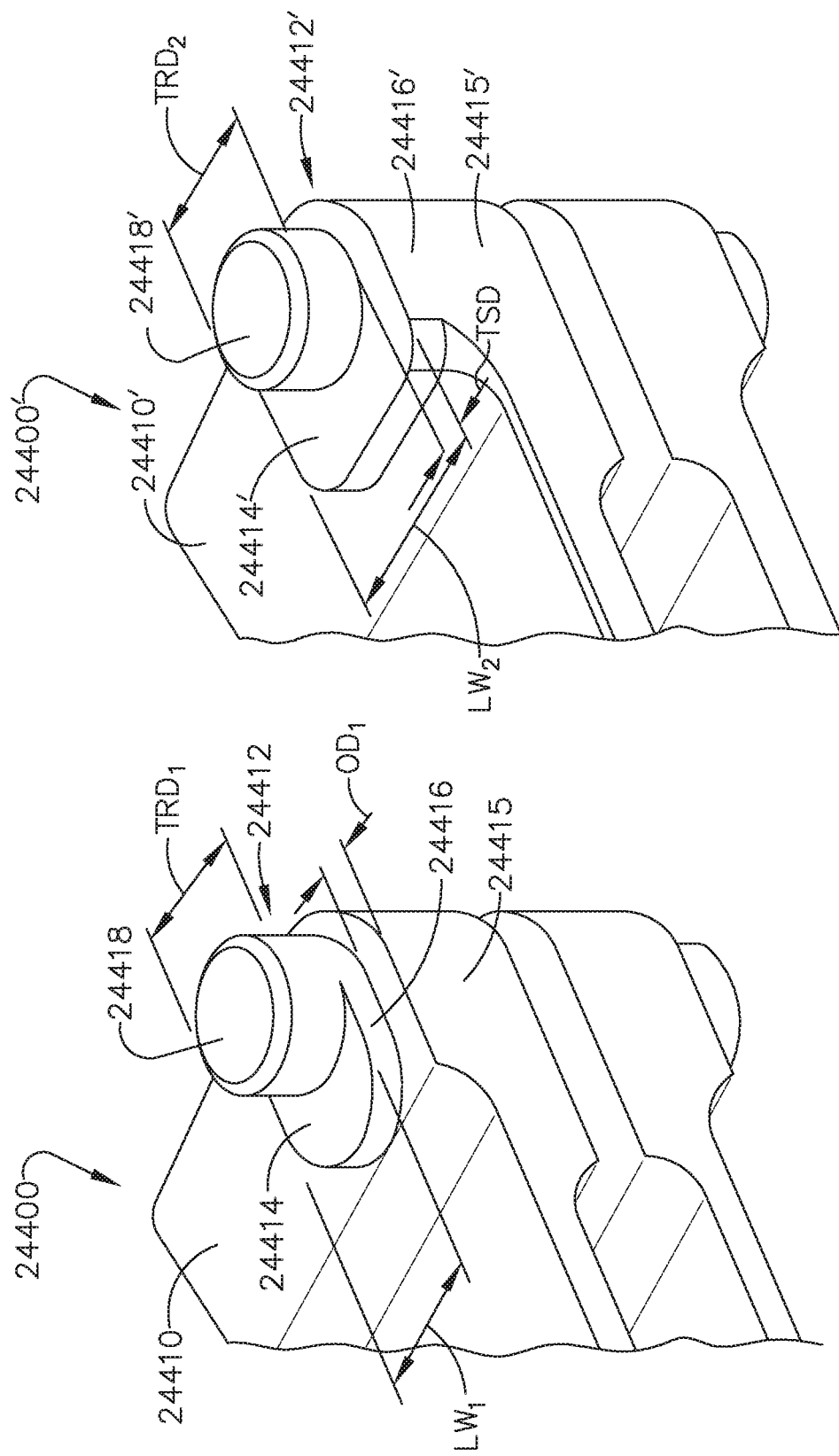
FIG. 44 is a partial perspective view of a proximal end portion of the anvil of the surgical end effector of FIG. 43.

FIG. 43 is a partial cross-sectional end elevational view of a surgical end effector 24100 that comprises an anvil 24400 that is pivotally supported on an elongate channel 24310. The anvil 24400 comprises an anvil mounting portion 24410 that has trunnion formations 24412 formed thereon. Each trunnion formation 24412 comprises a laterally protruding actuator lobe 24414 that defines a bottom lobe surface 24416 that is configured to interact with an anvil locking system 24700 in the manner described above. As can be seen in FIG. 44, the bottom lobe surface 24416 is vertically offset (distance $OD_1$) from a bottom surface 24415 of the anvil mounting portion 24410. A trunnion pin 24418 protrudes outwardly from the actuator lobe 24414 and is sized to translate and pivot within a corresponding trunnion slot 24320 formed in the elongate channel 24310. In this example, the trunnion pin 24418 has a trunnion pin diameter $TRD_1$ that is approximately equal to the width $LW_1$ of the actuator lobe 24414.

Figure 45:
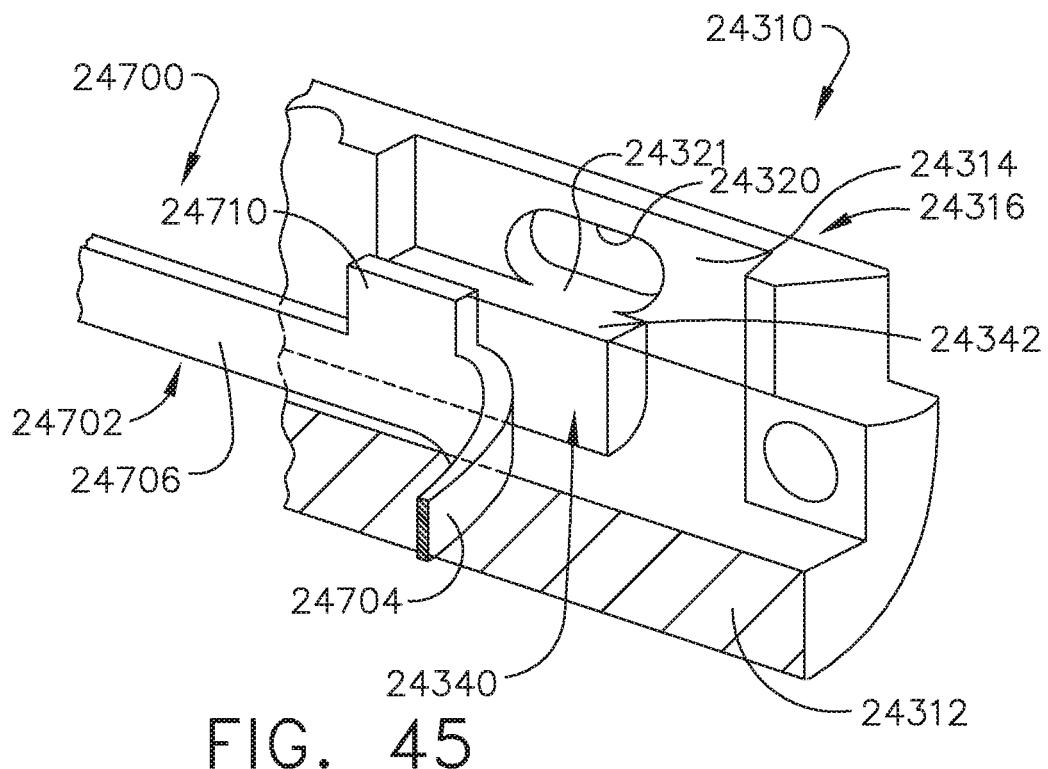
FIG. 45 is a partial cross-sectional perspective view of a portion of a channel and anvil lock of the surgical end effector of FIG. 43, with the anvil lock in a locked position.

Channel 20310 comprises a channel bottom 24312 and a pair of upstanding sidewalls 24314. The channel 24310 may be coupled to an elongate shaft assembly 1200 (FIG. 5) by a channel mount feature 20340 which may facilitate articulation thereof about articulation joint 3020 (FIG. 5). FIG. 45 illustrates a portion of a proximal end 24316 of the channel 24310. In one example, each channel wall 24314 has a trunnion slot 24320 formed therein. In the illustrated arrangement, a lobe ledge 24340 is formed in each channel wall 24314 such that a top surface 24342 of the lobe ledge 24340 is coextensive with a bottom surface 24321 of the corresponding trunnion slot 24320. Each trunnion 24418 is received within a corresponding trunnion slot 24320 and is free to rotate and translate therein.

Still referring to FIG. 45, a portion of an anvil lock 24702 of the anvil locking system 24700 is shown. The anvil lock 24702 operates in the same manner as the anvil lock 20702 described above and includes a lockout body 24706 that has an actuator tab (not shown) that is formed on a distal end thereof that is configured to be contacted by an unlocking feature that protrudes proximally from a compatible cartridge. The anvil lock 24702 may be fabricated from spring steel or other suitable metal and include a proximal biasing arm 24704 that may be configured to be seated in a transverse spring mounting slot (not shown) that is provided in the body portion of a channel mount feature (not shown). The anvil lock 24702 further includes an upwardly extending anvil lockout tab 24710 that protrudes therefrom that is configured to extend above the corresponding lobe ledge 24340 and contact a corresponding lobe 24414 as will be described below.

Figure 47:
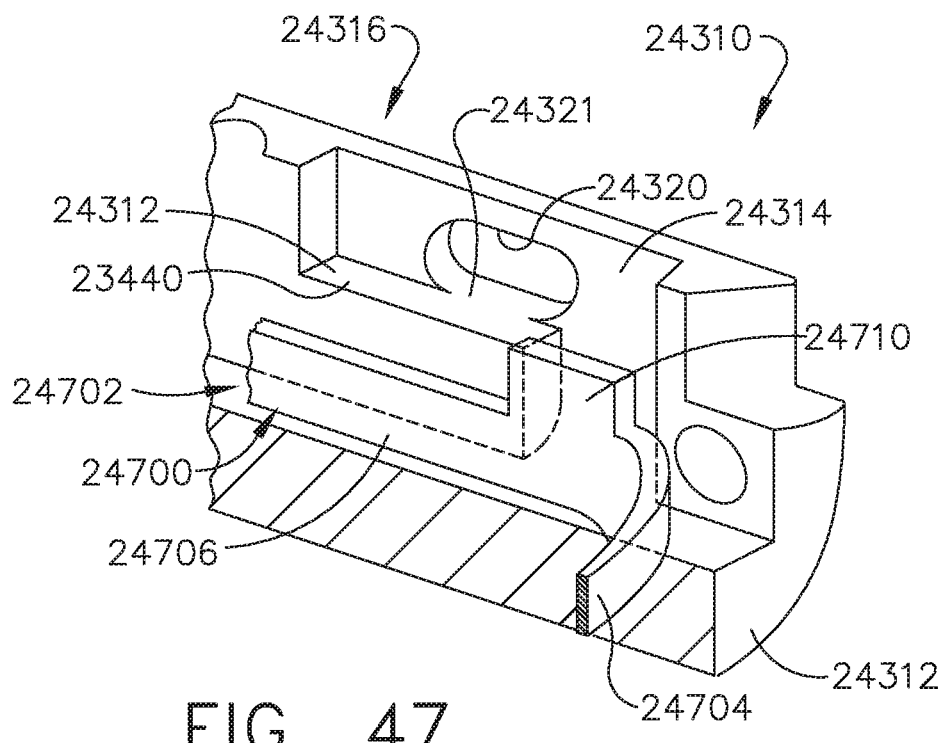
FIG. 47 is another partial cross-sectional perspective view of a portion of the channel and anvil lock of the surgical end effector of FIG. 43, with the anvil lock in an unlocked position.
Figure 46:
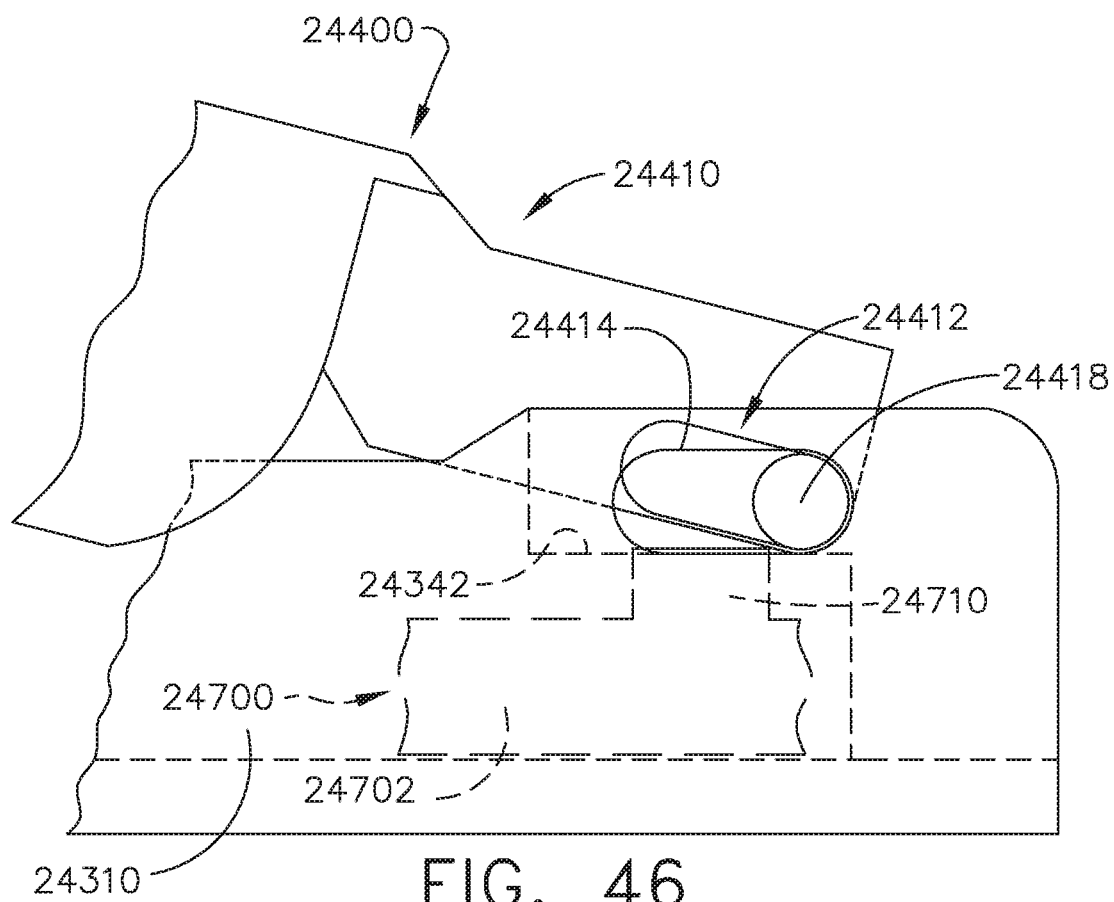
FIG. 46 is a partial side elevational view of the surgical end effector of FIG. 43 with the anvil in an open position and the anvil lock thereof shown in a locked position in phantom lines.
Figure 48:
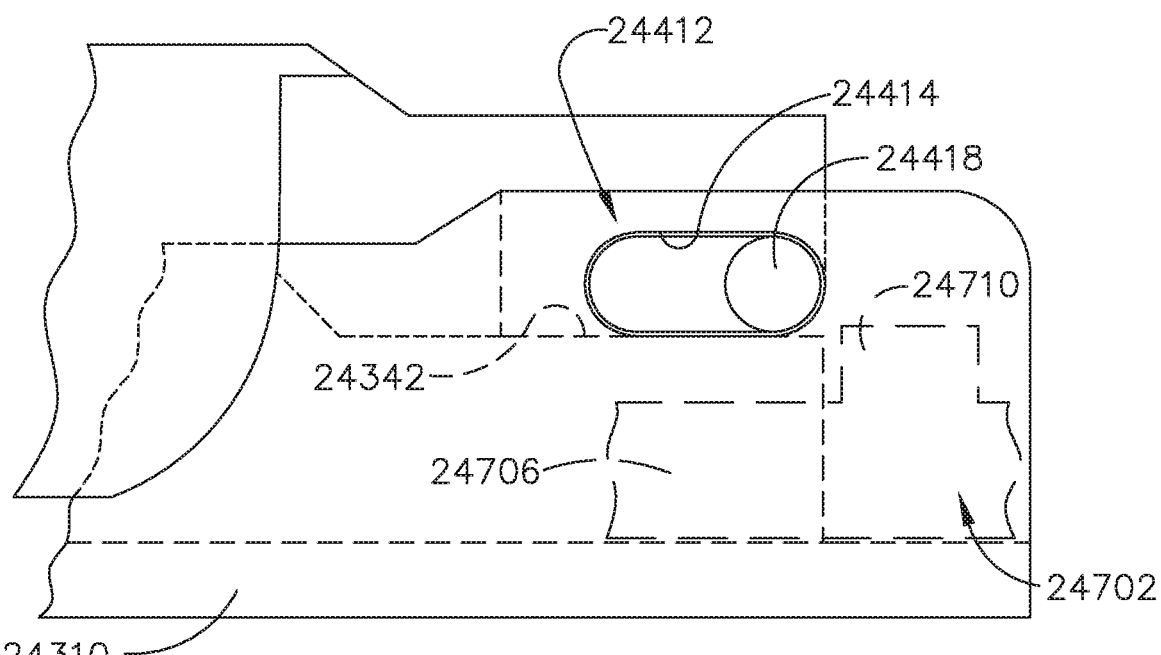
FIG. 48 is another partial side elevational view of the surgical end effector of FIG. 43 with the anvil in a closed position and the anvil lock thereof shown in the unlocked position in phantom lines.

FIGS. 45 and 46 illustrate the anvil lock 24702 in the locked position wherein the anvil 24400 is pivoted to an open position. This may occur when no cartridge has been inserted into the channel 24310 or a non-compatible cartridge (e.g. a cartridge that lacks, among other things, the proper anvil unlocking feature that is necessary to bias the anvil lock spring proximally) has been inserted into the channel 24310. Should the user unwittingly attempt to close the anvil 24400 when the anvil lock 24702 is in the distal locked position shown in FIGS. 45 and 46, the corresponding lobe 24414 will contact the anvil lockout tab 24710 and prevent the anvil 24400 from pivoting to the closed position. FIGS. 47 and 48 illustrate the position of the anvil lock 24702 in the proximal unlocked position wherein the anvil lockout tab 24710 is positioned proximal to the lobe 24414 to permit the lobe 24414 to pivot to the closed position.

Figure 49:
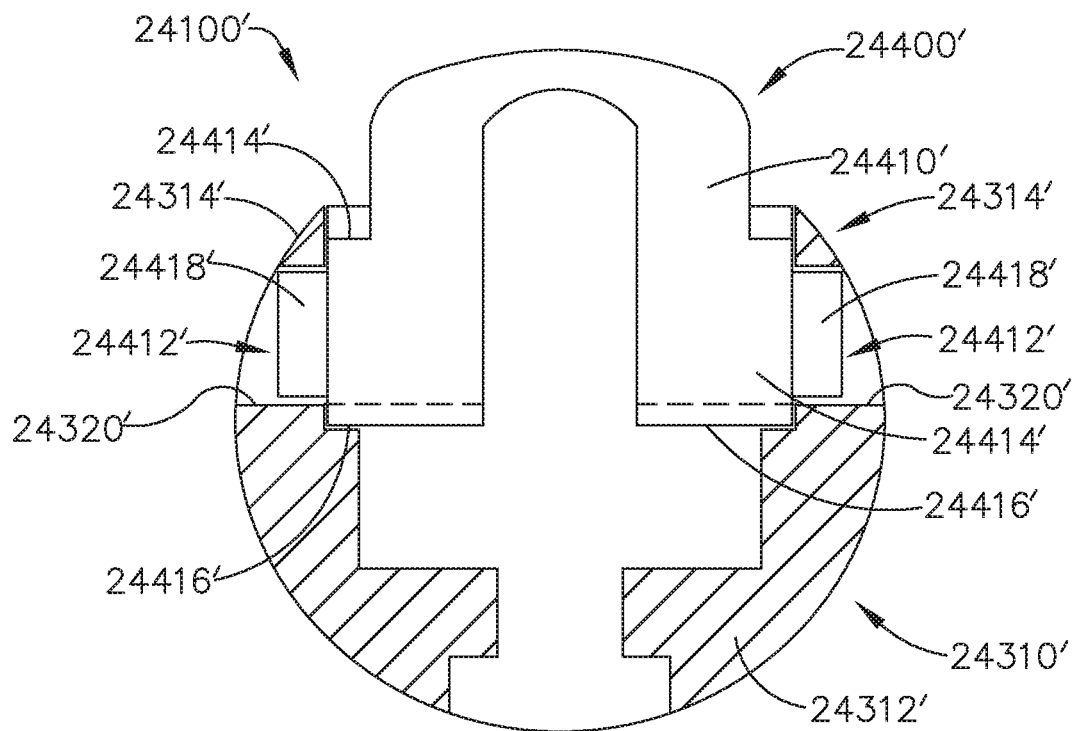
FIG. 49 is a partial cross-sectional end view of portions of another surgical end effector.

FIG. 49 is a partial cross-sectional end elevational view of a surgical end effector 24100' that comprises an anvil 24400' that is pivotally supported on an elongate channel 24310'. The anvil 24400' comprises an anvil mounting portion 24410' that has trunnion formations 24412' formed thereon. Each trunnion formation 24412' comprises a laterally protruding actuator lobe 24414' that defines a bottom lobe surface 24416' that is configured to interact with an anvil locking system 24700' in the manner described above. As can be seen in FIG. 50, the bottom lobe surface 24416' is coextensive with a bottom surface 24415' of the anvil mounting portion 24410'. A trunnion pin 24418' protrudes outwardly from the actuator lobe 24414' and is sized to translate and pivot within a corresponding trunnion slot 24320' formed in the elongate channel 24310'. In this example, the trunnion pin 24418' has a trunnion pin diameter $TRD_2$ that is smaller than the width $LW_2$ of the actuator lobe 24414'.

Figure 51:
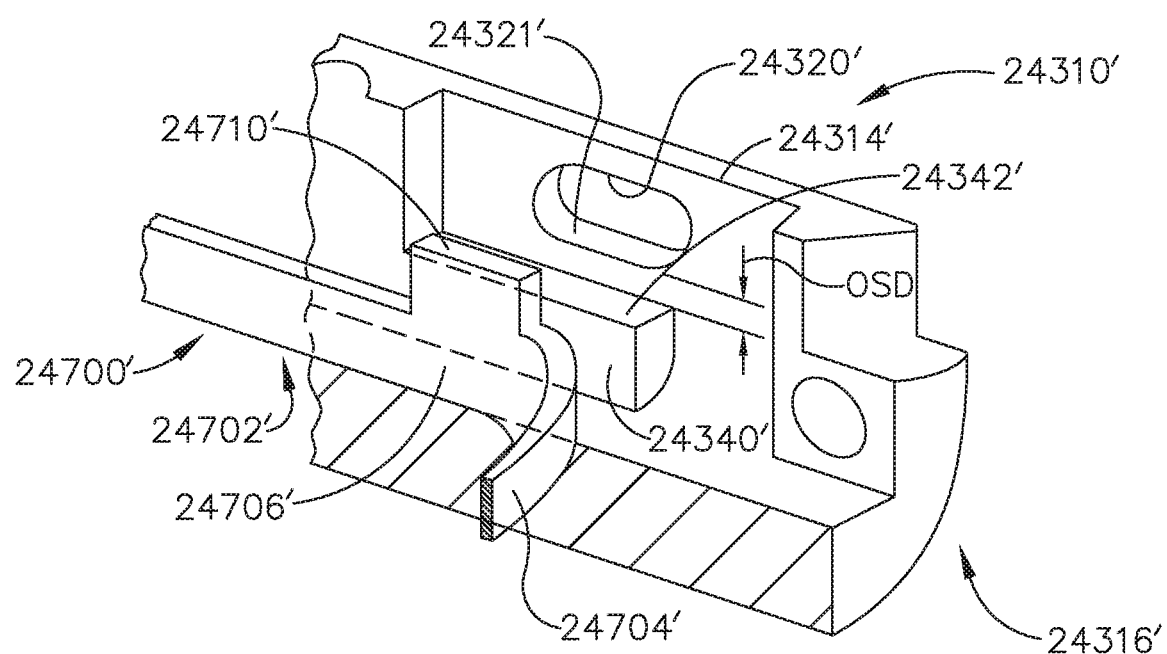
FIG. 51 is a partial cross-sectional side view of a portion of a channel and anvil lock of the surgical end effector of FIG. 49, with the anvil lock in a locked position.

Channel 20310' comprises a channel bottom 24312' and a pair of upstanding sidewalls 24314'. The channel 24310' may be coupled to an elongate shaft assembly 1200 (FIG. 5) by a channel mount feature 20340 which may facilitate articulation thereof about articulation joint 3020 (FIG. 5). FIG. 51 illustrates a portion of a proximal end 24316' of the channel 24310'. In one example, each channel wall 24314' has a trunnion slot 24320' formed therein. In the illustrated arrangement, a lobe ledge 24340' is formed in each channel wall 24314' such that a top surface 24342' of the lobe ledge 24340' is offset vertically from a bottom surface 24321' of the corresponding trunnion slot 24320' an offset distance OSD. Offset distance OSD may be approximately equal to a distance TSD between the trunnion pin 24418' and the bottom lobe surface 24416'. See FIG. 50. Each trunnion pin 24418' is received within a corresponding trunnion slot 24320' and is free to rotate and translate therein.

Still referring to FIG. 51, a portion of an anvil lock 24702' of the anvil locking system 24700' is shown. The anvil lock 24702' operates in the same manner as the anvil lock 20702 described above and includes a lockout body 24706' that has an actuator tab (not shown) formed on a distal end thereof that is configured to be contacted by an unlocking feature that protrudes proximally from a compatible cartridge. The anvil lock 24702' may be fabricated from spring steel or other suitable metal and include a proximal biasing arm 24704' that may be configured to be seated in a transverse spring mounting slot (not shown) provided in the body portion of a channel mount feature (not shown). The anvil lock 24702' further includes an upwardly extending anvil lockout tab 24710' that protrudes therefrom that is configured to extend above the corresponding lobe ledge 24340' and contact a corresponding lobe 24414' as was described above.

FIG. 51 illustrates the anvil lock 24702' in the locked position wherein the anvil 24400 is pivoted to an open position. This may occur when no cartridge has been inserted into the channel or a non-compatible cartridge (e.g. a cartridge that lacks, among other things, the proper anvil unlocking feature that is required to bias the anvil lock spring proximally) has been inserted into the channel 24310'. Should the user unwittingly attempt to close the anvil 24400' when the anvil lock 24702' is in the distal locked position shown in FIG. 45, the corresponding lobe 24414' will contact the anvil lockout tab 24710' and prevent the anvil 24400' from pivoting to the closed position. Once a compatible surgical staple cartridge has been loaded into the end effector 24100', the anvil lock 24702' will be biased to the unlocked position (see e.g., FIG. 47) and the anvil 24400' will be free to pivot to the closed position.

Figure 52:
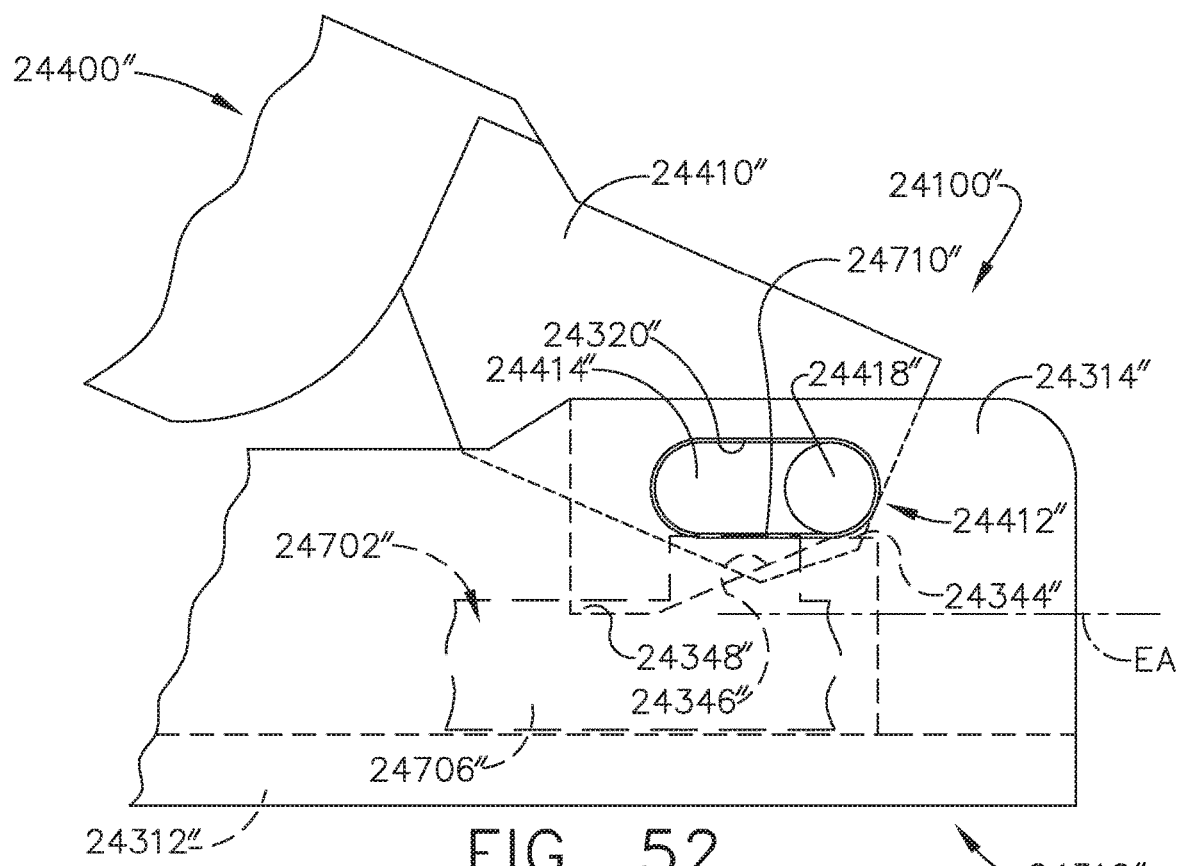
FIG. 52 is a partial side elevational view of another surgical end effector with an anvil thereof in an open position and an anvil lock thereof shown in a locked position in phantom lines.

FIG. 52 depicts a portion of a surgical end effector 24100" that comprises an anvil 24400" that is pivotally supported on an elongate channel 24310". The anvil 24400" comprises an anvil mounting portion 24410" that has trunnion formations 24412" formed thereon. As can be seen in FIGS. 53 and 54, each trunnion formation 24412" comprises a laterally protruding actuator lobe 24414" that defines a bottom lobe surface 24416" that is configured to interact with an anvil locking system 24700" in the manner described above. As can be seen in FIG. 53, the actuator lobe 24414", as well as the bottom lobe surface 24416" of the actuator lobe 24414", are located at an angle relative to an end effector axis EA as well as a bottom edge 24419" of the anvil mounting portion 24410" and/or the bottom 24312" of the channel 24310". As further illustrated in FIG. 53, the bottom lobe surface 24416" is parallel to a lobe axis LBA that is located at a lobe angle LA relative to the end effector axis EA. A trunnion pin 24418" protrudes outwardly from the actuator lobe 24414" and is sized to translate and pivot within a corresponding trunnion slot 24320" that is formed in the elongate channel 24310". See FIG. 55. In this example, the trunnion pin 24418" has a trunnion pin diameter $TRD_3$ that is equal to the width $LW_3$ of the actuator lobe 24414".

Figure 55:
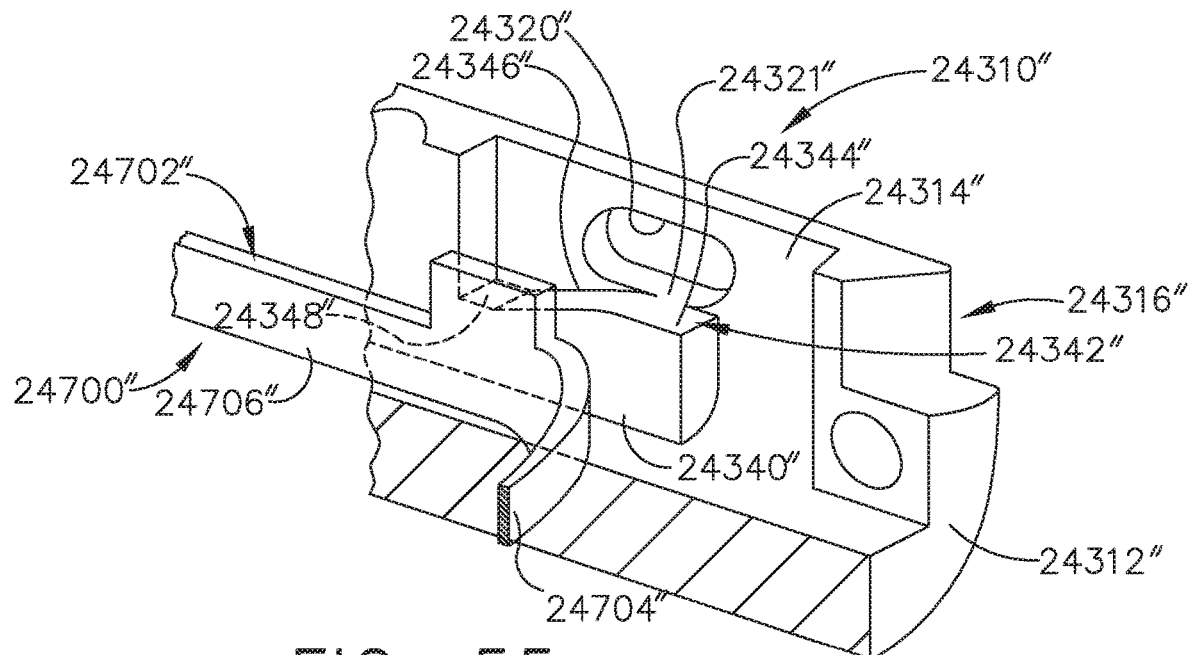
FIG. 55 is a partial cross-sectional perspective view of a portion of a channel and anvil lock of the surgical end effector of FIG. 52 with the anvil lock in a locked position.
Figure 56:
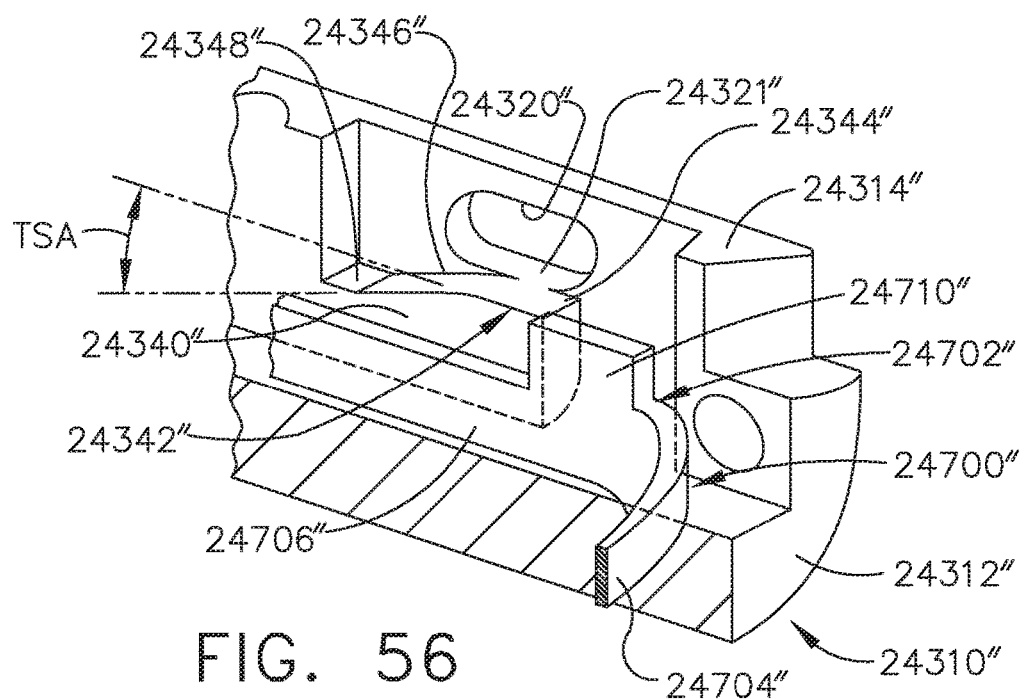
FIG. 56 is another partial cross-sectional perspective view of a portion of the channel and anvil lock of the surgical end effector of FIG. 52, with the anvil lock in an unlocked position.

Referring to FIG. 55, the channel 24310" comprises a channel bottom 24312" and a pair of upstanding sidewalls 24314". The channel 24310" may be coupled to an elongate shaft assembly 1200 (FIG. 5) by a channel mount feature 20340 which may facilitate articulation thereof about articulation joint 3020 (FIG. 5) in the various manners described herein. FIG. 55 illustrates a portion of a proximal end 24316" of the channel 24310". In one example, each channel wall 24314" has a trunnion slot 24320" formed therein. In the illustrated arrangement, a lobe ledge 24340" is formed in each channel wall 24314" such that a proximal surface portion 24344" of a top surface 24342" of the lobe ledge 24340" is coextensive with a bottom surface 24321" of the corresponding trunnion slot 24320". In the illustrated arrangement, the bottom surface 24321" of the trunnion slot 24320" is approximately parallel to the end effector axis EA and/or the bottom 24312" of the channel 24310". As can be seen in FIG. 56, a ramped portion 24346" of the top surface 24342" extends distally from the proximal surface portion 24344" at an angle TSA and terminates in a horizontal distal surface portion 24348". In one arrangement, for example, the distal surface portion 24348" is approximately parallel with the end effector axis EA and/or the bottom 24312" of the channel 24310" and the angle TSA=angle LA. However, angle TSA may be different from angle LA in other embodiments. Each trunnion 24418" is received within a corresponding trunnion slot 24320" and is free to rotate and translate therein.

Referring to FIGS. 55 and 56, a portion of an anvil lock 24702" of the anvil locking system 24700" is shown. The anvil lock 24702" operates in the same manner as the anvil lock 20702 described above and includes a lockout body 24706" that has an actuator tab (not shown) formed on a distal end thereof that is configured to be contacted by an unlocking feature that protrudes proximally from a compatible surgical staple cartridge. The anvil lock 24702" may be fabricated from spring steel or other suitable metal and include a proximal biasing arm 24704" that may be configured to be seated in a transverse spring mounting slot (not shown) that is provided in the body portion of a channel mount feature (not shown). The anvil lock 24702" further includes an upwardly extending anvil lockout tab 24710" that protrudes therefrom and is configured to extend above the distal surface portion 24348" of the corresponding lobe ledge 24340" and be even or level with the proximal surface portion 24344" of the lobe ledge 24340".

Figure 57:
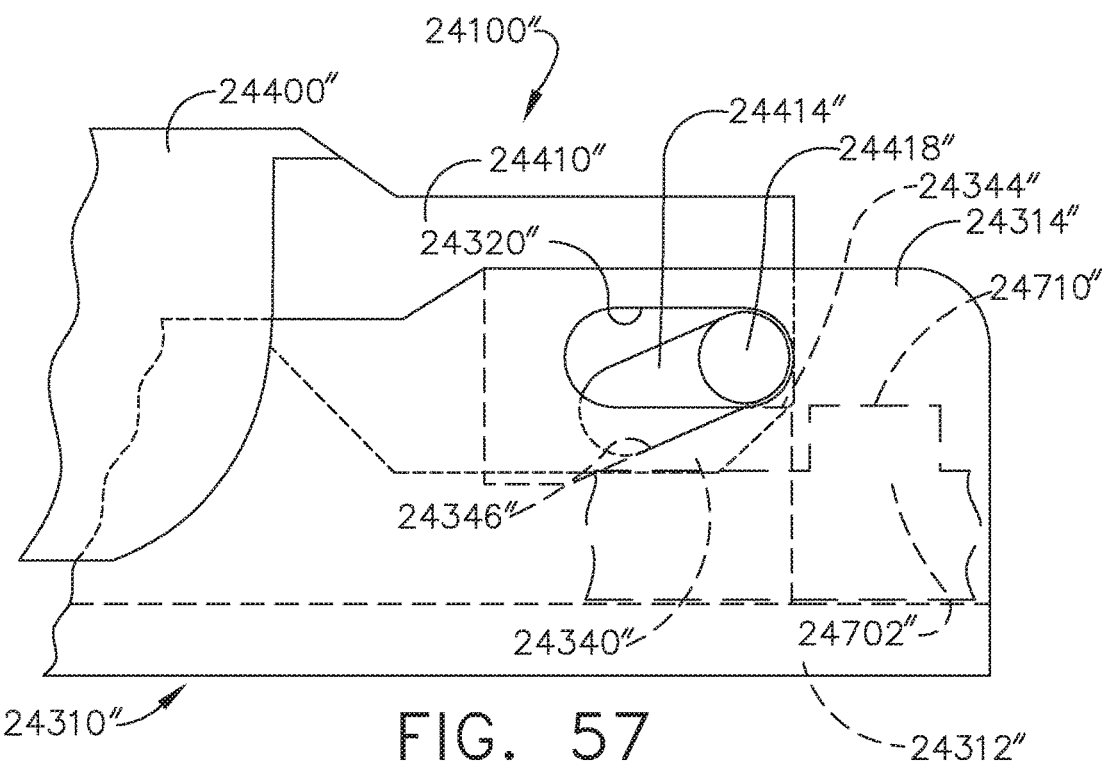
FIG. 57 is a partial side elevational view of the surgical end effector of FIG. 52 with the anvil in a closed position and the anvil lock thereof shown in the unlocked position in phantom lines.

FIG. 55 illustrates the anvil lock 24702' in the distal, locked position with the anvil 24400" pivoted to an open position. This may occur when no surgical staple cartridge has been inserted into the channel 24310" or a non-compatible surgical staple cartridge (e.g., a surgical staple cartridge that lacks, among other things, a proper anvil unlocking feature required to bias the anvil lock 24702" proximally) has been inserted into the channel 24310". When the anvil lock 24702" is in that position, the anvil trunnions 24418" are located in the proximal end of their respective trunnion slot 24320" and the bottom lobe surface 24416" of at least one lobe 24414" is resting on the proximal surface portion 24344" of the corresponding lobe ledge 24340" as well as on the anvil lockout tab 24710". Should the user unwittingly attempt to close the anvil 24400" when the anvil lock 24702" is in the distal, locked position shown in FIGS. 52 and 55, the anvil lockout tab 24710" will prevent the lobe 24414" from pivoting downward onto the ramp surface portion 24346" of the lobe ledge 24340" which prevents the anvil 24400" from pivoting to the closed position. See FIG. 52. Once a compatible surgical staple cartridge has been loaded into the end effector 24100", the anvil lockout feature thereon will bias the anvil lock 24702" proximally into to the unlocked position. See FIGS. 56 and 57. When the anvil lock 24702" is in the proximal unlocked position, the anvil lock out tab 24710" is locked proximal to the ramp surface 24346" on the lobe ledge 24340" to thereby permit the lobe 24414" to pivot downwardly thereon which results in the closure of the anvil 24400".

FIG. 58 depicts a proximal portion of another anvil 24400''' that is configured to be pivotally supported in an elongate channel 24310''' that is similar to channel 24310" except for the differences discussed below. The anvil 24400''' comprises an anvil mounting portion 24410''' that has trunnion formations 24412''' formed thereon. Each trunnion formation 24412''' comprises a laterally protruding actuator lobe 24414''' that defines a bottom lobe surface 24416''' that is configured to interact with an anvil locking system 24700" in the manner described above. The actuator lobe 24414''' as well as the bottom lobe surface 24416''' of the actuator lobe 24414''' are located at an angle that is the same as the angle LA described above with respect to actuator lobe 24414". A trunnion pin 24418''' protrudes outwardly from the actuator lobe 24414''' and is sized to translate and pivot within a corresponding trunnion slot 24320''' that is formed in the elongate channel 24310'''. See FIG. 59. In this example, the trunnion pin 24418''' has a trunnion pin diameter $TRD_4$ that is equal to the width $LW_4$ of the actuator lobe 24414'''.

Figure 59:
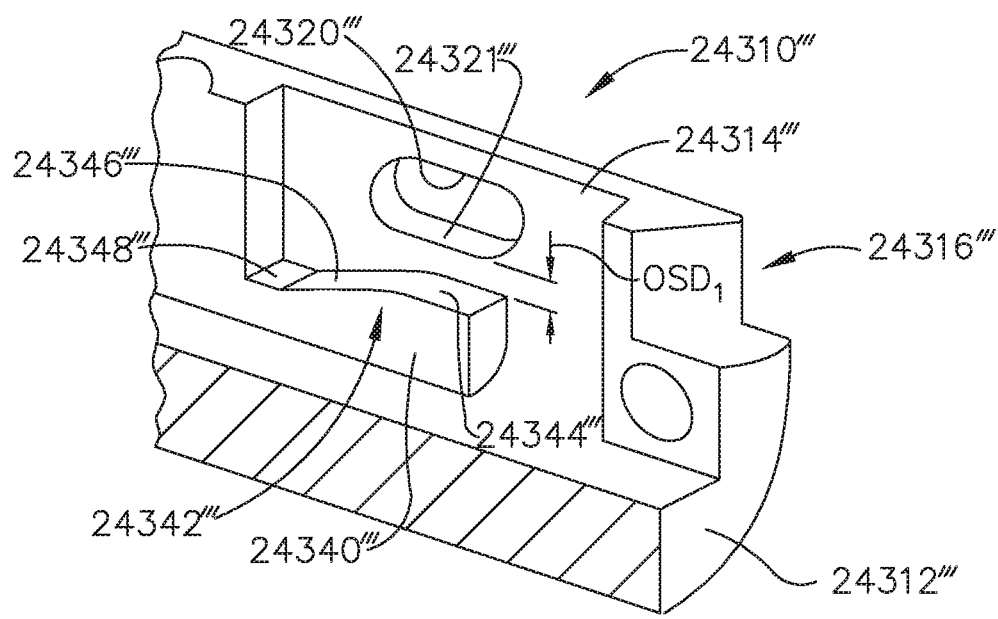
FIG. 59 is a partial cross-sectional perspective view of a portion of another channel that may be used in connection with the anvil of FIG. 58.

As can be seen in FIG. 59, the channel 24310''' comprises a channel bottom 24312''' and a pair of upstanding sidewalls

24314'''. The channel 24310''' may be coupled to an elongate shaft assembly 1200 (FIG. 5) by a channel mount feature 20340 which may facilitate articulation thereof about articulation joint 3020 (FIG. 5). FIG. 59 illustrates a portion of a proximal end 24316''' of the channel 24310'''. In one example, each channel wall 24314''' has a trunnion slot 24320''' formed therein. In the illustrated arrangement, a lobe ledge 24340''' is formed in each channel wall 24314''' such that a top surface 24342' of the lobe ledge 24340''' is offset vertically from a bottom surface 24321''' of the corresponding trunnion slot 24320''' an offset distance $OSD_1$. Offset distance $OSD_1$ may be approximately equal to a distance between the trunnion 24418''' and the bottom lobe surface 24416'''. In the illustrated arrangement, the top surface 24342' of the lobe ledge 24340''' is identical to the top surface 24342" of the lobe ledge 24340" and includes a proximal portion 24344' that is parallel to the bottom surface 24321''' of the trunnion slot 24320''' as well as a ramped surface 24346' and a distal surface 24348'.

The anvil locking system 24700" works in the same manner to prevent the anvil 24400''' from closing. When no cartridge is present in the channel 24310''' or a non-compatible cartridge (e.g. a cartridge that lacks the proper anvil unlocking feature to bias the anvil lock spring proximally) has been inserted into the channel 24310''' the anvil lock tab 24710" is in its distal-most locked position preventing the corresponding actuator lobe 24414''' from pivoting down onto the ramp surface 24346' thereby retaining the anvil 24400''' in the open position. Once a compatible surgical staple cartridge has been loaded into the end effector 24100''', the anvil lockout feature thereon will bias the anvil lock 24702" proximally into to the unlocked position. When the anvil lock 24702" is in the proximal, unlocked position, the anvil lock out tab 24710" is locked proximal to the ramp surface 24346' on the lobe ledge 24340''' to thereby permit the lobe 24414''' to pivot downwardly thereon which results in the closure of the anvil 24400'''.

Figure 60:
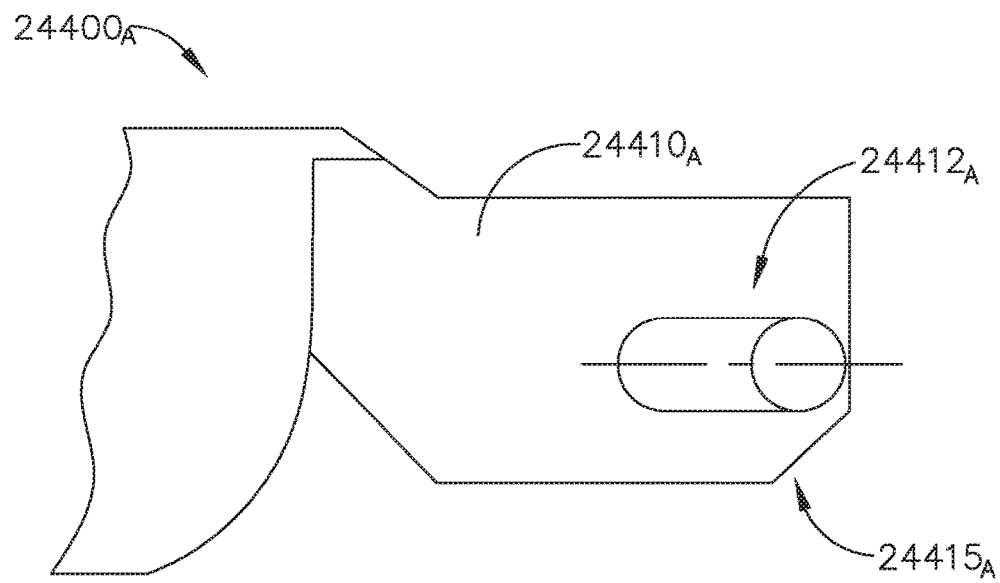
FIG. 60 is a side elevational view of a portion of another anvil.
Figure 61:
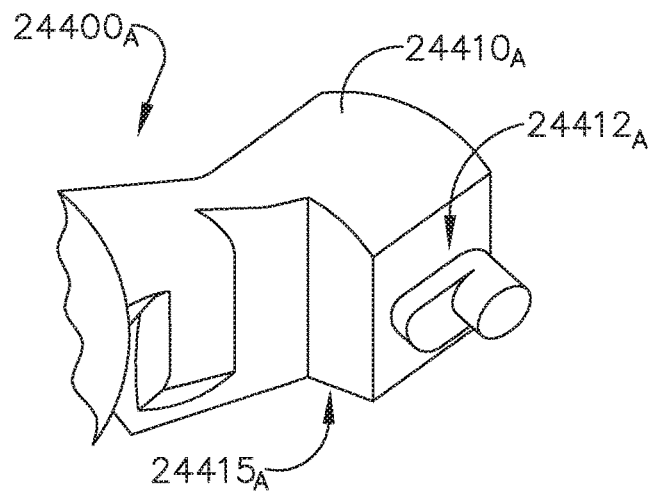
FIG. 61 is a perspective view of a portion of the anvil of FIG. 60.
Figure 62:
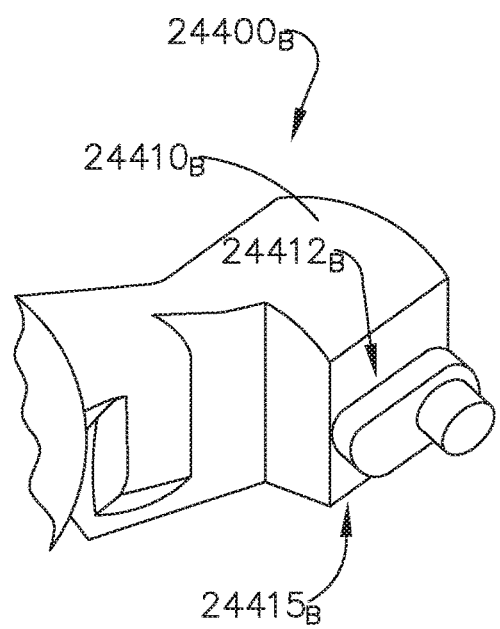
FIG. 62 is a perspective view of a portion of another anvil.

FIGS. 60 and 61 illustrate another anvil 24400A that is identical in construction and operation to anvil 24400 described above, except that the trunnion formation 24412A is offset vertically from a bottom edge 24415A of an anvil mounting portion 24410A of the anvil 24400A FIG. 62 illustrates another anvil 24400B that is identical in construction and operation to anvil 24400' described above, except that the trunnion formation 24412E is offset vertically from a bottom edge 24415E of an anvil mounting portion 24410E of the anvil 24400B.

The examples depicted in FIGS. 41-62 employ trunnion formations that comprise various shapes and configurations of lobe structures that serve to interact with an anvil lock feature such that the interaction between the anvil lock feature and the corresponding lobe structure serves to facilitate positioning of the anvil trunnions within their respective trunnion slots. This positioning of the lob structures permits the anvil to close upon application of closure motions thereto when a compatible surgical staple cartridge has been loaded into the end effector. In instances wherein an incompatible surgical staple cartridge has been loaded into the end effector, the anvil lock feature will retain the corresponding trunnion formation in a position wherein the anvil will be unable to close even upon application of a closure motion thereto. Thus, the initial positions of the trunnion formations prevent closure, but loading of a proper or compatible surgical staple cartridge into the channel changes positions of the trunnion formations to allow closure to occur. The various lobe features described herein are also generally more robust that previous trunnion arrangements which may lead to improved anvil reliability.

FIGS. 63-69 depict a surgical end effector 25300 that may be used for example in connection with the powered surgical instrument 1010 described above. The surgical end effector 25300 comprises an anvil 25400 that is pivotally supported on an elongate channel 25310 that is configured to operably support a surgical staple cartridge 25600. The anvil 25400 is movable between an open position and a closed position through interaction with an axially movable closure member in the various manners disclosed herein. In the illustrated example, the anvil 25400 comprises an anvil body 25402 and an anvil mounting portion 25410. The anvil mounting portion 25410 comprises a pair of laterally extending trunnions 25412 that are operably received within corresponding trunnion slots provided in upstanding sidewalls 25314 of the channel 25310 in the various manners disclosed herein. As was discussed above with respect to end effector 1300, anvil 25400 may be pivoted between an open and a closed position by interaction with an end effector closure tube 3050 in the various manners described herein. For example, the end effector closure tube 3050 may be axially moved by actuation of a closure trigger 1032 of the surgical instrument 1010. In other arrangements, the end effector 25300 and shaft assembly to which it is attached may operably interface with a robotic system as is described in detail in many of the references which have been incorporated herein by reference. In such applications, the end effector closure tube 3050 may be axially advanced and retracted through actuation of a closure control system of the robotic system.

In the illustrated arrangement, distal movement of the end effector closure tube 3050 causes a distal end 3051 of the end effector closure tube 3050 to operably interact with a camming surface 25411 that is formed on the anvil mounting portion 25410 to cam the anvil 25400 to a closed position. When the end effector closure tube 3050 is axially retracted in the proximal direction, the end effector closure tube 3050 may be configured to interact with various formations, ledges or tabs to apply an opening motion to the anvil 25400. Further details may be found in various other references which have been herein incorporated by reference.

The elongate channel 25310 may be coupled to an elongate shaft assembly 1200 (FIG. 5) by a channel mount feature 20340 which may facilitate articulation thereof about articulation joint 3020 (FIG. 5) in the various manners described herein. The illustrated example also includes a firing member 20500 (FIG. 20) that is attached to a distal end of a firing member beam 1900 (FIG. 5) and is configured to operably interface with a camming assembly in a surgical staple cartridge 25600 that has been loaded into the channel 25310. To ensure that a compatible surgical staple cartridge 25600 has been loaded into the end effector 25300 prior to closure of the anvil 25400, the end effector employs a closure lockout system 25700. In the illustrated example, the closure lockout system 25700 is configured to prevent a distal movement of the end effector closure tube 3050 unless a compatible cartridge 25600 has been properly seated within the channel 25310. In one example, the closure lockout system 25700 comprises a closure lock 25702 that is configured to move between a locked position and an unlocked position in response to installation of a compatible surgical staple cartridge 25600 therein. FIGS. 65-69 illustrate one form of a closure lock 25702 that may be fabricated from spring steel or other suitable metal and include a body portion 25706 that is pivotally pinned to the body portion 20342 of the channel mount feature 20340 by a pivot pin 25709 that extends through a pivot hole 25707 in the body portion 25706. The closure lock 25702 further includes a proximal biasing arm 25704 that may be configured to be seated in a slot (not shown) that is provided in the body portion 20342 of the channel mount feature 20340. Such arrangement serves to bias the closure lock 25702 downward within the channel 25310.

Figure 65:
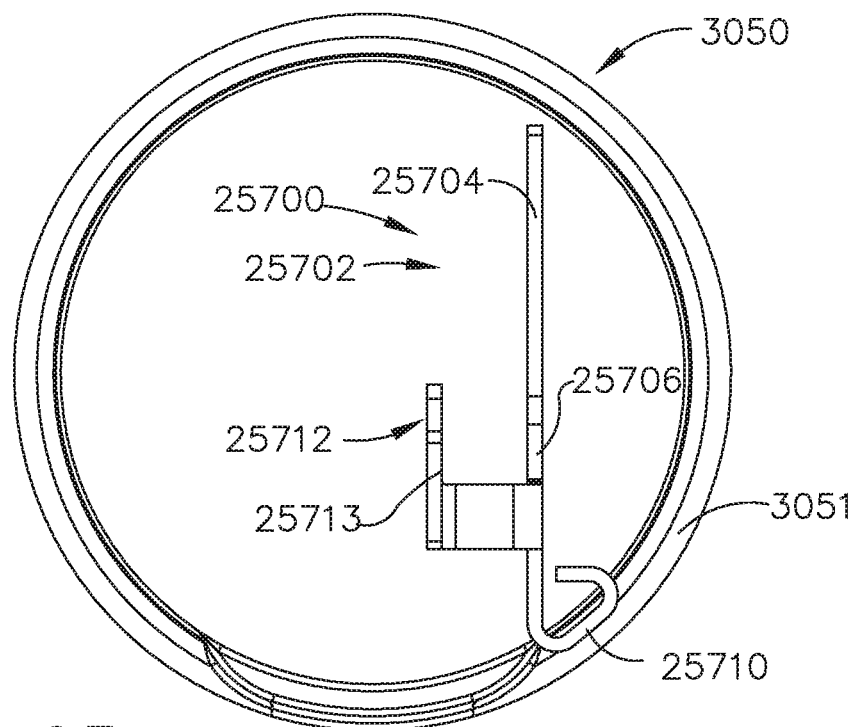
FIG. 65 is an end elevational view of an surgical end effector closure tube of the surgical end effector of FIG. 63 and with a closure lock thereof in a locked position.
Figure 66:
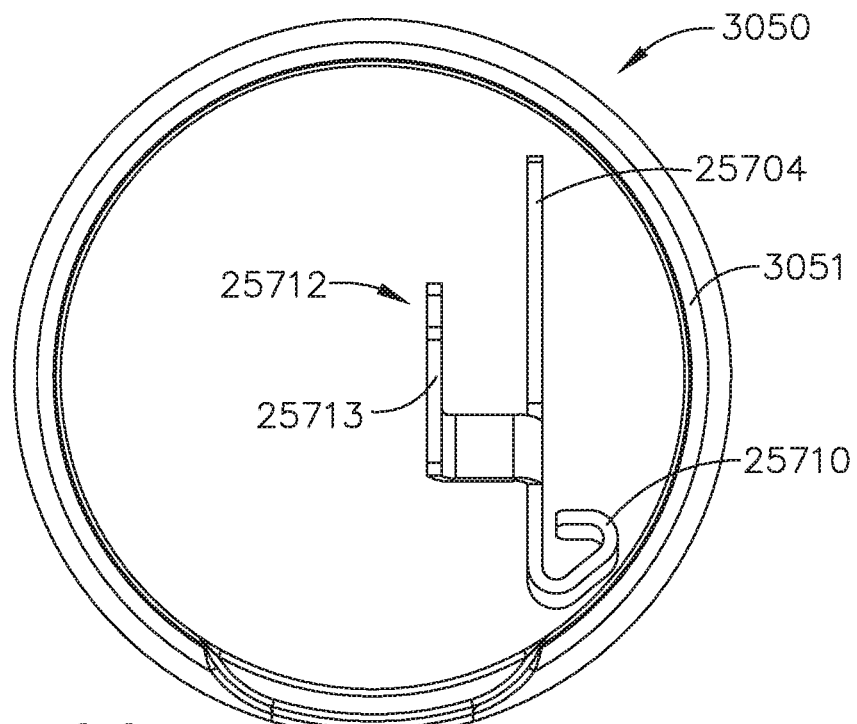
FIG. 66 is another end elevational view of the surgical end effector closure tube and closure lock of FIG. 65, with the closure lock shown in an unlocked position.

As can be most particularly seen in FIGS. 65 and 66, in the illustrated example, the closure lock 25702 further includes a blocking feature 25710 that protrudes from a bottom of the body portion 25706 and extends laterally outward. As illustrated in FIG. 65, when the closure lock 25702 is in the locked position, the blocking feature 25710 is positioned to block the distal advancement of the end effector closure tube 3050. When the closure lock 25702 is in the unlocked position as shown in FIG. 66, the blocking feature 25710 is moved away from the blocking position to permit the distal advancement of the end effector closure tube 3050.

Figure 67:
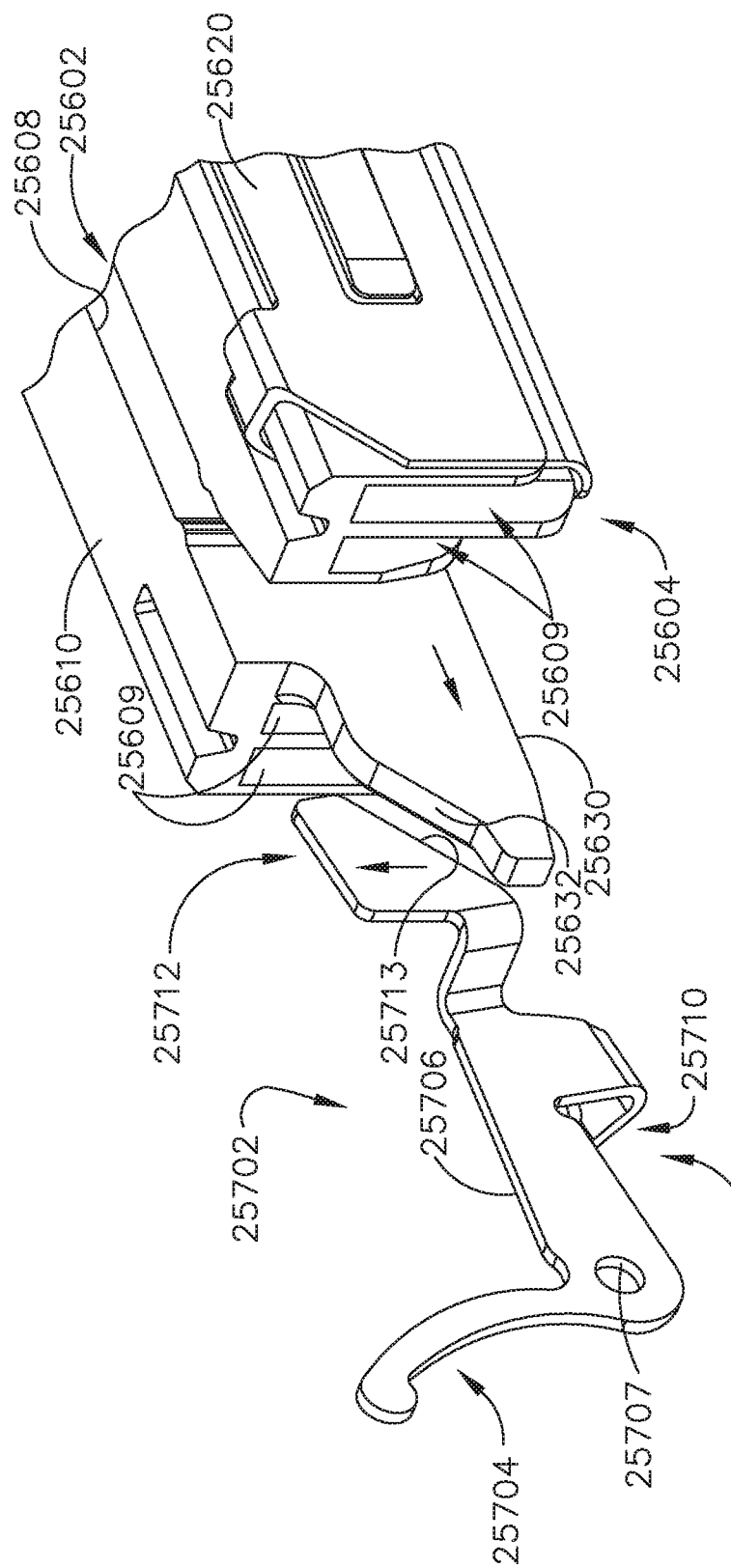
FIG. 67 is a partial perspective view of a portion of a compatible surgical staple cartridge and the closure lock of the surgical end effector of FIG. 63.

Turning to FIG. 67, the closure lock 25702 further includes an actuator portion 25712 that extends proximally to be engaged by a closure unlocking feature 25630 formed on a proximal end 25604 of a compatible surgical staple cartridge 25600. In at least one arrangement, the surgical staple cartridge 25600 comprises an elongate cartridge body 25602 that is sized to be removably seated in the elongate channel 25310. The cartridge body 25602 includes a cartridge slot 25608 that extends from the proximal end portion 25604 to a distal end portion 25606 (FIG. 64) of the cartridge body 25602. The cartridge body 25602 further comprises a cartridge deck surface 25610 that confronts a staple-forming undersurface 25404 of the anvil 25400 when the cartridge 25600 is seated in the channel 25310 and the anvil 25400 is pivoted to a closed position. Although not shown in FIG. 67, the surgical staple cartridge 25600 may have a plurality of (usually three) lines of surgical staple pockets on each side of the cartridge slot 25608 that open through the cartridge deck surface 25610. Each staple pocket may have a staple driver (not shown) associated therewith that supports a surgical staple or fastener (not shown) thereon. In at least one example, the cartridge body 25602 is molded from a polymer material with the staple pockets molded or machined therein. In one arrangement, the staple pockets also open through a bottom of the cartridge body 25602 to facilitate installation of the drivers and fasteners into their respective pockets. Once the drivers and fasteners are inserted into their respective staple pockets, a cartridge pan 25620 is attached to the bottom of the cartridge body 25602. When installed, the cartridge pan 25620 may, among other things, prevent the drivers and fasteners from falling out of the bottom of the cartridge body 25602 during handling and installation of the cartridge 25600 into the elongate channel 25310. As was discussed above in connection with cartridge 20040, cartridge 25600 operably supports a camming assembly therein. The camming assembly comprises a series of spaced cam members that are configured to move axially within corresponding cam slots 25609 formed on each side of the cartridge slot 25608 in the cartridge body 25602. The cam slots 25609 are aligned with corresponding lines of drivers in the cartridge body 25602 to facilitate camming contact with a corresponding cam member as the camming assembly is driven through the staple cartridge 25600 from a beginning position within the proximal end portion 25604 of the cartridge body 25602 to an ending position within the distal end portion 25606.

Figure 63:
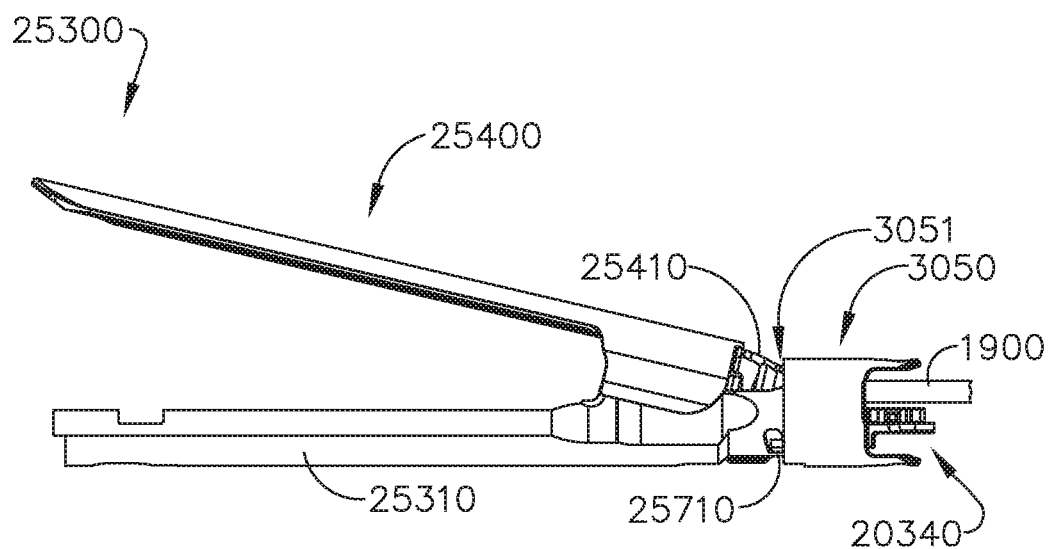
FIG. 63 is a side elevational view of another surgical end effector with an anvil thereof in an open position prior to installation of a surgical staple cartridge therein.
Figure 68:
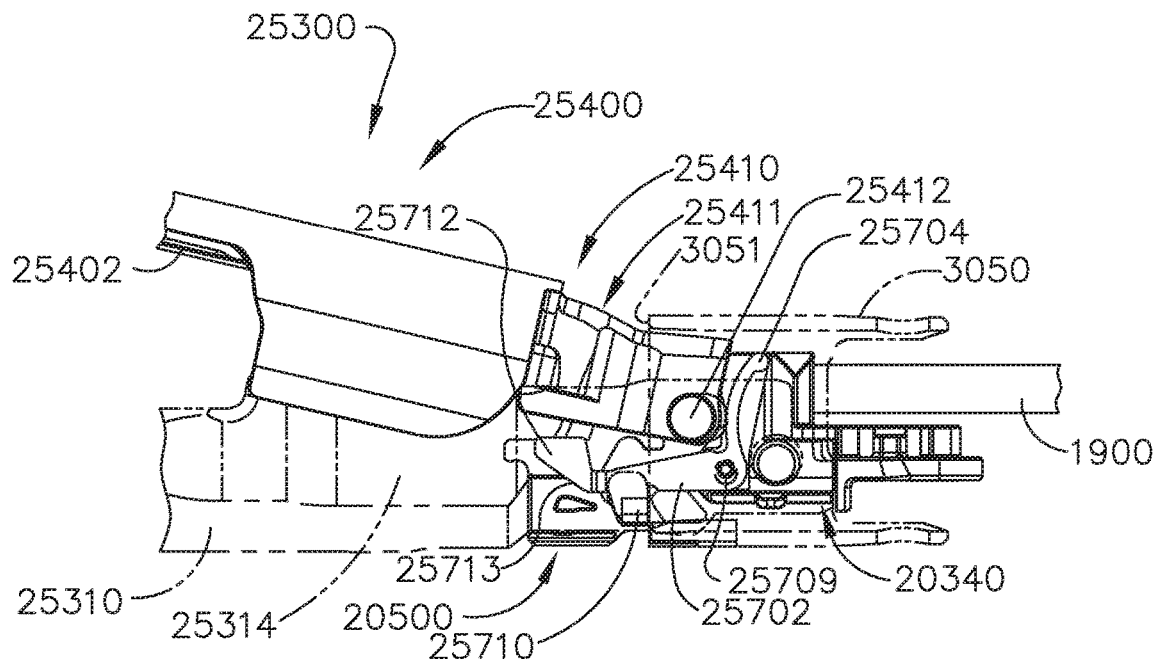
FIG. 68 is a partial side elevational view of the surgical end effector of FIG. 63 with the anvil thereof in an open position and prior to installation of a surgical staple cartridge therein.

FIGS. 63 and 68 illustrate the surgical end effector 25300 without a surgical staple cartridge installed therein. As can be seen in FIG. 68, the proximal biasing arm 25704 has biased the closure lock 25702 downward in the channel 25310 which results in the blocking feature 25710 moving into blocking alignment with the distal end 3051 of the end effector closure tube 3050 (locked position). Should the user activate the closure system to move the end effector closure tube 3050 distally, the blocking feature 25710 will block the distal advancement of the end effector closure tube 3050 thereby preventing an application of closure motions to the anvil 25400. Returning to FIG. 67, in at least one arrangement, the staple cartridge 25600 includes an anvil unlocking feature or tab 25630 that protrudes proximally from the cartridge body 25602 and is aligned to unlockingly engage the actuation tab 25712 that is formed on the distal end of the closure lock 25702 when the cartridge 25600 has been operably installed in the elongate channel 25310. In one example, the unlocking feature 25630 has a somewhat ramped surface 25632 that is configured to operably interact with an angled surface 25713 on the actuation tab 25712 so that the when the ramped surface 25632 and the angled surface 25713 are brought into engagement, the closure lock 25702 is pivoted in an upward direction. When the closure lock 25702 is pivoted upward into the unlocked position, the blocking feature 25710 is no longer in blocking alignment with the end effector closure tube 3050. See FIG. 66.

Figure 64:
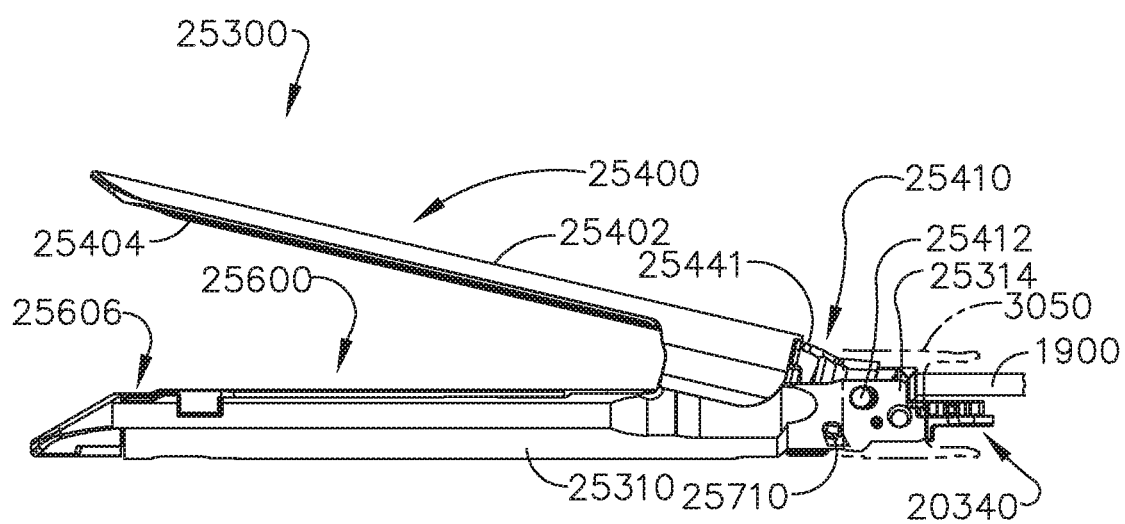
FIG. 64 is another side elevational view of the surgical end effector of FIG. 63 after a compatible surgical staple cartridge has been installed therein.
Figure 69:
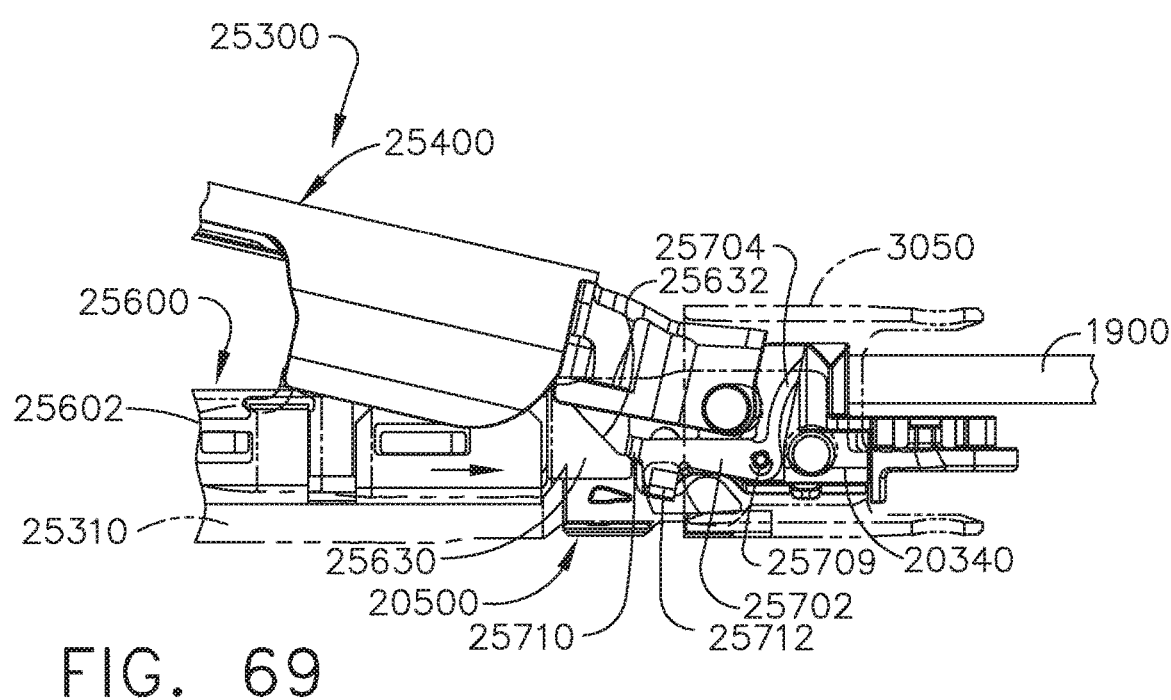
FIG. 69 is another partial side elevational view of the surgical end effector of FIG. 68 with the anvil thereof in an open position and during installation of a compatible surgical staple cartridge therein.

FIGS. 64 and 69 depict the surgical end effector 25300 with a compatible surgical staple cartridge 25600 operably installed in the elongate channel 25310. As can be seen in FIG. 69, the ramped surface 25632 on the unlocking feature 25630 on the staple cartridge body 25602 has contacted the angled surface 25713 (shown in FIG. 68) on the actuation tab 25712 on the closure lock 25702 to bias the closure lock 25702 into the unlocked position. When in that position, the user may distally advance the end effector closure tube 3050 distally to apply closing motions to the anvil 25400. Should the user attempt to install an inappropriate cartridge that lacks the unlocking feature 25630 in an appropriate position or similar feature designed to unlocking engage the closure lock 25702, the user will be unable to distally advance the end effector closure tube 3050 to close the anvil 25400.

Figure 70:
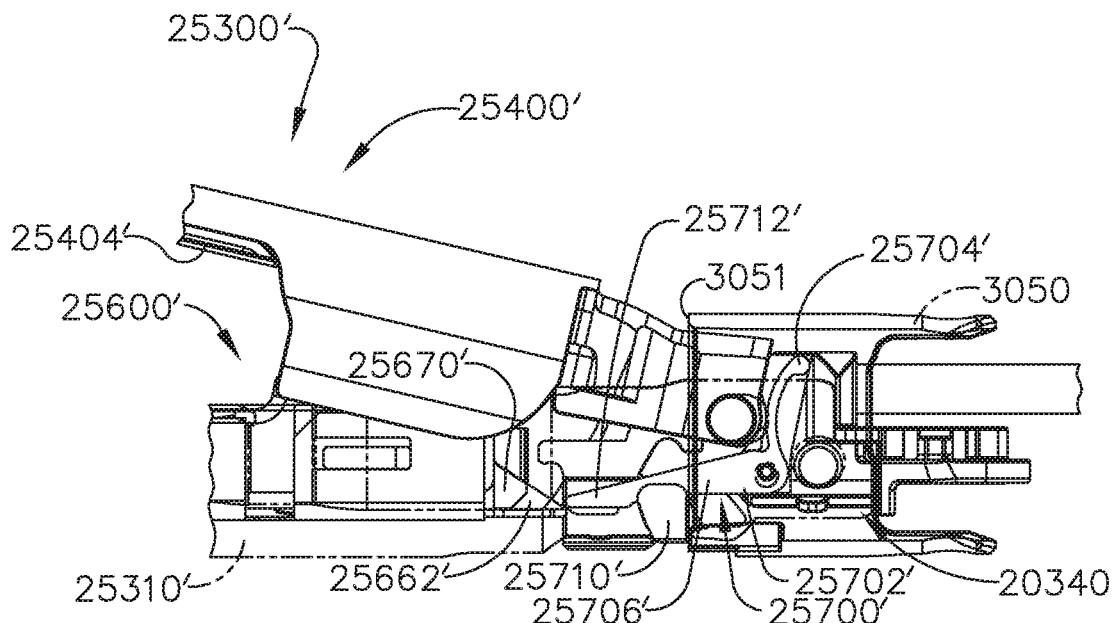
FIG. 70 is a partial side elevational view of the surgical end effector of FIG. 68 with the anvil thereof in an open position and during initial installation of a compatible surgical staple cartridge therein.
Figure 71:
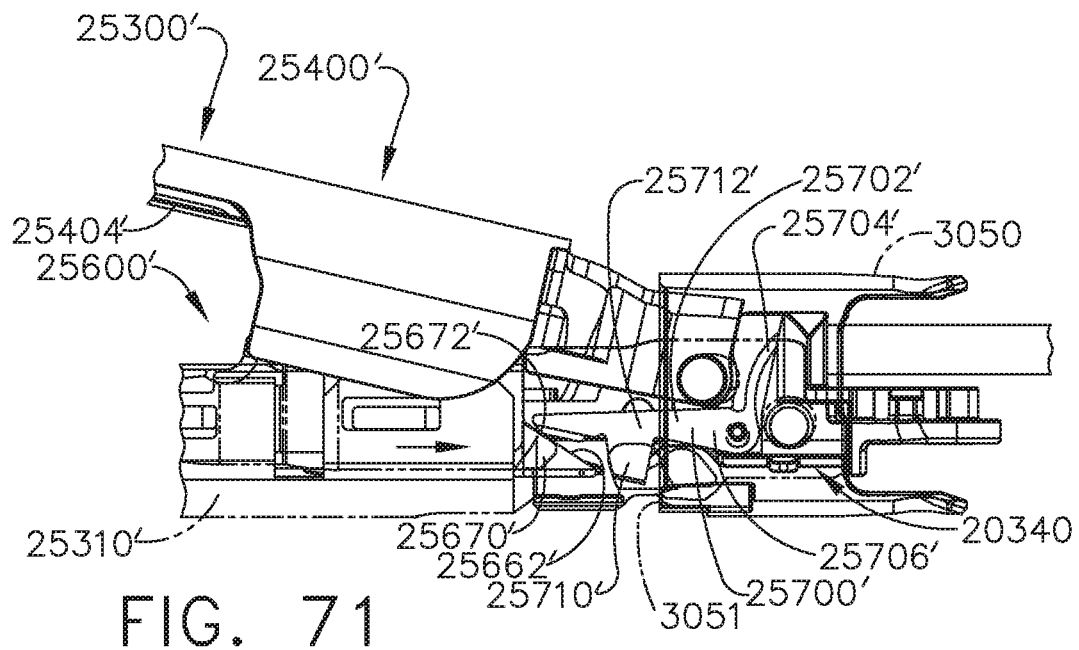
FIG. 71 is another partial side elevational view of the surgical end effector of FIG. 70 with the anvil thereof in an open position and after the compatible surgical staple cartridge has been operably seated therein.

FIGS. 70 and 71 illustrate a surgical end effector 25300' that comprises an anvil 25400' that is pivotally supported on a channel 25310' and is substantially identical to end effector 25300 described above except that the closure locking system 25700' employs a different closure lock 25702' that is configured to interact with an unlocking feature provided on a camming assembly 25650' within a surgical staple cartridge 25600'. As can be seen in FIGS. 70 and 71, the closure lock 25702' comprises an elongate body 25706' that has a tapered actuator tab portion 25712' on its distal end. The body 25706' is pivotally attached to the channel mount feature 20340 and a proximal biasing arm 25704' biases the closure lock 25702' within the channel 25310'.

Figure 72:
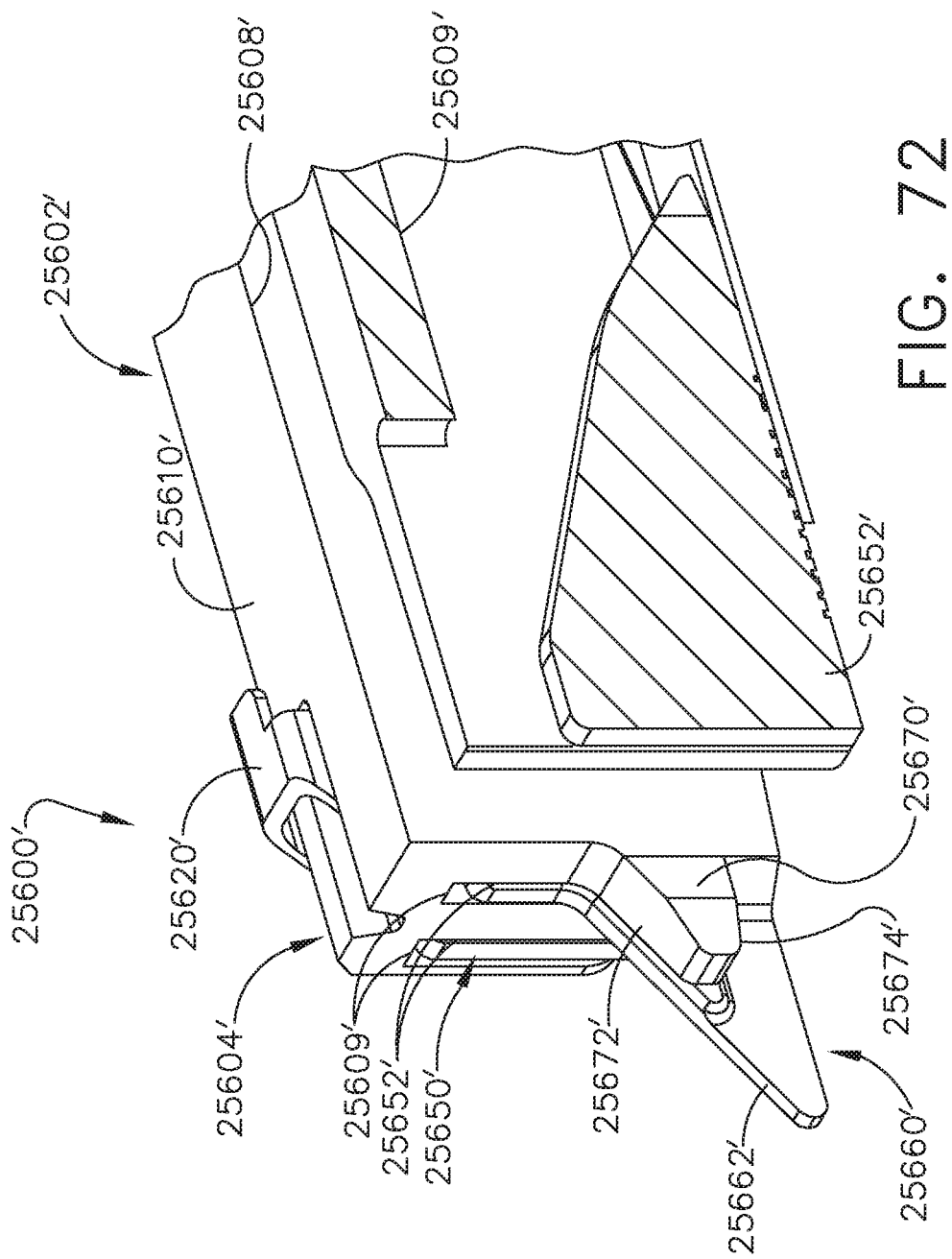
FIG. 72 is a partial cross-sectional perspective view of a portion of the compatible surgical staple cartridge shown in FIGS. 70 and 71.

FIG. 72 illustrates a surgical staple cartridge 25600' that comprises an elongate cartridge body 25602' that is sized to be removably seated in the elongate channel 25310'. The cartridge body 25602' includes a cartridge slot 25608' that extends from a proximal end portion 25604' to a distal end portion of the cartridge body 25602'. The cartridge body 25602' further comprises a cartridge deck surface 25610' that confronts a staple-forming undersurface 25404' of the anvil 25400' when the cartridge 25600' is seated in the channel 25310' and the anvil 25400' is pivoted to a closed position. Although not shown in FIG. 72, the surgical staple cartridge 25600' may have a plurality of (usually three) lines of surgical staple pockets on each side of the cartridge slot 25608' that open through the cartridge deck surface 25610'. Each staple pocket may have a staple driver (not shown)

associated therewith that supports a surgical staple or fastener (not shown) thereon. In at least one example, the cartridge body 25602' is molded from a polymer material with the staple pockets molded or machined therein. In one arrangement, the staple pockets also open through a bottom of the cartridge body 25602' to facilitate installation of the drivers and fasteners into their respective pockets. Once the drivers and fasteners are inserted into their respective staple pockets, a cartridge pan 25620' is attached to the bottom of the cartridge body 25602'. When installed, the cartridge pan 25620' may, among other things, prevent the drivers and fasteners from falling out of the bottom of the cartridge body 25602' during handling and installation of the cartridge 25600' into the elongate channel 25310'. A camming assembly 25650' is operably supported in the cartridge body 25602'. In at least one arrangement, the camming assembly 25650' comprises a series of spaced cam members 25652' that are configured to move axially within corresponding cam slots 25609' that are formed on each side of the cartridge slot 25608' in the cartridge body 25602'. The cam slots 25609' are aligned with corresponding lines of drivers in the cartridge body 25602' to facilitate camming contact with a corresponding cam member 25652' as the camming assembly 25650' is driven through the staple cartridge 25600' from a beginning position within the proximal end portion 25604' of the cartridge body 25602' to an ending position within the distal end portion. In at least one example, the camming assembly 25650' includes a closure unlocking feature or tab 25660' that protrudes proximally from the camming assembly 25650' and is aligned to unlockingly engage the actuation tab 25712' that is formed on the distal end of the closure lock 25702' when the cartridge 25600' has been operably installed in the elongate channel 25310' and the camming assembly 25650' is in its unfired beginning position within the cartridge 25600'.

Returning to FIG. 71, in one example, the unlocking feature 25660' has a tapered nose portion 25662' that is configured to operably interact with the actuation tab 25712' so that the when the tapered nose portion 25662' is brought into engagement with the actuation tab 25712', the closure lock 25702' is pivoted upward. When the closure lock 25702' is pivoted upward into the unlocked position, a blocking feature 25710' on the closure lock 25702' is no longer in blocking alignment with the end effector closure tube 3050.

As can be seen in FIG. 72, the cartridge body 25602' may further include a locking safety 25670' that protrudes proximally from a proximal end of the cartridge body 25602' and adjacent to the tapered nose portion 25662'. An upper surface 25672' of the locking safety 25670' is angled to match the tapered nose portion 25662' but when the camming assembly 25650' is in its proximal-most beginning position, the tapered nose portion 25662' protrudes proximally beyond the end of the locking safety 25670'.

FIG. 70 illustrates an initial insertion of an unfired compatible surgical staple cartridge 25600' into the channel 25310'. As can be seen in FIG. 70 the tapered nose portion 25662' has made initial contact with the actuator tab portion 25712' on the closure lock 25702'. The closure lock 25702' remains biased downward to a locked position wherein the blocking feature 25710' of the closure lock 25702' is in blocking alignment with the distal end 3051 of the end effector closure tube 3050. As the cartridge 25600' is further advanced proximally into a seated position within the channel 25310', the tapered nose portion 25662' on the camming assembly 25650' lifts the actuation tab 25712' upward above the angled upper surface 25672' of the locking safety 25670' to enable the closure lock 25702' to pivot into the unlocked position wherein the blocking feature 25710' is no longer in blocking alignment with the distal end 3051 of the end effector closure tube 3050. When in that position, the user may advance the end effector closure tube 3050 distally to apply closing motions to the anvil 25400'. Thus, in this embodiment, the closure locking system 25700' is actuated by the camming assembly 25650', but only when the camming assembly 25650' is in an unfired beginning position.

Figure 73:
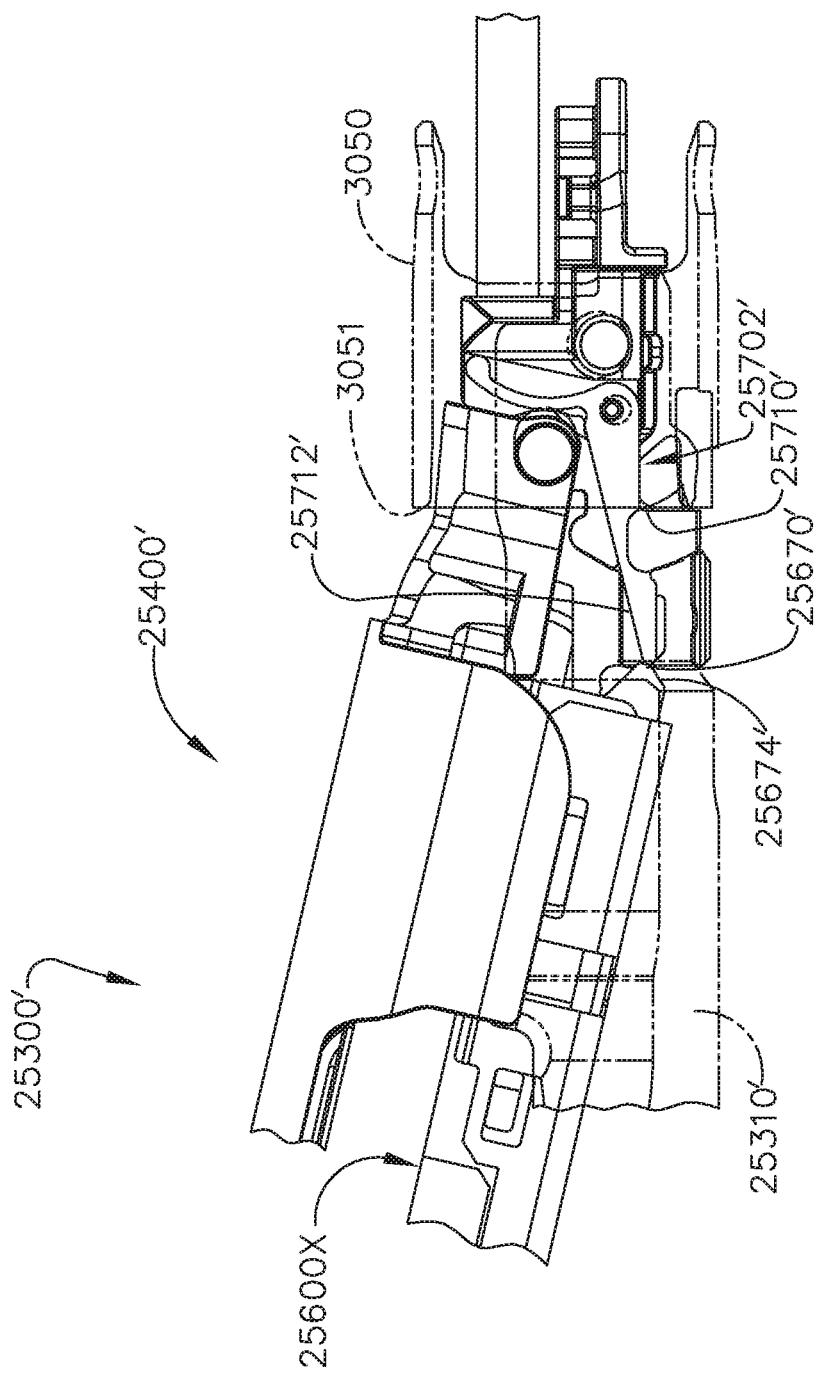
FIG. 73 is another partial side elevational view of the surgical end effector of FIG. 70 with the anvil thereof in an open position and during installation thereof of a surgical staple cartridge lacking a compatible camming assembly in a starting position.

FIG. 73 illustrates insertion of a staple cartridge 25600X wherein the camming assembly thereof is not in a proximal-most unfired position. This may occur when the user attempts to use the staple cartridge 25600X that has been previously used, for example. Because the camming assembly is not in its unfired beginning position, the tapered nose portion is absent to begin to bias the closure lock 25702' into an upward position above the closure safety 25670'. When the cartridge 25600X is fully seated in the channel 25310', the action tab 25712' of the closure lock 25702' is positioned under a lower lock surface 25674'. The closure lock 25702' remains in the locked position wherein the blocking feature 25710' thereof is in blocking alignment with the distal end 3051 of the end effector closure tube 3050. Should the user unwittingly attempt to distally advance the end effector closure tube 3050 to close the anvil 25400', the distal end 3051 will contact the blocking feature 25710' and the closure safety 25670' will further prevent the closure lock 25702' from pivoting upwardly to an unlocked position under the closure load.

Figure 74:
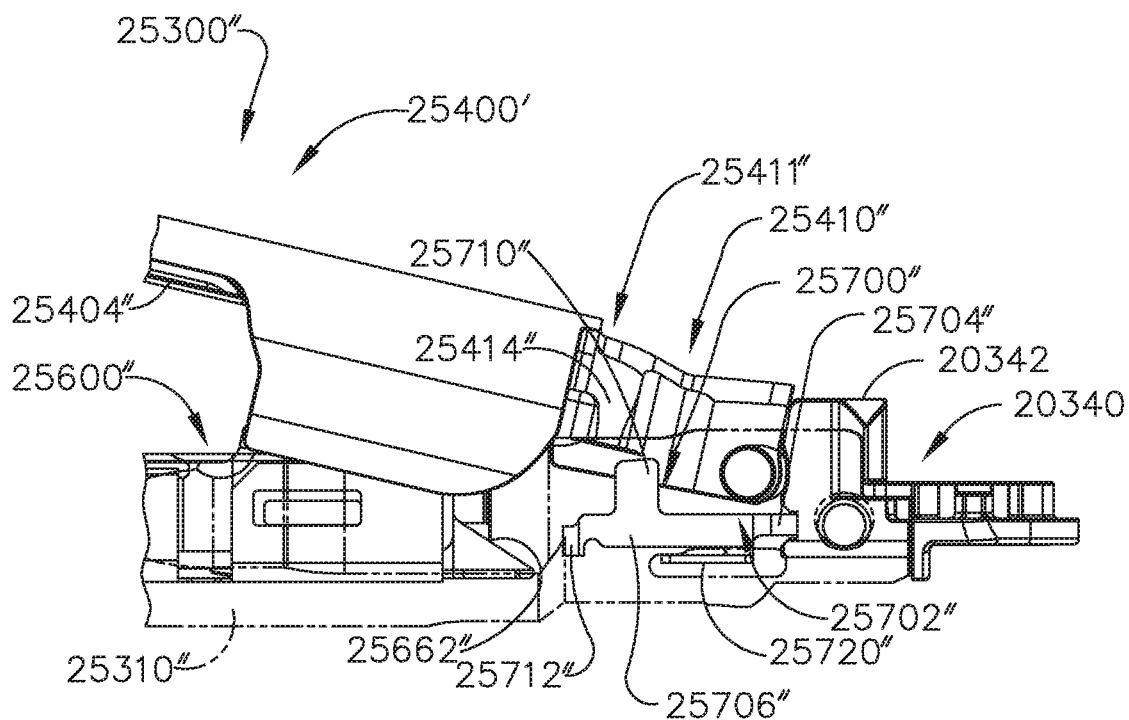
FIG. 74 is a partial side elevational view of another surgical end effector with an anvil thereof in an open position and during initial installation of a compatible surgical staple cartridge therein.
Figure 75:
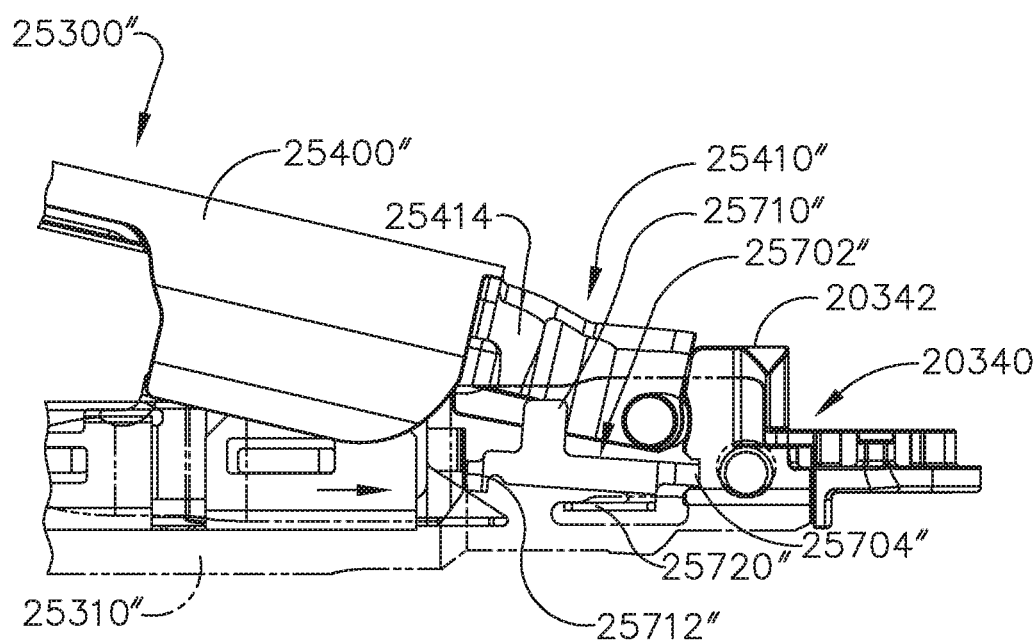
FIG. 75 is another partial side elevational view of the surgical end effector of FIG. 74 with the anvil thereof in an open position and after the compatible surgical staple cartridge has been operably seated therein.
Figure 76:
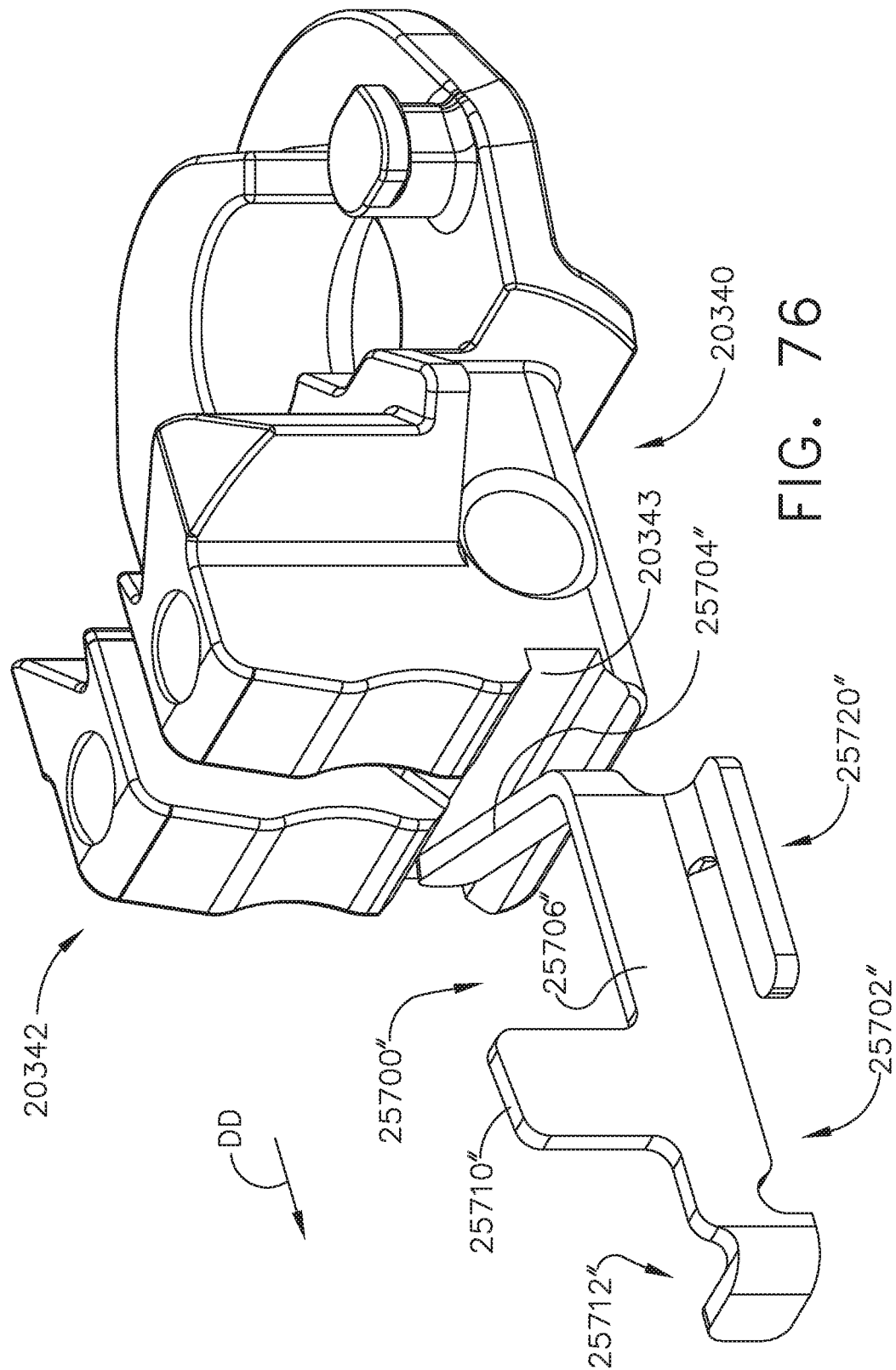
FIG. 76 is a perspective view of an anvil lock and channel mounting feature of the surgical end effector of FIGS. 74 and 75.

FIGS. 74 and 75 illustrate a surgical end effector 25300" that comprises an anvil 25400" that is pivotally supported on a channel 25310" and is substantially identical to end effector 25300' described above. End effector 25300" employs a closure locking system 25700" that comprises a closure lock 25702". As can be seen in FIG. 76, the closure lock 25702" comprises an elongate body 25706" that has an actuator tab portion 25712" on its distal end. The body 25706" includes a lower spring arm 25720" that is mounted within the channel 25310". The lower spring arm 25720" is mounted so as to apply a downwardly biasing force to the closure lock 25702" which will be discussed below. As will also be discussed in further detail below, the closure lock 25702" further includes a vertically extending anvil locking tab 25710" that is configured to lockingly interact with a lock lug 25414" that is formed on an anvil mounting portion 25410" of the anvil 25400". In addition, the closure lock 25702" comprises a proximal biasing spring 25704" which serves to bias the closure lock 25702" in the distal direction DD (FIG. 76). As can be seen in FIG. 74, the elongate channel 25310" may be coupled to an elongate shaft assembly 1200 (FIG. 5) by a channel mount feature 20340 which may facilitate articulation thereof about articulation joint 3020 (FIG. 5) in the various manners described herein. As can be seen in FIG. 76, the proximal biasing spring 25704" is configured to be seated within the transverse slot 20343 in the body portion 20342 of the channel mount feature 20340.

Similar to the closure of anvil 25400' discussed above, distal movement of an end effector closure tube causes a distal end of the end effector closure tube to operably interact with a camming surface 25411" formed on an anvil mounting portion 25410" of the anvil 25400" to cam the anvil 25400" to a closed position. When the end effector closure tube is axially retracted in the proximal direction, the end effector closure tube may be configured to interact with various formations, ledges or tabs to apply an opening motion to the anvil 25400". Further details may be found in various other references which have been herein incorporated by reference.

Figure 77:
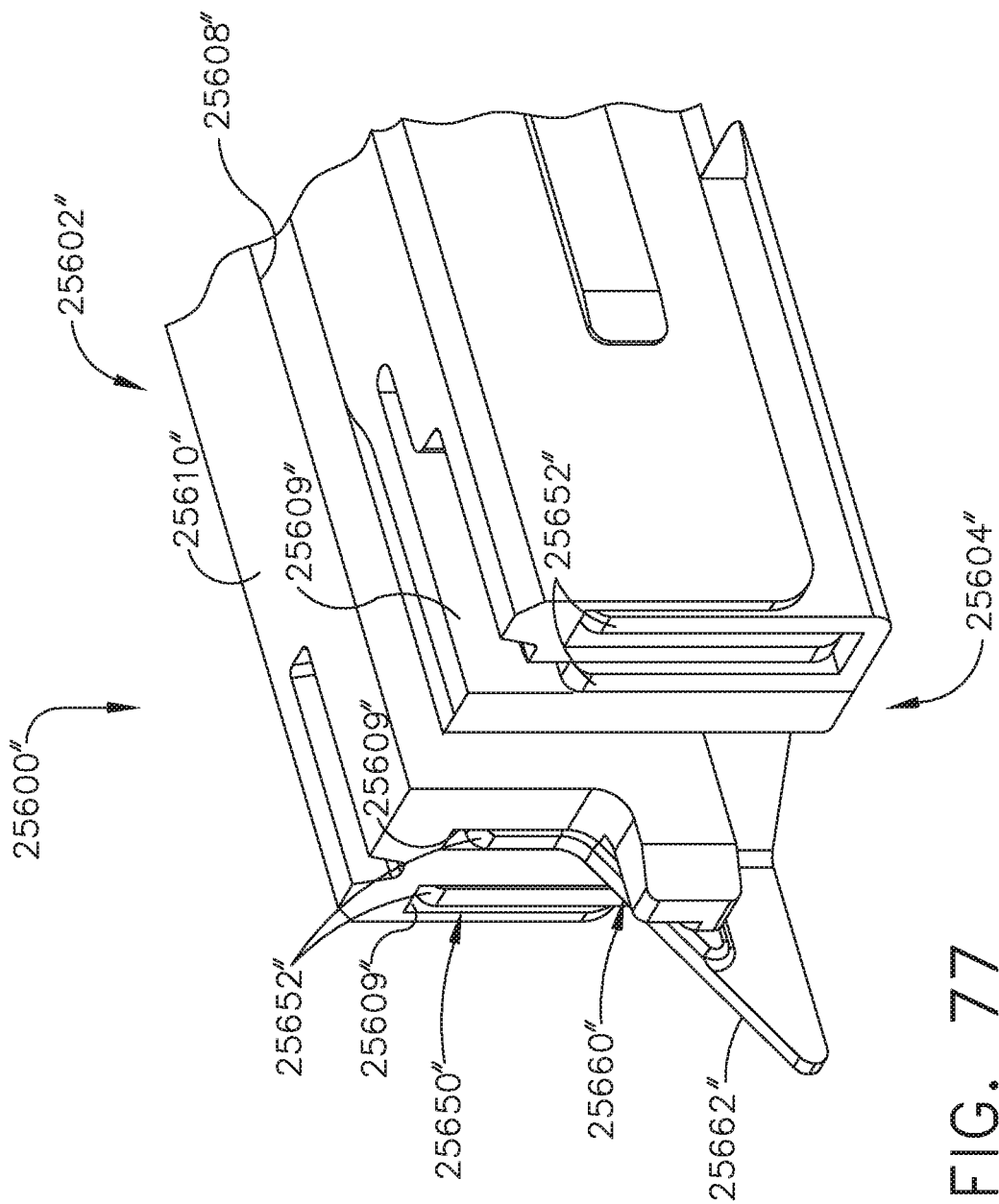
FIG. 77 is a perspective view of a portion of a surgical staple cartridge that is compatible with the surgical end effector of FIGS. 74 and 75.

FIG. 77 illustrates a surgical staple cartridge 25600" that comprises an elongate cartridge body 25602" that is sized to be removably seated in the elongate channel 25310". The cartridge body 25602" includes a cartridge slot 25608" that extends from a proximal end portion 25604" to a distal end portion of the cartridge body 25602". The cartridge body 25602" further comprises a cartridge deck surface 25610' that confronts a staple-forming undersurface 25404" of the anvil 25400" when the cartridge 25600" is seated in the channel 25310" and the anvil 25400" is pivoted to a closed position. Although not shown in FIG. 77, the surgical staple cartridge 25600" may have a plurality of (usually three) lines of surgical staple pockets on each side of the cartridge slot 25608" that open through the cartridge deck surface 25610". Each staple pocket may have a staple driver (not shown) associated therewith that supports a surgical staple or fastener (not shown) thereon. In at least one example, the cartridge body 25602' is molded from a polymer material with the staple pockets molded or machined therein. In one arrangement, the staple pockets also open through a bottom of the cartridge body 25602" to facilitate installation of the drivers and fasteners into their respective pockets. A camming assembly 25650" is operably supported in the cartridge body 25602". In at least one arrangement, the camming assembly 25650" comprises a series of spaced cam members 25652" that are configured to move axially within corresponding cam slots 25609" that are formed on each side of the cartridge slot 25608" in the cartridge body 25602". The cam slots 25609" are aligned with corresponding lines of drivers in the cartridge body 25602" to facilitate camming contact with a corresponding cam member 25652" as the camming assembly 25650" is driven through the staple cartridge 25600" from a beginning position within the proximal end portion 25604" of the cartridge body 25602" to an ending position within the distal end portion. In at least one example, the camming assembly 25650' includes a closure unlocking feature or tab 25660" that protrudes proximally from the camming assembly 25650" and is aligned to unlockingly engage the actuation tab 25712" that is formed on the distal end of the closure lock 25702" when the surgical staple cartridge 25600" has been operably installed in the elongate channel 25310" and the camming assembly 25650" is in its unfired beginning position within the cartridge 25600".

Returning to FIG. 77, in one example, the unlocking feature 25660" has a tapered nose portion 25662" that is configured to operably interact with the actuation tab 25712" so that the when the tapered nose portion 25662" is brought into engagement with the actuation tab 25712", the closure lock 25702" is moved upward against a downward biasing force established by the lower spring 25720". When the closure lock 25702" is pivoted upward into the unlocked position, the anvil locking tab 25710" on the closure lock 25702" is no longer in blocking alignment with the lock lug 25414" on the anvil mounting portion 24410".

FIG. 74 illustrates an initial insertion of an unfired compatible surgical staple cartridge 25600" into the channel 25310". As can be seen in FIG. 74, the tapered nose portion 25662" of the camming assembly 25650" has not yet interacted with the actuator tab portion 25712" on the closure lock 25702". The closure lock 25702" remains biased downward to a locked position wherein the anvil locking tab 25710" of the closure lock 25702" is in blocking alignment with the lock lug 25414" on the anvil mounting portion 25410" of the anvil 25400". As the surgical staple cartridge 25600" is further advanced proximally into a seated position within the channel 25310", the tapered nose portion 25662" on the camming assembly 25650" contacts the actuation tab 25712" and biases the closure lock 25702" upward to an unlocked position wherein the anvil locking tab 25710" is no longer aligned with the anvil lock lug 25414". When in that position, the user may close the anvil 25400" by distally advancing the end effector closure tube to apply closing motions to the anvil 25400". Thus, in this embodiment, the closure locking system 25700" is actuated by the camming assembly 25650", but only when the camming assembly 25650" is in an unfired beginning position. Once the surgical staple cartridge 25600" has been removed from the channel 25310", the lower spring 25720" on the closure lock 25702" will bias the closure lock 25702" downwardly back into its locked position wherein the anvil locking tab 25710" is in blocking alignment with the lock lug 25414" on the anvil 25400".

Figure 78:
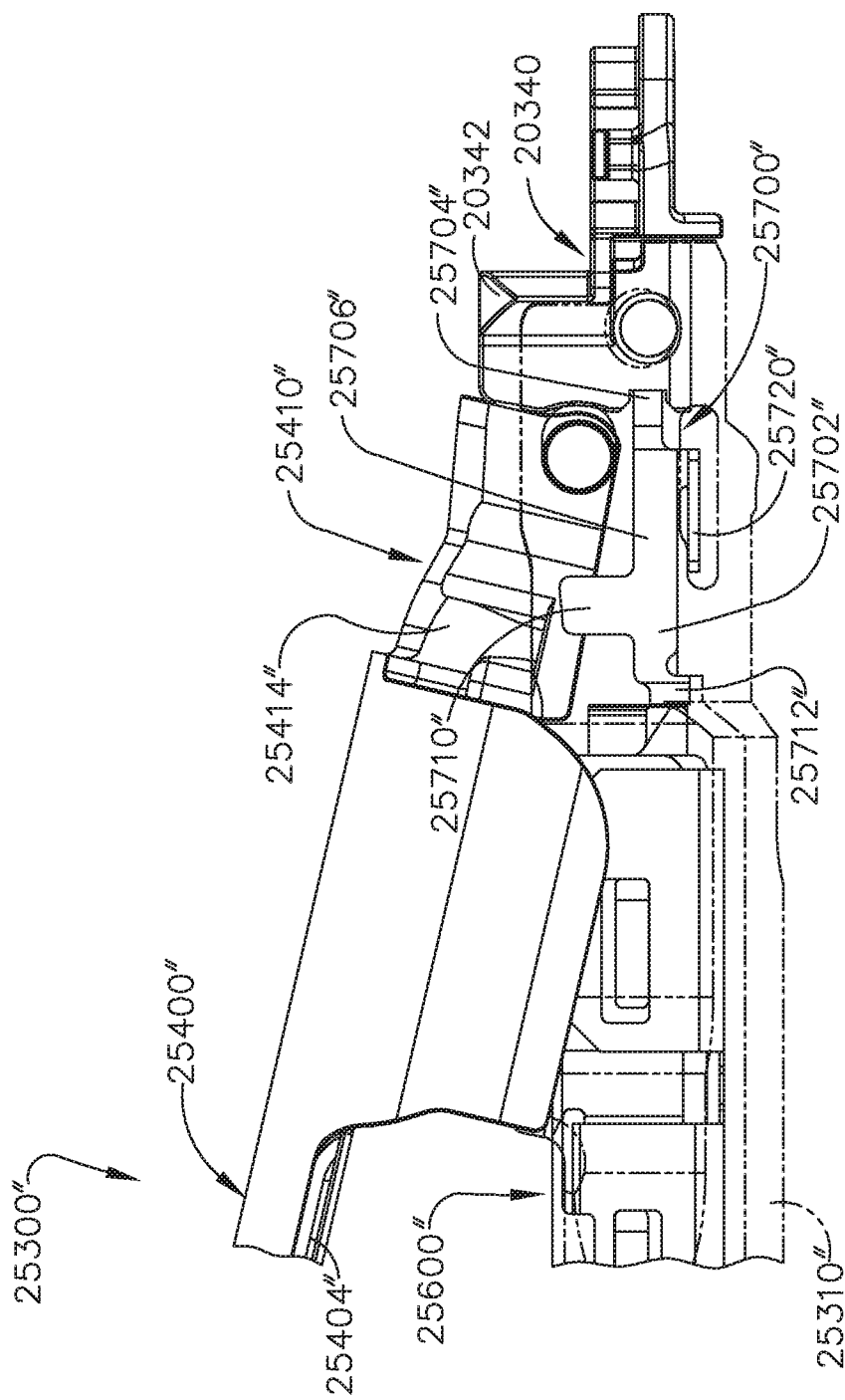
FIG. 78 is another partial side elevational view of the surgical end effector of FIG. 74 with the anvil thereof in an open position and after an incompatible surgical staple cartridge has been seated therein.
Figure 79:
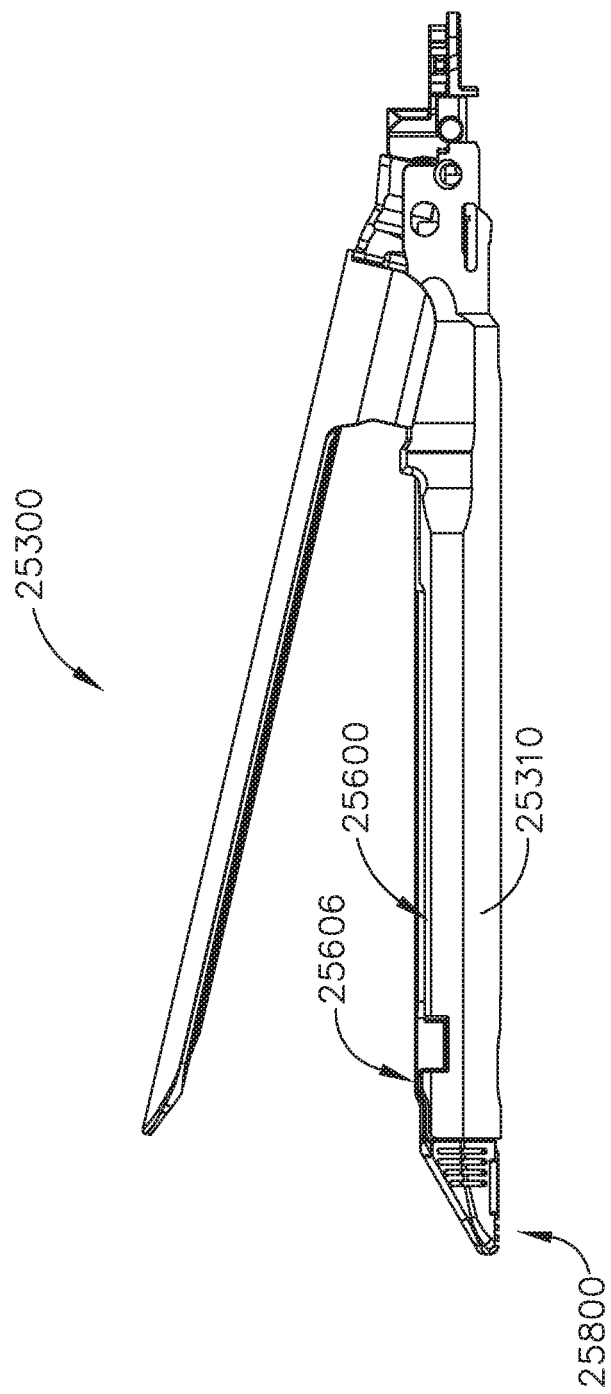
FIG. 79 is a side elevational view of another surgical end effector with a compatible surgical staple cartridge loaded therein and an anvil thereof in an open position.
Figure 80:
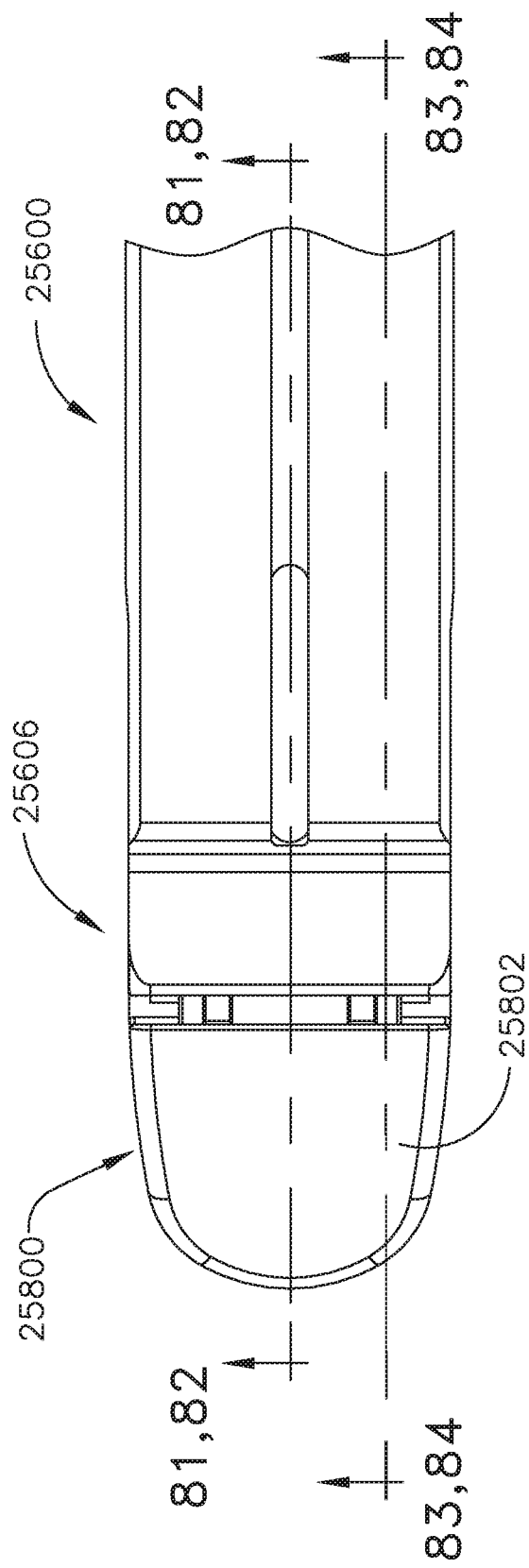
FIG. 80 is a top view of a portion of a surgical staple cartridge that is compatible with the surgical end effector of FIG. 79 with portions thereof omitted for clarity.

FIG. 78 illustrates insertion of a staple cartridge 25600X" that has a camming assembly therein that is not in a proximal-most unfired position. Because the camming assembly is not in its unfired, beginning position, the tapered nose portion is absent to bias the closure lock 25702" upward into the unlocked position. The closure lock 25702' remains in the locked position wherein the anvil locking tab 25710" thereof is in blocking alignment with the anvil lock lug 25414" on the anvil 25400". Should the user unwittingly attempt to close the anvil 25400", the anvil lock lug 25414" will contact the anvil locking tab 25710" on the closure lock 25702" and prevent the anvil 25400" from pivoting to the closed position.

Figure 81:
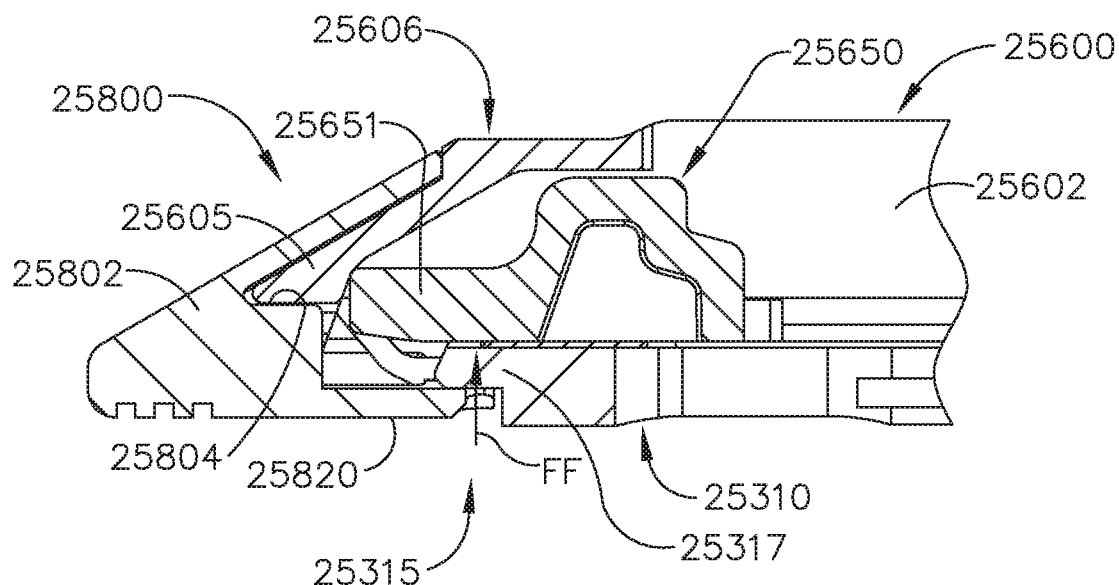
FIG. 81 is a partial cross-sectional side view of a portion of the surgical staple cartridge of FIG. 80 installed in the surgical end effector of FIG. 79 taken along line 81-81 in FIG. 80 showing the cartridge nose assembly in a locked position.
Figure 82:
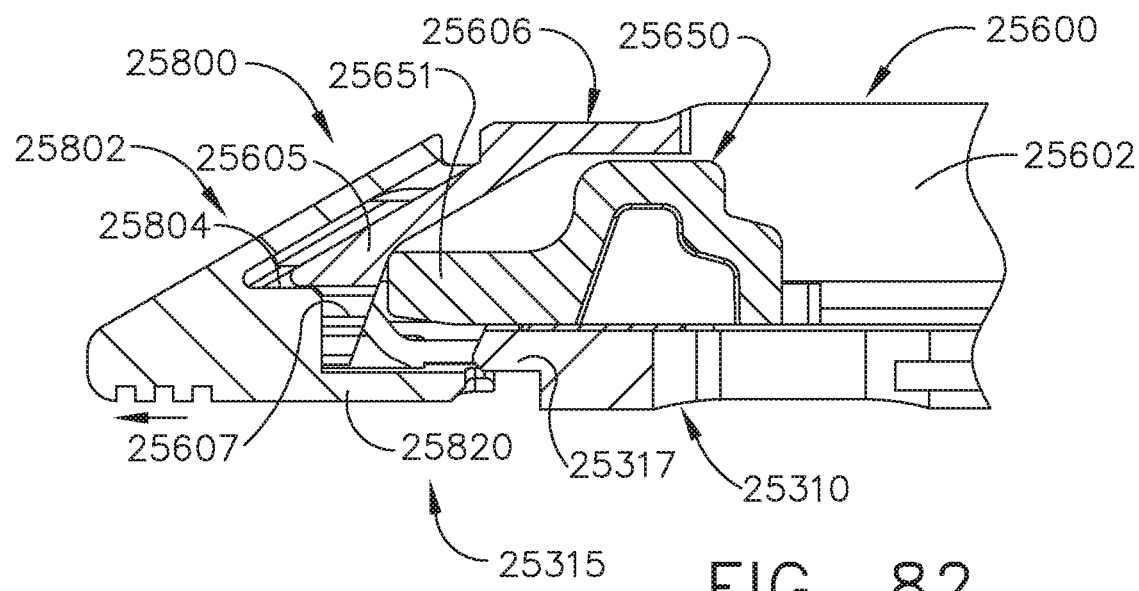
FIG. 82 is another partial cross-sectional side view of a portion of the surgical staple cartridge of FIG. 80 installed in the surgical end effector of FIG. 79 taken along line 82-82 in FIG. 80 showing the cartridge nose assembly in an unlocked position.

FIGS. 79-83 illustrate an alternative cartridge nose assembly 25800 that may be employed with any of the cartridges and channel arrangements disclosed herein to provide another mechanism for ensuring that a surgical staple cartridge that is inserted into the end effector channel is compatible with the end effector and to provide the user with another visual indicator that the cartridge has been fired. For example, the cartridge nose assembly 25800 may be employed with the cartridge 25600 and the channel 25310 of the end effector 25300 (FIG. 64). In the illustrated arrangement, cartridge nose assembly 25800 comprises a nose assembly body 25802 that is movably coupled to a distal end 25606 of the cartridge body 25602. As can be seen in FIGS. 81 and 82, the distal end portion 25606 of the cartridge body 25602 comprises a distally extending tapered portion 25605 that is adapted to be received within complementary shaped nose notch 25804 in the nose assembly body 25802. In addition, the nose assembly body 25802 is configured with axial alignment features (not shown) that may be slidably supported in axial grooves 25607 provided in the distal end portion 25606 of the cartridge body 25602.

Figure 83:
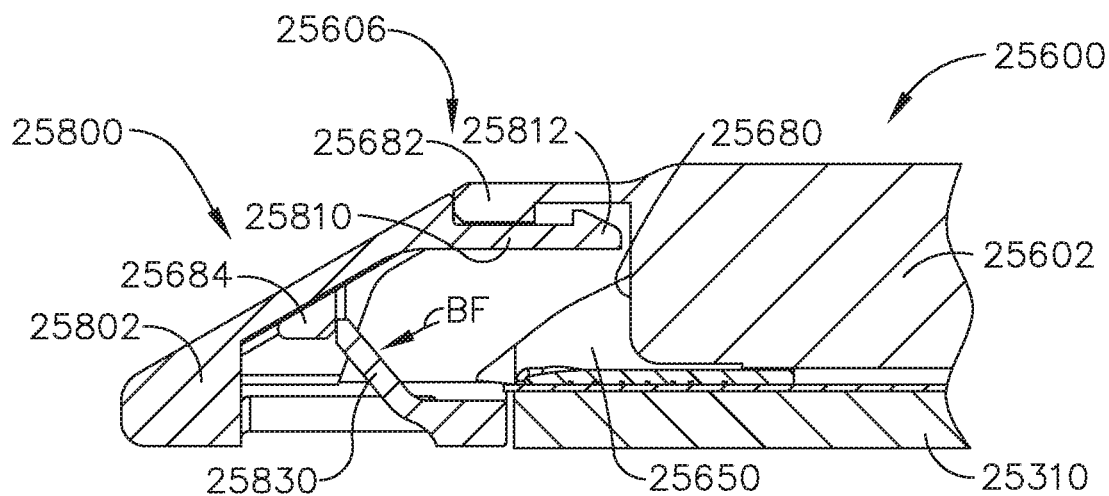
FIG. 83 is another partial cross-sectional side view of a portion of the surgical staple cartridge of FIG. 80 installed in the surgical end effector of FIG. 79 taken along line 83-83 in FIG. 80 showing the cartridge nose assembly in a locked position.
Figure 84:
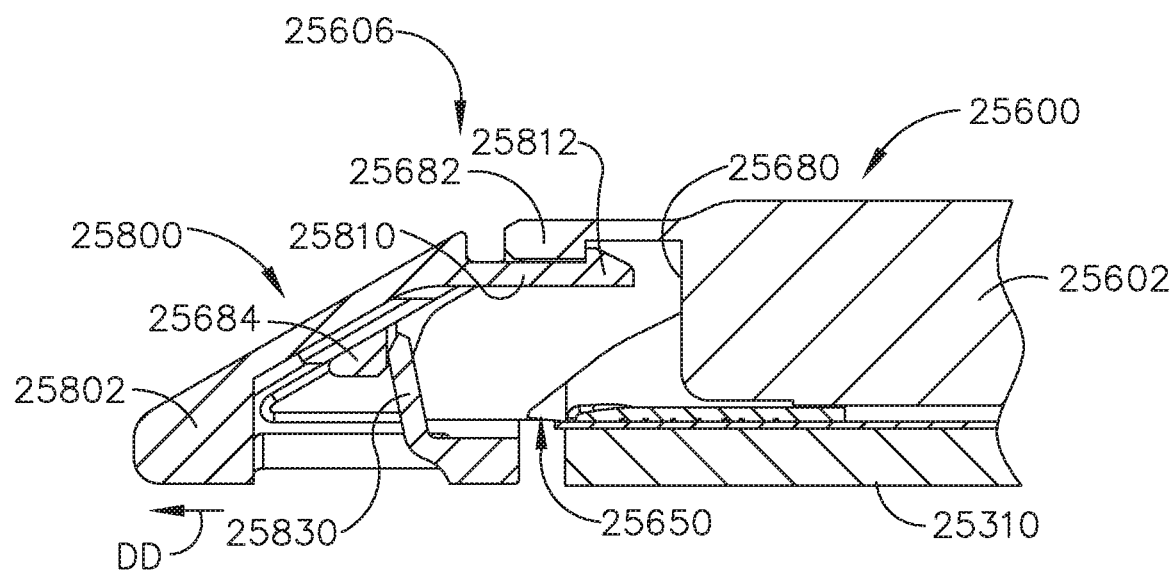
FIG. 84 is another partial cross-sectional side view of a portion of the surgical staple cartridge of FIG. 80 installed in the surgical end effector of FIG. 79 taken along line 84-84 in FIG. 80 showing the cartridge nose assembly in an unlocked position.

As can be seen in FIGS. 83 and 84, a nose retainer latch arm 25810 extends proximally from an upper portion of the nose assembly body 25802 into a latch cavity 25680 formed in the cartridge body 25602. The nose assembly body 25802 is axially movable from a locked position shown in FIGS. 81 and 83 to an unlocked position shown in FIGS. 82 and 84. When the nose assembly body 25802 is in the unlocked position, a retention latch 25812 that is formed on a proximal end of the retainer latch arm 25810 engages a retention lug 25682 that is formed on the distal end portion 25606 of the cartridge body 25602 to retain the cartridge nose assembly 25800 on the distal end 25606 of the cartridge body 25602.

Referring now to FIGS. 81 and 82, the nose assembly body 25802 further comprises proximally extending nose tab portions 25820 that are sized to frictionally engage corresponding distal extending channel ledges 25317 formed on a distal end 25315 of the channel 25310 to retain the nose assembly 25800 in the proximally forward "locked position". As can be seen in FIGS. 83 and 84, the nose assembly body 25802 may further include an integral spring arm 25830 that is configured to interact with a spring lug 25684 that is formed on the distally extending tapered portion 25605 of the cartridge body 25602. The spring arm 25830 applies a distal biasing force BF to the cartridge nose assembly 25800 to increase the frictional force between the nose tab portions 25820 and the channel ledges 25317 to retain the cartridge nose assembly 25800 in the locked position.

In operation, the cartridge nose assembly 25800 is in the locked position when the cartridge 25600 is in its unfired state and is ready to be installed in the channel 25310. To install the unfired cartridge 25600 into the end effector 25300, the cartridge body 25602 is placed in the channel 25310 and then advanced proximally therein to engage the channel ledges 25317 with the nose tab portions 25820 as shown in FIGS. 81 and 82. As discussed above, when the cartridge 25600 is unfired, the camming assembly 25650 is in its proximal-most beginning position. During the firing process, the camming assembly 25650 is driven in the cartridge body 25602 to its distal-most position therein. When the camming assembly 25650 reaches its distal-most position, a central body portion 25651 of the camming assembly 25650 contacts the cartridge nose assembly 25800 with a sufficient amount of force to overcome the frictional forces FF retaining the cartridge nose assembly 25800 in the locked position and moves the cartridge nose assembly 25800 axially into the unlocked position. In the alternative, the user may disengage the cartridge nose assembly 25800 by pulling it distally to the unlocked position. Once the cartridge nose assembly 25800 is moved to the unlocked position, the cartridge 25600 may be removed from the elongate channel 25310. In addition, the distally extending cartridge nose assembly 25800 may provide the user with a visual indication that the cartridge has been fired (spent).

Figure 85:
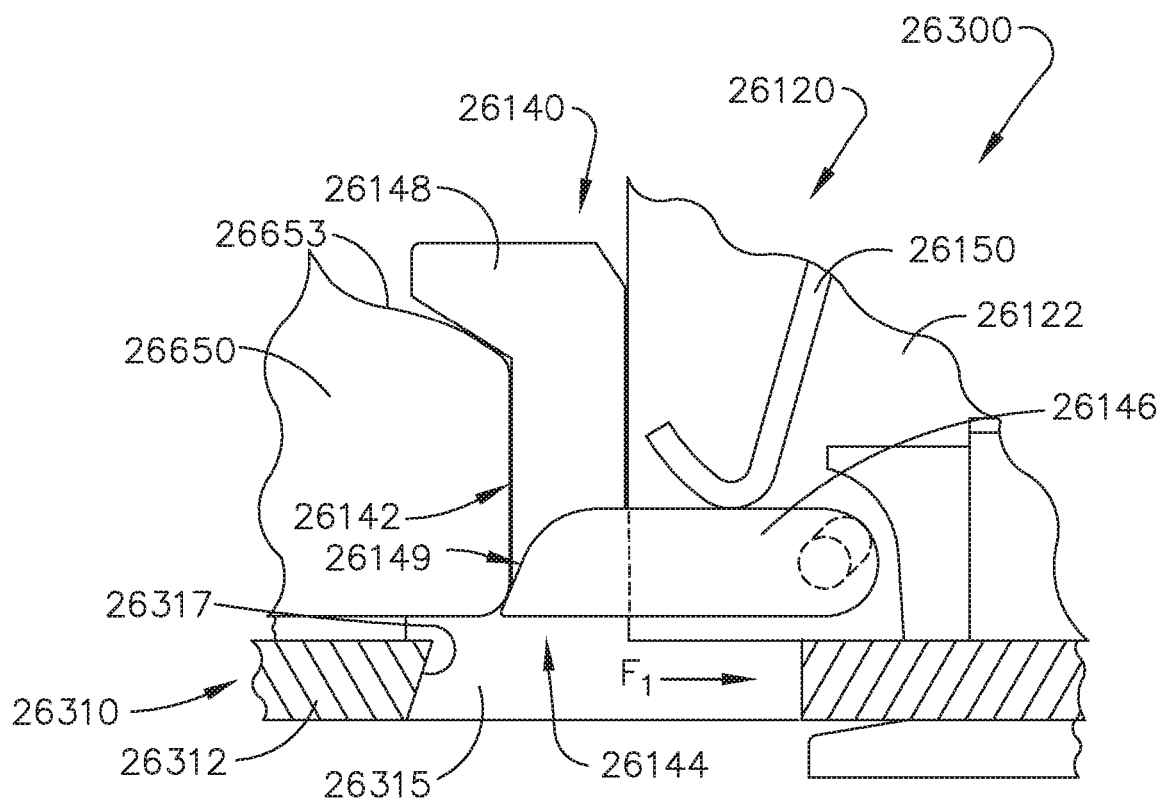
FIG. 85 is a partial cross-sectional view of a portion of a firing member and camming assembly of a surgical staple cartridge wherein the camming assembly is in a starting position and in unlocking engagement with a firing member lock on a firing member.
Figure 86:
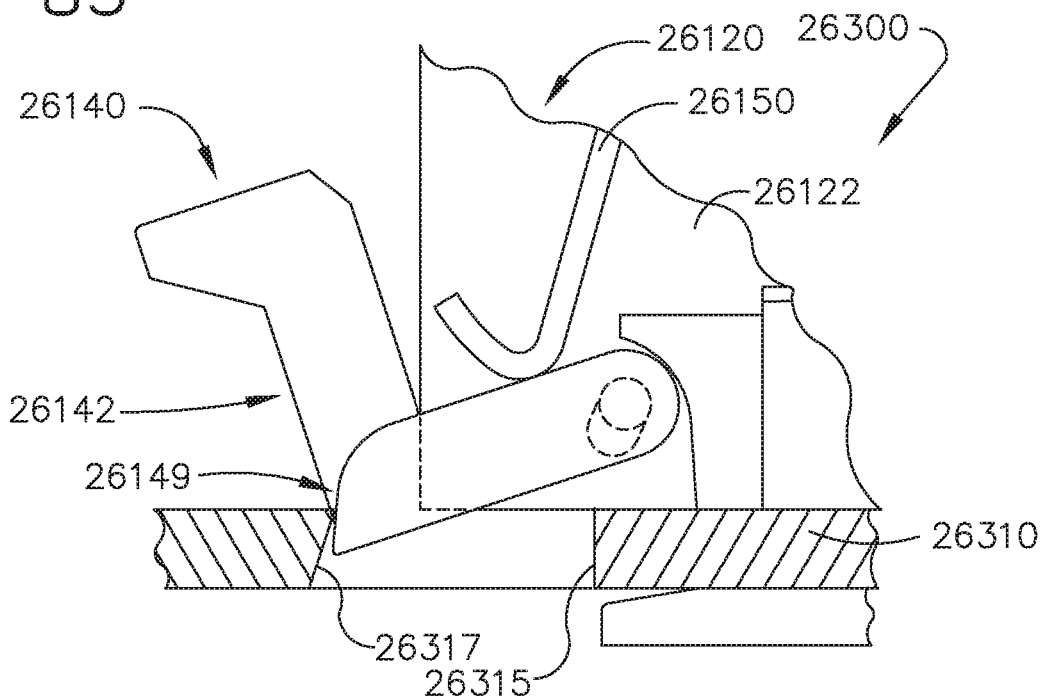
FIG. 86 is another partial cross-sectional view of a portion of a firing member of FIG. 85, with the firing member lock in a locked position.

FIGS. 85 and 86 illustrate a portion of a surgical end effector 26300 that employs a firing member 26120 that may be configured to be distally advanced by a rotary powered firing system or an axial powered (non-rotary powered) firing system. In particular, the firing member 26120 may be employed in connection with any of the various end effector arrangements and firing drive system configurations disclosed herein, as well as in connection with those end effector and firing drive system configurations described in the various references incorporated by reference herein.

As can be seen in FIGS. 85 and 86, the firing member 26120 comprises a firing member body 26122 that includes a firing member lockout system 26140 that comprises a firing member lockout 26142 that is pivotally attached to the firing member body 26122. The firing member lockout 26142 comprises a lockout body 26144 that comprises a pair of legs 26146 that straddle the firing member body 26122 and are pivotally attached thereto. The lockout body 26144 further includes a sled latch 26148 that is configured for contact with a camming sled or camming assembly 26650 that is operably supported in a staple cartridge (not shown). FIG. 85 illustrates the firing member 26120 in a proximal-most starting position. As can be seen in FIGS. 85 and 86, a firing lockout hole 26315 is provided through a bottom portion 26312 of an elongate channel 26310 of the end effector 26300. A lockout spring 26150 is mounted in the elongate channel 26310 and is configured to bias the firing member lockout 26142 downward such that, if a fresh unfired staple cartridge has not been properly loaded into the elongate channel 26310, a distal edge 26149 of the lockout body 26144 engages an angled distal edge 26317 of the firing lockout hole 26315. When in that position, should the user inadvertently attempt to distally advance the firing member 26120, the firing member lockout 26142 prevents the distal advancement of the firing member 26120 as shown in FIG. 86.

A fresh, unfired surgical staple cartridge contains a camming assembly 26650 that is located in a starting or unfired position that is proximal to the lines of staple drivers that are supported in the cartridge body. As used herein, the terms "fresh, unfired" means that the staple cartridge has all of its intended staples or fasteners in their respective unfired positions and the camming assembly is in a proximal unfired starting position. When a fresh, unfired surgical staple cartridge has been properly seated within the elongate channel 26310, a proximally extending unlocking portion 26653 on the camming assembly 26650 engages the sled latch 26148 on the firing member lockout 26142 to pivot the firing member lockout 26142 into an unlocked position wherein the firing member lockout 26142 does not extend into the firing lockout hole 26315 in the elongate channel 26310. FIG. 85 illustrates a camming assembly 26650 in the starting position and the firing member 26120 is free to be advanced distally by actuating the firing drive system.

At the completion of the firing process, the camming assembly 26650 may remain at the distal end of the staple cartridge (i.e., in a "fired" position") while the firing member 26120 is retracted back to its starting position wherein the anvil may be opened and the spent cartridge removed from the channel 26310. Thus, once a surgical staple cartridge has been spent (e.g., completely fired) the camming assembly 26650 is not returned to its starting position. As such, if the spent cartridge were to be inadvertently re-installed in the end effector 26300, the camming assembly 26650 is not in a starting position wherein the camming assembly 26650 can unlock the firing member lockout 26142. Thus, the firing member lockout system 26140 may also be referred to herein as a "spent cartridge lockout system".

Figure 87:
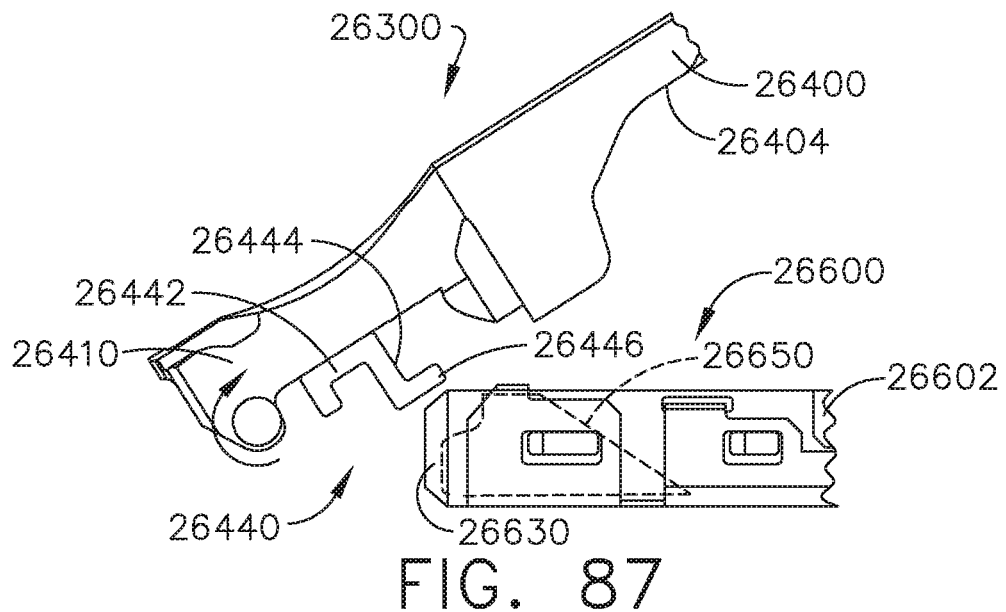
FIG. 87 is a side elevational view of a portion of an anvil of another surgical end effector with the anvil in an open position in relation to compatible surgical staple cartridge installed within a corresponding channel that has been omitted for clarity.
Figure 88:
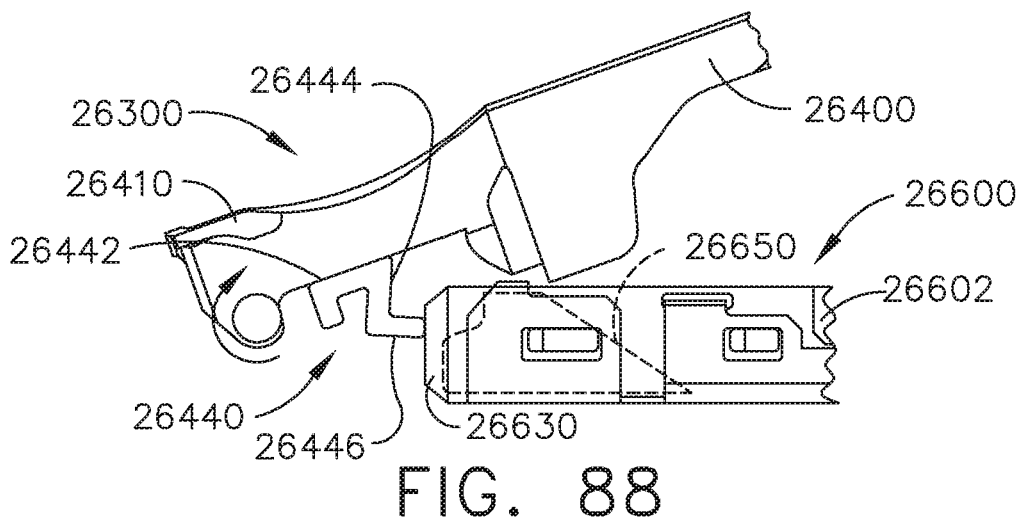
FIG. 88 is another side elevational view of the anvil and surgical staple cartridge of FIG. 87 during initial closure of the anvil.
Figure 89:
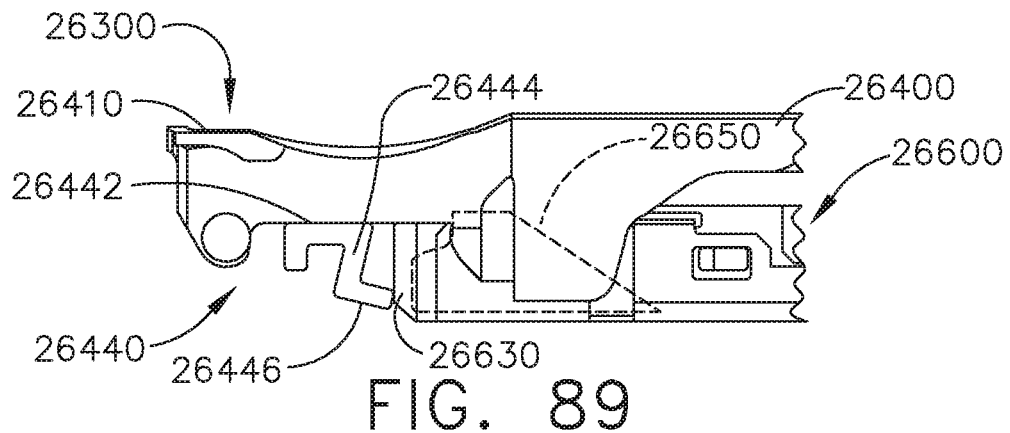
FIG. 89 is another side elevational view of the anvil and surgical staple cartridge of FIG. 87 after the anvil has been moved to a closed position.

FIGS. 87-90 illustrate an anvil 26400 that is configured to be pivotally supported on the channel 26310 or a similar channel of the various types disclosed herein. In FIGS. 87-89, the channel has been omitted for clarity. In the illustrated arrangement, the anvil 26400 includes a cartridge verification system 26440 that may be configured to prevent firing of an incompatible cartridge that has been otherwise seated in the cartridge. The anvil 26400 and cartridge verification system 26440 may be used in connection with a surgical end effector 26300 that employs a firing member 26120 that is equipped with an onboard firing member lockout system 26140 that is configured to prevent the distal advancement of the firing member 26120 unless the firing member lockout 26142 has been moved to an unlocked position through interaction with a corresponding camming assembly located in the surgical staple cartridge. The cartridge verification system 26440 may also be used in connection with surgical end effectors that employ an axially advanced (non-rotary) firing member that is otherwise equipped with a firing member lockout system that is similar to the firing member lockout system 26140.

Figure 90:
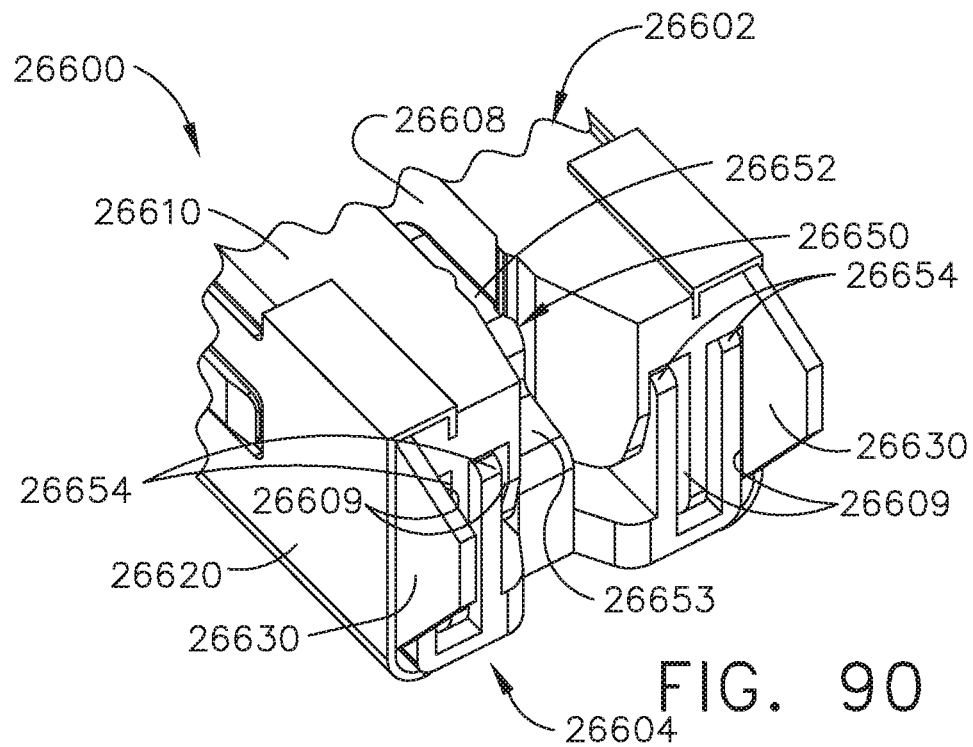
FIG. 90 is a perspective view of a portion of the compatible surgical staple cartridge depicted in FIGS. 87-89.

FIG. 90 illustrates a portion of a surgical staple cartridge 26600 that is compatible with the surgical end effector 26300. In at least one arrangement, the surgical staple cartridge 26600 comprises an elongate cartridge body 26602 that is sized to be removably seated in the elongate channel of the end effector 26300. The cartridge body 26602 includes a cartridge slot 26608 that extends from a proximal end portion 26604 to a distal end portion of the cartridge body 26602. The cartridge body 26602 further comprises a cartridge deck surface 26610 that confronts a staple-forming undersurface 26404 of the anvil 26400 when the cartridge 26600 is seated in the channel and the anvil 26400 is pivoted to a closed position. Although not shown in FIG. 90, the surgical staple cartridge 26600 may have a plurality of (usually three) lines of surgical staple pockets on each side of the cartridge slot 26608 that open through the cartridge deck surface 26610. Each staple pocket may have a staple driver (not shown) associated therewith that supports a surgical staple or fastener (not shown) thereon. In at least one example, the cartridge body 26602 is molded from a polymer material with the staple pockets molded or machined therein. In one arrangement, the staple pockets also open through a bottom of the cartridge body 26602 to facilitate installation of the drivers and fasteners into their respective pockets. Once the drivers and fasteners are inserted into their respective staple pockets, a cartridge pan 26620 is attached to the bottom of the cartridge body 26602. When installed, the cartridge pan 26620 may, among other things, prevent the drivers and fasteners from falling out of the bottom of the cartridge body 26602 during handling and installation of the cartridge 26600 into the elongate channel 26310.

In the illustrated arrangement, the cartridge 26600 operably supports a camming assembly 26650 therein. The camming assembly 26650 comprises a central body portion 26652 and a series of spaced cam members 26654 that are configured to move axially within corresponding cam slots 26609 formed on each side of the cartridge slot 26608 in the cartridge body 26602. The cam slots 26609 are aligned with corresponding lines of drivers in the cartridge body 26602 to facilitate camming contact with a corresponding cam member 26654 as the camming assembly 26650 is driven through the staple cartridge 26600 from a beginning position within the proximal end portion 26604 of the cartridge body 26602 to an ending position within the distal end portion of the cartridge body 26602. The central body portion 26652 includes the proximally extending unlocking portion 26653 that is configured to engage the sled latch 26148 on the firing member lock 26142 when the cartridge 26600 has been properly loaded into the channel 26310. As can be seen in FIG. 90, when the camming assembly 26650 is in its proximal-most starting position wherein the unlocking portion 26653 can move the firing member lockout 26142 to the unlocked position, each of the cam members 26654 may protrude proximally out of their respective cam slots 26609.

Figure 91:
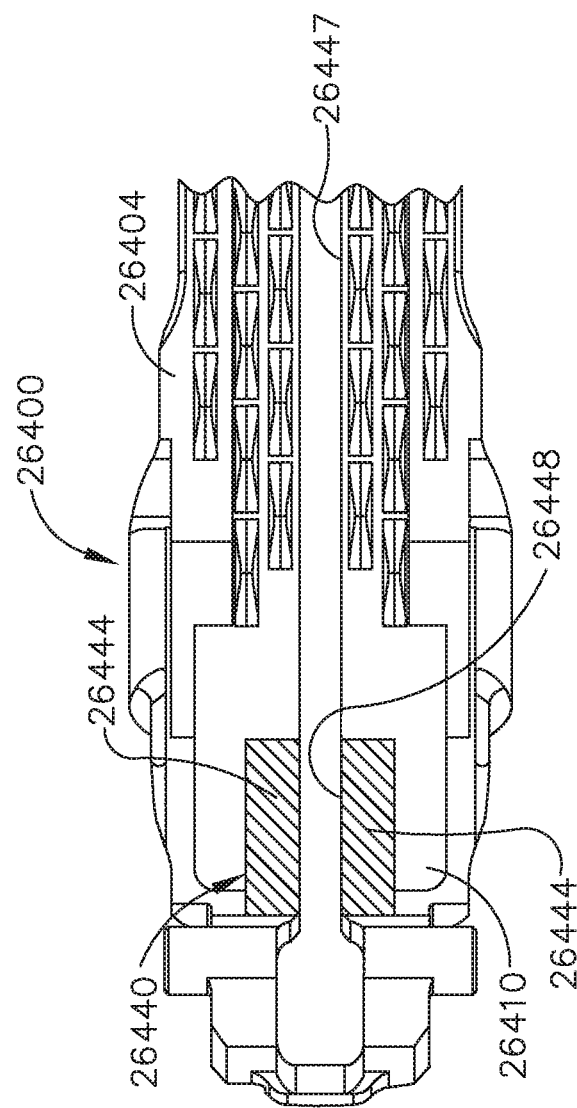
FIG. 91 is a partial bottom view of the anvil of FIGS. 87-89.

Referring now to FIGS. 87 and 91, in the illustrated arrangement, the cartridge verification system 26440 comprises a cartridge verification member or shuttle member 26442 that is attached to an underside of an anvil mounting portion 26410 of the anvil 26400. The cartridge verification member 26442 may be of one-piece construction and include a pair of downwardly extending shuttle legs 26444 that are bifurcated by a firing member slot 26447 (FIG. 91) to facilitate passage of the firing member 26120 therebetween. In other arrangements, the cartridge verification member 26442 may be of two-piece construction which consists of two separate downwardly extending shuttle legs 26444 that are separated from each other by a space 26448 that is configured to accommodate passage of the firing member body 26122 therethrough. In either case, the shuttle member 26442 may be fabricated from a compliant polymer or rubber material and be attached to the underside of the anvil mounting portion 26410 by appropriate adhesive of fastener arrangements.

In the illustrated example, each shuttle leg 26444 includes a distally protruding sled actuator arm 26446. Returning to FIG. 90, the cartridge body 26602 includes two proximally protruding verification features or cartridge key portions 26630 that are configured to unlockingly engage the sled actuator arm 26446 on a corresponding shuttle leg 26444 when the cartridge 26600 is operably seated in the channel 26310. As will be discussed further below, if the verification features 26630 are not present to contact the corresponding sled actuator arm 26446, the sled actuator arms 26446 would otherwise contact the protruding cam members 26654 and push or urge the camming assembly 26650 distally into a position wherein the unlocking portion 26653 on the camming assembly 26650 is no longer in unlocking engagement with the sled latch 26148 on the firing member lock 26142.

Interaction between the cartridge verification system 26440 and cartridge 26600 may be understood from reference to FIGS. 87-92. FIG. 87 illustrates initial installation of a compatible surgical staple cartridge 26600 into the end effector 26300. Although the channel has been omitted from the drawings, the anvil 26400 is shown in a fully open position. In the illustrated example, the anvil 26400 is movably journaled on the channel such that upon application of an initial closure motion thereto from a closure member arrangement of many of the various closure systems described herein, the anvil 26400 pivots to a partially closed position or intermediate position shown in FIG. 88. When in that position, each sled actuator arm 26446 is confrontingly aligned with the corresponding verification feature 26630 on the cartridge body 26602. Further application of the closure motion to the anvil 26400 may also cause the anvil 26400 to translate distally into a closed position. When the anvil 26400 moves distally, the verification features 26630 block the distal movement of the corresponding compliant sled actuator arms 26446 to prevent the sled actuator arm 26446 from contacting the proximally protruding cam members 26654. Thus, the camming assembly 26650 remains in its starting position wherein the unlocking portion 26653 on the camming assembly 26650 remains in unlocking engagement with the sled latch 26148 on the firing member lock 26142. Thus, the firing member 26120 is free to move distally through the cartridge 26600 upon actuation of the firing drive system.

Figure 92:
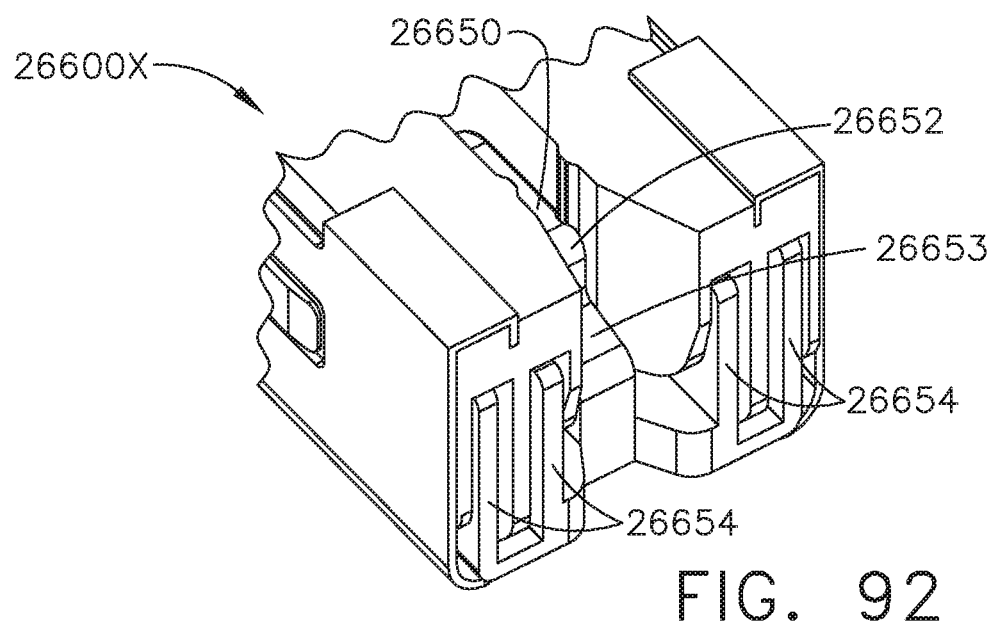
FIG. 92 is a perspective view of a portion of surgical staple cartridge that is incompatible with the anvil of FIGS. 87-89.

FIG. 92 illustrates a cartridge 26600X that may be very similar to cartridge 26600 but is "incompatible" with the surgical end effector 26300. For example, the cartridge 26600X lacks the verification features or key portions 26630 of the cartridge 26600. In addition, to lacking the verification features or keys 26630, the cartridge 26600X may also differ from the cartridge 26600 in the numbers, sizes, locations, etc. of the fasteners contained therein, notwithstanding the fact that the cartridge 26600X may have a camming assembly 26650 that is identical in construction and use as the camming assembly 26650 employed in cartridges 26600.

Figure 93:
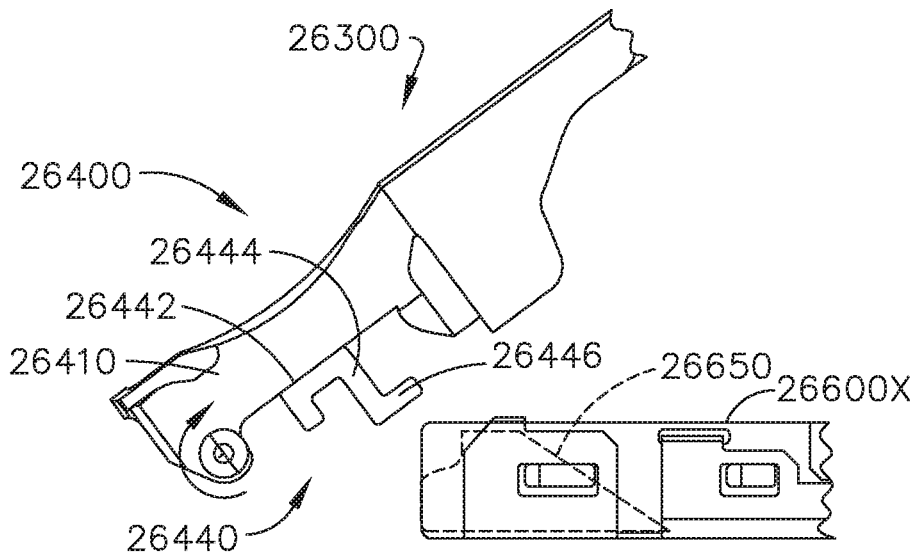
FIG. 93 is a side elevational view of the anvil of FIGS. 87-89 in an open position in relation to an incompatible surgical staple cartridge of FIG. 92 installed within a corresponding channel that has been omitted for clarity.
Figure 94:
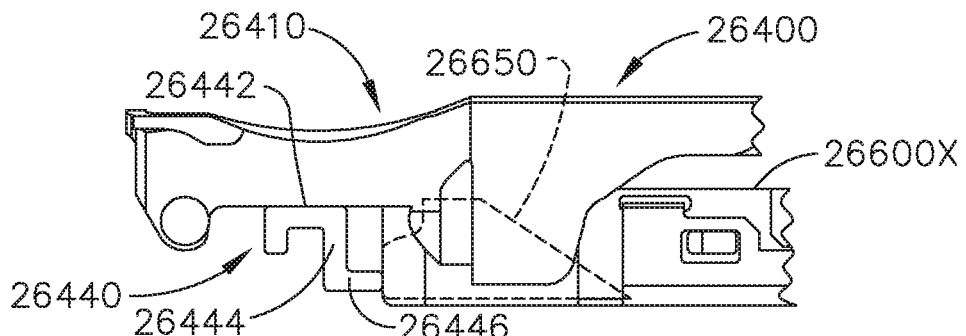
FIG. 94 is another side elevational view of the anvil and surgical staple cartridge of FIG. 93 during initial closure of the anvil.
Figure 95:
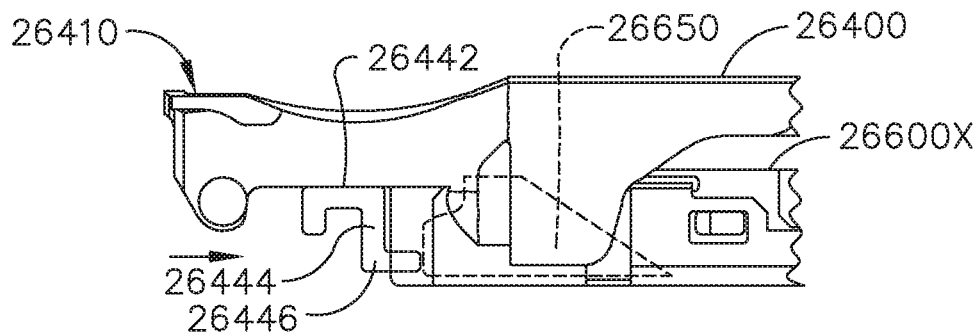
FIG. 95 is another side elevational view of the anvil and surgical staple cartridge of FIG. 93 after the anvil has been moved to a closed position.

FIGS. 93-95 illustrate insertion of an incompatible cartridge 26600X into the surgical end effector 26300. FIG. 93 illustrates initial installation of an incompatible surgical staple cartridge 26600X into the end effector 26300. Although the channel has been omitted from the drawings, the anvil 26400 is shown in a fully open position. FIG. 94 illustrates the anvil 26400 in an intermediate position upon application of an initial closure motion thereto. When in that position, each sled actuator arm 26446 is confrontingly aligned with corresponding cam members 26654 that protrude proximally out of their respective cam slots 26609. Further application of the closure motion to the anvil 26400 may cause the anvil 26400 to translate distally into a final closed position. When the anvil 26400 moves distally, the sled actuator arms 26446 contact the proximally protruding cam members 26654 and move the camming assembly 26650 distally to a point wherein the unlocking portion 26653 thereon is no longer in engagement with the sled latch 26148 on the firing member lock 26142. Thus, the firing member lockout 26142 remains in locking engagement with the elongate channel 26310 of the end effector 26300 to prevent the distal advancement of the firing member 26120 upon actuation of the firing drive system.

Figure 96:
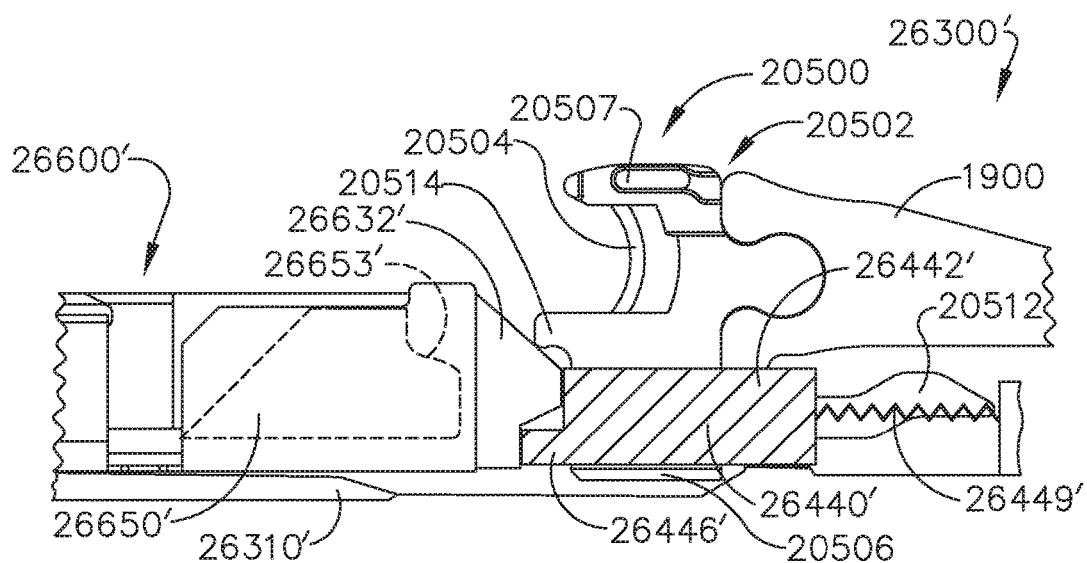
FIG. 96 is a partial cross-sectional side view of a portion of another surgical end effector with a compatible surgical staple cartridge loaded therein and an anvil thereof omitted for clarity.
Figure 97:
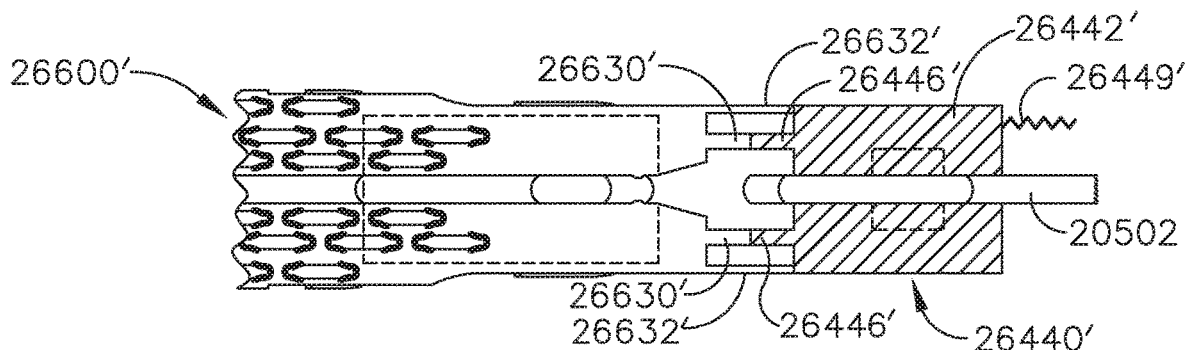
FIG. 97 is a top view of a portion of the surgical staple cartridge and surgical end effector of FIG. 96.
Figure 98:
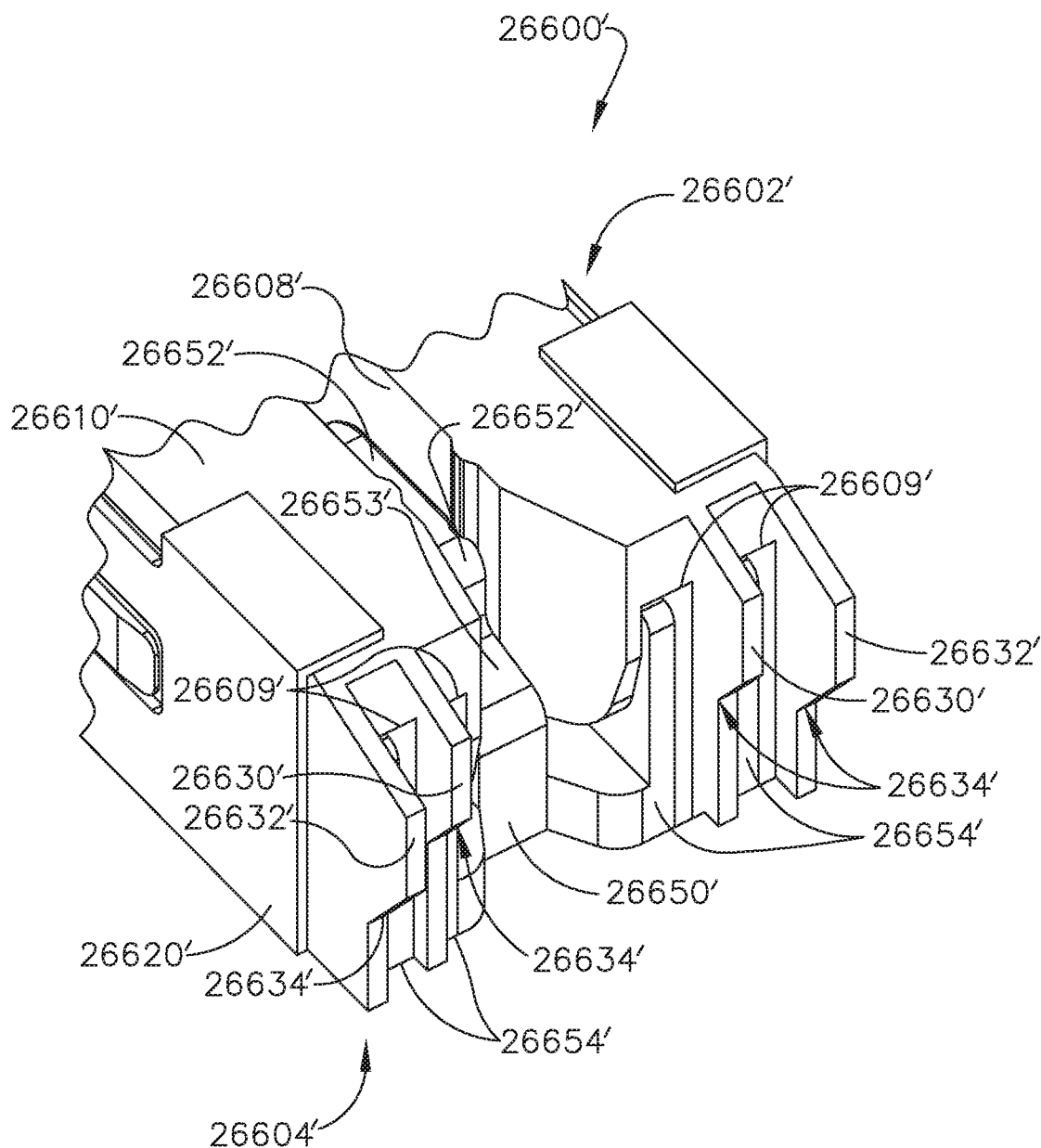
FIG. 98 is a perspective view of a portion of proximal end of a compatible surgical staple cartridge depicted in FIG. 97.

FIGS. 96-98 illustrate another cartridge verification system 26440' that may be employed with an end effector 26300' that employs a firing member 20500 that is axially advanced by a firing member beam 1900 in the various manners discussed herein. As was discussed above, the firing member 20500 comprises a firing member body 20502 that is configured to axially pass through vertically aligned slots in the anvil (not shown), a staple cartridge 26600', and the elongate channel 26310'. A lower foot assembly 20506 that comprises a pair of laterally extending lower flanges extends from a bottom end of the firing member body 20502 to slidably engage corresponding channel ledges that are formed on each side of the channel slot. An upper foot that comprises two laterally extending anvil tabs 20507 may be formed on an upper end of the firing member body 20502 and is configured to slidably engage anvil ledges (not shown) that are formed on each side of the anvil slot. In at least one arrangement, the firing member 20500 further includes a pair of central tabs (not shown) that extend laterally from each side of the firing member body 20502.

The firing member body 20502 is also configured with a proximally extending spring tail 20512 that may be configured to operably interface with a firing member lockout spring (not shown) that is mounted in the elongate channel 26310' and is configured to bias the firing member 20500 downward in the elongate channel 26310' into a locked position. When in the locked position, the firing member foot 20506 and/or the central tabs are misaligned with corresponding passages in the channel 20310' and as such, should the user attempt to distally advance the firing member 20500 when in that locked out state, the firing member 20500 would not move distally due to such misalignment. That is, the foot 20506 and/or central tabs contact portions of the elongate channel 20310' to thereby prevent the distal advancement of the firing member 20500. In one arrangement, a sled latch 20514 is formed on the firing member body 20502 and is configured to be engaged by a proximally extending unlocking portion 26653' on a camming assembly 26650' that is operably supported in a proximal-most unfired or starting position within a compatible cartridge 26600' that has been operably seated in the channel 26310'. When a fresh, unfired staple cartridge 26600' with the camming assembly 26650' thereof in its unfired position has been operably installed in the elongate channel 26310', the unlocking portion 26653' on the camming assembly 26650' engages the sled latch 20514 on the firing member body 20502 and moves the firing member 20500 upward into an unlocked position wherein the lower foot assembly 20506 and/or the central tabs are aligned with their respective passages in the channel 26310' to permit the firing member 20500 to axially advance therein. As the user distally advances the firing member 20500 into the cartridge 26600', the firing member 20500 also drives the camming assembly 20650' therein which cams the drivers upward to drive the staples or fasteners supported thereon into forming contact with the underside of the anvil. The tissue cutting member 20504 on the firing member 20500 then cuts through the stapled tissue. Once the firing member 20500 has been driven to its distal-most position corresponding to the ending position of the camming assembly 26650', the firing member 20500 is retracted back to its proximal-most position, leaving the camming assembly 26650' in the distal end of the cartridge 26600'. When the firing member 20500 returns to its proximal-most beginning position, the lock spring once again biases the firing member 20500 back into its locked position. Thus, should the user inadvertently try to reuse the spent cartridge, the camming assembly 26650' is not in its starting position which is required to unlock the firing member 20500. Thus, this firing member lockout arrangement may also be referred to herein as a "spent cartridge lockout arrangement".

In the arrangement depicted in FIGS. 96 and 97, the cartridge verification system 26440' comprises an axially movable, cartridge verification member or seating shuttle 26442' that is supported within the channel 26310' for axial movement from a distal-most cartridge engagement position to a proximal verification location within the channel 26310'. A shuttle spring 26449' is mounted within the channel 26310' and serves to bias the cartridge verification member or seating shuttle 26442' into the distal-most cartridge engagement position. As can be seen in FIGS. 96 and 97, the cartridge verification member or shuttle 26442' further includes a pair of distally protruding sled actuator arms 26446'. The sled actuator arms 26446' are positioned to contact corresponding cam members on a camming assembly of a non-compliant cartridge as will be discussed below.

FIG. 98 illustrates a proximal end portion 26604' of the surgical staple cartridge 26600' that is compatible with the surgical end effector 26300'. In at least one arrangement, the surgical staple cartridge 26600' comprises an elongate cartridge body 26602' that is sized to be removably seated in the elongate channel 26310'. The cartridge body 26602' includes a cartridge slot 26608' that extends from the proximal end portion 26604' to a distal end portion of the cartridge body 26602'. The cartridge body 26602' further comprises a cartridge deck surface 26610' that confronts a staple-forming undersurface of the anvil when the cartridge 26600' is seated in the channel 26310' and the anvil is pivoted to a closed position. Although not shown in FIG. 98, the surgical staple cartridge 26600' may have a plurality of (usually three) lines of surgical staple pockets on each side of the cartridge slot 26608' that open through the cartridge deck surface 26610'. Each staple pocket may have a staple driver (not shown) associated therewith that supports a surgical staple or fastener (not shown) thereon. In at least one example, the cartridge body 26602' is molded from a polymer material with the staple pockets molded or machined therein. In one arrangement, the staple pockets also open through a bottom of the cartridge body 26602' to facilitate installation of the drivers and fasteners into their respective pockets. Once the drivers and fasteners are inserted into their respective staple pockets, a cartridge pan 26620' is attached to the bottom of the cartridge body 26602'. When installed, the cartridge pan 26620' may, among other things, prevent the drivers and fasteners from falling out of the bottom of the cartridge body 26602' during handling and installation of the cartridge 26600' into the elongate channel 26310'.

In the illustrated arrangement, cartridge 26600' operably supports a camming assembly 26650' therein. The camming assembly 26650' comprises a central body portion 26652' and a series of spaced cam members 26654' that are configured to move axially within corresponding cam slots 26609' formed on each side of the cartridge slot 26608' in the cartridge body 26602'. The cam slots 26609' are aligned with corresponding lines of drivers in the cartridge body 26602' to facilitate camming contact with a corresponding cam member 26654' as the camming assembly 26650' is driven through the staple cartridge 26600' from a beginning position within the proximal end portion 26604' of the cartridge body 26602' to an ending position within the distal end portion of the cartridge body 26602'. The central body portion 26652' includes the proximally extending unlocking portion 26653' that is configured to engage the sled latch 20514 on the firing member 20500 when the cartridge 26600' has been properly loaded into the channel 26310'.

The compatible cartridge 26600' further includes proximally protruding verification features or key formations 26630' that are configured to engage the sled actuator arms 26446' when the cartridge 26600' is operably seated in the channel 26310'. In the illustrated arrangement, the cartridge body 26602' additional has two side verification features or cartridge key formations 26632' that are also configured to engage the cartridge verification member or shuttle 26442'. As will be discussed further below, if the verification formations 26630', 26632' are not present to contact the corresponding sled actuator arm 26446' and the cartridge verification member or shuttle 26442', the sled actuator arms 26446' would otherwise contact the protruding cam members 26654' and push or urge the camming assembly 26650' distally into a position wherein the unlocking portion 26653' on the camming assembly 26650' is no longer in unlocking engagement with the sled latch 20514 on the firing member 20500.

Figure 99:
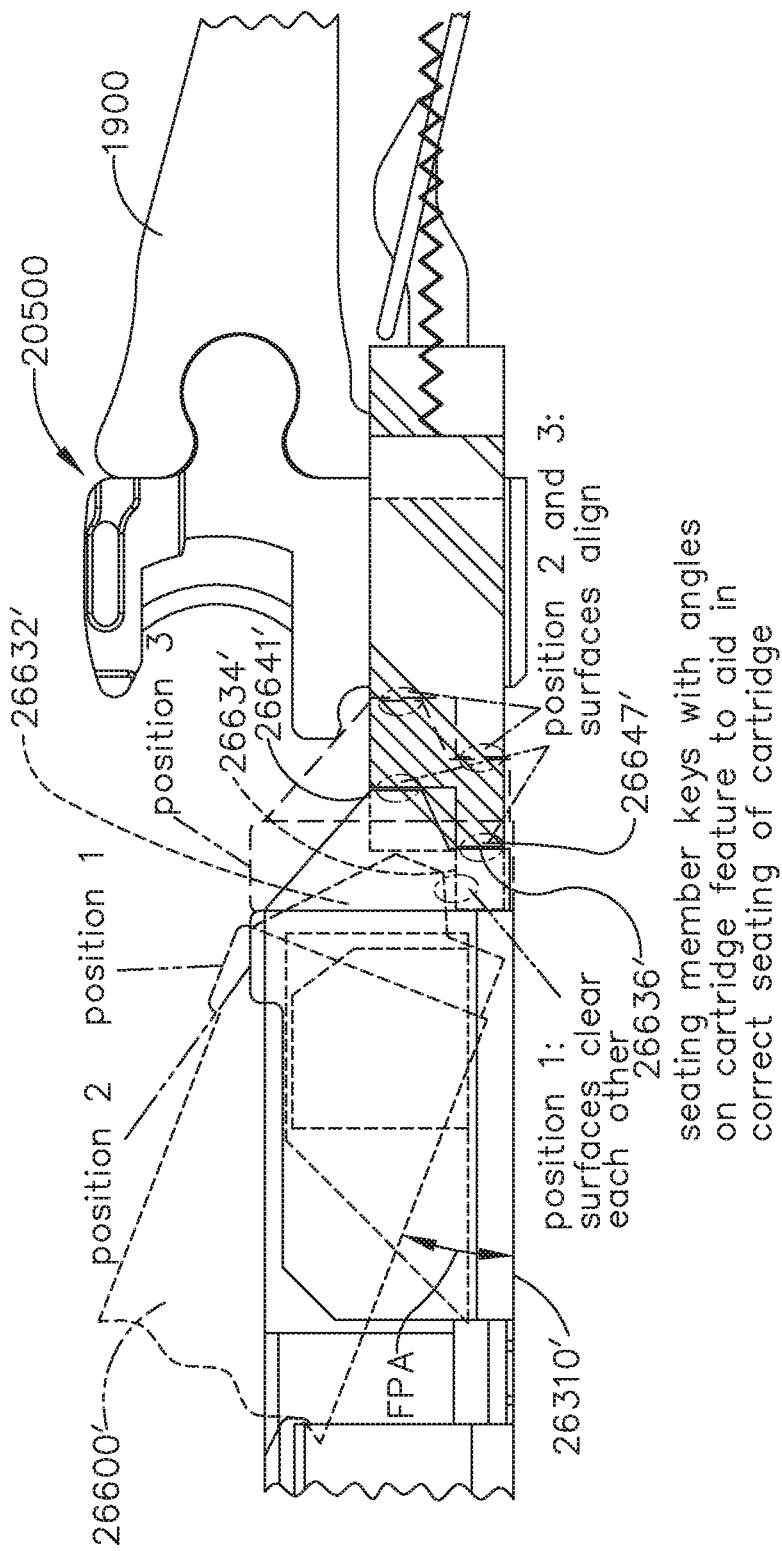
FIG. 99 is another partial cross-sectional side view of a portion of the surgical end effector of FIG. 96 illustrating the installation of a compatible surgical staple cartridge therein.
Figure 100:
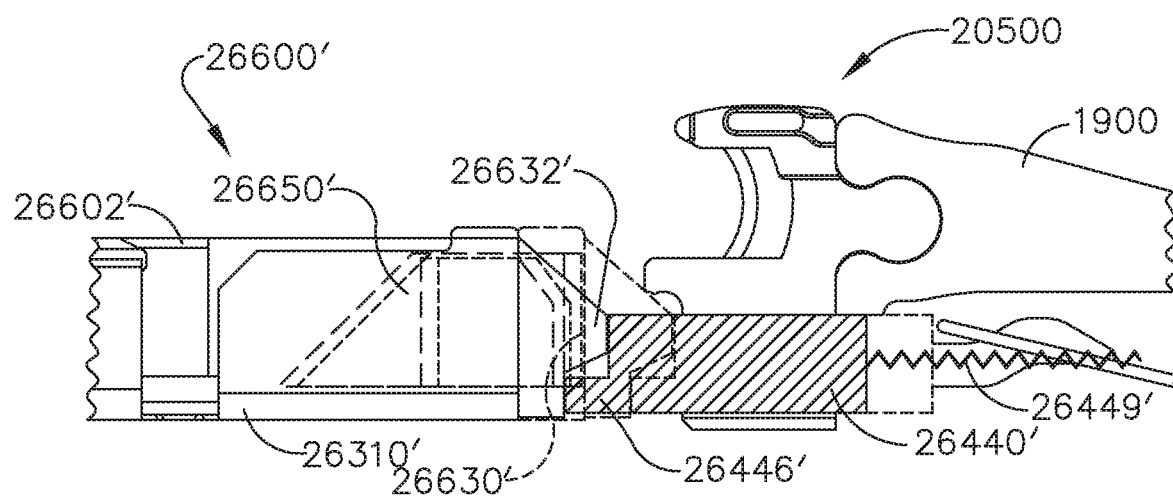
FIG. 100 is another partial cross-sectional side view of a portion of the surgical end effector of FIG. 96 illustrating the installation of a compatible surgical staple cartridge therein.
Figure 101:
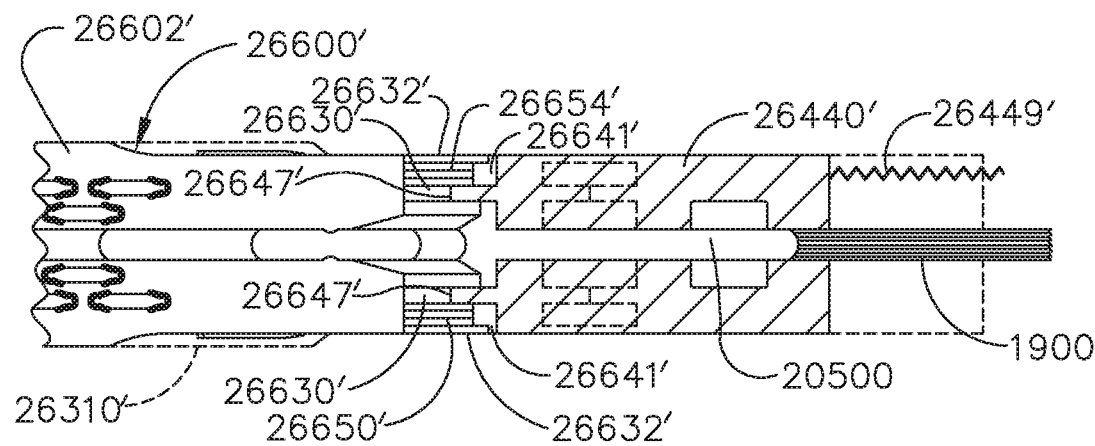
FIG. 101 is a top view of the surgical end effector and compatible surgical staple cartridge of FIG. 98.

Turning now to FIGS. 99-101, in the illustrated arrangement, the verification features or key formations 26630', 26632' each have an angled lower alignment surface 26634' thereon that facilitate initial insertion of the cartridge 26600' into the channel 26310' at a first position angle FPA wherein the angled lower alignment surfaces 26634' avoid abutting contact with the sled actuator arms 26446'. The surfaces 26634' may be referred to herein as secondary surfaces. Once the user has positioned the surgical staple cartridge 26600' in the first installation position, the cartridge 26600' is then pivoted downward into the channel 26310' into position 2 wherein vertical abutment surfaces 26636' (secondary surfaces) on the verification features or cartridge key formations 26630', 26632' abut the corresponding vertical abutment surfaces 26641' and 26647' (primary surfaces) on the cartridge verification member or shuttle 26442'. The user may then advance the cartridge 26600' proximally into position 3 within the elongate channel 26310'.

Figure 102:
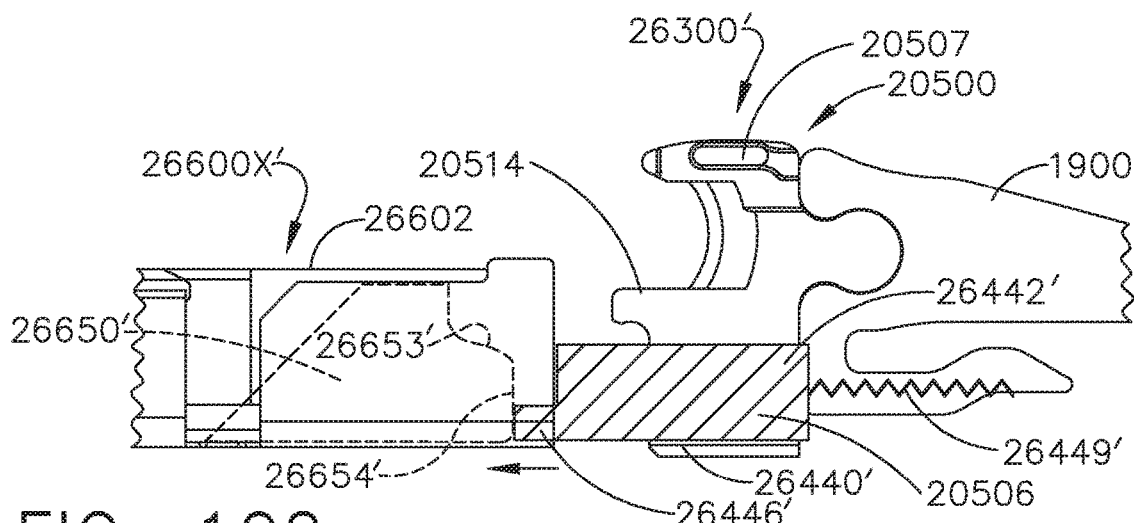
FIG. 102 is another partial cross-sectional side view of a portion of the surgical end effector of FIG. 96 illustrating the installation of an incompatible surgical staple cartridge therein.

FIG. 102 illustrates insertion of an incompatible cartridge 26600X' into the surgical end effector 26300'. In this example, the incompatible cartridge 26600X' lacks the verification features or cartridge key formations 26630', 26632' that were provided on the compatible cartridge 26600' to engage the cartridge verification member or shuttle 26442'. Thus, as the cartridge 26600X' is seated in the channel 26310', the sled actuator arms 26446' contact the protruding cam members 26654' and push or urge the camming assembly 26650' distally into a position wherein the unlocking portion 26653' on the camming assembly 26650' is not in unlocking engagement with the sled latch 20514 on the firing member 20500. Thus, the firing member 20500 remains locked in position and the user would be unable to distally advance the firing member 20500 into the incompatible cartridge 26600X'.

Figure 103:
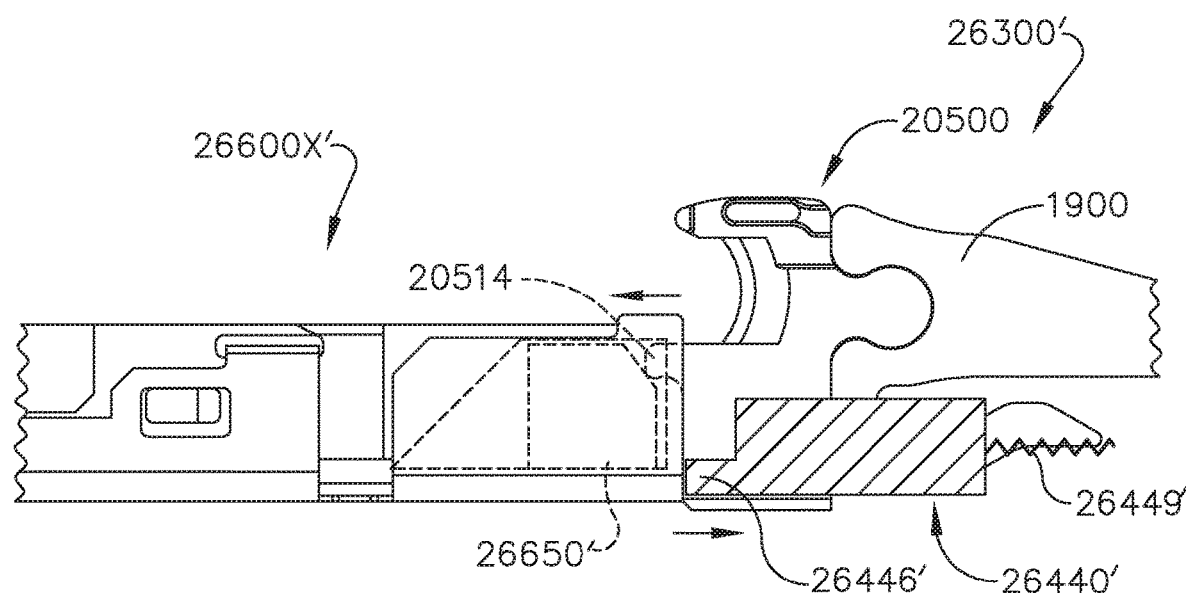
FIG. 103 is another partial cross-sectional side view of a portion of the surgical end effector of FIG. 96 illustrating the installation of an incompatible surgical staple cartridge therein.
Figure 104:
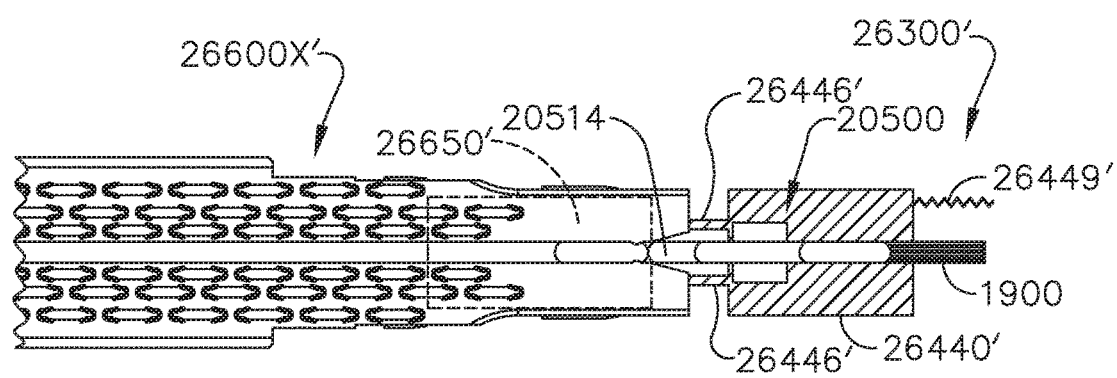
FIG. 104 is a top view of the surgical end effector and incompatible surgical staple cartridge of FIG. 103.
Figure 105:
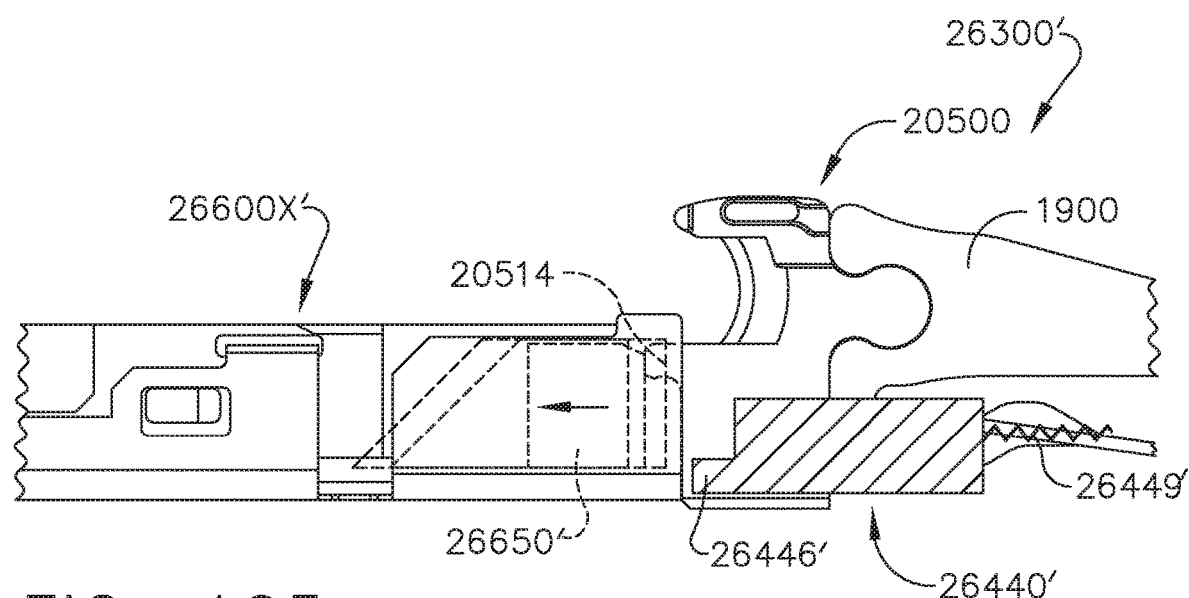
FIG. 105 is another partial cross-sectional side view of a portion of the surgical end effector of FIG. 96 illustrating the installation of an incompatible surgical staple cartridge therein.
Figure 106:
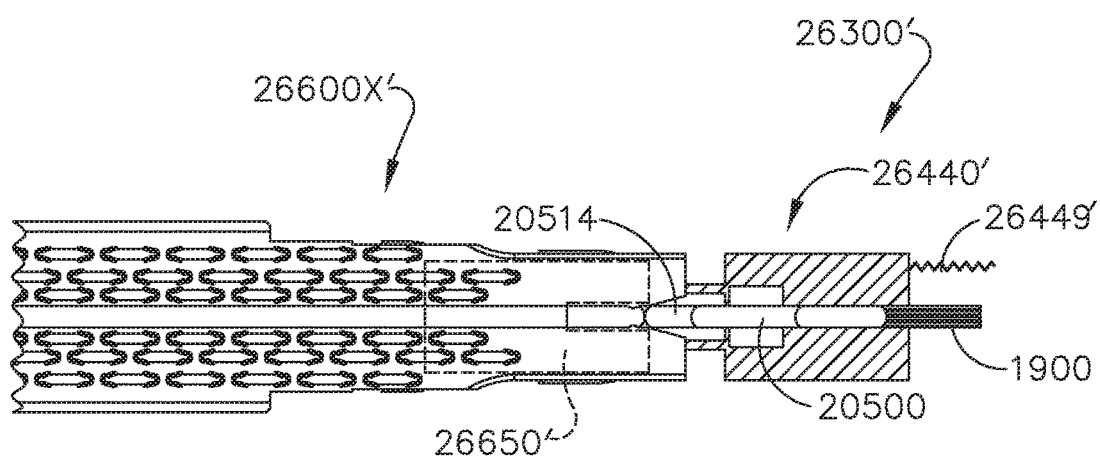
FIG. 106 is a top view of the surgical end effector and incompatible surgical staple cartridge of FIG. 105.

FIGS. 103 and 104 illustrate insertion of the incompatible cartridge 26600X' into the end effector 26300' wherein the incompatible cartridge 26600X' has been initially inserted too far proximally into the channel 26310' such that the distal end of the firing member 20500 has contacted and pushed the camming assembly 26650' or "sled" too far distally within the cartridge 26600X' so as to be in the appropriate position to unlockingly engage the sled latch 20514 portion of the firing member 20500 after the cartridge 26600X' has ultimately been seated in the channel 26310' in a proper position. Likewise, when the incompatible cartridge 26600X' is initially inserted in a diagonal position 1 as was described above an then moved to positions 2 and 3, the firing member 20500 may bump the camming assembly 26650' or sled distally out of the firing member unlocking position such that once properly seated, the camming assembly 26650' would fail to unlock the firing member 20500. See FIGS. 105 and 106.

Figure 107:
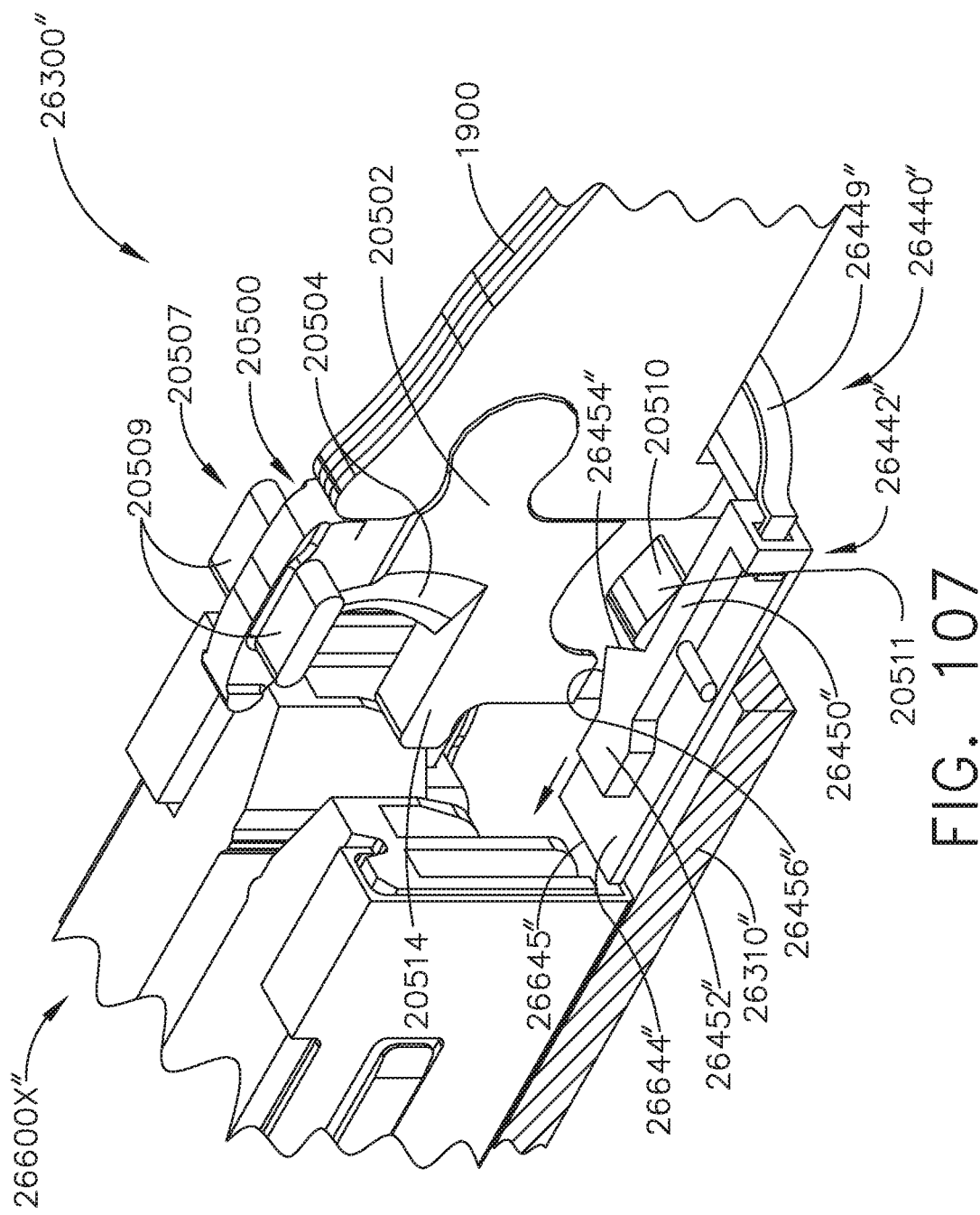
FIG. 107 is a partial cross-sectional perspective view of portions of another surgical end effector with an incompatible surgical staple cartridge installed therein.
Figure 108:
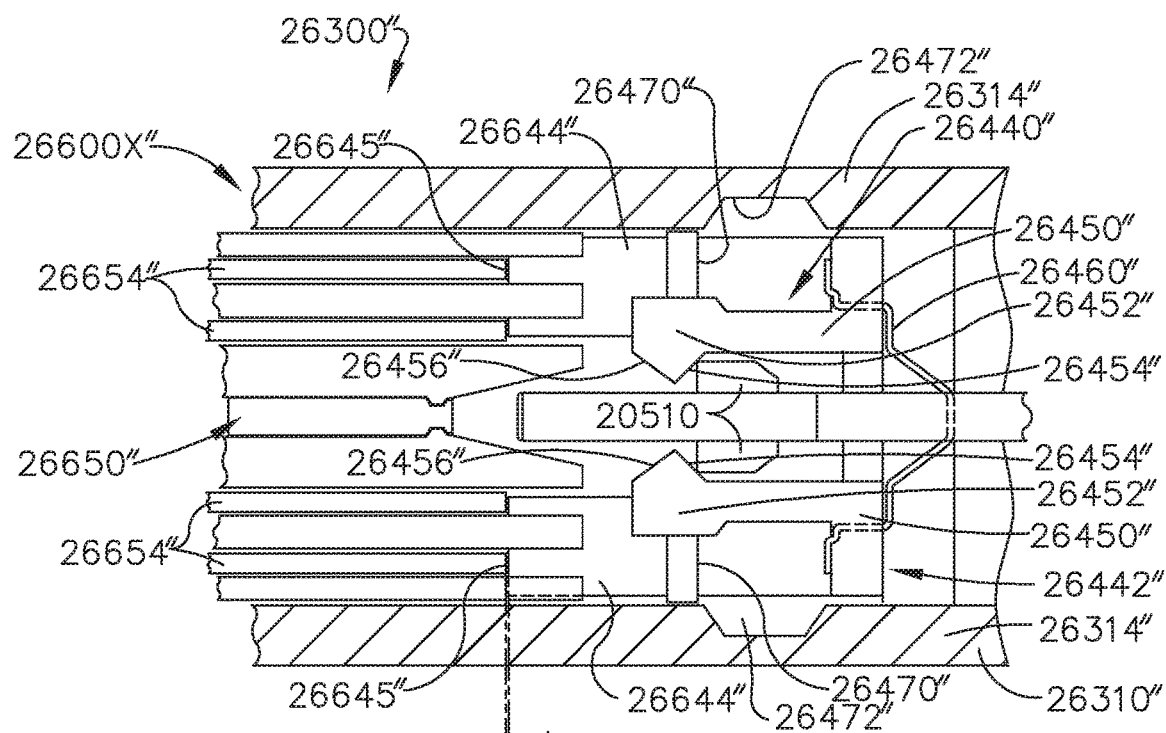
FIG. 108 is a partial top view of portions of the surgical end effector an incompatible surgical staple cartridge of FIG. 107.
Figure 109:
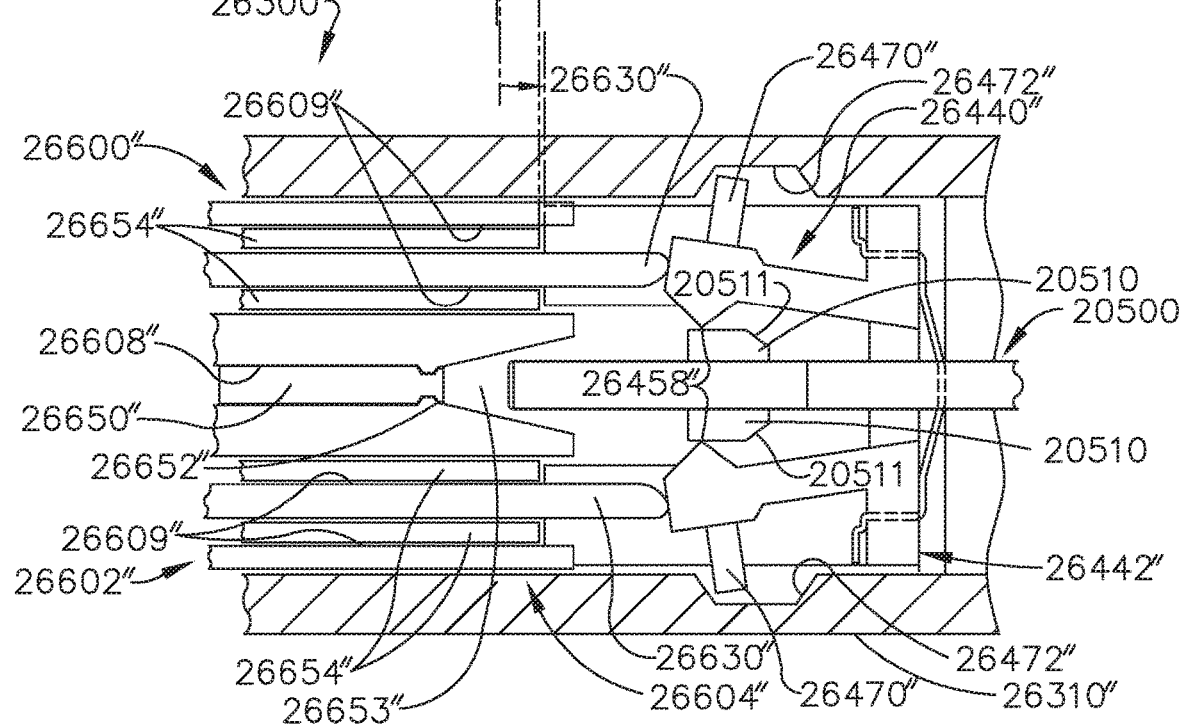
FIG. 109 is another partial top view of the surgical end effector of FIG. 105, with a compatible surgical staple cartridge installed therein.

FIGS. 107-109 illustrate another cartridge verification system 26440" that may be employed with an end effector 26300" that employs a firing member 20500 that is axially advanced by a firing member beam 1900 in the various manners discussed herein. As was discussed above, the firing member 20500 comprises a firing member body 20502 that is configured to axially pass through vertically aligned slots in the anvil (not shown), a staple cartridge, and the elongate channel 26310". A lower foot assembly (not shown) that comprises a pair of laterally extending lower flanges extends from a bottom end of the firing member body 20502 to slidably engage corresponding channel ledges that are formed on each side of the channel slot. An upper foot 20507 that comprises two laterally extending anvil tabs 20509 may be formed on an upper end of the firing member body 20502 and is configured to slidably engage anvil ledges (not shown) that are formed on each side of the anvil slot. In at least one arrangement, the firing member 20500 further includes a pair of central tabs 20510 that extend laterally from each side of the firing member body 20502.

The firing member body 20502 is also configured with a proximally extending spring tail (not shown) that may be configured to operably interface with a firing member lockout spring (not shown) that is mounted in the elongate channel 26310" and is configured to bias the firing member 20500 downward in the elongate channel 26310' into a locked position. When in the locked position, the firing member foot and/or the central tabs 20510 are misaligned with corresponding passages in the channel 20310" and as such, should the user attempt to distally advance the firing member 20500 when in this locked out state, the firing member 20500 would not move distally due to such misalignment. That is, the foot and/or central tabs 20510 contact portions of the elongate channel 26310" to thereby prevent the distal advancement of the firing member 20500. In one arrangement, a sled latch 20514 is formed on the firing member body 20502 and is configured to be engaged by a proximally extending unlocking portion on a camming assembly that is operably supported in a proximal-most starting position within a compatible cartridge that has been operably seated in the channel 26310".

When a fresh, unfired compatible staple cartridge with the camming assembly thereof in its starting (unfired) position has been operably installed in the elongate channel 26310", an unlocking portion on the camming assembly engages the sled latch 20514 on the firing member body 20502 and moves the firing member 20500 upward into an unlocked position wherein the lower foot assembly and/or the central tabs 20510 are aligned with their respective passages in the channel 26310" to permit the firing member 20500 to axially advance therein. As the user distally advances the firing member 20500 into the cartridge, the firing member 20500 also drives the camming assembly therein which cams the drivers upward to drive the staples or fasteners supported thereon into forming contact with the underside of the anvil. A tissue cutting member 20504 on the firing member 20500 then cuts through the stapled tissue. Once the firing member 20500 has been driven to its distal-most position corresponding to the ending position of the camming assembly, the firing member 20500 is retracted back to its proximal-most position, leaving the camming assembly in the distal end (fired position) of the cartridge. When the firing member 20500 returns to its proximal-most beginning position, the lock spring once again biases the firing member 20500 back into its locked position. Thus, should the user inadvertently try to reuse the spent cartridge, the camming assembly is not in its starting position which is required to unlock the firing member 20500. Such firing member locking system may also be referred to herein as a "spent cartridge lockout system".

In the arrangement depicted in FIGS. 107-109, the cartridge verification system 26440" comprises an axially movable, cartridge verification shuttle 26442" that is supported within the channel 26310" for axial movement from a distal-most cartridge engagement position to a proximal verification location within the channel 26310". A shuttle spring 26449" is mounted within the channel 26310" and serves to bias the cartridge verification shuttle 26442" into the distal-most cartridge engagement position. As can be seen in FIGS. 107 and 108, the cartridge verification shuttle 26442" further includes distally extending shuttle base members 26644" and pair of laterally movable shuttle drive arms 26450". Each shuttle drive arm 26450" has a drive latch feature 26452" thereon that has an angled proximal drive surface 26454" and an angled distal drive surface 26456" that converge together to form a point 26548". The shuttle drive arms 26450" are biased laterally inward into a driving position by the shuttle spring 26449". When the shuttle drive arms 26450" are in the driving position, the angled proximal drive surfaces 26454" are in driving engagement with the central tabs 20510 on the firing member 20500 as shown in FIGS. 107 and 108. When the shuttle drive arms 26450" are in that position, distal advancement of the firing member 20500 will cause the seating shuttle 26442" to move distally therewith.

FIG. 109 illustrates a proximal end portion 26604" of a surgical staple cartridge 26600" that is compatible with the surgical end effector 26300" and seated within the channel 26310". In at least one arrangement, the surgical staple cartridge 26600" comprises an elongate cartridge body 26602" that is sized to be removably seated in the elongate channel 26310". The cartridge body 26602" includes a cartridge slot 26608" that extends from the proximal end portion 26604" to a distal end portion of the cartridge body 26602". The cartridge 26600" operably supports a camming assembly 26650" therein. The camming assembly 26650" comprises a central body portion 26652" and a series of spaced cam members 26654" that are configured to move axially within corresponding cam slots 26609" formed on each side of the cartridge slot 26608" in the cartridge body 26602". The cam slots 26609" are aligned with corresponding lines of drivers in the cartridge body 26602" to facilitate camming contact with a corresponding cam member 26654" as the camming assembly 26650" is driven through the staple cartridge 26600" from a beginning position within the proximal end portion 26604" of the cartridge body 26602" to an ending position within the distal end portion of the cartridge body 26602". The central body portion 26652" includes the proximally extending unlocking portion 26653" that is configured to engage the sled latch 20514 on the firing member 20500 when the cartridge 26600" has been properly loaded into the channel 26310".

The compatible cartridge 26600" further includes proximally protruding unlocking features or cartridge key formations 26630" that are configured to engage the shuttle drive arms 26450" when the cartridge 26600" is operably seated in the channel 26310". As can be seen in FIG. 109, during the distal advancement of the firing member 20500, the verification shuttle 26442" is driven distally until each shuttle drive arm 26450" contacts a corresponding cartridge key formation 26630" which causes the shuttle drive arms 26450" to bias laterally outward. As the firing member 20500 continues to move distally, the drive latch features 26452" on the shuttle drive arms 26450" disengage from the corresponding central tabs 20510 on the firing member body 20502 to permit the firing member 20500 to move distally without driving the verification shuttle 26442" distally. Thus, in such case, the verification shuttle 26442" has not moved sufficiently distally so as to move the camming assembly 26650" out of unlocking engagement with the sled latch 20514 on the firing member 20500. Therefore, the firing member 20500 may be driven distally through the compatible cartridge 26600" to drive the fasteners therefrom and to cut the tissue that has been clamped in the end effector 26300". When the firing member 20500 is retracted back into its starting position, a tapered surface 20511 on each central tab 20510 contacts the angled distal drive surface 26456" on the corresponding drive latch feature 26452" to bias the shuttle arms 26450" laterally to permit the central tabs 20510 to reengage the angled proximal drive surfaces 26454" so that the verification shuttle 26442" can once again be driven distally with the firing member 20500.

FIGS. 107 and 108 illustrate an incompatible cartridge 26600X" loaded into the surgical end effector 26300". As can be seen in those Figures, the incompatible cartridge 26600X" lacks the proximally protruding unlocking features or cartridge key formations 26630" that are provided on the compatible cartridge 26600". Thus, when the firing member 20500 is distally advanced, the cartridge verification shuttle 26442" also moves distally with the firing member 20500. As the cartridge verification shuttle 26442" moves distally, the distal ends 26645" of the distally extending shuttle base members 26644" contact the camming assembly 26650" and move the camming assembly 26650" out of unlocking engagement with the sled latch 20514 on the firing member 20500. When the unlocking portion 26653" of the camming assembly 26650" disengages the sled latch 20514, the firing member body 20502 will drop into locking engagement with the elongate channel 26310" thereby preventing further distal advancement of the firing member 20500.

As can be further seen in FIGS. 108 and 109, in the illustrated arrangement, a lateral stiffener member 26470" protrudes laterally outward from each shuttle arm 26450". When the firing member 20500 and the verification shuttle 26442" are located in their respective proximal-most starting positions, each lateral stiffener member 26470" is laterally aligned with a corresponding channel notch 26472" provided in each channel sidewall 26314" to provide clearance for the shuttle arms 26450" to move laterally when a compatible cartridge 26600" has been properly loaded into the end effector 26300". However, when an incompatible cartridge 26600X" has been loaded into the end effector 26300" and the user begins to advance the firing member 20500 as well as the verification shuttle 26442" distally, the lateral stiffener members 26470" are no longer aligned with the channel notches 26472" in the channel sidewalls 26314" as can be seen in FIG. 108. In such instance, the lateral stiffener members 26470" prevent the shuttle arms 26450" from biasing laterally outward out of engagement with the central tabs 20510 that extend laterally from each side of the firing member body 20502.

The cartridge verification systems described herein may address various problems that may, from time-to-time, be encountered when using an end effector that is capable of initially accepting a variety of cartridges wherein some of the cartridges are not otherwise particularly compatible with the end effector. For example, a cartridge may operably fit into the channel of the end effector, but the cartridge may lack proper fastener configurations that are compatible with the forming pockets on the end effector anvil. The incompatible cartridge may not have the proper numbers and forms of staples, etc. The cartridge may not have a camming assembly that is compatible with the firing member lockout arrangement employed by the end effector. Some cartridges may have an appropriate camming assembly, but the camming assembly may at some point have moved to a marginal unlocking position wherein the camming assembly may or may not unlockingly engage the firing member lockout arrangement. At least some of the cartridge verification systems may address that issue. The cartridge verification systems disclosed herein may also provide the ability to differentiate between an old obsolete cartridge and a newer more appropriate cartridge that has, for example, features that are better paired to the end effector components. The cartridge verification systems may also ensure that a cartridge is properly seated in the end effector channel and minimize any misalignment of the cartridge in the channel wherein the proximal end of the cartridge is positioned relative to the firing member in an undesirable position wherein the central tabs on the firing member may get under the cartridge pan rather than on top of it as desired. Such misalignment may result in the damage and bending of the cartridge pan which could lead to premature locking of the firing member.

FIGS. 110-115 illustrate another cartridge verification system 27440 that may be employed with an end effector 27300 that employs a firing member 20500 (described above) that is axially advanced by a firing member beam 1900 in the various manners discussed herein. In the illustrated arrangement, the cartridge verification system 27440 comprises an axially movable cartridge verification member or shuttle 27442 that is supported within a channel 27310 of the end effector 27300 for axial movement from a distal-most cartridge engagement position to a proximal verification location within the channel 27310. The cartridge verification member or shuttle 27442 may be fabricated from spring steel and include an elongate body 27444 that has a blocking hook 27446 that is formed on a distal end 27445 of the elongate body 27444. See FIG. 111. The cartridge verification member or shuttle 27442 further includes an actuator portion 27448 that is formed on a proximal end 27447 of the elongate body 27444.

Figure 111:
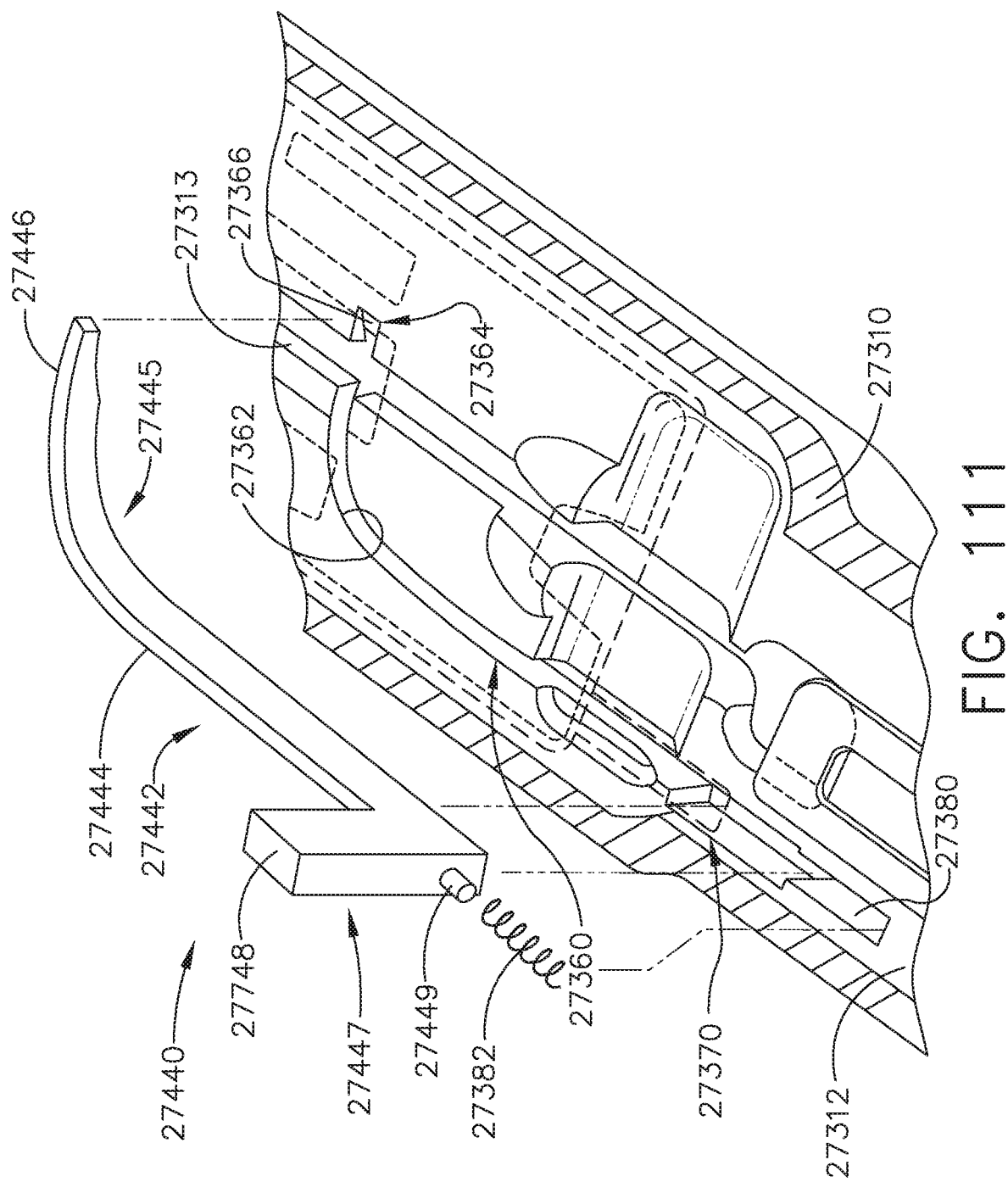
FIG. 111 is a partial exploded assembly view of portions of the surgical end effector of FIG. 110.

Still referring to FIG. 111, the cartridge verification member or shuttle 27442 is configured to axially move within a shuttle track 27360 that is formed in a channel bottom 27312 of the channel 27310. As can be seen in FIG. 111, the shuttle track 27360 comprises a curved transverse portion 27362 that extends transversely relative to a channel slot 27313 that is centrally disposed in the channel bottom 27312 to accommodate axial passage of the firing member 20500 therethrough. The transverse curved portion 27362 of the shuttle track 27360 terminates in a ramped track portion 27364 that is located on another side of the channel slot 27313. As can be seen in FIG. 111, the ramped track portion 27364 has an angled bottom surface 27366. A proximal end 27370 of the shuttle track 27360 abuts an axial spring cavity 27380 that is configured to support a shuttle spring 27382 that is journaled on a spring retainer pin 27449 that protrudes proximally from the actuator portion 27448 of the cartridge verification member or shuttle 27442. The shuttle spring 27382 serves to bias the verification shuttle 27442 into a distal-most, locked position wherein the cartridge verification member or shuttle 27442 blocks distal advancement of a camming assembly 27650 and the firing member 20500.

Figure 110:
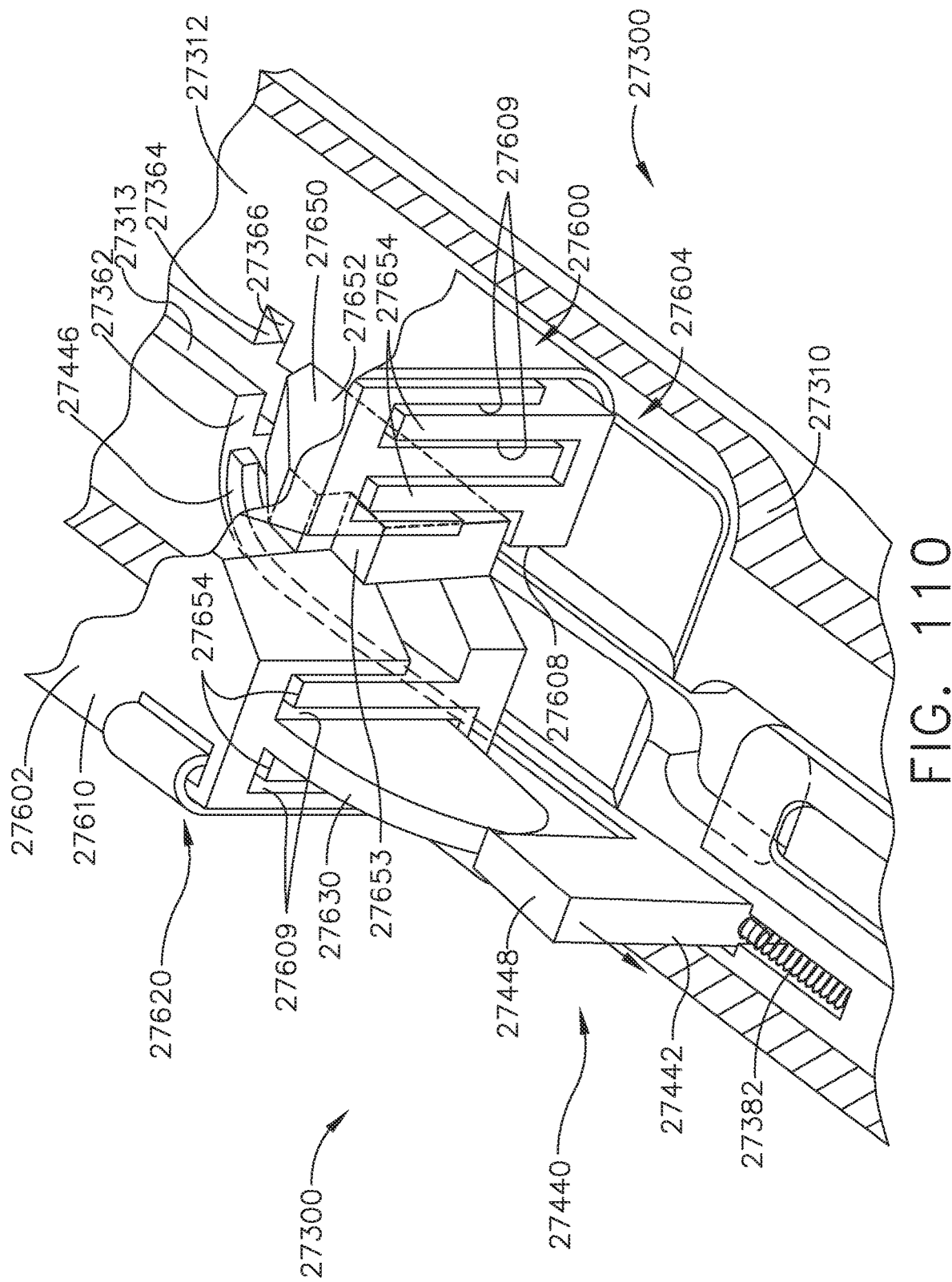
FIG. 110 is a partial cross-sectional perspective view of portions of another surgical end effector with a compatible surgical staple cartridge installed therein.

FIG. 110 illustrates a proximal end portion 27604 of a surgical staple cartridge 27600 that is compatible with the surgical end effector 27300. In at least one arrangement, the surgical staple cartridge 27600 comprises an elongate cartridge body 27602 that is sized to be removably seated in the elongate channel 27310. The cartridge body 27602 includes a cartridge slot 27608 that extends from the proximal end portion 27604 to a distal end portion of the cartridge body 27602. The cartridge body 27602 further comprises a cartridge deck surface 27610 that confronts a staple-forming undersurface of the anvil when the cartridge 27600 is seated in the channel 27310 and the anvil is pivoted to a closed position. Although not shown in FIG. 110, the surgical staple cartridge 27600 may have a plurality of (usually three) lines of surgical staple pockets on each side of the cartridge slot 27608 that open through the cartridge deck surface 27610. Each staple pocket may have a staple driver (not shown) associated therewith that supports a surgical staple or fastener (not shown) thereon. In at least one example, the cartridge body 27602 is molded from a polymer material with the staple pockets molded or machined therein. In one arrangement, the staple pockets also open through a bottom of the cartridge body 27602 to facilitate installation of the drivers and fasteners into their respective pockets. Once the drivers and fasteners are inserted into their respective staple pockets, a cartridge pan 27620 is attached to the bottom of the cartridge body 27602. When installed, the cartridge pan 27620 may, among other things, prevent the drivers and fasteners from falling out of the bottom of the cartridge body 27602 during handling and installation of the cartridge 27600 into the elongate channel 27310.

In the illustrated arrangement, cartridge 27600 operably supports a camming assembly 27650 therein. The camming assembly 27650 comprises a central body portion 27652 and a series of spaced cam members 27654 that are configured to move axially within corresponding cam slots 27609 formed on each side of the cartridge slot 27608 in the cartridge body 27602. The cam slots 27609 are aligned with corresponding lines of drivers in the cartridge body 27602 to facilitate camming contact with a corresponding cam member 27654 as the camming assembly 27650 is driven through the staple cartridge 27600 from a beginning position within the proximal end portion 27604 of the cartridge body 27602 to an ending position within the distal end portion of the cartridge body 27602. The central body portion 27652 includes a proximally extending unlocking portion 27653 that is configured to engage the sled latch 20514 on the firing member 20500 when the cartridge 27600 has been properly loaded into the channel 27310.

The compatible cartridge 27600 further includes a proximally protruding verification feature or cartridge key formation 27630 that is configured to engage the sled actuator 27448 when the cartridge 27600 is operably seated in the channel 27310. The verification feature 27630 biases the cartridge verification member or shuttle 27442 into the proximal-most, unlocked position wherein the camming assembly 27650 and the firing member 20500 may be distally displaced through the cartridge 27600. When the cartridge verification member or shuttle 27442 is in the unlocked position, the blocking hook 27446 that is formed on the distal end 27445 of the elongate body 27444 of the cartridge verification member or shuttle 27442 is retracted into the curved transverse portion 27362 of the shuttle track 27360 and does not extend across the channel slot 27313 in the channel bottom 27312. When the blocking hook 27446 is not extending across the channel slot 27313, the firing member 20500 and the camming assembly 27650 can be advanced into the cartridge 27310".

Figure 115:
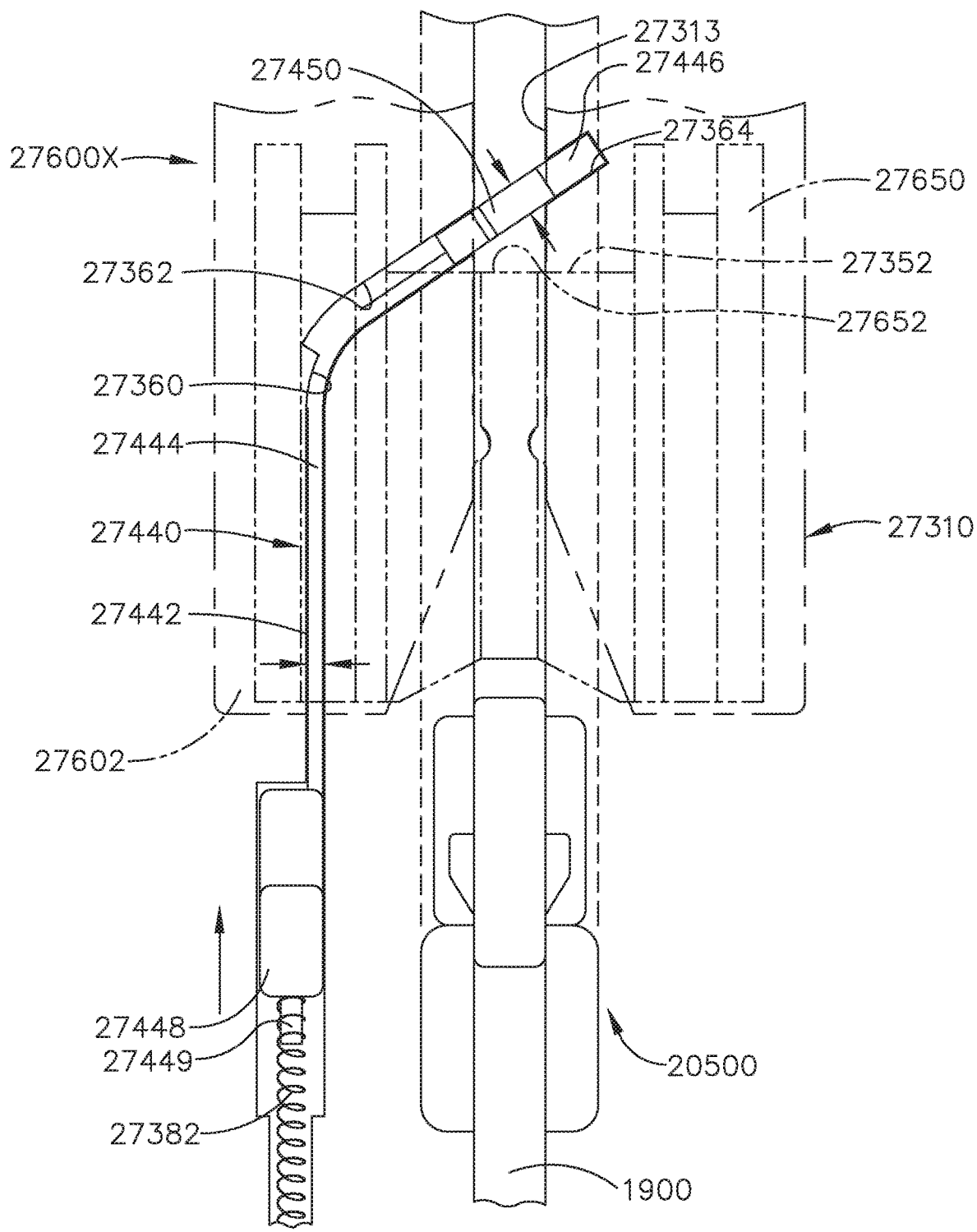
FIG. 115 is a top view of the surgical end effector and surgical staple cartridge of FIG. 114.
Figure 116:
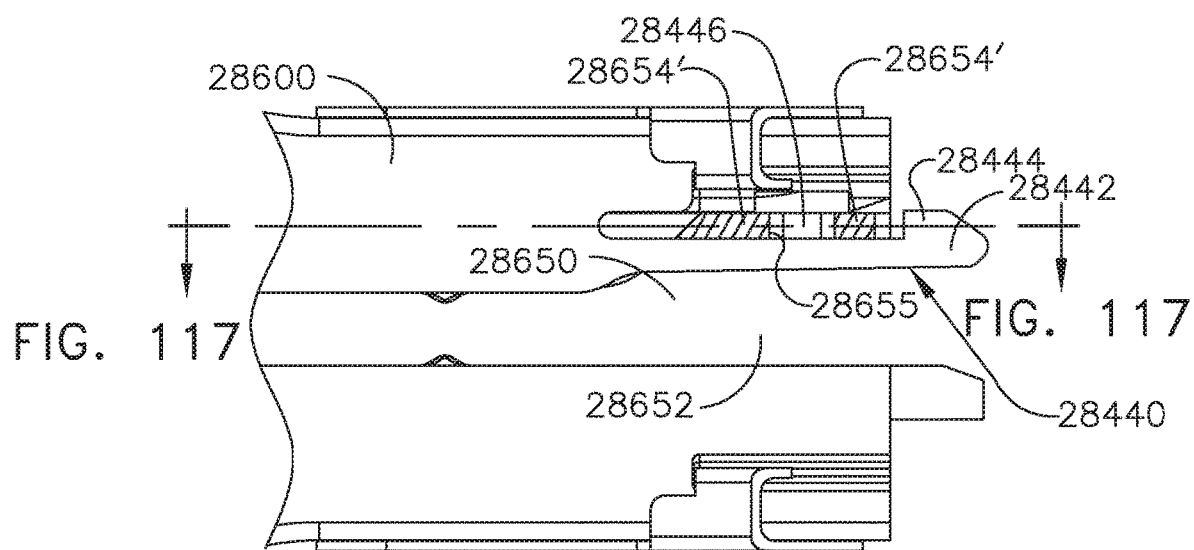
FIG. 116 is a top view of a portion of another surgical staple cartridge.
Figure 118:
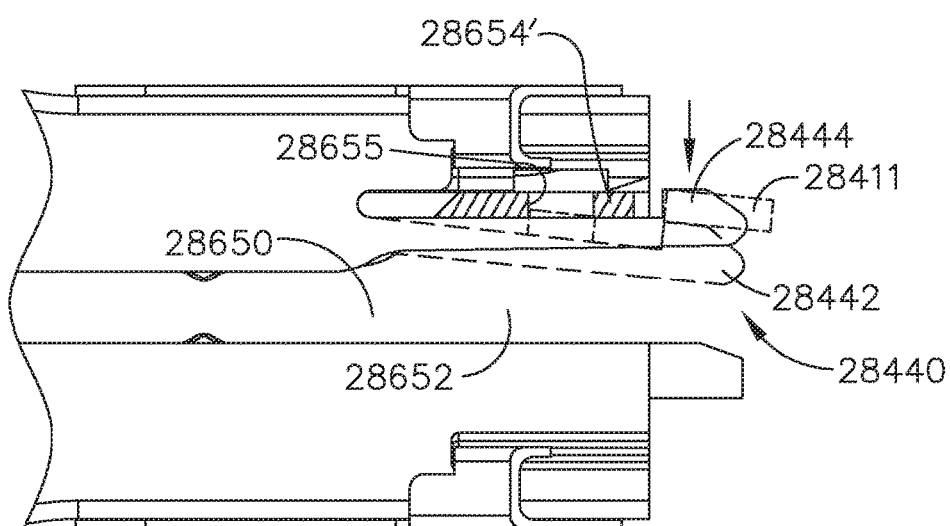
FIG. 118 is another top view of the surgical staple cartridge of FIG. 116 interacting with a compatible actuator portion of a surgical end effector.

FIGS. 114 and 115 illustrate the surgical end effector 27300 with an incompatible cartridge 27600X installed therein. In this example, the incompatible cartridge 27600X lacks the verification feature or cartridge key formation 27630 that was provided on the compatible cartridge 27600 to engage the actuator portion 27448 of the cartridge verification member or shuttle 27442. Thus, the shuttle spring 27382 has biased the cartridge verification member or shuttle 27442 distally into its locked position wherein the blocking hook 27446 that is formed on the distal end 27445 of the elongate body 27444 of the cartridge verification member or shuttle 27442 extends transversely across the channel slot 27313 and into the ramped track portion 27364. As the blocking hook 27446 enters the ramped track portion 27364, the angled bottom surface 27366 causes the blocking hook 27446 to move upward into a position wherein the blocking hook 27446 blocks the distal advancement of the camming assembly 27650 and the firing member 20500. Thus, when in that position, should the user unwittingly attempt to distally advance the firing member 20500, the blocking hook 27446 will block the distal advancement of the camming assembly 27650 and the firing member 20500.

In at least one arrangement as shown in FIG. 115, the portion of the blocking hook 27446 that transversely spans the channel slot 27313 may be reinforced with an additional reinforcement block portion 27450 that is attached thereto. That is the portion of the blocking hook 27446 that is reinforced has a cross-sectional thickness that is greater than a cross-sectional thickness of the remaining body portions of the cartridge verification member or shuttle 26442. Alternative arrangements are contemplated for use with those end effectors disclosed herein that employ an axially movable closure member for moving the anvil to a closed position such as, for example, an end effector closure tube. In such end effector arrangements, for example, the end effector closure tube may be configured to bias the verification shuttle to the locked, blocking position when the closure member is actuated to close the anvil. The cartridge verification system 27440 may also be effectively employed with surgical end effectors that have rotary powered firing member arrangements with firing member lockout systems of the types disclosed herein.

Figure 117:
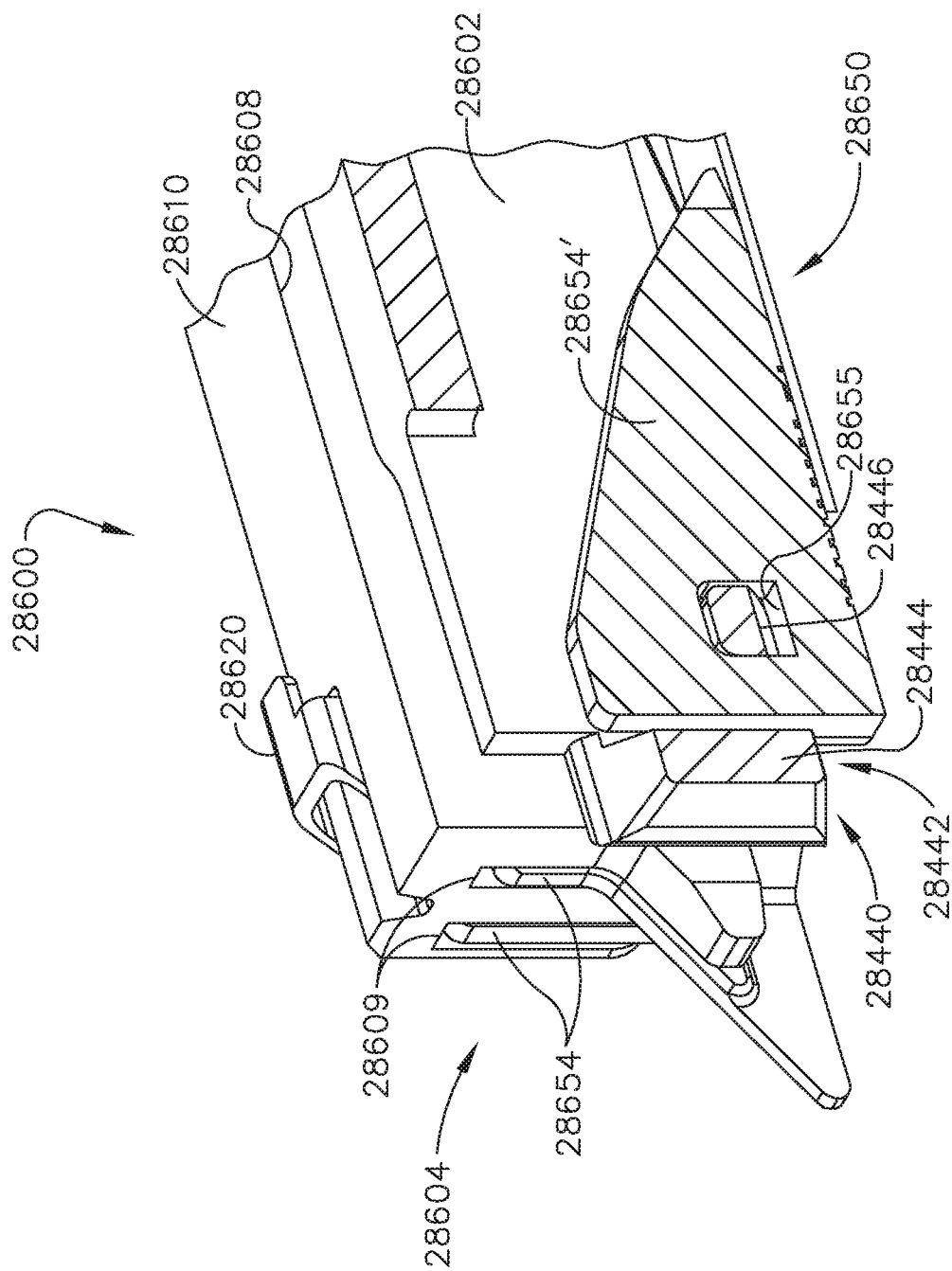
FIG. 117 is a partial cross-sectional perspective view of a portion of the surgical staple cartridge of FIG. 116 with a camming assembly thereof in a locked position.
Figure 119:
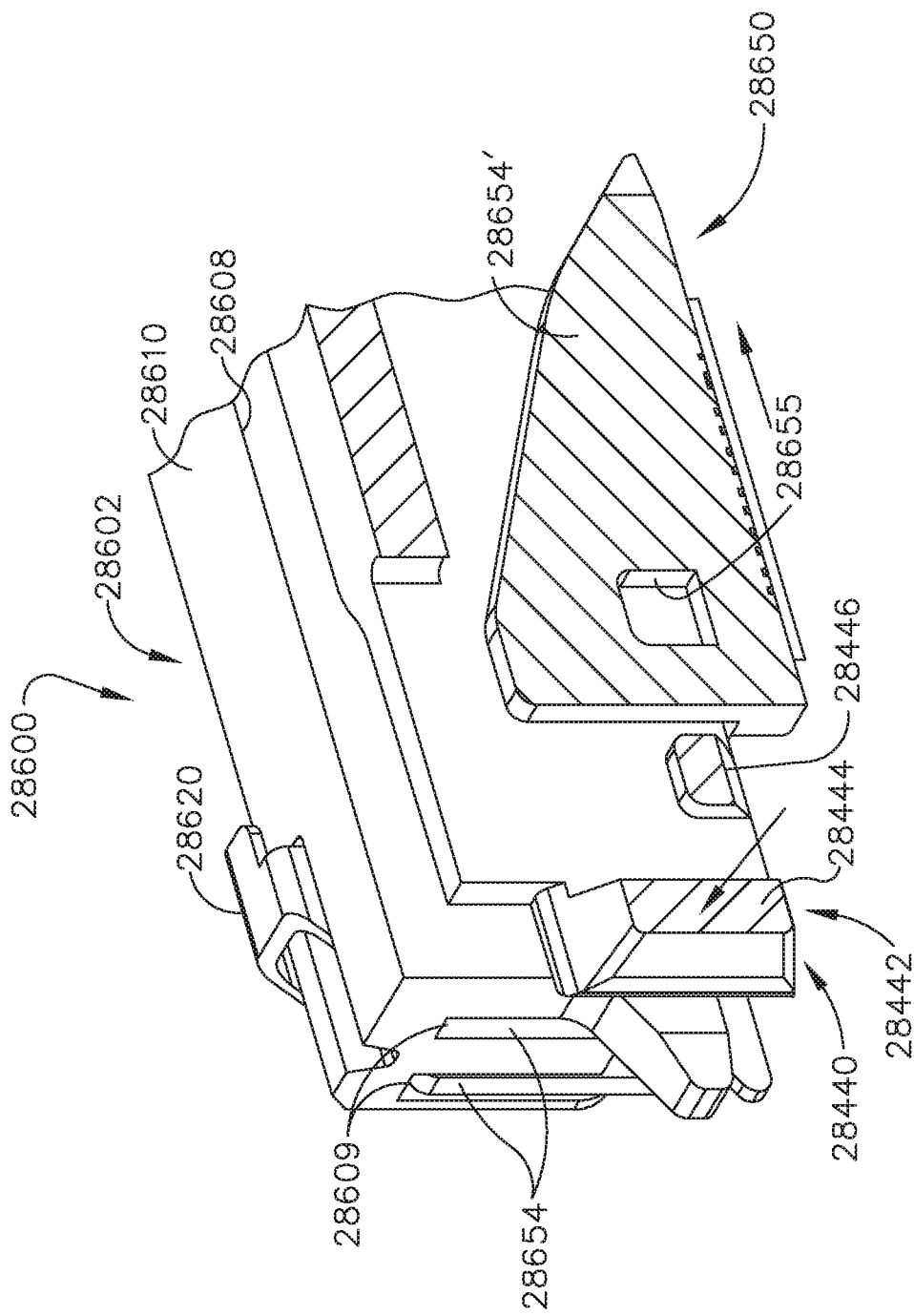

FIGS. 116-119 illustrate an alternative surgical staple cartridge 28600 that may be employed in connection with various end effector arrangements disclosed herein. In the illustrated arrangement, the surgical staple cartridge 28600 comprises an elongate cartridge body 28602 that is sized to be removably seated in the elongate channel of the end effector. As can be seen in FIG. 117, the cartridge body 28602 includes a cartridge slot 28608 that extends from a proximal end portion 28604 of the cartridge body 28602 to a distal end portion of the cartridge body 28602. The cartridge body 28602 further comprises a cartridge deck surface 28610 that confronts a staple-forming undersurface of the anvil when the cartridge 28600 is seated in the channel and the anvil is pivoted to a closed position. Although not shown in FIG. 117, the surgical staple cartridge 28600 may have a plurality of (usually three) lines of surgical staple pockets on each side of the cartridge slot 28608 that open through the cartridge deck surface 28610. Each staple pocket may have a staple driver (not shown) associated therewith that supports a surgical staple or fastener (not shown) thereon. In at least one example, the cartridge body 28602 is molded from a polymer material with the staple pockets molded or machined therein. In one arrangement, the staple pockets also open through a bottom of the cartridge body 28602 to facilitate installation of the drivers and fasteners into their respective pockets. Once the drivers and fasteners are inserted into their respective staple pockets, a cartridge pan 28620 is attached to the bottom of the cartridge body 28602. When installed, the cartridge pan 28620 may, among other things, prevent the drivers and fasteners from falling out of the bottom of the cartridge body 28602 during handling and installation of the cartridge 28600 into the elongate channel.

In the illustrated arrangement, cartridge 28600 operably supports a camming assembly 28650 therein. The camming assembly 28650 comprises a central body portion 28652 and a series of spaced cam members 28654, 28654' that are configured to move axially within corresponding cam slots 28609 formed on each side of the cartridge slot 28608 in the cartridge body 28602. The cam slots 28609 are aligned with corresponding lines of drivers in the cartridge body 28602 to facilitate camming contact with a corresponding cam member 28654, 28654' as the camming assembly 28650 is driven through the staple cartridge 28600 from a beginning position within the proximal end portion 28604 of the cartridge body 28602 to an ending position within the distal end portion of the cartridge body 28602.

Still referring to FIG. 117, the cartridge 28600 is equipped with a camming assembly locking system 28440 that is configured to retain the camming assembly 28650 in its starting position unless the cartridge 28600 has been loaded into a compatible end effector. In the illustrated arrangement for example, the camming assembly locking system 28440 comprises a laterally displaceable lock feature 28442 that comprises an actuator portion 28444 and a locking tab 28446. As can be seen in FIG. 117, the locking tab 28446 is configured to be received within a lock cavity 28655 provided in a corresponding cam member 28654' when the camming assembly 28650 is in a locked position. See FIGS. 116 and 117. The actuator portion 28444 is configured to be contacted by an actuator lug or other portion of the end effector anvil when the anvil is moved to a closed position. For example, an actuator lug 28411 may be formed on an anvil mounting portion of any of the various anvils disclosed herein and be configured to laterally bias the actuator portion 28444 laterally into an unlocked position when the anvil is moved to a closed position. When the actuator portion 28444 is in an unlocked position, the locking tab 28446 is moved laterally out of the lock cavity 28655 in the cam member 28654' and the cam assembly 28650 may then be distally advanced through the cartridge 28600 when the firing drive system is activated as described herein. See FIGS. 118 and 119.

In various instances, a surgical stapling instrument comprises a cartridge jaw configured to receive a replaceable staple cartridge. The stapling instrument further comprises a staple firing system configured to eject, or fire, staples from the staple cartridge and an anvil comprising forming surfaces, or pockets, configured to deform the staples. The staple firing system comprises a tissue cutting knife which is moved from a proximal end of the staple cartridge toward a distal end during a staple firing stroke. During the staple firing stroke, the tissue cutting knife abuts and pushes a sled in the staple cartridge which drives the staples toward and against the anvil. As the staples are deformed against the anvil, the staples are implanted in the tissue in longitudinal rows and the tissue cutting knife incises the tissue between two of the longitudinal staple rows. After the staple firing stroke has been completed, and/or after a sufficient length of the staple firing stroke has been completed, the tissue cutting knife is retracted proximally. However, the cartridge sled is not retracted proximally with the tissue cutting knife. Instead, the cartridge sled is left behind at the distal-most position in which it was pushed by the tissue cutting knife. After a staple cartridge has been fired, or at least partially fired, it is removed from the cartridge jaw and then replaced with another replaceable staple cartridge, if desired. At such point, the stapling instrument can be re-used to continue stapling and incising the patient tissue. In some instances, however, a previously-fired staple cartridge can be accidentally loaded into the cartridge jaw. If the tissue cutting knife were to be advanced distally within such a previously-fired staple cartridge, the stapling instrument would cut the patient tissue without stapling it. The stapling instrument would similarly cut the patient tissue without stapling it if the tissue cutting knife were advanced distally through a staple firing stroke without a staple cartridge positioned in the cartridge jaw at all. To this end, the stapling instrument comprises one or more lockouts which prevents this from happening, as discussed in greater detail below.

The disclosures of U.S. Patent Application Publication No. 2004/0232200, entitled SURGICAL STAPLING INSTRUMENT HAVING A SPENT CARTRIDGE LOCKOUT, filed on May 20, 2003, U.S. Patent Application Publication No. 2004/0232199, entitled SURGICAL STAPLING INSTRUMENT HAVING A FIRING LOCKOUT FOR AN UNCLOSED ANVIL, U.S. Patent Application Publication No. 2004/0232197, entitled SURGICAL STAPLING INSTRUMENT INCORPORATING AN E-BEAM FIRING MECHANISM, filed on May 20, 2003, U.S. Patent Application Publication No. 2004/0232196, entitled SURGICAL STAPLING INSTRUMENT HAVING SEPARATE DISTINCT CLOSING AND FIRING SYSTEMS, filed on May 20, 2003, U.S. Patent Application Publication No. 2004/0232195, entitled SURGICAL STAPLING INSTRUMENT HAVING A SINGLE LOCKOUT MECHANISM FOR PREVENTION OF FIRING, filed on May 20, 3003, and U.S. Patent Application Publication No. 2018/0085123, entitled ARTICULATING SURGICAL STAPLING INSTRUMENT INCORPORATING A TWO-PIECE E-BEAM FIRING MECHANISM, filed on Aug. 17, 2017 are incorporated by reference in their entireties.

Figure 120:
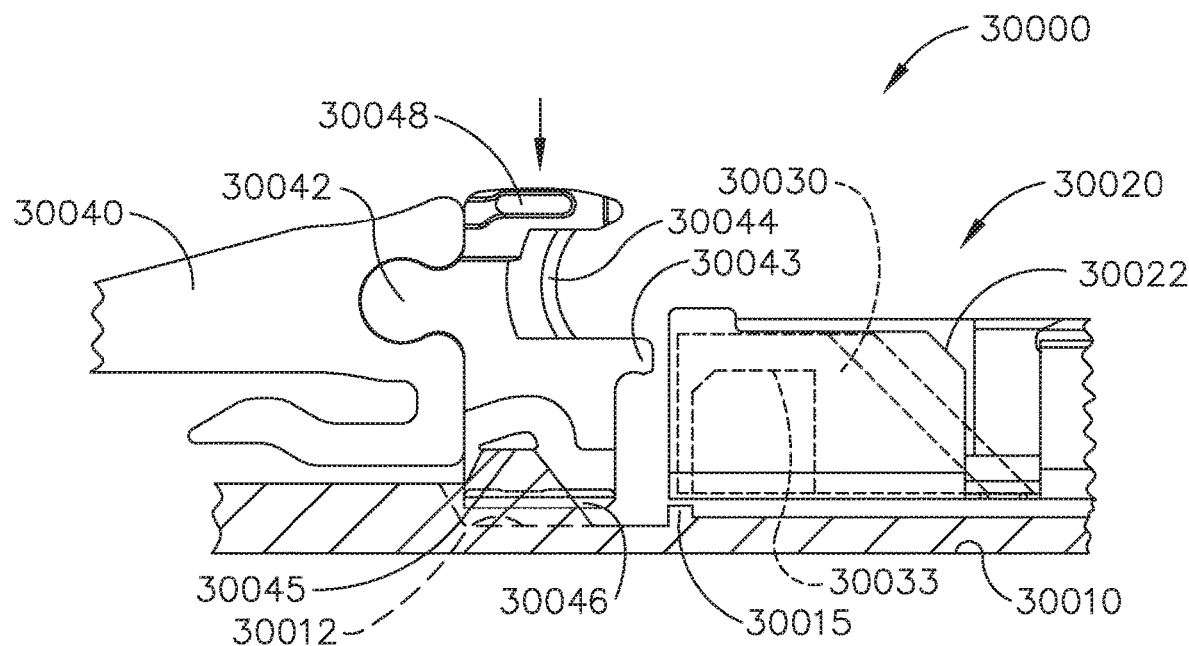

Referring to FIG. 120, a surgical stapling instrument 30000 comprises a cartridge jaw, or channel, 30010 and a staple cartridge 30020 seated in the cartridge jaw 30010. The staple cartridge 30020 comprises a cartridge body 30022, staple cavities defined in the cartridge body 30022, and staples removably stored in the staple cavities. The staple cartridge 30020 further comprises a sled 30030 and staple drivers which are driven by the sled 30030 to eject the staples from the staple cavities as the sled 30030 is advanced distally during a staple firing stroke. The stapling instrument 30000 further comprises a firing member 30040 which is configured to engage the sled 30030 and push the sled 30030 distally, as discussed in greater detail below.

Further to the above, the firing member 30040 comprises a cutting portion 30042 including a tissue knife 30044. The cutting portion 30042 further comprises a distal nose 30043 which is configured to sit on a shoulder 30033 defined on the sled 30030 when the sled 30030 is in its unfired position in the staple cartridge 30020 and the firing member 30040 is moved distally from its unfired position illustrated in FIG. 120. Once the distal nose 30043 is on the sled shoulder 30033, the firing member 30040 can be advanced distally to perform the staple firing stroke. Notably, the cutting portion 30042 further comprises a first camming member 30046 configured to engage a cam surface of the channel 30010 and a second camming member 30048 configured to engage a cam surface on the anvil of the stapling instrument 30000 which co-operate to position the anvil and the staple cartridge 30020 relative to one another. That said, embodiments are envisioned without one or both of the camming members 30046 and 30048.

Figure 121:
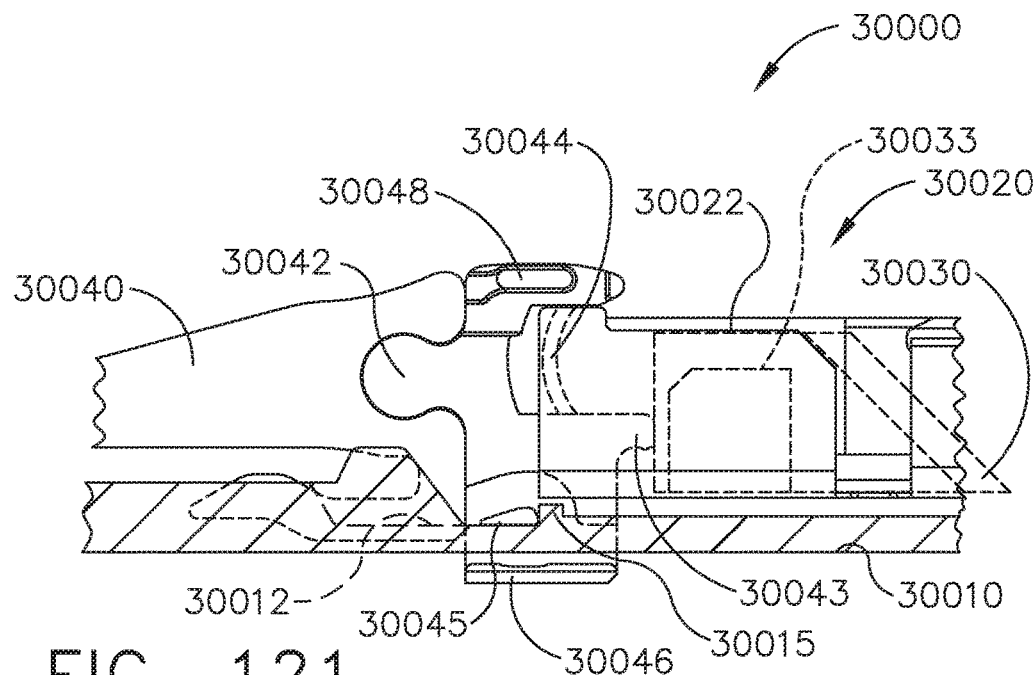

Referring to FIG. 121, the firing member 30040 is biased toward the channel 30010 by a spring and, if the sled 30030 is not in its unfired position when the firing member 30040 is advanced distally to start the staple firing stroke, the distal nose 30043 of the cutting portion 30042 will miss, or not land on, the shoulder 30033 and the cutting portion 30042 will dive downwardly toward the channel 30010 instead. The cutting portion 30042 comprises lockout pins 30045 extending laterally therefrom which enter a lockout window, or recess, 30012 defined in the channel 30010 when the distal nose 30043 does not land on the shoulder 30033 of the sled 30030. In such instances, the firing member 30040 is permitted to travel distally within the lockout window 30012; however, the distal end of the lockout window 30012 comprises a lockout shoulder 30015 which is contacted by the lockout pins 30045 to stop the distal advancement of the firing member 30040. In such instances, as a result, the firing member 30040 is locked out and prevented from performing its staple firing stroke. Had the sled 30030 been its unfired position, however, the interaction between the distal nose 30043 of the cutting portion 30042 and the shoulder 30033 of the sled 30030 would have prevented the firing member 30040 from diving into the lockout window 30012 and the staple firing stroke could have been performed.

Further to the above, the firing member 30040 would dive into the lockout window 30012 if the firing member 30040 were advanced distally without a staple cartridge positioned in and/or a staple cartridge properly seated in the cartridge channel 30010. In view of the above, the surgical instrument 30000 comprises a lockout which prevents the staple firing stroke if the staple cartridge in the surgical instrument 30000 is missing, improperly seated, and/or has been at least partially spent. That said, various instances can arise where a staple cartridge has not been fired, i.e., all of its staples are still positioned in their staple cavities, and, yet, the distal nose 30043 of the cutting portion 30042 can miss the shoulder 30033 of the sled 30030 owing to various manufacturing tolerances, for instance. Such instances would cause the firing member 30040 to be locked out unnecessarily and require a clinician to replace the staple cartridge with another staple cartridge. Such instances may not happen that often, but if they do they are inconvenient to the clinician.

Figure 122:
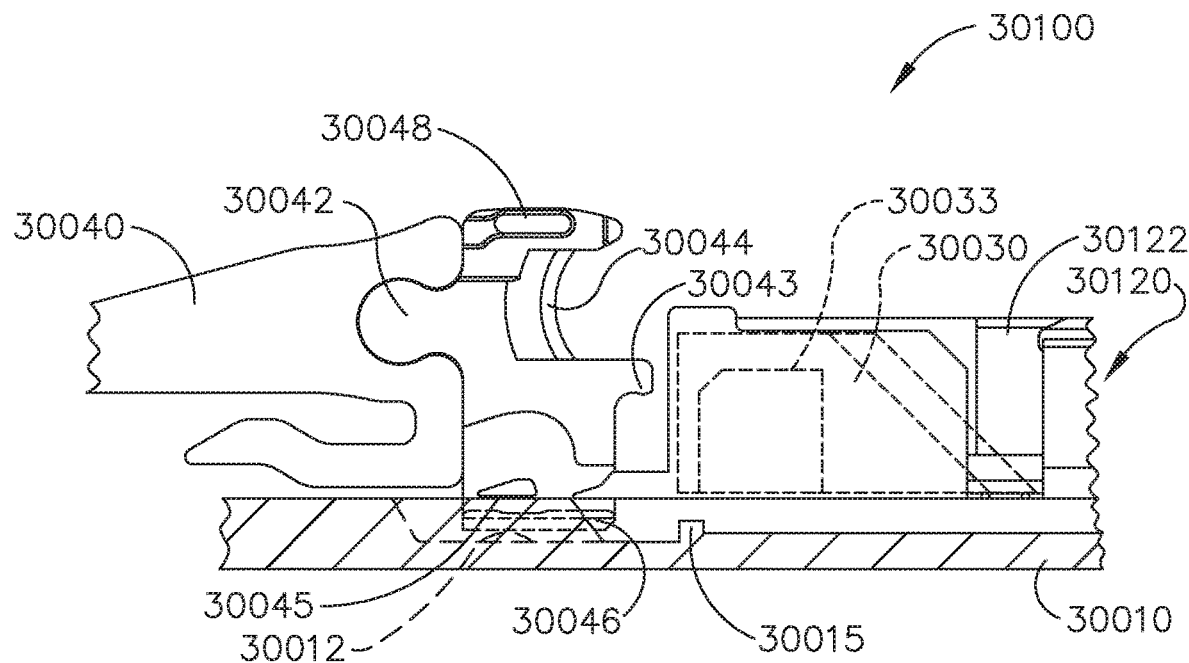
Figure 123:
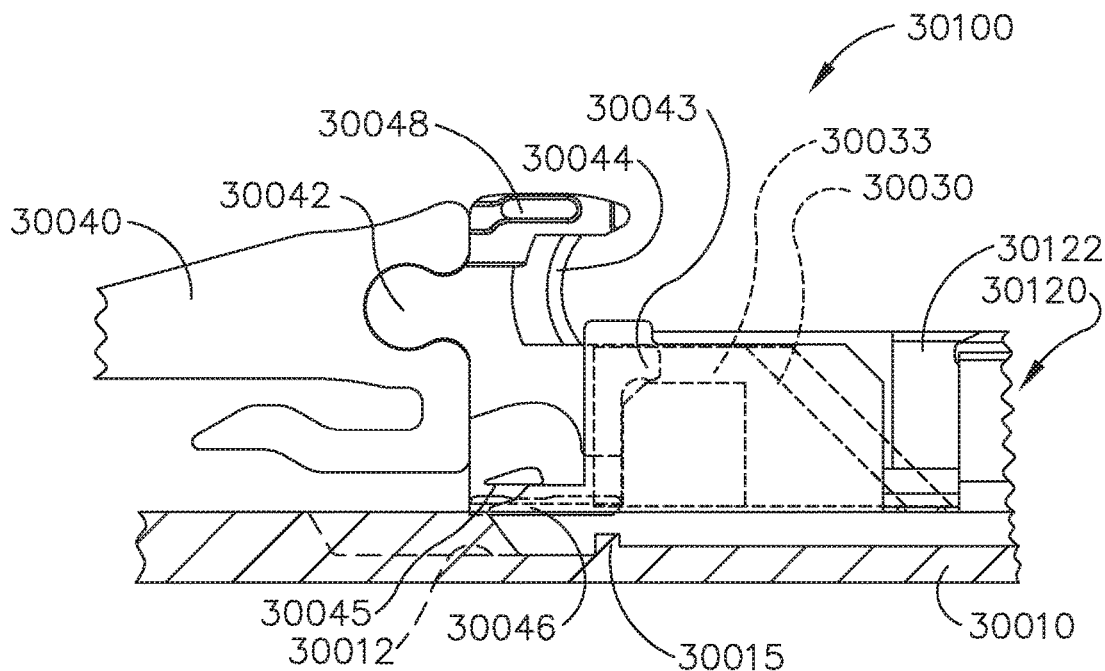
Figure 124:
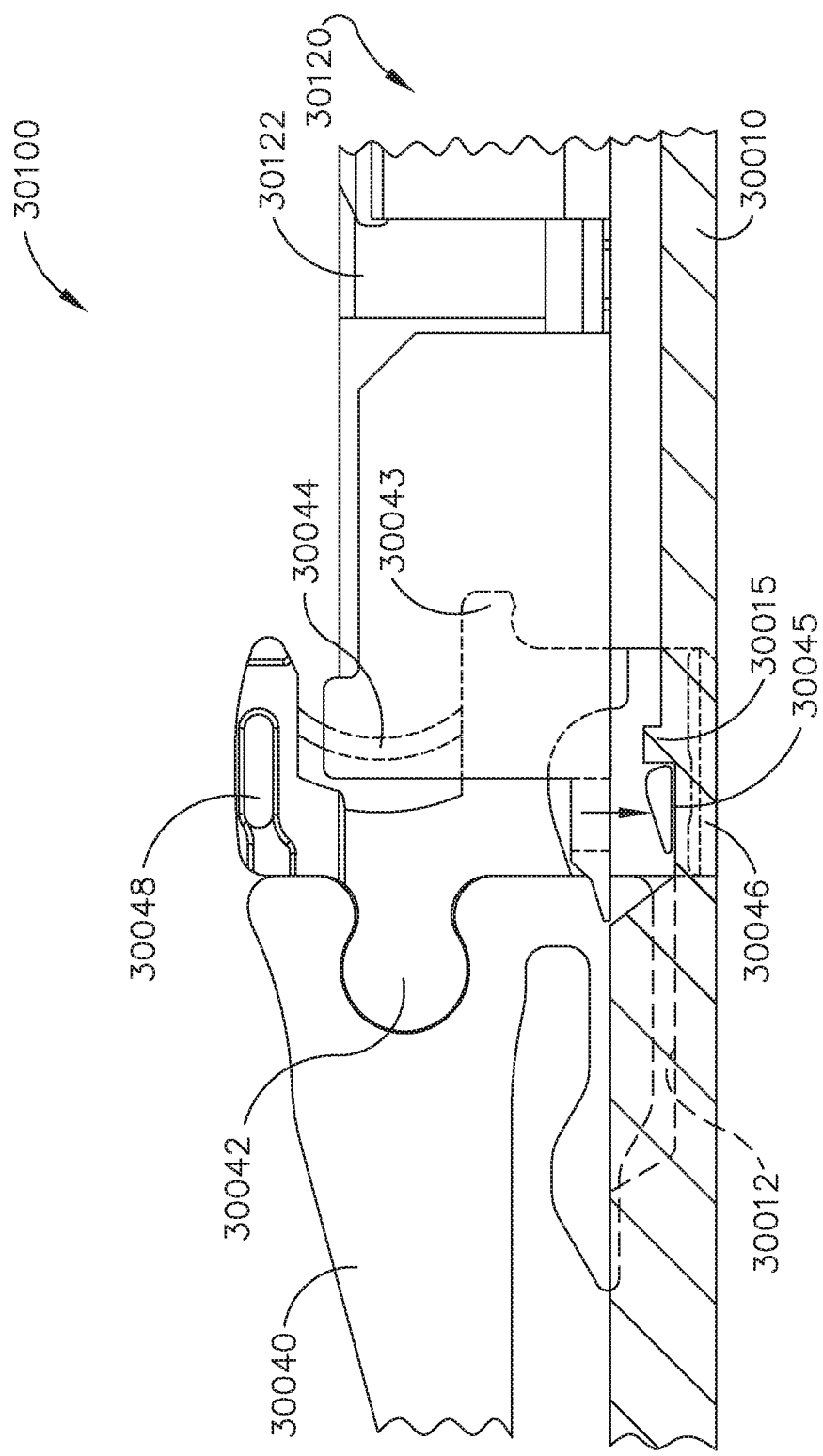

A surgical instrument 30100 is illustrated in FIG. 122 and includes an improvement which can reduce the possibility of the distal nose 30043 of the cutting portion 30042 missing the shoulder 30033 of the sled 30030. The surgical instrument 30100 is similar to the surgical instrument 30000 in many respects but includes a staple cartridge 30120 instead of the staple cartridge 30020. The staple cartridge 30120 comprises a cartridge body 30122, staple cavities defined in the cartridge body 30122, and staples removably stored in the staple cavities. Referring to FIG. 123, the staple cartridge 30120 further comprises a sled 30030 which, similar to the above, is movable distally from an unfired position during a staple firing stroke if the distal nose 30043 of the cutting portion 30042 catches the shoulder 30033 of the sled 30030. If not, referring to FIG. 124, the cutting portion 30042 is pushed into the lockout window 30012 defined in the cartridge channel 30010 when the firing member 30040 is advanced distally.

Figure 125:
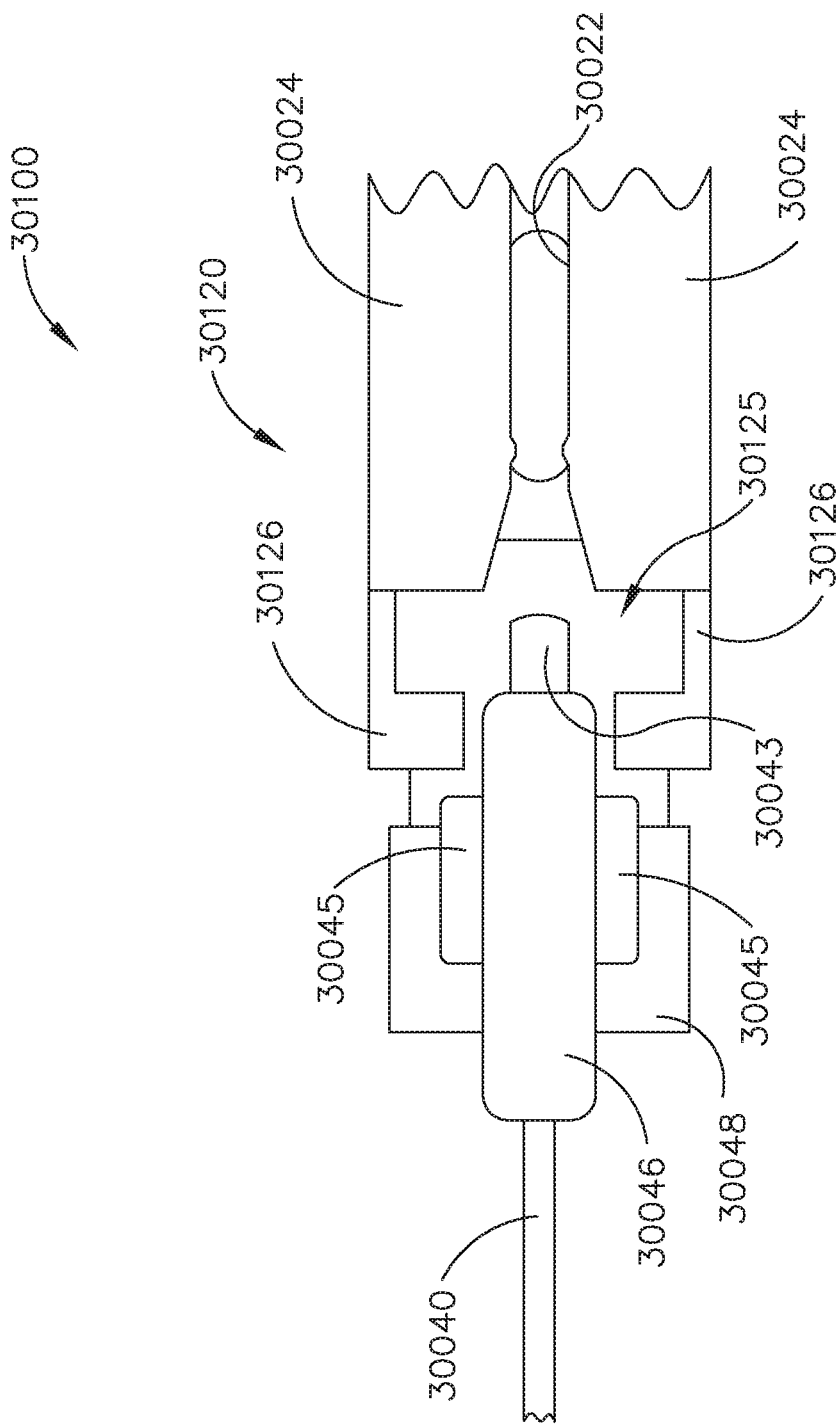
Figures 126, 127:
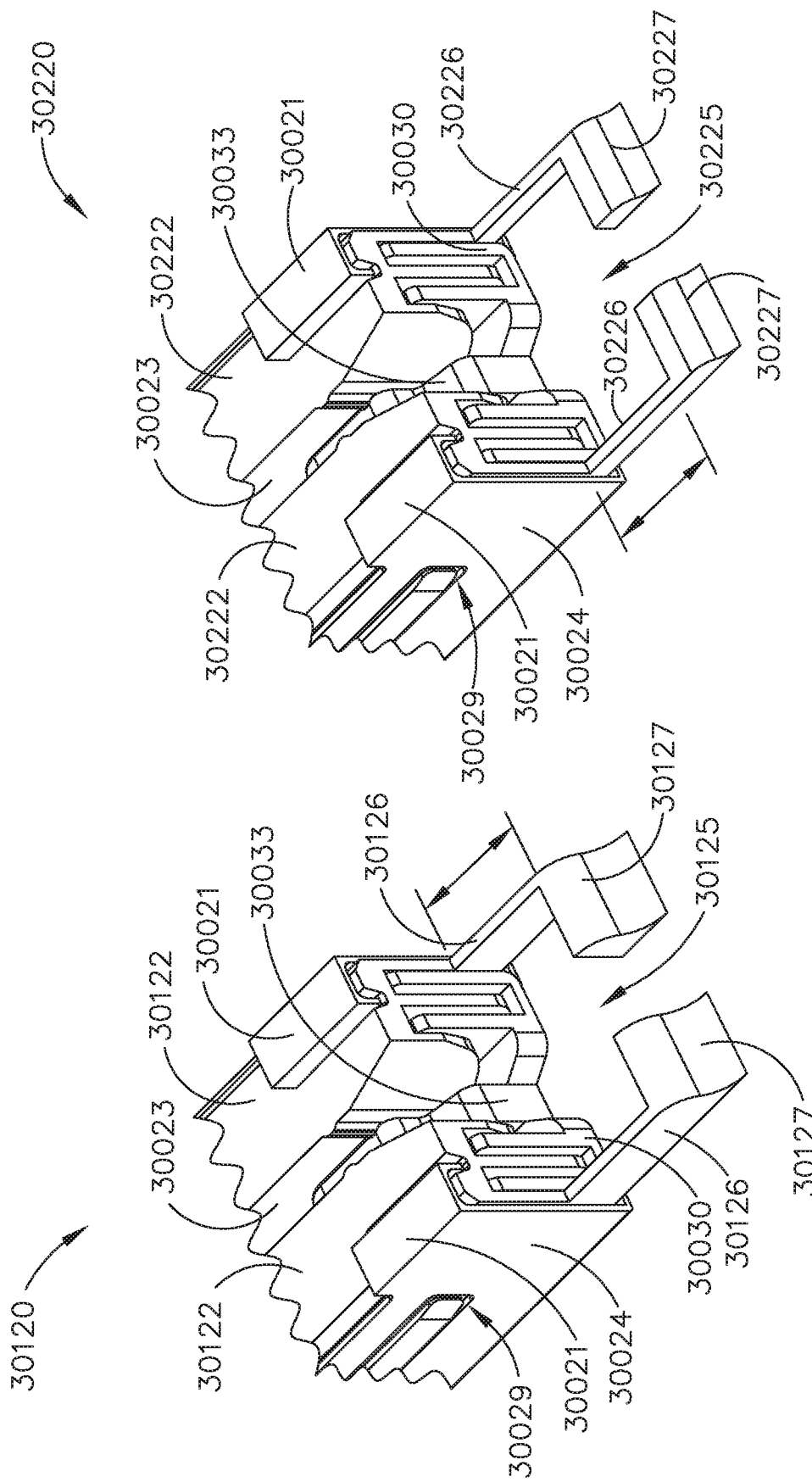

Referring to FIGS. 125 and 126, the cartridge body 30122 comprises proximal ramps 30126 configured to lift the firing member 30040 upwardly when the firing member 30040 is advanced distally. More specifically, the lockout pins 30045 extending laterally from the firing member 30040 contact ramp surfaces 30127 defined on the proximal ramps 30126 which guide the cutting portion 30042 away from the lockout window 30012 when the firing member 30040 is advanced distally. They do so, further to the above, against the biasing force of the spring pushing the firing member 30040 toward the cartridge channel 30010. The lifting of the firing member 30040 in this manner increases the probability that the nose 30043 of the firing member 30040 will land on the shoulder 30033 of the sled 30030—even if the sled 30030 has been accidentally pushed slightly distally from its unfired position. Thus, the possibility of an unfired staple cartridge becoming unintentionally locked out is reduced. If the staple cartridge 30120 has been at least partially fired, however, the nose 30043 will miss the shoulder 30033 and the lockout pins 30045 will fall through a window 30125 defined between the proximal ramps 30126 and into the lockout window 30012. Thus, as above, the surgical instrument 30100 will be locked out if an at least partially spent staple cartridge 30120 is seated in the cartridge channel 30010. Moreover, as above, the surgical instrument 30100 will be locked out if a staple cartridge is missing from the cartridge channel 30010 and the staple firing stroke is initiated as the firing member 30040 will immediately enter the lockout window 30012 owing to the absence of the proximal ramps 30126.

Notably, further to the above, the ramps 30126 are positioned proximally with respect to the shoulder 30033 of the sled 30030. As such, the firing member 30040 must consecutively pass the missing cartridge/improper cartridge lockout provided by the ramps 30126 and the spent cartridge lockout provided by the sled 30030 as the firing member 30040 is moved distally to perform the staple firing stroke. Moreover, the ramps 30126 lift the firing member 30040 to a proper height to be supported by the sled 30030. Ultimately, the ramps 30126 of the cartridge body 30122 and the shoulder 30033 of the sled 30030 work together to defeat the lockouts of the stapling instrument 30100.

A staple cartridge 30220 is illustrated in FIG. 127 in accordance with at least one alternative embodiment. The staple cartridge 30220 comprises a cartridge body 30222 which is similar to the cartridge body 30122 in many respects. That said, the cartridge body 30222 comprises proximal ramps 30226 which extend further proximally than the proximal ramps 30126. As such, the firing member 30040 will be lifted earlier in its staple firing stroke when a staple cartridge 30220 is used. In various instances, the staple cartridge 30220 can include a larger drop window 30225 than the drop window 30125. Moreover, the proximal ramps 30226 comprise ramp surfaces 30227 which are shorter than the ramp surfaces 30127. In such instances, the firing member 30040 will not be lifted as high when a staple cartridge 30220 is used as compared to when a staple cartridge 30120 is used. In any event, such parameters can be used to hone an appropriate lifting motion for the firing member 30040.

As discussed above, the lockout pins 30045 of the firing member 30040 are configured to contact the ramps 30226 which lift the firing member 30040 such that the firing member 30040 can land on the shoulder 30033 of the sled 30030 if the sled 30030 is properly positioned in the staple cartridge 30220. That said, alternative embodiments are envisioned in which ramps can lift any suitable portion of a staple firing member onto the shoulder 30033 of the sled 30030. For instance, the firing member 30040 can comprise laminate bars attached to the cutting portion 30042 which contact the ramps 30226 and cause the firing member 30040 to be lifted upwardly when the staple firing stroke is initiated.

Referring again to FIG. 127, the staple cartridge 30220 comprises a pan 30024 at least partially extending under the cartridge body 30222. The pan 30024 is configured to prevent the staple drivers and/or staples within the cartridge body 30222 from falling out of the bottom of the cartridge body 30222. The pan 30024 comprises latches 30021 engaged with slots defined in the cartridge body 30222. The pan 30024 further comprises windows 30029 defined therein which, in co-operation with projections extending from the cartridge body 30222, align the pan 30024 with the cartridge body 30222. In addition to or in lieu of the above, the lifts ramps 30226, for example, can extend from the pan 30024.

Figure 130:
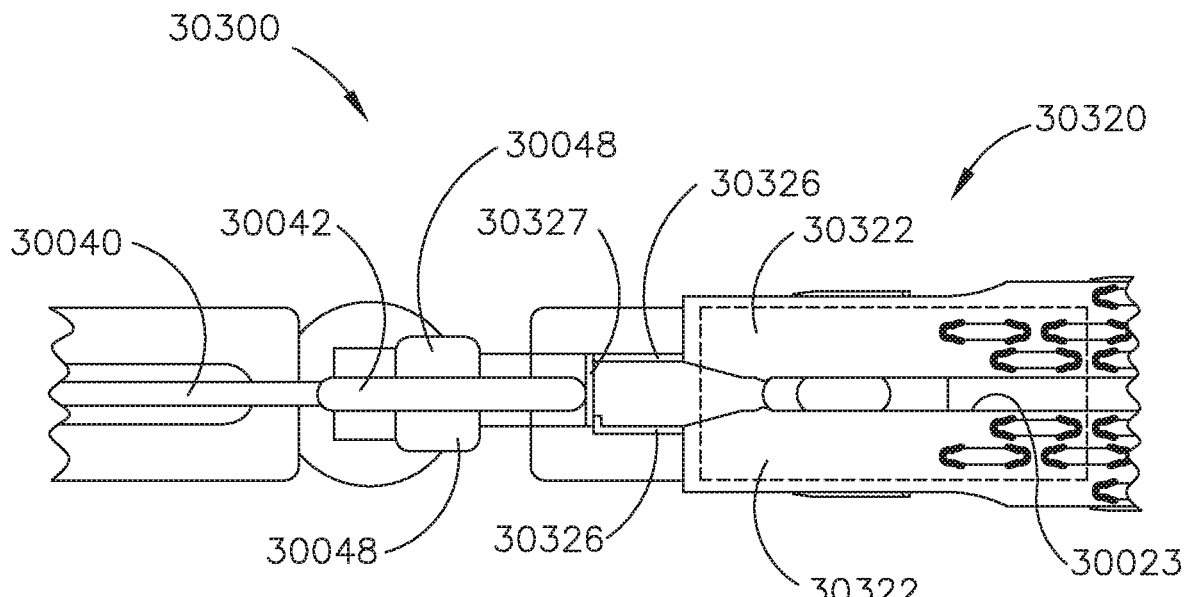

A surgical stapling instrument 30300 is illustrated in FIG. 128. The stapling instrument 30300 is similar to the stapling instrument 30200 in many respects. That said, the stapling instrument 30300 comprises a staple cartridge 30320 instead of the staple cartridge 30220. The staple cartridge 30320 comprises a cartridge body 30322, staple cavities defined in the cartridge body 30322, and staples removably stored in the staple cavities. The cartridge body 30322 further comprises a longitudinal slot 30023 defined therein which is configured to receive the firing member 30040 and, in addition, a proximal ramp 30327 extending in front of the longitudinal slot 30023 which lofts the firing member 30040 onto the sled 30030 if the sled 30030 is in, or at least nearly in, its unfired position, as illustrated in FIG. 129. If the sled 30030 has been at least partially advanced through its staple firing stroke, the shoulder 30033 will not catch the nose 30043 of the firing member 30040 and the cutting portion 30042 will fall through a window defined between ramp supports 30326 and into the lockout window 30012. [0401] Referring to FIGS. 130 and 132, the ramp 30327 also comprises a gate configured to pivot out of the way of the firing member 30040 when a sufficient pushing force is applied to the firing member 30040. The ramp 30327 comprises a first end rotatably mounted to one of the ramp supports 30326 and a second end releasably attached to the other ramp support 30326. Referring to FIGS. 131 and 133, the second end of the ramp 30327 is configured to release from its ramp support 30326 after the firing member 30040 has been lofted upwardly such that, once the ramp 30327 gives way, the nose 30043 of the firing member 30040 falls on the shoulder 30033 of the sled 30030—if the sled 30030 is in its unfired position, or at least close to its unfired position. At such point, the ramp 30327 no longer impedes the distal movement of the firing member 30040 and the firing member 30040 can be advanced distally through the longitudinal slot 30023. The ramp 30327 remains displaced to the side throughout the staple firing stroke and after the firing member 30040 has been retracted back into its unfired position. As such, the displaced ramp 30327 cannot lift the firing member 30040 if the firing member 30040 were to be advanced distally once again. In such instances, the lockout pins 30045 of the cutting portion 30042 would be pushed into the lockout window 30012 by the spring acting against the firing member 30040 if the firing member 30040 were advanced distally before the spent staple cartridge 30320 is replaced. Thus, the ramp 30327 acts as a spent cartridge lockout. In at least one alternative embodiment, the ramp 30327 is configured to break away from the cartridge body 30322 to release the firing member 30040.

Moreover, further to the above, the lockout arrangement of the stapling instrument 30300 also acts as an improper/incompatible cartridge lockout. If an improper, or incompatible, staple cartridge not having the ramp 30327, or another suitably configured ramp, were to be seated in the cartridge channel 30010, the firing member 30040 would not be lofted onto a sled of the improper staple cartridge and, instead, the lockout pins 30045 would be forced into the lockout window 30012 thereby locking out the staple firing system. In such instances, the firing member 30040 can be retracted back into its unfired position and the improper/incompatible staple cartridge can be replaced with a proper/compatible staple cartridge. The accidental swapping of an improper staple cartridge for a proper staple cartridge can happen in an operating room where certain staple cartridges are meant to be only used with certain stapling instruments, among other instances.

As discussed above, the ramp 30327 extends behind the sled 30030. As a result, the ramp 30327 can protect the sled 30030 from being bumped distally accidentally. In various instances, the staple cartridge 30320 is loaded into the stapling instrument 30300 by inserting the proximal end of the staple cartridge 30320 into the cartridge channel 30010 first and then seating the staple cartridge 30320 in the cartridge channel 30010. As such, the possibility exits that the sled 30030 will contact the cartridge channel 30010, for example, and be pushed distally within the staple cartridge 30320 from its proximal unfired position. In such instances, the sled 30030 may no longer be positioned to defeat the staple firing lockout of the stapling instrument 30300 when the staple firing stroke is initiated and, thus, the stapling firing lockout will treat this staple cartridge 30320 as being spent and it must be replaced to use the stapling instrument 30300. The ramp 30327 can prevent this as it extends proximally behind the sled 30030 and can prevent the sled 30030 from being bumped distally within the staple cartridge 30320 when the staple cartridge 30320 is being installed.

As discussed above, the sled 30030, when properly positioned in the staple cartridge, defeats the staple firing lockout of the stapling instrument such that the staple firing stroke can be completed. In use, the firing member 30040 is advanced distally, at least partially, to assess whether or not the sled 30030 is properly positioned and that the staple firing lockout has been defeated. More specifically, the firing member 30040 is advanced distally until the firing member 30040 is supported by the sled 30030 to perform the staple firing stroke—if the sled 30030 is properly positioned in the staple cartridge 30320—or contact the lockout shoulder 30015 if the sled 30030 is not properly positioned in the staple cartridge 30320 or the staple cartridge 30320 is missing from the cartridge channel 30010. If the firing member 30040 contacts the lockout shoulder 30015, the firing member 30040 may need to be retracted to be able to insert an unspent staple cartridge 30320 into the cartridge channel 30010 and/or retracted to start another staple firing stroke. With this in mind, the surgical instrument 30400 of FIGS. 134 and 135 is configured to limit the travel of a firing member such that the firing member can be stopped before it reaches the lockout shoulder 30015 if the staple cartridge is missing from the cartridge channel, as discussed in greater detail below.

The firing member 30440 of the surgical instrument 30400, further to the above, is similar to the firing member 30040 in many respects but comprises a cutting member 30442 including secondary lockout pins 30449 extending laterally therefrom. If the staple cartridge 30320 is not positioned in the cartridge channel 30410 of the stapling instrument 30400, the cutting member 30442 will immediately enter the lockout window 30012 when the firing member 30440 is advanced distally and the secondary lockout pins 30449 will quickly contact a secondary lockout shoulder 30419 in the lockout window 30012. Thus, if a staple cartridge 30320 is not present in the cartridge channel 30410, the firing member 30440 will not have to travel distally until it contacts the lockout shoulder 30015. In such instances, the distance in which the firing member 30440 needs to be retracted is at least reduced. In certain instances, the secondary lockout shoulder 30419 is positioned such that the cutting member 30442 does not need to be retracted at all. In such instances, as a result, an unspent staple cartridge 30320 can be inserted into the channel 30410 and the staple firing stroke can be completed without having to retract the firing member 30440.

Further to the above, the interaction between the lockout pins 30449 and the lockout shoulder 30419 provides a missing cartridge lockout. If the staple cartridge 30320 is seated in the cartridge channel 30410, the cutting member 30442 engages the ramp 30327 of the staple cartridge 30320 which lifts the lockout pins 30449 over the lockout shoulder 30419. Stated another way, the presence of the staple cartridge 30320 in the cartridge channel 30010 defeats the secondary staple firing lockout. That said, the sled 30030 of the staple cartridge 30320 must be properly positioned in the staple cartridge 30320 in order for the staple firing stroke to be completed as the nose 30043 of the cutting member 30442 must still land on the shoulder 30033 of the sled 30030 in order for the lockout pins 30045 to be lifted over the lockout shoulder 30015, as described above. Stated another way, the presence of the sled 30030 in the staple cartridge 30320 in its unfired position defeats the primary firing lockout and the presence of the staple cartridge 30320 in the cartridge channel 30410 defeats the secondary firing lockout. Thus, the stapling instrument 30400 comprises a primary missing cartridge lockout and a secondary missing cartridge lockout, where the primary missing cartridge lockout also serves as a spent cartridge lockout.

A surgical stapling instrument 30500 is illustrated in FIG. 136. The stapling instrument 30500 is similar to the stapling instrument 30000 in many respects. Among other things, the stapling instrument 30500 comprises a cartridge channel 30510, a staple cartridge 30520 removably positionable in the cartridge channel 30510, a firing member 30040, and a staple firing lockout 30514. The staple firing lockout 30514 comprises a resilient metal spring, for example, mounted in the cartridge channel 30510. That said, the staple firing lockout 30514 can be comprised of any suitable material. The staple firing lockout 30514 comprises a base mounted in the cartridge channel 30510 and flexible lock arms 30516 extending from the base. Each flexible lock arm 30516 moves independently of the other and comprises a lock window 30515 defined therein which is configured to receive and releasably capture a lockout pin 30045 extending from the firing member 30040. The flexible lock arms 30516 are configured such that they extend inwardly toward and/or against the side of the firing member 30040 and are, thus, biased to capture the lockout pins 30045. When one or both of the lockout pins 30045 are captured in a lock window 30515, the staple firing member 30040 is prevented from being advanced distally through a staple firing stroke.

Further to the above, the staple cartridge 30520 comprises a cartridge body 30522, staple cavities defined in the cartridge body 30522, and staples removable stored in the staple cavities. The staple cartridge 30520 further comprises a pan 30024 attached to the cartridge body 30522 and a sled configured to travel distally within the staple cartridge 30520 to eject the staples from the staple cavities during a staple firing stroke. Similar to the above, the firing member 30040 is configured to push the sled distally to perform the staple firing stroke once the firing member 30040 has been unlocked. To this end, referring to FIGS. 136 and 139, the cartridge body 30522 comprises projections, or keys, 30526 extending proximally therefrom which are configured to engage the lock arms 30516 when the staple cartridge 30520 is seated in the cartridge channel 30510. Notably, the ends of the lock arms 30516 flare outwardly such that, when the projections 30526 contact the lock arms 30516, the lock arms 30516 aren't trapped between the projections 30526 and the firing member 30040. As a result, the projections 30526 flex the lock arms 30516 laterally outwardly such that the lockout pins 30045 extending from the firing member 30040 are no longer positioned in the lockout windows 30515 of the firing lockout 30514 when the staple cartridge 30520 is seated in the cartridge channel 30510. Thus, the act of seating the staple cartridge 30520 in the cartridge channel 30510 unlocks the stapling instrument 30500.

If a staple cartridge 30520 is not seated in the cartridge channel 30510, as discussed above, the firing member 30040 remains locked by the firing lockout 30514 and the stapling instrument 30500 cannot be used to staple the patient's tissue. If a staple cartridge is seated in the cartridge channel 30510 that does not have the projections, or keys, 30526, such as the staple cartridge 30020, for example, it will not unlock the firing lockout 30514, as illustrated in FIGS. 137 and 138, and, as a result, the stapling instrument 30500 cannot be used to staple the patient's tissue. As depicted in FIGS. 137 and 138, the proximal end of the cartridge body 30022 does not engage, and/or sufficiently displace, the lock arms 30516. Thus, in this instance, the staple cartridge 30020 would be an improper staple cartridge as it does not unlock the staple firing drive of the stapling instrument 30500 and, correspondingly, the staple cartridge 30520 would be a proper staple cartridge as it can unlock the staple firing drive of the stapling instrument 30500. As such, the firing lockout 30514 is both a missing cartridge lockout and an improper cartridge lockout. The stapling instrument 30500 can further comprise a spent cartridge lockout. In the event that an improper staple cartridge is seated in the stapling instrument 30500 and the stapling instrument 30500 cannot be fired, the improper staple cartridge can be removed and a proper staple cartridge, i.e., a staple cartridge 30520, can be seated in the stapling instrument 30500 to unlock the staple firing drive.

As discussed above in connection with the stapling instrument 30000, referring again to FIG. 121, the lockout pins 30045 of the firing member 30040 engage the lock shoulder 30015 if the sled 30030 is not in its proper position in the staple cartridge 30020. As also discussed above, the firing member 30040 of the stapling instrument 30000 is advanced distally before engaging the lock shoulder 30015 and, thus, has time to accelerate before contacting the lock shoulder 30015. As such, the firing member 30040 of the stapling instrument 30000 can impact the lock shoulder 30015 with significant speed and energy. As such, the lock shoulder 30015 is robustly designed to absorb this impact; however, there exists a possibility that the firing member 30040 can plow or blow through the lock shoulder 30015 thereby unintentionally defeating the staple firing lockout of the stapling instrument 30000. The lockout 30514 of FIGS. 136 and 137 can reduce, if not eliminate, these potential problems. For instance, the lock windows 30515 of the firing lockout 30514 are sized and configured to prevent little, if any, proximal and distal translation of the staple firing member 30040 while the lock arms 30516 are engaged with the lockout pins 30045 and, thus, the staple firing member 30040 has little, if any, time to accelerate before being stopped by the distal ends of the lock windows 30515. Moreover, once the lockout pins 30045 engage the distal ends of the lock windows 30515, the lock arms 30516 are placed in tension and, as a result, are capable of handling significant loads before failing, if they fail at all.

As discussed above, both lock arms 30516 are disengaged from the firing member 30040 by the cartridge body 30522 when the staple cartridge 30520 is seated in the stapling instrument 30500. That said, alternative embodiments are envisioned in which a first component of a staple cartridge unlocks a first lock arm 30516 and a second component of the staple cartridge unlocks a second lock arm 30516 when the staple cartridge is seated in the stapling instrument 30500. For instance, a cartridge body of the staple cartridge can unlock the first lock arm 30516 and a sled of the staple cartridge can unlock the second lock arm 30516.

A surgical stapling instrument 30600 is illustrated in FIG. 140 and a surgical stapling instrument 30700 is illustrated in FIG. 141. The stapling instruments 30600 and 30700 are similar to the stapling instrument 30500 in many respects. Referring to FIG. 140, the stapling instrument 30600 comprises a cartridge channel 30610, a staple cartridge 30620 removably positionable in the cartridge channel 30610, and a staple firing lockout 30614 mounted to the cartridge channel 30610 which prevents the firing member 30040 from being advanced through a staple firing stroke unless the staple cartridge 30620 is seated in the cartridge channel 30610. Similarly, referring to FIG. 141, the stapling instrument 30700 comprises a cartridge channel 30710, a staple cartridge 30720 removably positionable in the cartridge channel 30710, and a staple firing lockout 30714 mounted to the cartridge channel 30710 which prevents the firing member 30040 from being advanced through a staple firing stroke unless the staple cartridge 30720 is seated in the cartridge channel 30710. Notably, however, seating the staple cartridge 30720 in the stapling instrument 30600 does not unlock the staple firing system of the stapling instrument 30600 and, likewise, seating the staple cartridge 30620 in the stapling instrument 30700 does not unlock the staple firing system of the stapling instrument 30700. Thus, the stapling instruments 30600 and 30700 can be used in the same operating room at the same time without the possibility of being used with the wrong staple cartridge, despite the fact that the staple cartridges 30620 and 30720 may be confusingly similar.

Referring to FIG. 142, further to the above, the staple cartridge 30620 further comprises a cartridge body 30622 including a proximal end 30626 that is angled such that the center of the cartridge body 30622, i.e., the portion closest to the longitudinal slot 30023, extends further proximally than the lateral sides of the cartridge body 30622. The staple cartridge 30620 further comprises a sled 30630, which is similar to the sled 30030 in many respects, that comprises a proximal end 30636 having a profile that matches, or at least substantially matches, the profile of the proximal end 30626 of the cartridge body 30622. Referring again to FIG. 140, the firing lockout 30614 is similar to the firing lockout 30514. Among other things, the firing lockout 30614 comprises lock arms 30616 which releasingly hold the firing member 30040 in its unfired position until the lock arms 30616 are displaced laterally by the proximal end of the cartridge body 30622 and/or the proximal end of the sled 30630 to release the lockout pins 30045 from lock windows defined in the lock arms 30616. If the staple cartridge 30620 is removed from the cartridge channel 30610, the lock arms 30616 resiliently return to their locked position.

Referring to FIG. 143, further to the above, the staple cartridge 30700 further comprises a cartridge body 30722 including a proximal end 30726 that is angled such that the laterals sides of the cartridge body 30722, i.e., the portions furthest away from the longitudinal slot 30023, extend further proximally than the center of the cartridge body 30722. The staple cartridge 30720 further comprises a sled 30730, which is similar to the sled 30030 in many respects, that comprises a proximal end 30736 having a profile that matches, or at least substantially matches, the profile of the proximal end 30726 of the cartridge body 30722. Referring again to FIG. 141, the firing lockout 30714 is similar to the firing lockout 30514. Among other things, the firing lockout 30714 comprises lock arms 30716 which releasingly hold the firing member 30040 in its unfired position until the lock arms 30716 are displaced laterally by the proximal end of the cartridge body 30722 and/or the proximal end of the sled 30730 to release the lockout pins 30045 from lock windows defined in the lock arms 30716. If the staple cartridge 30720 is removed from the cartridge channel 30710, the lock arms 30716 resiliently return to their locked position.

Notably, further to the above, the proximal end of the staple cartridge 30620 would not displace, or at least sufficiently displace, the lock arms 30716 of the firing lockout 30714 to disengage the firing lockout 30714 from the firing member 30040 if the staple cartridge 30620 were to be seated in the stapling instrument 30700. Moreover, the proximal end of the staple cartridge 30720 would not displace, or at least sufficiently displace, the lock arms 30616 of the firing lockout 30614 to disengage the firing lockout 30614 from the firing member 30040 if the staple cartridge 30720 were to be seated in the stapling instrument 30600. Thus, the staple cartridges 30620 and 30720 each comprise unique keying features which unlock their respective, or proper, stapling instruments.

In various instances, further to the above, the cartridge body and/or sled of a staple cartridge, or staple cartridge type, can comprise one or more unique keying features which can only unlock its respective stapling instrument. In certain instances, the pan extending under the cartridge body can comprise a proximal feature, or key, configured to unlock the staple firing drive of its stapling instrument. Referring to FIG. 144, a cartridge pan 30824, which is similar to the pan 30024 in many respects, comprises a proximal projection, or key, 30826 configured to unlock the staple firing drive of a stapling instrument. The projection 30826 is comprised of folded sheet metal to form a tubular structure, for example. The tubular structure is strengthened by a nested interconnection including a tab 30827 and a slot 30828.

A surgical stapling instrument 30900 is illustrated in FIGS. 145 and 147 and a surgical stapling instrument 31000 is illustrated in FIG. 148. The stapling instruments 30900 and 31000 are similar to the stapling instrument 30500 in many respects. Referring to FIG. 145, the stapling instrument 30900 comprises a cartridge channel 30910, a staple cartridge 30920 removably positionable in the cartridge channel 30910, and a staple firing lockout 30914 mounted to the cartridge channel 30910 which prevents the firing member 30040 from being advanced through a staple firing stroke unless the staple cartridge 30920 is seated in the cartridge channel 30910. Similarly, referring to FIG. 148, the stapling instrument 31000 comprises a cartridge channel, a staple cartridge 31020 removably positionable in the cartridge channel, and a staple firing lockout 31014 mounted to the cartridge channel which prevents the firing member 30040 from being advanced through a staple firing stroke unless the staple cartridge 31020 is seated in the cartridge channel.

Notably, the staple firing lockout 30914 comprises only one lock arm 30916 which extends alongside the right side of the firing member 30040. That said, the one lock arm 30916 comprises a lock window defined therein which is configured to capture and suitably hold a lockout pin 30045 of the firing member 30040 to hold the firing member 30040 in its unfired position, as illustrated in FIG. 147, until the staple cartridge 30920 is seated in the cartridge channel 30910, as illustrated in FIG. 145. More specifically, the cartridge body 30922 of the staple cartridge 30920 comprises a proximal projection, or key, 30926 extending from the right side of the cartridge body 30922 that engages the lock arm 30916 and flexes the lock arm 30916 laterally outwardly when the staple cartridge 30920 is seated in the cartridge channel 30910. Notably, the cartridge body 30922 does not comprise a projection, or key, 30926 extending from the left side of the cartridge body 30922.

Also, notably, the staple firing lockout 31014 comprises only one lock arm 31016 which extends alongside the left side of the firing member 30040. That said, the one lock arm 31016 comprises a lock window defined therein which is configured to capture and suitably hold a lockout pin 30045 of the firing member 30040 to hold the firing member 30040 in its unfired position, as illustrated in FIG. 148, until the staple cartridge 31020 is seated in the cartridge channel of the stapling instrument 31000. More specifically, the cartridge body 31022 of the staple cartridge 31020 comprises a proximal projection, or key, 31026 extending from the left side of the cartridge body 31022 that engages the lock arm 31016 and flexes the lock arm 31016 laterally outwardly when the staple cartridge 31020 is seated in the stapling instrument 31000. Notably, the cartridge body 31022 does not comprise a projection, or key, 31026 extending from the right side of the cartridge body 31022.

Owing to the asymmetry of the cartridge bodies 30922 and 31022 and the corresponding asymmetry of the staple firing lockouts 30914 and 31014, seating the staple cartridge 31020 in the stapling instrument 30900 does not unlock the staple firing system of the stapling instrument 30900 and, likewise, seating the staple cartridge 30920 in the stapling instrument 31000 does not unlock the staple firing system of the stapling instrument 31000. Thus, the stapling instruments 30900 and 31000 can be used in the same operating room at the same time without the possibility of being used with the wrong staple cartridge despite the fact that the staple cartridges 30920 and 31020 may be confusingly similar. In some instances, the staple pattern produced by the staple cartridge 30920 is different than the staple pattern produced by the staple cartridge 30120 and, as a result, the anvil of the stapling instrument 30900 will have a different forming pocket arrangement than the anvil of the stapling instrument 31000. In such instances, the asymmetrical key/firing lockout arrangements disclosed herein can prevent a mismatch between the arrangement of the staple cavities and the arrangement of the staple forming pockets.

Referring to FIGS. 149 and 150, a staple cartridge 31120 comprises a cartridge body 31122 including parallel longitudinal rows of staple cavities while a staple cartridge 31220 comprises a cartridge body 31222 including rows of staple cavities oriented in transverse directions. Similar to the above, referring to FIG. 149, the proximal end of the cartridge body 31122 comprises keys 31126 extending from the left side of the cartridge body 31122—but not the right, or opposite, side of the cartridge body 31122—and the proximal end of the cartridge body 31222, referring to FIG. 150, comprises keys 31226 extending from the right side of the cartridge body 31222—but not the left side of the cartridge body 31222. The staple cartridge 31120 (FIG. 149) is used with a first stapling instrument having parallel longitudinal rows of anvil staple forming pockets and a left-side staple firing lockout, such as the firing lockout 31014 (FIG. 148), for example. The staple cartridge 31220 (FIG. 150) is used with a second stapling instrument having longitudinal rows of transverse staple forming pockets and a right-side staple firing lockout, such as the firing lockout 30914 (FIG. 147), for example. The staple cartridge 31220 does not unlock the first stapling instrument and, similarly, the staple cartridge 31120 does not unlock the second stapling instrument. As such, the keys 31126 of the staple cartridge 31120 cannot unlock a stapling instrument having staple forming pockets which extend in transverse directions and, correspondingly, the keys 31226 of the staple cartridge 31220 cannot unlock a stapling instrument having staple forming pockets which extend in parallel longitudinal rows.

Notably, the staple cartridge 31120 and the staple cartridge 31220 are substantially the same length and have substantially the same shape. Moreover, the staple cartridges 31120 and 31220 are both configured to produce staple lines in the patient tissue which are approximately 60 mm in length. However, the staple cartridges 31120 and 31220 could both be configured to produce staple lines which are approximately 30 mm in length or 45 mm in length, for example. Moreover, it is entirely possible that the cartridge body 31122 and the cartridge body 31222 have the same color. In various instances, a commercial supplier may color-code the cartridge bodies of the staple cartridges that they sell to indicate the size of the staples stored therein. For instance, the cartridge bodies containing unformed staples having an approximately 4 mm unformed height are green, for example. The cartridge bodies containing unformed staples having an approximately 2.5 mm unformed height could be white, for example. Thus, it is entirely possible that the staple cartridges 31120 and 31220 have the same color. As such, it is possible that a clinician could grab one staple cartridge when they intended to grab the other and install the staple cartridge in the wrong stapling instrument. The improvements disclosed herein account for such possibilities and lockout the stapling instrument in such instances.

A surgical instrument 30800 is illustrated in FIGS. 151-155. Referring primarily to FIGS. 153 and 154, the surgical instrument 30800 comprises a cartridge channel 30810, a staple cartridge 30820 removably positioned in the cartridge channel 30810, a firing member 30040, and a lockout 30814 mounted to the cartridge channel 30810. The lockout 30814 comprises a leaf spring 30816 including a proximal end anchored in an aperture defined in the cartridge channel 30810 and a distal end which is movable relative to the fixed proximal end. Referring primarily to FIGS. 153 and 155, the lockout 30814 further comprises a lockout box 30815 configured to capture one of the lockout pins 30045 extending from the cutting portion 30042 of the firing member 30040 and hold the firing member 30040 in an unfired position when the staple cartridge 30820 is not seated in the cartridge channel 30810. The lockout box 30815 comprises a distal wall configured to prevent the firing member 30040 from being advanced distally, a proximal wall configured to prevent the firing member 30040 from being retracted proximally, and a bottom wall connecting the proximal wall and the distal wall of the lockout box 30815. The top of the lockout box 30815, however, is open but could be closed.

The staple cartridge 30820 comprises a cartridge body 30822, a sled, and a pan 30824 attached to and extending under the cartridge body 30822. Further to the above, the pan 30824 comprises a proximal projection 30826 configured to engage the leaf spring 30816 of the lockout 30814 when the staple cartridge 30820 is seated in the cartridge channel 30810, as illustrated in FIGS. 152 and 154. When the projection 30826 contacts the leaf spring 30816, the leaf spring 30816 flexes laterally such that the lockout pin 30045 is no longer captured in the lockout box 30815 of the lockout 30814. At such point, the firing member 30040 has been unlocked and the firing member 30040 can be advanced distally to perform a staple firing stroke. Referring primarily to FIG. 154, the distal, or free, end of the leaf spring 30816 extends into a window 30819 defined in the cartridge channel 30810. The window 30819 provides clearance for the leaf spring 30816 when the leaf spring 30816 is flexed by the staple cartridge 30820. Also, a bottom sidewall of the window 30819 supports the distal end of the leaf spring 30816 such that the distal end is at least simply supported. In any event, the lockout 30814 provides a missing cartridge lockout and an improper cartridge lockout for staple cartridges, such as the staple cartridge 30020, that do not have an appropriate key for unlocking the stapling instrument 30800.

As discussed above, the lockout 30814 is moved from a locked position (FIGS. 152 and 153) to an unlocked position (FIG. 154) when the staple cartridge 30820 is seated in the cartridge channel 30810 of the stapling instrument 30800. This deflection is seen in FIG. 155 which illustrates the lockout 30814 in its locked position in solid and its unlocked position in phantom. In instances where an improper or incompatible staple cartridge, i.e., a staple cartridge not having a suitable key, is seated in the cartridge channel 30810, the leaf spring 30816 will not be deflected, or at least suitably deflected, to unlock the firing member 30040. Notably, the lockout 30814 further comprises a tab 30817 extending from the leaf spring 30816 such that the tab 30817 moves laterally with the leaf spring 30816 when the lockout 30814 is deflected. When the lockout 30814 is in its locked position, as illustrated in FIG. 153, the tab 30817 prevents the anvil of the surgical instrument 30800, i.e., the anvil 30050, from being moved into a closed, or fully-clamped, position, as described in greater detail below.

The anvil 30050 is rotatably coupled to the cartridge channel 30810 about pivot pins 30051 mounted in apertures defined in the cartridge channel 30810. When the anvil 30050 is rotated toward the cartridge channel 30810 by a closure system of the surgical instrument 30800, and the staple cartridge 30820 is not seated in the cartridge channel 30810, a bottom surface 30057 of the anvil 30050 contacts the tab 30817 and the anvil 30050 is blocked from being moved into its closed or fully-clamped position. When the staple cartridge 30820 is seated in the cartridge channel 30810, however, the tab 30817 is displaced laterally such that, when the anvil 30050 is closed, the anvil 30050 does not contact the tab 30817 and the anvil 30050 can be moved into its closed or fully-clamped position. Thus, the lockout 30814 also comprises an anvil closure lockout as the lockout 30814 prevents the anvil 30050 from being closed when the staple cartridge 30820 is not seated in the cartridge channel 30810. In such instances, the clinician will become quickly aware that an improper staple cartridge is positioned in the cartridge channel 30810 and/or that a staple cartridge is missing altogether as they won't be able to close the anvil 30050. Because the anvil 30050 can't be closed onto the tissue, the staple firing stroke of the stapling instrument 30800 would also be prevented in such instances. In alternative embodiments where the staple cartridge jaw is rotatable instead of the anvil, such a lockout could be used to prevent the staple cartridge jaw from being rotated into a closed or fully-clamped position if an improper staple cartridge is positioned in the staple cartridge jaw or a staple cartridge is missing from the cartridge jaw altogether.

As discussed above, the lockout 30814 is configured to resist the closure of the anvil 30050. To this end, further to the above, the proximal end of the lockout 30814 is fixedly supported in the cartridge channel 30810 and the distal end of the lockout 30814 is simply supported by the sidewalls of the window 30819. This is the case when the lockout 30814 is in both of its locked (FIG. 153) and unlocked (FIG. 154) configurations. As such, the lockout 30814 can act as a beam supported at both ends and is well-suited to withstand the clamping load applied by the anvil 30050. Similarly, the tab 30817 extending from the lockout 30814 is also supported by the cartridge channel 30810. More specifically, the tab 30817 is slidably supported in a slot 30818 defined in the cartridge channel 30810 when the lockout 30814 is in both of its locked (FIG. 153) and unlocked (FIG. 154) configurations. As such, the lockout 30814 can act as a beam supported at both ends and an intermediate position and is well-suited to withstand the clamping load applied by the anvil 30050. That said, any suitable support arrangement could be used.

As discussed above, the lockout 30814 is configured to prevent the anvil 30050 of the stapling instrument 30800 from being moved into a closed, or fully-clamped, position when the staple cartridge 30820 is not seated in the cartridge channel 30810. That said, the lockout 30814 is configured to prevent the anvil 30050 from being substantially closed at all when the staple cartridge 30820 is not seated in the cartridge channel 30810. In such instances, the anvil 30050 can be moved slightly toward the cartridge channel 30810; however, the anvil 30050 is noticeably open when the anvil 30050 contacts the tab 30817 of the lockout 30814. In various alternative embodiments, the anvil 30050 is prevented from moving at all until the staple cartridge 30820 is seated in the cartridge channel 30810. In either event, the stapling instrument 30800 is not insertable into a patient through a trocar when the anvil 30050 is locked out. More specifically, a trocar comprises an inner passageway, or cannula, that is sized and configured to closely receive a surgical instrument therein and, when the anvil 30050 is locked out as described above, the distance between the anvil 30050 and the cartridge channel 30810 is too large for the stapling instrument 30800 to fit through the inner passageway. As a result, in such instances, the clinician using the stapling instrument 30800 will become aware that an improper staple cartridge is positioned in the stapling instrument 30800 before the stapling instrument 30800 is inserted into the patient.

A staple cartridge 31520 is illustrated in FIG. 155A. The staple cartridge 31520 comprises a cartridge body 31522 and a pan 31524 attached to the cartridge body 31522. The pan 31524 comprises lock arms 31521 engaged with lateral channels defined in the cartridge body 31522 which hold the pan 31524 to the cartridge body 31522. The pan 31524 is comprised of stamped metal, such as stainless steel, for example. The pan 31524 comprises two lateral sides—one on each side of the longitudinal slot 30023. Each lateral side of the pan 31524 extends along a lateral side of the cartridge body 31522 and under a portion of the cartridge body 31522. Each lateral side of the pan 31524 further comprises a proximal end 31527 that wraps around the proximal end of the cartridge body 31522. The proximal ends 31527 extend orthogonally, or at least substantially orthogonally, to the lateral sides of the pan 31524. Each proximal end 31527 comprises a tab which is folded to form a proximally-extending key 31526. Similar to the above, the keys 31526 are configured to unlock a staple firing system of a stapling instrument when the staple cartridge 31520 is seated in the stapling instrument.

Further to the above, each key 31526 comprises a rounded proximal end created by folding over the tabs outwardly such that the ends of the tab are brought back into contact with the proximal end 31527. As a result, the keys 31526 are sturdy and deflection of the keys 31526 is prevented, or at least substantially reduced. As such, the keys 31526 will reliably deflect the firing system locks to unlock the firing system when the staple cartridge 31520 is seated in the stapling instrument. Each proximal end 31527 further comprises one or more retention teeth 31529 which extend into slots 31528 defined in the proximal end 31527. The slots 31528 facilitate the folding of the proximal ends 31527 and also prevent, or at least limit, movement and/or deflection within the keys 31526. The teeth 31529 bite into the proximal end 31527 and hold the key 31526 in its folded configuration.

A staple cartridge 31620 is illustrated in FIG. 155B. The staple cartridge 31620 comprises a cartridge body 31522 and a pan 31624 attached to the cartridge body 31522. The pan 31624 comprises lock arms 31621 engaged with lateral channels defined in the cartridge body 31522 which hold the pan 31624 to the cartridge body 31522. The pan 31624 is comprised of stamped metal, such as stainless steel, for example. The pan 31624 comprises two lateral sides—one on each side of the longitudinal slot 30023. Each lateral side of the pan 31624 extends along a lateral side of the cartridge body 31522 and under a portion of the cartridge body 31522. Each lateral side of the pan 31624 further comprises a proximal end that wraps downwardly around the proximal end of the cartridge body 31522. The proximal ends extend orthogonally, or at least substantially orthogonally, to the lateral sides of the pan 31624. Each proximal end comprises a tab which is folded to form a proximally-extending key 31626. Similar to the above, the keys 31626 are configured to unlock a staple firing system of a stapling instrument when the staple cartridge 31620 is seated in the stapling instrument.

Further to the above, each key 31626 comprises a laterally-facing U-shaped channel. More specifically, each key 31626 comprises an inner base 31627, a laterally-extending top side 31628 extending from the inner base 31627, and a laterally-extending bottom side 31629 extending from the opposite side of the inner base 31627. The U-shaped configuration of the keys 31626 prevents the keys 31626 from buckling under a longitudinal load and/or deflecting under a laterally-directed torque. Notably, the keys 31626 are folded from tabs extending from the pan 31624 in such a manner so as to create clearance gaps 31625 under the keys 31626. The clearance gaps 31625 are sized and configured to permit the locking pins of a firing member to pass under the keys 31626 during a staple firing stroke of the firing member.

A staple cartridge 31720 is illustrated in FIG. 155C. The staple cartridge 31720 comprises a cartridge body 31522 and a pan 31724 attached to the cartridge body 31522. The pan 31724 comprises lock arms 31721 and 31721' engaged with lateral channels defined in the cartridge body 31522 which hold the pan 31724 to the cartridge body 31522. The pan 31724 is comprised of stamped metal, such as stainless steel, for example. The pan 31724 comprises two lateral sides—one on each side of the longitudinal slot 30023. Each lateral side of the pan 31724 extends along a lateral side of the cartridge body 31522 and under a portion of the cartridge body 31522. One lateral side of the pan 31724 further comprises a proximal end 31727 that wraps downwardly around the proximal end of the cartridge body 31522. The proximal end 31727 extends orthogonally, or at least substantially orthogonally, to the lateral side of the pan 31724. The proximal end 31727 comprises a tab which is folded to form a proximally-extending key 31726. Similar to the above, the key 31726 is configured to unlock a staple firing system of a stapling instrument when the staple cartridge 31720 is seated in the stapling instrument.

Further to the above, the lateral side of the pan 31724 comprises an arcuate or circular cut-out and the proximal end 31727 comprises an arcuate or circular projection 31723 that is bent around the side of the cartridge body 31522 into the circular cut-out. The projection 31723 is closely received in the cut-out such that the proximal end 31727 of the pan 31724 is greatly stiffened or strengthened by this arrangement. The key 31726 comprises an L-shaped tab bent proximally from the pan 31724. The key 31726 comprises a shoulder 31728 bent upwardly from the proximal end 31727 to create this L-shaped configuration. The shoulder 31728 comprises at least one notch, or strain relief, 31729 configured to facilitate the bending of the key 31726. The L-shaped configuration of the key 31726 prevents the key 31726 from buckling under a longitudinal load and/or deflecting under a laterally-directed torque. Notably, the key 31726 is folded from a tab extending from the pan 31724 in such a manner so as to create a clearance gap 31725 under the key 31726. The clearance gap 31725 is sized and configured to permit the locking pin of a firing member to pass under the key 31726 during a staple firing stroke of the firing member.

A staple cartridge 31920 is illustrated in FIG. 155E. The staple cartridge 31920 comprises a cartridge body 31522 and a pan 31924 attached to the cartridge body 31522. The pan 31924 comprises lock arms 31921 engaged with lateral channels defined in the cartridge body 31522 which hold the pan 31924 to the cartridge body 31522. The pan 31924 is comprised of stamped metal, such as stainless steel, for example. The pan 31924 comprises two lateral sides—one on each side of the longitudinal slot 30023. Each lateral side of the pan 31924 extends along a lateral side of the cartridge body 31522 and under a portion of the cartridge body 31522. One lateral side of the pan 31924 further comprises a proximal end 31927 that wraps around the proximal end of the cartridge body 31522. The proximal end 31927 extends orthogonally, or at least substantially orthogonally, to the lateral side of the pan 31924. The proximal end 31927 comprises a tab which is folded to form a proximally-extending key 31926. Similar to the above, the key 31926 is configured to unlock a staple firing system of a stapling instrument when the staple cartridge 31920 is seated in the stapling instrument.

Further to the above, the key 31926 comprises an L-shaped tab bent proximally from the pan 31924. The key 31926 comprises a shoulder 31928 bent upwardly from the proximal end 31927 to create this L-shaped configuration. The L-shaped configuration of the key 31926 prevents the key 31926 from buckling under a longitudinal load and/or deflecting under a laterally-directed torque. Moreover, a free edge of the shoulder 31928 is welded, soldered, and/or brazed to the proximal end 31927 in order to strengthen the key 31926. That said, any suitable number of welds 31929 can be used to secure or strengthen the key 31926. Notably, the key 31926 is folded from a tab extending from the pan 31924 in such a manner so as to create a clearance gap 31925 under the key 31926. The clearance gap 31925 is sized and configured to permit the locking pin of a firing member to pass under the key 31926 during a staple firing stroke of the firing member.

A staple cartridge 31820 is illustrated in FIG. 155D. The staple cartridge 31820 comprises a cartridge body 31522 and a pan 31824 attached to the cartridge body 31522. The pan 31824 comprises lock arms 31821 engaged with lateral channels defined in the cartridge body 31522 which hold the pan 31824 to the cartridge body 31522. The pan 31824 is comprised of stamped metal, such as stainless steel, for example. The pan 31824 comprises two lateral sides—one on each side of the longitudinal slot 30023. Each lateral side of the pan 31824 extends along a lateral side of the cartridge body 31522 and under a portion of the cartridge body 31522. One lateral side of the pan 31824 further comprises a proximal end 31827 that wraps around the proximal end of the cartridge body 31522. The proximal end 31827 extends orthogonally, or at least substantially orthogonally, to the lateral side of the pan 31824. The proximal end 31827 comprises a tab which is folded to form a proximally-extending key 31826. Similar to the above, the key 31826 is configured to unlock a staple firing system of a stapling instrument when the staple cartridge 31820 is seated in the stapling instrument.

Further to the above, the key 31826 comprises a rounded proximal end created by folding over the tab outwardly such that the end of the tab is brought back into contact with the proximal end 31827. As a result, the key 31826 is sturdy and deflection of the key 31826 is prevented, or at least substantially reduced. As such, the key 31826 will reliably deflect the firing system locks to unlock the firing system when the staple cartridge 31820 is seated in the stapling instrument. The proximal end 31827 further comprises one or more retention teeth 31829 which extend into slots 31828 defined in the proximal end 31827. The slots 31828 facilitate the folding of the proximal end 31827 and also prevent, or at least limit, movement and/or deflection within the key 31826. The teeth 31829 bite into the proximal end 31827 and hold the key 31826 in its folded configuration. Notably, the key 31826 is folded from a tab extending from the pan 31824 in such a manner so as to create a clearance gap 31825 under the key 31826. The clearance gap 31825 is sized and configured to permit the locking pin of a firing member to pass under the key 31826 during a staple firing stroke of the firing member.

Many of the lockouts disclosed herein are defeated when a compatible or proper staple cartridge is seated in the stapling instrument. When seated, a staple cartridge is locked into position within the stapling instrument. In such instances, there is little, if any, relative movement possible between the staple cartridge and the stapling instrument until the staple cartridge is uninstalled from the stapling instrument.

In various instances, a surgical stapling assembly comprises a shaft and an end effector extending distally from the shaft including a first jaw and a second jaw rotatable relative to the first jaw. The surgical stapling assembly may comprise a lockout member configured to prevent the inadvertent firing of the surgical stapling assembly and/or the clamping of the surgical stapling assembly until a lockout key unlocks the lockout member. The lockout key may be a part of a staple cartridge configured to be installed in one of the first jaw and the second jaw, for example. Particularly, the lockout key may be a part of a sled of the staple cartridge such that the staple cartridge can unlock the lockout member when the sled is in its unfired position indicating that the staple cartridge is unspent when the staple cartridge is installed within the surgical stapling assembly. In at least one instance, further action may be required to unlock the lockout with the lockout key. For example, an end effector may be required to attain a fully clamped configuration before the lockout key can unlock the lockout member. One example of a lockout can be found in U.S. Patent Application Publication No. 2016/0249921 entitled SURGICAL APPARATUS WITH CONDUCTOR STRAIN RELIEF, now U.S. Pat. No. 10,085,749, the entire disclosure of which is hereby incorporated by reference herein.

In at least one instance, surgical stapling assemblies, such as the one described above, may be used with a surgical robot. The surgical stapling assemblies can be configured to be attached to robotic systems and operated by way of robotic arms of the robotic systems. These robotic systems allow for surgeons to be outside of a sterile field within which the patient is present. In at least one instance, a technician and/or another surgeon, for example, may be located within the bounds of the sterile field to monitor the interface between the tools and the patient. This technician and/or surgeon may attach and detach instruments to the robotic arms during a surgical procedure. In some instances, it may be advantageous to be able to actively bypass the lockout member of a surgical stapling assembly. Providing this ability can enable a surgeon or technician to manually defeat a lockout means of a staple cartridge when the lockout means, for whatever reason, cannot be automatically defeated. Providing this ability may also enable a surgeon to test the operability of the lockout member to ensure that the lockout member is functional prior to using the surgical stapling assembly. In an instance where a surgeon wants to manually override the lockout member to fire a staple cartridge, a surgeon or clinician may know that the installed staple cartridge is a proper unfired staple cartridge and may want to fire the staple cartridge regardless of the fact that the lockout member was not actually defeated. In at least one instance, the clinician may want remove that lockout member from the firing sequence and prevent it from being a part of the firing stroke. Moreover, providing direct access to the lockout member within the end effector itself for manual unlocking can provide an advantage with or without a system that automatically defeats the lockout member. Direct access to the lockout member within the end effector can eliminate additional components that otherwise may be present in a system utilizing an unlocking mechanism to unlock the lockout member that is further upstream of the lockout member. Using an unlocking mechanism further upstream to the lockout member within the shaft of the surgical instrument, for example, can introduce additional components that might jam or fail during the application of an unlocking actuation.

FIGS. 156-160 depict a surgical stapling assembly 41000 configured to clamp, staple, and cut the tissue of a patient. The surgical stapling assembly 41000 is configured to be attached to, detached from, and operated by a surgical robot and/or a surgical instrument handle. The surgical stapling assembly 41000 comprises a shaft 41100, a first jaw 41200 pivotably supported within the shaft 41100, and a second jaw 41300 attached to the shaft 41100. The first jaw 41200 is movable between an unclamped configuration and a clamped configuration to clamp and unclamp tissue positioned between the first jaw 41200 and the second jaw 41300. The surgical stapling assembly 41000 further comprises a staple cartridge 41230 comprising a plurality of staples removably stored therein. The staple cartridge 41230 is configured to be installed into the first jaw 41200 and replaced with other staple cartridges. The surgical stapling assembly 41000 further comprises a firing member 41400 extending through the shaft 41100 that is configured to move the first jaw 41200 relative to the second jaw 41300 between the unclamped configuration and the clamped configuration, deploy staples from the staple cartridge 41230, and cut tissue during a firing stroke with a knife, or blade, 41422. The firing member 41400 is configured to be actuated by a drive system of a surgical robot and/or a surgical instrument handle. Embodiments are envisioned where the firing member 41400 is driven with a rotary drive shaft. Embodiments are also envisioned where the jaw configured to receive the staple cartridge is fixed to the shaft and the jaw containing the anvil is movable between a clamped configuration and an unclamped configuration.

The surgical stapling assembly 41000 further comprises a lockout 41500 (FIG. 160) configured to prevent the firing member 41400 from moving distally past a specific position unless a proper unspent staple cartridge is installed within the first jaw 41200 and the first jaw 41200 is in a fully clamped configuration. In at least one instance, the firing member 41400 is permitted to move a first distance between a home position and the specific position regardless of the condition of the lockout 41500 to permit clamping and unclamping of tissue, as discussed in greater detail below. The lockout 41500 is biased toward a locked configuration where the firing member 41400 is prevented from moving distally beyond the specific position. The lockout 41500 is movable into an unlocked configuration where the firing member 41400 is permitted to move distally beyond the specific position to deploy staples from the staple cartridge 41230. Discussed in greater detail below, the surgical stapling assembly 41000 further comprises a direct access orifice defined therein configured to allow a clinician to manually, or artificially, unlock the lockout 41500, i.e., move the lockout 41500 into the unlocked configuration.

The first jaw 41200 comprises a channel 41210 configured to receive the staple cartridge 41230 therein. The staple cartridge 41230 is configured to be installed within the channel 41210 and readily replaced with another staple cartridge. The staple cartridge 41230 further comprises a sled 41235 movable between an unfired position and a fired position to eject the staples from the staple cartridge 41230 as the sled 41235 is pushed distally through a cartridge body 41232 of the staple cartridge 41230 by the firing member 41400. The second jaw 41300 comprises an anvil 41320 comprising a staple-forming surface 41310 configured to form the staples ejected from the staple cartridge 41230.

The first jaw 41200 is movable relative to the second jaw 41300 between an unclamped configuration and a clamped configuration by the firing member 41400. Embodiments are envisioned where the second jaw 41300 is movable relative to the first jaw 41200. To clamp tissue, the firing member 41400 is moved distally a first distance from a home position to cam the first jaw 41200 into a clamped configuration. Referring to FIG. 159, the firing member 41400 comprises anvil-camming portions 41423 configured to engage a ramp 41332 of an anvil channel 41330 defined within the second jaw 41300 and channel-camming portions 41424 configured to engage a ramp 41222 of a bottom surface 41220 of the first jaw 41200. The anvil-camming portions 41423 and the channel-camming portions 41424 extend laterally from a distal portion 41420 of the firing member 41400 and are configured to control the distance between the first jaw 41200 and the second jaw 41300 as the distal portion 41420 of the firing member moves through its firing stroke. During the first distance discussed above, the anvil-camming portions 41423 and the channel-camming portions 41424 engage the first and second jaws 41200, 41300 and cam the first jaw 41200 into a clamped configuration. Further distal movement of the distal portion 41420 of the firing member 41400 holds the first and second jaws 41200, 41300 relative to each other during the firing stroke and pushes the sled 41235 distally to eject staples stored within the staple cartridge 41230.

The surgical stapling assembly 41000 further comprises a lockout 41500 configured to prevent the firing member from being advanced distally beyond the first distance unless a proper unspent staple cartridge is installed within the first jaw 41200 and the first jaw 41200 is fully clamped. The lockout 41500 comprises a lockout member 41510 pivotably supported within the shaft 41100 and movable between an unlocked configuration (FIG. 157) where the firing member 41400 is permitted to move beyond the first distance to complete the firing stroke and a locked configuration (FIG. 158) where the firing member 41400 is prevented from moving beyond the first distance. The lockout member 41510 is biased into the locked configuration by a spring 41520. A proper unspent staple cartridge installed within the channel 41210 can overcome the bias provided by the spring 41520 when the first jaw 41200 is moved into the clamped configuration.

To unlock the lockout 41500, the first jaw 41200 must be moved into its clamped configuration to present the sled 41235 to engage and unlock the lockout member 41510. The sled 41235 cannot defeat the lockout 41500 when the first jaw 41200 is not in its clamped configuration. Embodiments are envisioned where the cartridge jaw is not pivotable but, rather, the anvil jaw is pivotable. In such embodiments, mere insertion of the staple cartridge presents the sled 41235 to defeat the lockout 41500. In such embodiments, the lockout 41500 can be defeated prior to the application of any clamping motions to the anvil jaw.

To unlock the lockout 41500, as discussed above, a proper unspent staple cartridge must be installed in the first jaw 41200 of the surgical stapling assembly 41000. The staple cartridge 41230 comprises a sled 41235 comprising a lockout key 41237 extending proximally therefrom. The lockout key 41237 is configured to move the lockout member 41510 into the unlocked configuration when the sled 41235 is in an unfired position and the first jaw 41200 is moved into the clamped configuration. To unlock the lockout, the lockout key 41237 pivots the lockout member 41510 into the unlocked configuration by moving a lockout ledge, or leg, 41511 of the lockout member 41510 away from a lockout notch 41412 defined in a firing shaft, or bar, 41410 of the firing member 41400 which would otherwise prevent distal movement of the firing member 41400 beyond an initial distance used for clamping when the first jaw 41200 is moved into the clamped configuration. The lockout member 41510 comprises a pair of arms 41512 extending distally from the lockout ledge 41511 which are configured to straddle the firing member 41400 as the firing member 41400 moves through its firing stroke.

FIG. 157 illustrates the lockout key 41237 engaged with distal ends 41516 of the arms 41512 on a distal end 41515 of the lockout member 41510. As illustrated in FIG. 157, the lockout member 41510 has pivoted relative to the shaft 41100 about nubs 41513 (FIG. 160) of the lockout member 41510 into the unlocked configuration. When the lockout member 41510 is in the unlocked configuration, the lockout notch 41412 of the firing shaft 41410 will clear the lockout ledge 41511 of the lockout member 41510 thereby permitting the firing member 41400 to move distally through the staple cartridge 41230. Referring to FIG. 158, if the lockout key 41237 is not present upon clamping the first jaw 41200 into the clamped configuration, the lockout member 41510 remains biased in the locked configuration by way of the spring 41520 (FIG. 159) pushing against the tabs 41514 (FIG. 160) of the lockout member 41510 where the lockout ledge 41511 engages the notch 41412 of the firing shaft 41410 to block distal movement of the firing member 41400 beyond the initial distance used for clamping.

As discussed above, the surgical stapling assembly 41000 further comprises a direct access orifice 41425 defined therein configured to allow a clinician to artificially move the lockout member 41510 into the unlocked configuration. The orifice 41425 can be positioned in any suitable component such that a tool 41590 can access the lockout member 41510 through the orifice 41425 to move the lockout member 41510 into the unlocked configuration. The orifice 41425 is defined in the channel-camming portions 41424 of the distal portion 41420 of the firing member 41400. The orifice 41425 may comprise access slits defined in the channel-camming portions 41424, for example. In at least one instance, the orifice 41425 is defined in the shaft 41100 and/or a component thereof. Nonetheless, the lockout member 41510 is directly accessible through the orifice 41425. The tool 41590 comprises a hook portion 41591 configured to be inserted through the orifice 41425 and an opening 41517 defined between the arms 41512 of the lockout member 41510 to hook, or latch, onto an upper side of the ledge 41511 to pull the ledge 41511 and thus pivot the lockout member 41510 into the unlocked configuration overcoming the spring bias which encourages the lockout member 41510 into the locked configuration. The orifice 41425 can be configured such that commonly-avoidable tools, such as a screwdriver, for example, do not fit within the orifice, or exterior access aperture, 41425. Portions of the lockout member 41510 are illustrated in phantom in the unlocked configuration where tool 41590 has positioned the lockout member 41510 into the unlocked configuration. Arms 41512' and ledge 41511' are phantom versions of the arms 41512 and ledge 41511 of the lockout member 41510 illustrated in the unlocked configuration.

Once the lockout member 41510 is manually, or artificially, defeated to move the lockout 41500 into the unlocked configuration, the firing member 41400 is permitted to move distally past an unfired location and into the staple cartridge 41230. The unfired location is defined as the position after clamping but before firing. Once the firing member 41400 is advanced distally past its unfired position, the tool 41590 can be disengaged from the lockout member 41510 and removed from the orifice 41425 to allow the lockout 41500 to resume normal operation. For instance, the lockout member 41510 will pivot into the locked configuration when the firing member 41400 returns to the unfired location after having at least partially fired a staple cartridge. During the firing stroke, the lockout member 41510 is accessible with the tool 41590 through a secondary access aperture 41160 defined between a proximal end of the channel 41210 and a distal end of the shaft 41100. That said, the lockout member 41510 will remain defeated during the staple firing stroke. In at least one instance, the direct access orifice is positioned within the shaft 41100, for example, and can provide access to the lockout member 41510 during the firing stroke of the firing member 41400. In at least one instance, the secondary access aperture 41160 comprises the primary lockout access aperture.

The lockout 41500 can be positioned in any suitable location. In at least one instance, the lockout 41500 may be positioned proximal to the distal portion 41420 of the firing member 41400 when the firing member 41400 is in its proximal most position (such as the position illustrated in FIG. 159). In such an instance, the access aperture may be defined in a shaft housing, or frame, of the surgical stapling assembly 41000. In at least one instance, the access aperture is defined in the channel 41210.

In at least one instance, the tool 41590 can be inserted through the direct access aperture 41425 to unlock the lockout 41500 prior to the insertion of the staple cartridge 41230 into the channel 41210. Moving the lockout 41500 to its unlocked configuration prior to the insertion of a staple cartridge can aid the staple cartridge installation by preventing the lockout 41500 from engaging the staple cartridge during installation. Some lockouts disable improper staple cartridges by bumping a sled of the staple cartridge from its unfired, firable position to an unfired, unfirable position which can cause the staple cartridge to become instantly spent. Moreover, such lockouts may bump a sled of a proper staple cartridge during installation of the proper staple cartridge. Unlocking the lockout 41500 prior to installation of the staple cartridge can ensure that the proper staple cartridge is not disabled accidentally during installation.

FIGS. 161 and 162 depict a surgical stapling assembly 42000 for use in clamping, stapling, and cutting the tissue of a patient. The surgical stapling assembly 42000 is similar to other stapling assemblies described herein in many respects. The surgical stapling assembly 42000 comprises a firing assembly 42100 and a cartridge channel 42200 configured to receive a staple cartridge therein. The firing assembly 42100 is configured to push a sled of a proper unspent staple cartridge installed within the cartridge channel 42200 to deploy the staples of the staple cartridge and cut the stapled tissue. The surgical stapling assembly 42000 further comprises a lockout 42300 configured to prevent the firing assembly 42100 from being advanced through an improper staple cartridge. The lockout 42300 comprises a spring 42310 which biases the lockout 42300 toward a locked configuration. The lockout 42300 is configured to be pushed proximally by a proper unspent staple cartridge to unlock the firing assembly 42100. Notably, the lockout 42300 is configured such that lockout 42300 does not accidentally push the sled of the proper staple cartridge into a position which would induce a lockout condition for the firing assembly 42100. The lockout 42300 can employ any suitable lockout method. The firing assembly 42100 is similar to other firing assemblies described herein.

The surgical stapling assembly 42000 further comprises a direct access cutout, or aperture, 42210 defined in the bottom of the cartridge channel 42200 at a proximal end of a longitudinal slot 42230 defined in the cartridge channel 42200. The firing assembly 42100 is movable through the slot 42230 of the cartridge channel 42200 during a staple firing stroke. The direct access cutout 42210 allows for a tool to be inserted within the surgical stapling assembly 42000 to access the lockout 42300 directly. The tool can be inserted through the direct access cutout 42210 to move the lockout 42300 into an unlocked configuration (FIG. 162). Unlocking the lockout 42300 in this manner can be referred to as artificially unlocking the lockout 42300 because an unspent staple cartridge has not automatically unlocked the lockout 42300 for whatever reason. The direct access cutout 42210 comprises a proximal end 42211 and a distal end 42213 comprising a wider cutout portion than the proximal end 42211. The wider cutout portion of the distal end 42213 can aid in the proper insertion of the tool into the channel 42200. For example, the tool can comprise a lock-engaging portion that fits in the distal end 42213 but not the proximal end 42211 thereby eliminating the possibility of mis-inserting the tool in the proximal end 42211. Moreover, the lockout 42300, and its position relative to other components of the surgical stapling assembly 42000, is also directly visible through the direct access cutout 42210. Nonetheless, a tool can be inserted through the cutout 42210 to pull and/or push the lockout 42300 proximally to overcome the spring bias and move the lockout 42300 into the unlocked configuration. The tool can also be removed and disengaged from the lockout 42300 such that the lockout 42300 can resume normal operation. Moreover, providing the ability to manually move the lockout 42300 may allow a clinician to move the lockout 42300 away from its locked position before installing a staple cartridge into the cartridge channel 42200 to prevent the lockout 42300 from moving a sled of the staple cartridge that is being installed into the cartridge channel 42200 prematurely.

FIGS. 163 and 164 depict a surgical stapling assembly 43000 comprising a firing assembly 43100, a frame 43400 that supports the firing assembly 43100 therein, a cartridge channel 43300 pivotably attached to the frame 43400, and a lockout key mechanism 43500 configured to defeat a lockout of the surgical stapling assembly 43000. The surgical stapling assembly 43000 can comprise any suitable lockout; however, a diving knife lockout where the firing assembly 43100 falls into a locking recess in the absence of a proper unspent staple cartridge being positioned in the cartridge channel 43300 is described below.

The firing assembly 43100 comprises a firing shaft 43110 and a firing member 43120 attached to the distal end of the firing shaft 43110. Although a linear firing shaft is illustrated, the firing assembly 43100 may be configured with a rotary drive shaft. The firing shaft 43110 is configured to be actuated by a firing driver of a surgical instrument handle and/or a surgical robot, for example. Any suitable drive mechanism may be used. The firing member 43120 comprises anvil-camming pins 43122 and channel camming pins 43123 extending laterally therefrom. The pins 43122, 43123 are configured to control the clamping pressure on the tissue captured within the surgical stapling assembly 43000 during a firing stroke. The firing member 43120 further comprises a cutting edge 43121 configured to cut the clamped tissue. The firing member 43120 further comprises a ledge, or distal nose, 43124 configured to engage and/or rest on top of a sled of an unfired proper staple cartridge such that the firing member 43120 does not fall into the lockout recess.

The firing assembly 43100 further comprises an extension 43111 configured to be biased downwardly toward the channel 43300 by a spring member mounted within the frame 43400. Discussed in greater detail below, the downward bias of the extension 43111 encourages the firing assembly 43100 toward its locked out condition. The downward bias is overcome when an unspent proper staple cartridge is installed within the cartridge channel 43300.

The lockout key mechanism 43500 comprises a spring 43530, a wedge 43520 slidably supported within the frame 43400, and a lifter spring 43510 comprising a proximal end 43511 mounted to the frame 43400. The wedge 43520 comprises a ramp 43521 on which a distal end 43512 of the lifter spring 43510 rests. When a staple cartridge is inserted into the cartridge channel 43300, the staple cartridge 43200 pushes the wedge 43520 proximally. Proximal movement of the wedge 43520 causes the lifter spring 43510 to lift the firing member 43120 to defeat a first stage of the lockout. The lifter spring 43510 comprises a notch 43513 defined on the distal end 43512 configured to engage lifter pins 43125 extending laterally from the firing member 43120 when the lifter spring 43510 is lifted by the wedge 43520 of the staple cartridge 43200.

Once the first stage of the lockout has been overcome, the firing assembly 43100 is advanced distally to assess the second stage of the lockout. This second stage of the lockout is defeated when the sled of the staple cartridge 43200 is in its proximal unfired position. Similar to the above, the firing shaft 43110 can be lifted onto the sled by the staple cartridge 43200 as the firing shaft 43110 is advanced distally.

To cause the nose 43124 of the firing member 43120 to land on an unfired sled of the staple cartridge 43200 to defeat the second stage of the lockout and prevent the firing member 43120 from falling into the lockout recess, a cartridge body key 43211 is provided on a proximal end 43201 of the cartridge body 43210. Referring now to FIG. 164, as the staple cartridge 43200 is installed in the cartridge channel 43300, the cartridge body key 43211 pushes the wedge 43520 proximally and overcomes the spring bias provided by the spring 43530. As the wedge 43520 is pushed proximally, the wedge 43520 lifts the lifter spring 43510. At this point, the notch 43513 can grab the lifter pins 43125 and lift the firing assembly 43100. Lifting the firing assembly 43100 in this manner can be referred to as defeating the first stage of the lockout. Notably, a staple cartridge without the proper cartridge lockout key may be able to be installed in the cartridge channel 43300 but will not be able to lift the firing assembly 43100. Once the staple cartridge 43200 is installed in the cartridge channel 43300 and the firing assembly 43100 is lifted, the firing assembly 43100 can be advanced distally such that the notch 43513 can hold the firing assembly 43100 at the proper height and for the proper distance so that the nose 43124 can land on the unfired sled in the staple cartridge 43200 thereby avoiding the lockout recess. Landing the nose 43124 on the unfired sled can be referred to as defeating the second stage of the lockout. If the sled in the staple cartridge 43200 is not in its unfired position, the firing assembly 43100 will fall into the lockout recess and not be able to be advanced distally beyond its locked configuration. In at least one instance, the cartridge body key 43211 extends proximally from a cartridge body pan 43220 of the staple cartridge 43200.

FIG. 165 depicts a first staple cartridge 43610 comprising a proximal end 43611 and a lockout key 43613 extending from the proximal end 43611. The lockout key 43613 comprises a first profile. FIG. 165 depicts a second staple cartridge 43620 comprising a proximal end 43621 and a lockout key 43623 extending from the proximal end 43621. The lockout key 43623 comprises a second profile that is different than the first profile of the lockout key 43613. The first staple cartridge 43610 is configured to unlock only the stapling instruments it is compatible with and the second staple cartridge 43620 is configured to unlock only the stapling instruments it is compatible with.

Referring back to the lockout key mechanism 43500 in FIGS. 163 and 164, cartridges using different key profiles can be used to ensure that the firing member is lifted at the appropriate location and with the appropriate height. Lifting the firing member at different locations, referring to FIG. 165, causes different lift timings of the firing member. This can be used to ensure that an improper staple cartridge can not unlock a non-compatible instrument. FIGS. 166 and 167 contain graphs illustrating the different lift timings 43610', 43620' and displacements 43610", 43620" provided by the cartridges 43610, 43620. The staple cartridge 43610 is configured to lift the firing member earlier than the staple cartridge 43620. In a compatible surgical instrument, the first staple cartridge 43610 will cause a wedge, for example, such as the wedge described herein, to lift the firing member at the appropriate time and location such that the firing member will land on an unfired sled of the first staple cartridge 43610 so as to defeat the lockout and enable the firing member to be advanced distally to perform a staple firing stroke. In an incompatible surgical instrument, the first staple cartridge 43610 will cause a wedge, for example, to lift the firing member at the incorrect time and location causing the firing member to fall before reaching the sled or causing the firing member to bump the sled distally before being lifted onto the sled. Both situations involving installing an incompatible cartridge and instrument will cause the firing member to enter a locked out condition upon an attempt to move the firing member through a firing stroke. The second staple cartridge 43620 works in a similar manner. That said, the second staple cartridge 43620 cannot unlock an instrument compatible with the first staple cartridge 43610, and vice versa.

FIGS. 168 and 169 depict a system 44000 comprising a first cartridge 44100 (FIG. 168) and a second cartridge 44200 (FIG. 169). The first staple cartridge 44100 comprises a cartridge body 44110 comprising a proximal end 44111, a distal end 44112, and a plurality of staple cavities 44114 arranged in rows extending between the proximal end 44111 and the distal end 44112. The first staple cartridge 44100 further comprises a cartridge pan 44130 configured to hold staples in the cartridge body 44110, and a sled 44120 configured to deploy the staples from the cartridge body 44110. The cartridge body 44110 further comprises a longitudinal slot 44113 defined therein configured to receive a firing member of a surgical stapling assembly. The longitudinal slot 44113 defines a first lateral side and a second lateral side labeled "A" and "B" respectively. The cartridge body 44110 further comprises a lockout key 44116 extending from a proximal face 44115 of the first lateral side "A" of the cartridge body 44110.

The second staple cartridge 44200 comprises a cartridge body 44210 comprising a proximal end 44211, a distal end 44212, and a plurality of staple cavities 44214 arranged in rows extending between the proximal end 44211 and the distal end 44212. The second staple cartridge 44200 further comprises a cartridge pan 44230 configured to hold staples in the cartridge body 44210, and a sled 44220 configured to deploy the staples from the cartridge body 44210. The cartridge body 44210 further comprises a longitudinal slot 44213 defined therein configured to receive a firing member of a surgical stapling assembly. The longitudinal slot 44213 defines a first lateral side and a second lateral side labeled "A" and "B" respectively. The cartridge body 44210 further comprises a lockout key 44216 extending from a proximal face 44215 of the second lateral side "B" of the cartridge body 44210.

The staple cavities 44114 comprise three rows on each side of the longitudinal slot 44113. Each row defines a row axis with which each staple cavity in that row is aligned. In other words, the proximal end and the distal end of each cavity in a single row is aligned with the row axis of that row. The staple cavities 44214 comprise three rows on each side of the longitudinal slot 44213. Each row defines a row axis with which each staple cavity in that row is transversely aligned. Each side of the staple cartridge 44200 comprises an outer row of staple cavities 44214, an inner row of staple cavities 44214, and a middle row of staple cavities 44214 positioned between the outer row of staple cavities 44214 and the inner row of staple cavities 44214. The staple cavities 44214 of the middle row define cavity axes that are transverse to cavity axes defined by the staple cavities 44214 in the inner row and the staple cavities 44214 in the outer row.

The system 44000 provides a way to prevent an improper staple cartridge from being used with a surgical stapling assembly by providing the lockout keys of each cartridge on different sides of the staple cartridge. Providing the lockout keys on different sides of the staple cartridge prevents the use of a stapling assembly comprising corresponding staple-forming pockets for the first staple cartridge 44100 with the second staple cartridge 44200 and the use of a stapling assembly comprising corresponding staple-forming pockets for the second staple cartridge 44200 with the first staple cartridge 44100. Thus, the first staple cartridge 44100 will not be able to unlock a firing lockout of a surgical stapling assembly meant for the second staple cartridge 44200 and the second staple cartridge 44200 will not be able to unlock a firing lockout of a surgical stapling assembly meant for the first staple cartridge 44100. This prevents improper cartridge installation which may result in deploying staples against an anvil with non-corresponding staple-forming pockets.

FIGS. 170-179 depict a surgical stapling assembly 45000 configured to clamp, staple, and cut the tissue of a patient. The surgical stapling assembly 45000 can be used with a surgical robot and/or a surgical instrument handle. The surgical stapling assembly 45000 comprises a first jaw 45200, a second jaw 45400 movable relative to the first jaw 45200 between an unclamped configuration and a clamped configuration, and a firing assembly 45500. The surgical stapling assembly 45000 further comprises a replaceable staple cartridge 45300 comprising a plurality of staples removably stored therein which are configured to be deployed by the firing assembly 45500. The first jaw 45200 comprises a channel 45210 configured to receive the replaceable staple cartridge 45300. The second jaw 45400 comprises an anvil 45410 comprising a staple-forming surface 45415 configured to form the staples deployed from the staple cartridge 45300. The first jaw 45200 further comprises pin apertures 45212 (FIG. 171) in which pivot pins 45413 of the second jaw 45400 are received to permit the second jaw 45400 to pivot relative to the first jaw 45200. Embodiments are envisioned where the fixed jaw comprises the anvil and the movable jaw comprises the channel and the staple cartridge.

To clamp tissue with the surgical stapling assembly 45000, the second jaw 45400 comprises a camming surface 45412 formed on a proximal end 45411 thereof which is configured to be engaged by a closure member. The closure member comprises a closure tube, for example, but can comprise any other suitable configuration. The closure member is configured to cam the second jaw 45400 from the unclamped configuration to the clamped configuration toward the channel 45210 by engaging and sliding along the camming surface 45412. To unclamp the surgical stapling assembly 45000, the closure member is retracted proximally. A spring may be provided to bias the second jaw 45400 into the unclamped configuration as the closure member disengages the camming surface 45412.

To staple and cut tissue with the surgical stapling assembly 45000, a proper unspent staple cartridge must be installed within the surgical stapling assembly 45000. When a proper unspent staple cartridge is installed within the channel 45210, the firing assembly 45500 can be actuated through the staple cartridge 45300 to push a sled 45340 of the staple cartridge 45300 distally from an unfired position to a fired position to deploy the staples stored within the staple cartridge 45300 during a staple firing stroke. As the firing assembly 45500 is moved through the staple firing stroke, a cutting edge 45523 of the firing assembly cuts the tissue clamped between the first jaw 45200 and the second jaw 45400. In at least one instance, the cutting edge 45523 trails behind the staple deployment to prevent tissue from being cut before the tissue is stapled.

Referring primarily to FIGS. 172-175, the firing assembly 45500 comprises a firing member 45520 comprising the cutting edge 45523, anvil-camming portions 45521 and channel-camming portions 45522 configured to control the distance between the first jaw 45200 and the second jaw 45400 during the staple firing stroke, and laterally-extending portions 45525 positioned between the anvil-camming portions 45521 and the channel-camming portions 45522 configured to fall into a lockout as discussed in greater detail below. The firing member 45520 further comprises a tail 45526 extending proximally therefrom which is configured to interface with a spring 45240 mounted in the shaft as discussed in greater detail below.

To prevent the firing assembly 45500 from being advanced through an improper and/or spent staple cartridge, the surgical stapling assembly 45000 further comprises a lockout system. The surgical stapling assembly 45000 comprises a diving-knife lockout such as those disclosed herein where the firing assembly 45500 falls into a lockout pocket if a proper unspent staple cartridge is not installed within the surgical stapling assembly 45000. A proper unspent staple cartridge, such as the staple cartridge 45300, is configured to prevent the firing assembly 45500 from falling into the lockout pocket by lifting the firing assembly 45500 when the staple cartridge 45300 is unspent. In such instances, a distal end of the firing assembly will land on an unfired sled of the staple cartridge 45300. The firing assembly 45500 may then be advanced through the staple cartridge 45300.

The staple cartridge 45300 includes a lockout key 45330 to lift the firing assembly 45500 to the proper height and proper distance to get the firing assembly 45500 to land on an unfired sled and defeat the lockout of the surgical stapling assembly 45000. The staple cartridge 45300 further comprises a cartridge body 45310 comprising a proximal end 45301 comprising a proximal face 45313 and a longitudinal slot 45311 configured to receive the firing assembly 45500 during the staple firing stroke. The lockout key 45330 extends proximally from the proximal face 45313 of the cartridge body 45310 and comprises a pair of protrusions defining a proximal longitudinal slot portion 45333 of the longitudinal slot 45311. The proximal longitudinal slot portion 45333 is configured to straddle the firing member 45520 when the staple cartridge 45300 is installed in the channel 45210. Each protrusion of the lockout key 45330 comprises a ramped surface, or portion, 45331 and a non-ramped portion, or surface, 45332. The staple cartridge 45300 further comprises a pan 45320 configured to hold the staples within the cartridge body 45310. The pan 45320 is configured to clip onto a deck 45312 of the cartridge body 45310. The pan 45320 may be removably affixed to the cartridge body 45310 by a series of hooks 45321 that are formed on the sidewalls of the cartridge pan 45320 and configured to hookingly engage corresponding portions of the cartridge body 45310. In at least one instance, the pan can comprise the lockout key.

The firing assembly 45500 comprises a firing shaft 45510 configured to transfer firing motions to the firing member 45520. The firing member 45520 is attached to a distal end 45513 of the firing shaft 45510. The firing member 45520 is biased downwardly by the spring 45420 mounted in the shaft. More specifically, the spring 45420 pushes the tail 45526 of the firing member 45520 downwardly to bias the firing member 45520 unless the firing member 45520 is lifted upwardly away from the firing lockout. To lift the firing assembly 45500, the surgical stapling assembly 45000 comprises a floating pin 45600 positioned behind the firing member 45520 of the firing assembly 45500. The floating pin 45600 is supported within a slot, or channel, 45213 defined in the sides of the staple cartridge channel 45210. The floating pin 45600 is configured to move vertically within the slot 45213 by the ramped surfaces 45331. More specifically, the floating pin 45600 is pushed upwardly by the lockout key 45330 into the staple cartridge channel 45210 which, in turn, contacts the bottom edge of the firing member 45520 and pushes the firing member 45520 upwardly. Thus, the floating pin 45600 keeps the firing member 45520 from diving into the firing lockout when the staple cartridge 45300 is seated in the staple cartridge channel 45210. As such, the lockout key 45330 overcomes the downward spring bias applied to the firing member 45520 by the spring 45240.

Once the staple cartridge 45300 is fully installed and the firing assembly 45500 is lifted to the position illustrated in FIG. 174, the firing assembly 45500 can then be advanced distally toward the sled 45340 of the staple cartridge 45300. Thus, with the proper lockout key, the first stage of the lockout is defeated. If the sled 45340 is in its unfired position, a distal nose, or shelf, 45524 of the firing member 45520 will land on a corresponding platform 45341 of the sled 45340 and avoid the lockout discussed above. Landing the distal nose 45524 of the firing member 45520 on the platform 45341 of the sled 45340 when the sled 45340 is in its unfired position defeats a second stage of the lockout. As the firing assembly 45500 is advanced distally, the bottom surface 45511 rides over the floating pin 45600 and the height of the firing assembly 45500 is governed by the engagement between the floating pin 45600, the bottom surface 45511 of the firing shaft 45510, and the lockout key 45600.

Because the height of the firing assembly 45500 is governed by the engagement between the floating pin 45600, the bottom surface 45511 of the firing shaft 45510, and the lockout key 45600, the firing shaft 45510 is configured such that the firing assembly 45500 may still fall into the lockout when the sled 45340 of the staple cartridge 45300 is not in its unfired position. Referring to FIGS. 176 and 177, the bottom surface 45511 comprises a notch 45515 defined proximal to the distal end 45513 of the firing shaft 45510. The notch 45515 is configured such that the firing shaft 45510 will fall into the lockout if the sled 45340 is not present in its unfired position. FIG. 176 illustrates the staple cartridge 45300 installed within the channel 45210; however, the sled 45340 is not present in its unfired position. Thus, turning to FIG. 177, the firing shaft 45510 is not sufficiently lifted upwardly by the floating pin 45600 to lift the firing shaft 45510 out of the lockout. Instead, the firing shaft 45510 is pulled down by the spring 45240 as the firing assembly 45500 is advanced distally owing to the floating pin 45600 fitting in the notch 45515. To perform a staple firing stroke, the improper cartridge must be removed and replaced with a proper unfired staple cartridge.

If a staple cartridge is installed in the surgical stapling assembly that does not have a proper lockout key, the floating pin 45600 will remain in its lower most position illustrated in FIG. 172. If an attempt is made to advance the firing assembly 45500 distally, the firing assembly 45500 will be unable to overcome the first stage of the lockout.

FIG. 180 depicts the staple cartridge 45300 discussed above. FIG. 181 depicts a second staple cartridge 45900 comprising a cartridge body 45910 and a pan 45920 configured to hold a plurality of staples in the staple cartridge 45900. The cartridge body 45910 further comprises a lockout key 45930 extending proximally from a proximal face 45913 of the cartridge body 45910. As can be seen from FIGS. 180 and 181, the staple cartridge 45300 and the second staple cartridge 45900 comprise similar features; however, they comprise lockout keys having different configurations. The lockout key 45330 of the staple cartridge 45300 comprises a first length 45338 and a first height 45339 while the lockout key 45930 of the second staple cartridge 45900 comprises a second length 45938 and a second height 45939 which are different than the first length 45338 and the first height 45339, respectively. The staple cartridges 45300, 45900 are part of a system in which the staple cartridge 45300 can only unlock a first instrument but not a second instrument while the second staple cartridge 45900 can only unlock the second instrument and not the first instrument. The lockout key 45930 comprises a ramped surface 45931 and a flat surface 45932 which have different dimensions than the surfaces 45331, 45332 of the lockout key 45330. The lockout key 45330 of the staple cartridge 45300 is shown in phantom lines in FIG. 181 for comparison purposes.

Differing lockout key configurations between similar looking cartridges, for example, can prevent a clinician from inserting and using an incompatible cartridge in a second instrument. In this instance, the lockout keys 45330, 45930 will cause a firing assembly of an instrument to lift to different heights and at different times during the firing stroke of the firing assembly. Referring back to the floating pin 45600, if the second staple cartridge 45900 is installed in the surgical stapling assembly 45000, the firing assembly 45500 will be lifted by the floating pin 45600 at a height which is less than a height at which the firing assembly 45500 will be lifted by the floating pin 45600 if the staple cartridge 45300 is installed. This will cause the firing assembly 45500 to not be able to land on the sled platform of the second staple cartridge and, instead, will become locked out. This will prevent the use of an improper staple cartridge within a stapling instrument.

The instrument with which the second staple cartridge 45900 may be used can comprise a similar floating pin system as discussed above; however, this floating pin may be located in a different position relative to the second staple cartridge 45900 such that the lockout key 45930 can lift the firing member of this instrument to the appropriate height and at the appropriate time to land on the sled of the second staple cartridge 45900 to bypass the lockout of the instrument. In at least one instance, the lockout keys described herein comprise cartridge body fins, for example.

Various aspects of the subject matter described herein are set out in the following examples.

Example 1

A surgical stapling assembly comprising a staple cartridge and a stapling instrument configured to receive the staple cartridge therein. The staple cartridge comprises a cartridge body comprising a lockout key, a plurality of staples stored within the staple cartridge, and a sled configured to deploy the staples during a staple firing stroke. The sled is movable between an unfired position and a fired position during the staple firing stroke. The staple cartridge is in an unspent configuration when the sled is in the unfired position. The stapling instrument comprises a first jaw, a second jaw movable relative to the first jaw, a firing member configured to move the sled through the staple firing stroke, and a lockout. The lockout key is configured to defeat a first stage of the lockout. The sled is configured to defeat a second stage of the lockout when the sled is in the unfired position. The lockout comprises a lockout pocket defined in one of the first jaw and the second jaw. The firing member is configured to move into the lockout pocket at the beginning of the staple firing stroke when the staple cartridge is not installed in the stapling instrument and the first stage of the lockout has not been defeated. The firing member is configured to move into the lockout pocket at the beginning of the staple firing stroke when the staple cartridge is installed in the stapling instrument but is not in the unspent configuration and the second stage of the lockout has not been defeated.

Example 2

The surgical stapling assembly of Example 1, wherein the lockout key comprises an arm and a ramp formed on a proximal end of the arm, wherein the arm extends proximally from the cartridge body, wherein a gap is defined between the proximal end of the cartridge body and the ramp, and wherein the gap is configured to permit the firing member to move into the lockout pocket when the staple cartridge is installed within the stapling instrument and the sled is not in the unfired position.

Example 3

The surgical stapling assembly of Examples 1 or 2, wherein the lockout key comprises two arms and a ramp formed on a proximal end of each arm.

Example 4

The surgical stapling assembly of Examples 1, 2, or 3, wherein the lockout key is configured to lift the firing member past a first length of the lockout pocket to defeat the first stage of the lockout.

Example 5

The surgical stapling assembly of Examples 1, 2, 3, or 4, wherein the cartridge body comprises a longitudinal slot configured to receive the firing member, wherein the lockout key comprises a gate, and wherein the gate extends across the longitudinal slot.

Example 6

The surgical stapling assembly of Example 5, wherein the gate is configured to lift the firing member past a first length of the lockout pocket to defeat the first stage of the lockout.

Example 7

The surgical stapling assembly of Examples 5 or 6, wherein the gate is configured to swing out of the path of the firing member during the staple firing stroke, and wherein the gate is not resettable after the staple firing stroke.

Example 8

The surgical stapling assembly of Examples 5, 6, or 7, wherein a first portion of the firing member is configured to engage the gate to lift the firing member past a first length of the lockout pocket, wherein a second portion of the firing member is configured to open the gate after the firing member is lifted past the first length of the lockout pocket, and wherein the first portion of the firing member is distal to the second portion.

Example 9

The surgical stapling assembly of Example 8, wherein the first portion of the firing member is configured to detect the position of the sled such that the second stage of the lockout is defeated when the sled is in the unfired position.

Example 10

The surgical stapling assembly of Examples 1, 2, 3, 4, 5, 6, 7, 8, or 9, further comprising a spring configured to bias the firing member toward the lockout pocket.

Example 11

The surgical stapling assembly of Examples 1, 2, 3, 4, 5, 6, 7, 8, 9, or 10, wherein the staple cartridge comprises a first staple cartridge and the lockout key comprises a first lockout key, wherein the surgical stapling assembly further comprises a second staple cartridge configured to be installed within the stapling instrument, wherein the second staple cartridge comprises a second lockout key, wherein the first lockout key is configured to lift the firing member a first height when the first staple cartridge is installed within the stapling instrument and the firing member advances through the first stage of the lockout, wherein the second lockout key is configured to lift the firing member a second height when the staple cartridge is installed within the stapling instrument and the firing member advances through the first stage of the lockout, wherein the first height and the second height are different, and wherein the second height is insufficient to overcome the first lockout.

Example 12

The surgical stapling assembly of Examples 1, 2, 3, 4, 5, 6, 7, 8, 9, 10, or 11, wherein when the lockout is not defeated when a second staple cartridge is seated in the stapling instrument that does not comprise the lockout key.

Example 13

The surgical stapling assembly of Examples 1, 2, 3, 4, 5, 6, 7, 8, 9, 10, 11, or 12, wherein defeating the first stage of the lockout and defeating the second stage of the lockout occur at different times and distances of the staple firing stroke.

Example 14

A surgical stapling assembly comprising a staple cartridge comprising a cartridge body including a lockout key, staples stored within the cartridge body, and a sled movable from an unfired position to deploy the staples during a staple firing stroke. The surgical stapling assembly further comprises a cartridge support configured to receive the staple cartridge, a firing member configured to move the sled through the staple firing stroke, a first lockout, and a second lockout. The lockout key is configured to defeat the first lockout when the staple cartridge is seated in the cartridge support. The firing member is prevented from performing the staple firing stroke by the first lockout if the staple cartridge is not seated in the cartridge support. The sled is configured to defeat the second lockout when the staple cartridge is seated in the cartridge support and the sled is in the unfired position. The firing member is prevented from performing the staple firing stroke by the second lockout if the sled is not in the unfired position.

Example 15

The surgical stapling assembly of Example 14, wherein the first lockout and the second lockout share a lockout shoulder on the cartridge support, wherein the cartridge body comprises a first shoulder configured to bypass the first lockout and prevent the firing member from being blocked by the lockout shoulder, and wherein the sled comprises a second shoulder configured to bypass the second lockout and prevent the firing member from being blocked by the lockout shoulder.

Example 16

The surgical stapling assembly of Examples 14 or 15, wherein the first lockout comprises a lockout shoulder on the cartridge support, and wherein the cartridge body comprises a first shoulder configured to bypass the first lockout and prevent the firing member from being blocked by the lockout shoulder.

Example 17

The surgical stapling assembly of Examples 14, 15, or 16, wherein the second lockout comprises a lockout shoulder on the cartridge support, and wherein the sled comprises a second shoulder configured to bypass the second lockout and prevent the firing member from being blocked by the lockout shoulder.

Example 18

The surgical stapling assembly of Examples 14, 15, 16, or 17, wherein defeating the first lockout and defeating the second lockout occur at different times and distances of the staple firing stroke.

Example 19

The surgical stapling assembly of Examples 14, 15, 16, 17, or 18, wherein the first lockout comprises a first lockout shoulder on the cartridge support, wherein the cartridge body comprises a first shoulder configured to bypass the first lockout and prevent the firing member from being blocked by the first lockout shoulder, wherein the second lockout comprises a second lockout shoulder on the cartridge support, and wherein the sled comprises a second shoulder configured to bypass the second lockout and prevent the firing member from being blocked by the second lockout shoulder.

Example 20

The surgical stapling assembly of Example 19, wherein the first lockout shoulder is positioned proximally with respect to the second lockout shoulder.

Example 21

The surgical stapling assembly of Examples 14, 15, 16, 17, 18, 19, or 20, wherein the first lockout is positioned proximally with respect to the second lockout.

Example 22

The surgical stapling assembly of Examples 14, 15, 16, 17, 18, 19, 20, or 21, wherein the firing member does not reach the second lockout if the firing member is stopped by the first lockout.

Example 23

The surgical stapling assembly of Examples 14, 15, 16, 17, 18, 19, 20, 21, or 22, wherein the lockout key contacts the first lockout to deactivate the first lockout when the staple cartridge is seated in the cartridge support.

Example 24

A surgical stapling assembly comprising a staple cartridge comprising a cartridge body including a lockout key, staples stored within the cartridge body, and a sled movable from an unfired position to deploy the staples during a staple firing stroke. The surgical stapling assembly further comprises a cartridge support configured to receive the staple cartridge, a firing member configured to move the sled through the staple firing stroke, a first lockout, and a second lockout. The lockout key is configured to deactivate the first lockout when the staple cartridge is seated in the cartridge support. The firing member is prevented from performing the staple firing stroke by the first lockout if the staple cartridge is not seated in the cartridge support. The sled is configured to defeat the second lockout when the staple cartridge is seated in the cartridge support and the sled is in the unfired position. The firing member is prevented from performing the staple firing stroke by the second lockout if the sled is not in the unfired position.

Example 25

The surgical stapling assembly of Example 24, wherein the lockout key contacts the first lockout to deactivate the first lockout when the staple cartridge is seated in the cartridge support.

Example 26

The surgical stapling assembly of Examples 24 or 25, wherein the first lockout prevents the staple firing stroke if a staple cartridge not having the lockout key is seated in the cartridge support.

Example 27

A staple cartridge configured to be installed within a surgical stapling instrument. The surgical stapling instrument comprises a firing member and a lockout configured to prevent the firing member from moving through a staple firing stroke. The staple cartridge comprises a cartridge body, staples removably stored within the cartridge body, and a sled configured to deploy the staples from the cartridge body during the staple firing stroke. The cartridge body comprises a proximal end and a ramp. The sled is movable between an unfired position and a fired position during the staple firing stroke. The staple cartridge is in an unspent configuration when the sled is in the unfired position. The sled comprises a shoulder. The ramp is configured to lift the firing member onto the shoulder of the sled to defeat the lockout if the sled is in the unfired position.

Example 28

The staple cartridge of Example 27, wherein a gap is defined between the ramp and the proximal end of the staple cartridge such that the firing member falls through the gap into a locked out position if the sled is not in the unfired position.

Example 29

A surgical stapling system comprising a stapling instrument and a staple cartridge configured to be installed within the stapling instrument. The stapling instrument comprises a firing member and a lockout configured to prevent the firing member from performing a staple firing stroke. The staple cartridge comprises a cartridge body, staples removably stored within the cartridge body, and a sled configured to deploy the staples from the cartridge body during the staple firing stroke. The cartridge body comprises a proximal end and a ramp. The sled is movable between an unfired position and a fired position during the staple firing stroke. The staple cartridge is in an unspent configuration when the sled is in the unfired position. The sled comprises a firing member support. The ramp is configured to lift the firing member onto the firing member support of the sled to defeat the lockout if the sled has not been advanced toward the fired position.

Example 30

The surgical stapling system of Example 29, wherein a gap is defined between the ramp and the proximal end of the staple cartridge such that the firing member falls through the gap into a locked out position if the sled has been previously advanced toward the fired position.

Example 31

The surgical stapling system of Examples 29 or 30, further comprising a spring configured to bias the firing member into a locked out position behind the lockout if the staple cartridge is not seated in the stapling instrument when the staple firing stroke is initiated.

Example 32

The surgical stapling system of Examples 29, 30, or 31, further comprising a spring configured to bias the firing member into a locked out position behind the lockout if a staple cartridge without the ramp is seated in the stapling instrument when the staple firing stroke is initiated.

Example 33

The surgical stapling system of Examples 29, 30, 31, or 32, wherein the cartridge body comprises a longitudinal slot configured to receive the firing member, wherein the ramp comprises a gate, and wherein the gate extends across the longitudinal slot.

Example 34

The surgical stapling system of Example 33, wherein the gate is configured to swing out of the path of the firing member during the staple firing stroke, and wherein the gate is not resettable after the staple firing stroke.

Example 35

A surgical stapling system comprising a stapling instrument and a staple cartridge seated in the stapling instrument. The stapling instrument comprise a firing member and a lockout configured to prevent the firing member from performing a staple firing stroke. The staple cartridge comprises a cartridge body comprising a first control surface, staples removably stored within the cartridge body, and a sled configured to deploy the staples from the cartridge body during the staple firing stroke. The sled is movable between an unfired position and a fired position during the staple firing stroke. The staple cartridge is in an unspent configuration when the sled is in the unfired position. The sled comprises a second control surface. The first control surface and the second control surface are configured to co-operatively defeat the lockout if the sled has not been advanced toward the fired position.

Example 36

The surgical stapling system of Example 35, wherein the first control surface comprises a ramp.

Example 37

The surgical stapling system of Examples 35 or 36, wherein the second control surface comprises a support surface configured to support the firing member during the staple firing stroke.

Example 38

A staple cartridge seatable in a stapling instrument including a lockout. The staple cartridge comprises a cartridge body comprising a first control surface, staples removably stored within the cartridge body, and a sled configured to deploy the staples from the cartridge body during the staple firing stroke. The sled is movable between an unfired position and a fired position during the staple firing stroke. The staple cartridge is in an unspent configuration when the sled is in the unfired position. The sled comprises a second control surface. The first control surface and the second control surface are configured to co-operatively defeat the lockout if the sled has not been advanced toward the fired position.

Example 39

The surgical staple cartridge of Example 38, wherein the first control surface comprises a ramp.

Example 40

The surgical staple cartridge of Examples 38 or 39, wherein the second control surface comprises a support surface configured to support the firing member during the staple firing stroke.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES, now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
U.S. patent application Ser. No. 12/235,782, entitled MOTOR-DRIVEN SURGICAL CUTTING INSTRUMENT, now U.S. Pat. No. 8,210,411;
U.S. patent application Ser. No. 12/235,972, entitled MOTORIZED SURGICAL INSTRUMENT, now U.S. Pat. No. 9,050,083.
U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
U.S. patent application Ser. No. 12/893,461, entitled STAPLE CARTRIDGE, filed Sep. 29, 2012, now U.S. Pat. No. 8,733,613;
U.S. patent application Ser. No. 13/036,647, entitled SURGICAL STAPLING INSTRUMENT, filed Feb. 28, 2011, now U.S. Pat. No. 8,561,870;
U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;
U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and
U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical stapling assembly, comprising:
    a staple cartridge, comprising:
        a cartridge body comprising a cartridge body proximal end, and wherein a lockout key protrudes from said cartridge body proximal end;
        a plurality of staples stored within said staple cartridge; and
        a sled configured to deploy said staples during a staple firing stroke, wherein said sled is movable between an unfired position and a fired position during said staple firing stroke, and wherein said staple cartridge is in an unspent configuration when said sled is in said unfired position; and
    a stapling instrument configured to receive said staple cartridge therein, wherein said stapling instrument comprises:
        a first jaw;
        a second jaw movable relative to said first jaw;
        a firing member configured to move said sled through said staple firing stroke; and
        a lockout, wherein said lockout key is configured to defeat a first stage of said lockout, wherein said sled is configured to defeat a second stage of said lockout when said sled is in said unfired position, wherein said lockout comprises a lockout pocket defined in one of said first jaw and said second jaw, wherein said firing member is configured to move into said lockout pocket from a starting position when said staple cartridge is not installed in said stapling instrument and said first stage of said lockout has not been defeated, and wherein said firing member is configured to move into said lockout pocket from said starting position when said staple cartridge is installed in said stapling instrument but is not in said unspent configuration and said second stage of said lockout has not been defeated.

2. The surgical stapling assembly of claim 1, wherein said lockout key comprises an arm and a ramp formed on a proximal end of said arm, wherein said arm extends proximally from said cartridge body, wherein a gap is defined between said cartridge body proximal end and said ramp, and wherein said gap is configured to permit said firing member to move into said lockout pocket when said staple cartridge is installed within said stapling instrument and said sled is not in said unfired position.

3. The surgical stapling assembly of claim 1, wherein said lockout key comprises two arms and a ramp formed on a proximal end of each said arm.

4. The surgical stapling assembly of claim 1, wherein said lockout key is configured to lift said firing member past a first length of said lockout pocket to defeat said first stage of said lockout.

5. The surgical stapling assembly of claim 1, further comprising a spring configured to bias said firing member toward said lockout pocket.

6. The surgical stapling assembly of claim 1, wherein said staple cartridge comprises a first staple cartridge and said lockout key comprises a first lockout key, wherein said surgical stapling assembly further comprises a second staple cartridge configured to be installed within said stapling instrument, wherein said second staple cartridge comprises a second lockout key, wherein said first lockout key is configured to lift said firing member a first height when said first staple cartridge is installed within said stapling instrument and said firing member advances through said first stage of said lockout, wherein said second lockout key is configured to lift said firing member a second height when said second staple cartridge is installed within said stapling instrument and said firing member advances through said first stage of said lockout, wherein said first height and said second height are different, and wherein said second height is insufficient to overcome said lockout.

7. The surgical stapling assembly of claim 1, wherein said lockout is not defeated when a second staple cartridge is seated in said stapling instrument that does not comprise said lockout key.

8. The surgical stapling assembly of claim 1, wherein defeating said first stage of said lockout and defeating said second stage of said lockout occur at different times and distances of said staple firing stroke.

9. A surgical stapling assembly, comprising:
    a staple cartridge comprising a cartridge body including a lockout key, staples stored within said cartridge body, and a sled movable from an unfired position to deploy said staples during a staple firing stroke;

a cartridge support configured to receive said staple cartridge;

a firing member configured to move said sled through said staple firing stroke;

a first lockout, wherein said lockout key is configured to defeat said first lockout when said staple cartridge is seated in said cartridge support, and wherein said firing member is prevented from performing said staple firing stroke by said first lockout if said staple cartridge is not seated in said cartridge support; and a second lockout, wherein said sled is configured to defeat said second lockout when said staple cartridge is seated in said cartridge support and said sled is in said unfired position, and wherein said firing member is prevented from performing said staple firing stroke by said second lockout if said sled is not in said unfired position.

10. The surgical stapling assembly of claim 9, wherein said first lockout and said second lockout share a lockout shoulder on said cartridge support, wherein said cartridge body comprises a first shoulder configured to bypass said first lockout and prevent said firing member from being blocked by said lockout shoulder, and wherein said sled comprises a second shoulder configured to bypass said second lockout and prevent said firing member from being blocked by said lockout shoulder.

11. The surgical stapling assembly of claim 9, wherein said first lockout comprises a lockout shoulder on said cartridge support, and wherein said cartridge body comprises a first shoulder configured to bypass said first lockout and prevent said firing member from being blocked by said lockout shoulder.

12. The surgical stapling assembly of claim 9, wherein said second lockout comprises a lockout shoulder on said cartridge support, and wherein said sled comprises a second shoulder configured to bypass said second lockout and prevent said firing member from being blocked by said lockout shoulder.

13. The surgical stapling assembly of claim 9, wherein defeating said first lockout and defeating said second lockout occur at different times and distances of said staple firing stroke.

14. The surgical stapling assembly of claim 9, wherein said first lockout comprises a first lockout shoulder on said cartridge support, wherein said cartridge body comprises a first shoulder configured to bypass said first lockout and prevent said firing member from being blocked by said first lockout shoulder, wherein said second lockout comprises a second lockout shoulder on said cartridge support, and wherein said sled comprises a second shoulder configured to bypass said second lockout and prevent said firing member from being blocked by said second lockout shoulder.

15. The surgical stapling assembly of claim 14, wherein said first lockout shoulder is positioned proximally with respect to said second lockout shoulder.

16. The surgical stapling assembly of claim 9, wherein said first lockout is positioned proximally with respect to said second lockout.

17. The surgical stapling assembly of claim 9, wherein said firing member does not reach said second lockout if said firing member is stopped by said first lockout.

18. The surgical stapling assembly of claim 9, wherein said lockout key contacts said first lockout to deactivate said first lockout when said staple cartridge is seated in said cartridge support.

19. A surgical stapling assembly, comprising:

a staple cartridge comprising a cartridge body including a lockout key, staples stored within said cartridge body, and a sled movable from an unfired position to deploy said staples during a staple firing stroke;

a cartridge support configured to receive said staple cartridge;

a firing member configured to move said sled through said staple firing stroke;

a first lockout, wherein said lockout key is configured to deactivate said first lockout when said staple cartridge is seated in said cartridge support, and wherein said firing member is prevented from performing said staple firing stroke by said first lockout if said staple cartridge is not seated in said cartridge support; and a second lockout, wherein said sled is configured to defeat said second lockout when said staple cartridge is seated in said cartridge support and said sled is in said unfired position, and wherein said firing member is prevented from performing said staple firing stroke by said second lockout if said sled is not in said unfired position.

20. The surgical stapling assembly of claim 19, wherein said lockout key contacts said first lockout to deactivate said first lockout when said staple cartridge is seated in said cartridge support.

21. The surgical stapling assembly of claim 19, wherein said first lockout prevents said staple firing stroke if a staple cartridge not having said lockout key is seated in said cartridge support.

22. A surgical stapling assembly, comprising:

a staple cartridge, comprising:
  a cartridge body comprising a lockout key comprising an arm and a ramp formed on a proximal end of said arm, wherein said arm extends proximally from a proximal end of said cartridge body, wherein a gap is defined between said proximal end of said cartridge body and said ramp;
  a plurality of staples stored within said staple cartridge; and
  a sled configured to deploy said staples during a staple firing stroke, wherein said sled is movable between an unfired position and a fired position during said staple firing stroke, and wherein said staple cartridge is in an unspent configuration when said sled is in said unfired position; and a stapling instrument configured to receive said staple cartridge therein, wherein said stapling instrument comprises:
  a first jaw;
  a second jaw movable relative to said first jaw;
  a firing member configured to move said sled through said staple firing stroke; and
  a lockout, wherein said lockout key is configured to defeat a first stage of said lockout, wherein said sled is configured to defeat a second stage of said lockout when said sled is in said unfired position, wherein said lockout comprises a lockout pocket defined in one of said first jaw and said second jaw, wherein said firing member is configured to move into said lockout pocket from a starting position when said staple cartridge is not installed in said stapling instrument and said first stage of said lockout has not been defeated, and wherein said gap is configured to permit said firing member to move into said lockout pocket from said starting position when said staple cartridge is installed in said stapling instrument but is not in said unspent configuration and said second stage of said lockout has not been defeated.

23. A surgical stapling assembly, comprising:

a staple cartridge, comprising:

a cartridge body comprising a lockout key comprising two arms and a ramp formed on a proximal end of each said arm;
a plurality of staples stored within said staple cartridge; and
a sled configured to deploy said staples during a staple firing stroke, wherein said sled is movable between an unfired position and a fired position during said staple firing stroke, and wherein said staple cartridge is in an unspent configuration when said sled is in said unfired position; and
a stapling instrument configured to receive said staple cartridge therein, wherein said stapling instrument comprises:
a first jaw;
a second jaw movable relative to said first jaw;
a firing member configured to move said sled through said staple firing stroke; and
a lockout, wherein said lockout key is configured to defeat a first stage of said lockout, wherein said sled is configured to defeat a second stage of said lockout when said sled is in said unfired position, wherein said lockout comprises a lockout pocket defined in one of said first jaw and said second jaw, wherein said firing member is configured to move into said lockout pocket from a starting position when said staple cartridge is not installed in said stapling instrument and said first stage of said lockout has not been defeated, and wherein said firing member is configured to move into said lockout pocket from said starting position when said staple cartridge is installed in said stapling instrument but is not in said unspent configuration and said second stage of said lockout has not been defeated.

24. A surgical stapling assembly, comprising:
a staple cartridge, comprising:
a cartridge body comprising a lockout key;
a plurality of staples stored within said staple cartridge; and
a sled configured to deploy said staples during a staple firing stroke, wherein said sled is movable between an unfired position and a fired position during said staple firing stroke, and wherein said staple cartridge is in an unspent configuration when said sled is in said unfired position; and
a stapling instrument configured to receive said staple cartridge therein, wherein said stapling instrument comprises:
a first jaw;
a second jaw movable relative to said first jaw;
a firing member configured to move said sled through said staple firing stroke; and
a lockout, wherein said lockout key is configured to defeat a first stage of said lockout, wherein said sled is configured to defeat a second stage of said lockout when said sled is in said unfired position, wherein said lockout comprises a lockout pocket defined in one of said first jaw and said second jaw, wherein said firing member is configured to move into said lockout pocket from a starting position when said staple cartridge is not installed in said stapling instrument and said first stage of said lockout has not been defeated, wherein said firing member is configured to move into said lockout pocket from said starting position when said staple cartridge is installed in said stapling instrument but is not in said unspent configuration and said second stage of said lockout has not been defeated, and wherein said lockout key is configured to lift said firing member past a first length of said lockout pocket to defeat said first stage of said lockout.

25. A surgical stapling assembly, comprising:
a first staple cartridge, comprising:
a first cartridge body comprising a first lockout key comprising an arm and a ramp formed on a proximal end of said arm, wherein said arm extends proximally from a proximal end of said first cartridge body, and wherein a gap is defined between said proximal end of said first cartridge body and said ramp;
a plurality of first staples stored within said first staple cartridge; and
a first sled configured to deploy said first staples during a first staple firing stroke, wherein said first sled is movable between a first unfired position and a first fired position during said first staple firing stroke, and wherein said first staple cartridge is in a first unspent configuration when said first sled is in said first unfired position, and wherein said surgical stapling assembly further comprises:
a second staple cartridge, comprising:
a second cartridge body comprising a second lockout key;
a plurality of second staples stored within said second staple cartridge; and
a second sled configured to deploy said second staples during a second staple firing stroke, wherein said second sled is movable between a second unfired position and a second fired position during said second staple firing stroke, and wherein said second staple cartridge is in a second unspent configuration when said second sled is in said second unfired position, and wherein said surgical stapling assembly further comprises:
a stapling instrument configured to receive said first and second staple cartridges therein, wherein said stapling instrument comprises:
a first jaw;
a second jaw movable relative to said first jaw;
a firing member configured to move said first sled through said first staple firing stroke and said second sled through said second staple firing stroke; and
a lockout, wherein said first lockout key is configured to defeat a first stage of said lockout, wherein said first sled is configured to defeat a second stage of said lockout when said first sled is in said first unfired position, wherein said lockout comprises a lockout pocket defined in one of said first jaw and said second jaw, wherein said firing member is configured to move into said lockout pocket from a starting position when one of said first staple cartridge and said second staple cartridge is not installed in said stapling instrument and said first stage of said lockout has not been defeated, and wherein said gap is configured to permit said firing member to move into said lockout pocket from said starting position when said first staple cartridge is installed in said stapling instrument but is not in said first unspent configuration and said second stage of said lockout has not been defeated, wherein said first lockout key is configured to lift said firing member a first height when said first staple cartridge is installed within said stapling instrument and said firing member advances through said first stage of said lockout, wherein said second lockout key is configured to lift said firing member a second height when said second staple cartridge is installed within said stapling instrument and said firing member advances through said first stage of said lockout, wherein said first height and said second height are different, and wherein said second height is insufficient to overcome said lockout.

\* \* \* \* \*